United States Patent
Beechem et al.

(10) Patent No.: US 11,473,142 B2
(45) Date of Patent: Oct. 18, 2022

(54) CHEMICAL COMPOSITIONS AND USES THEREOF

(71) Applicant: NanoString Technologies, Inc., Seattle, WA (US)

(72) Inventors: Joseph M. Beechem, Eugene, OR (US); Dae Kim, Bellevue, WA (US); Margaret Hoang, Seattle, WA (US); Mark Gregory, Boise, ID (US); Erin Piazza, Edmonds, WA (US); Denise Zhou, Seattle, WA (US)

(73) Assignee: NanoString Technologies, Inc., Seattle, WA (US)

(*) Notice: Subject to any disclaimer, the term of this patent is extended or adjusted under 35 U.S.C. 154(b) by 0 days.

(21) Appl. No.: 17/476,712

(22) Filed: Sep. 16, 2021

(65) Prior Publication Data

US 2021/0403999 A1   Dec. 30, 2021

Related U.S. Application Data

(63) Continuation of application No. 16/272,487, filed on Feb. 11, 2019.
(Continued)

(51) Int. Cl.
| | |
|---|---|
| *C12P 19/34* | (2006.01) |
| *C12Q 1/6876* | (2018.01) |
| *C12Q 1/6818* | (2018.01) |
| *C12Q 1/6858* | (2018.01) |
| *C12Q 1/6848* | (2018.01) |

(Continued)

(52) U.S. Cl.
CPC ......... *C12Q 1/6876* (2013.01); *C12Q 1/6804* (2013.01); *C12Q 1/686* (2013.01); *C12Q 1/6818* (2013.01); *C12Q 1/6841* (2013.01); *C12Q 1/6848* (2013.01); *C12Q 1/6851* (2013.01); *C12Q 1/6855* (2013.01);
(Continued)

(58) Field of Classification Search
USPC .......... 435/6.1, 6.11, 6.12, 91.1, 91.2, 91.51, 435/283.1, 287.1, 287.2; 436/94, 501; 536/23.1, 24.3, 24.33, 25.3
See application file for complete search history.

(56) References Cited

U.S. PATENT DOCUMENTS

| | | | |
|---|---|---|---|
| 5,320,814 | A | 6/1994 | Walt et al. |
| 5,543,838 | A | 8/1996 | Hosier et al. |

(Continued)

FOREIGN PATENT DOCUMENTS

| | | |
|---|---|---|
| JP | 2008-542783 A | 11/2008 |
| WO | WO 97/07245 A1 | 2/1997 |

(Continued)

OTHER PUBLICATIONS

U.S. Appl. No. 16/272,487, filed Feb. 11, 2019.
(Continued)

*Primary Examiner* — Frank W Lu
(74) *Attorney, Agent, or Firm* — Cooley LLP; Ivor R. Elrifi; Matthew Pavao

(57) ABSTRACT

The present invention relates to, among other things, probes, compositions, methods, and kits for simultaneous, multiplexed detection and quantification of protein and/or nucleic acid expression in a user-defined region of a tissue, user-defined cell, and/or user-defined subcellular structure within a cell that are adaptable for use with existing sequencing technologies.

13 Claims, 40 Drawing Sheets
(29 of 40 Drawing Sheet(s) Filed in Color)
Specification includes a Sequence Listing.

Related U.S. Application Data

(60) Provisional application No. 62/771,212, filed on Nov. 26, 2018, provisional application No. 62/629,180, filed on Feb. 12, 2018.

(51) Int. Cl.
  *C12Q 1/6869* (2018.01)
  *C12Q 1/686* (2018.01)
  *C12Q 1/6851* (2018.01)
  *C12Q 1/6855* (2018.01)
  *C12Q 1/6841* (2018.01)
  *C12Q 1/6804* (2018.01)

(52) U.S. Cl.
  CPC ......... *C12Q 1/6858* (2013.01); *C12Q 1/6869* (2013.01); *C12Q 2600/16* (2013.01)

(56) References Cited

U.S. PATENT DOCUMENTS

| | | | |
|---|---|---|---|
| 5,635,352 | A | 6/1997 | Urdea et al. |
| 6,100,030 | A | 8/2000 | McCasky Feazel et al. |
| 6,207,392 | B1 | 3/2001 | Weiss et al. |
| 6,429,027 | B1 | 8/2002 | Chee et al. |
| 6,596,257 | B2 | 7/2003 | Bryan |
| 6,602,661 | B1 | 8/2003 | Knezevic et al. |
| 6,690,470 | B1 | 2/2004 | Baer et al. |
| 6,942,968 | B1 | 9/2005 | Dickinson et al. |
| 7,060,507 | B2 | 6/2006 | Akeson et al. |
| 7,132,519 | B2 | 11/2006 | Monforte et al. |
| 7,214,477 | B1 | 5/2007 | Emmert-Buck |
| 7,255,999 | B2 | 8/2007 | Singh et al. |
| 7,402,399 | B2 | 7/2008 | Mukherjeei et al. |
| 7,569,392 | B2 | 8/2009 | Levy et al. |
| 7,648,828 | B2 | 1/2010 | Chan-Hui et al. |
| 7,728,287 | B2 | 6/2010 | Felton et al. |
| 8,003,312 | B2 | 8/2011 | Krutzik et al. |
| 8,221,972 | B2 | 7/2012 | Lemaire et al. |
| 8,309,306 | B2 | 11/2012 | Nolan et al. |
| 8,349,574 | B2 | 1/2013 | Bates et al. |
| 8,362,415 | B2 | 1/2013 | Felton et al. |
| 8,486,623 | B2 | 7/2013 | Monforte et al. |
| 8,637,650 | B2 | 1/2014 | Cherkasov et al. |
| 8,753,824 | B2 | 6/2014 | Papin et al. |
| 8,865,414 | B2 | 10/2014 | Hennig et al. |
| 8,906,700 | B2 | 12/2014 | Lim et al. |
| 9,046,477 | B2 | 6/2015 | Emedcoles et al. |
| 9,228,948 | B2 | 1/2016 | Emedcoles et al. |
| 9,297,762 | B2 | 3/2016 | Emedcoles et al. |
| 9,304,084 | B2 | 4/2016 | Emedcoles et al. |
| 9,376,677 | B2 | 6/2016 | Mir |
| 9,376,678 | B2 | 6/2016 | Gormley et al. |
| 9,644,204 | B2 | 5/2017 | Hindson et al. |
| 9,975,122 | B2 | 5/2018 | Masquelier et al. |
| 10,053,723 | B2 | 8/2018 | Hindson et al. |
| 10,071,377 | B2 | 9/2018 | Bharadwaj et al. |
| 10,501,777 | B2 | 12/2019 | Beechem et al. |
| 10,640,816 | B2 | 5/2020 | Beechem et al. |
| 2001/0002315 | A1 | 5/2001 | Schultz et al. |
| 2001/0007775 | A1 | 7/2001 | Seul et al. |
| 2001/0023078 | A1 | 9/2001 | Bawendi et al. |
| 2001/0029049 | A1 | 10/2001 | Walt et al. |
| 2001/0034034 | A1 | 10/2001 | Bruchez et al. |
| 2001/0053334 | A1 | 12/2001 | Chen et al. |
| 2002/0028457 | A1 | 3/2002 | Empedocles et al. |
| 2002/0034737 | A1 | 3/2002 | Drmanac |
| 2002/0034827 | A1 | 3/2002 | Singh et al. |
| 2002/0039728 | A1 | 4/2002 | Kain et al. |
| 2002/0051971 | A1 | 5/2002 | Stuelpnagel et al. |
| 2002/0068018 | A1 | 6/2002 | Pepper et al. |
| 2002/0177141 | A1 | 11/2002 | Chee et al. |
| 2002/0187515 | A1 | 12/2002 | Chee et al. |
| 2003/0008323 | A1 | 1/2003 | Ravkin et al. |
| 2003/0013091 | A1 | 1/2003 | Dimitrov |
| 2003/0028981 | A1 | 2/2003 | Chandler et al. |
| 2003/0148335 | A1 | 8/2003 | Shen et al. |
| 2003/0152952 | A1 | 8/2003 | Van Ness et al. |
| 2003/0186426 | A1 | 10/2003 | Brewer et al. |
| 2004/0000519 | A1 | 1/2004 | Yong et al. |
| 2005/0048498 | A1 | 3/2005 | Woudenberg et al. |
| 2005/0131006 | A1 | 6/2005 | Mukherjee et al. |
| 2005/0170439 | A1 | 8/2005 | Chan-Hui et al. |
| 2005/0196786 | A1 | 9/2005 | Levy |
| 2005/0233318 | A1 | 10/2005 | Chee et al. |
| 2006/0063196 | A1 | 3/2006 | Akeson et al. |
| 2007/0166708 | A1 | 7/2007 | Dimitrov et al. |
| 2008/0038725 | A1 | 2/2008 | Luo et al. |
| 2008/0038734 | A1 | 2/2008 | Sorge et al. |
| 2008/0118934 | A1 | 5/2008 | Gerdes et al. |
| 2010/0015607 | A1 | 1/2010 | Geiss et al. |
| 2010/0047924 | A1 | 2/2010 | Webster et al. |
| 2010/0075858 | A1 | 3/2010 | Davis et al. |
| 2010/0112710 | A1 | 5/2010 | Geiss et al. |
| 2010/0151472 | A1 | 6/2010 | Nolan et al. |
| 2010/0209913 | A1 | 8/2010 | Endress et al. |
| 2010/0261026 | A1 | 10/2010 | Ferree et al. |
| 2010/0262374 | A1 | 10/2010 | Hwang et al. |
| 2011/0086774 | A1 | 4/2011 | Dunaway et al. |
| 2011/0151451 | A1 | 6/2011 | Lemaire et al. |
| 2011/0172115 | A1 | 7/2011 | Thompson |
| 2011/0223613 | A1 | 9/2011 | Gut |
| 2011/0245111 | A1 | 10/2011 | Chee |
| 2013/0023433 | A1 | 1/2013 | Luo et al. |
| 2013/0178372 | A1 | 7/2013 | Geiss et al. |
| 2014/0120532 | A1 | 5/2014 | Lee et al. |
| 2014/0120550 | A1 | 5/2014 | Baranov |
| 2014/0121117 | A1 | 5/2014 | Tanner |
| 2014/0371088 | A1 | 12/2014 | Webster |
| 2015/0080233 | A1 | 3/2015 | Bendall et al. |
| 2015/0099650 | A1 | 4/2015 | Sood et al. |
| 2015/0132763 | A1 | 5/2015 | Amorese et al. |
| 2015/0141297 | A1 | 5/2015 | Lim et al. |
| 2015/0287578 | A1 | 10/2015 | Bendall et al. |
| 2015/0329852 | A1 | 11/2015 | Nolan |
| 2015/0368697 | A1 | 12/2015 | Samusik et al. |
| 2016/0194701 | A1 | 7/2016 | Beechem et al. |
| 2016/0362730 | A1 | 12/2016 | Alexander et al. |
| 2017/0016053 | A1 | 1/2017 | Beechem et al. |
| 2017/0275669 | A1 | 9/2017 | Weissleder et al. |
| 2018/0142286 | A1 | 5/2018 | Dunaway et al. |
| 2019/0249248 | A1 | 8/2019 | Beechem et al. |
| 2020/0040382 | A1 | 2/2020 | Beechem et al. |
| 2020/0040385 | A1 | 2/2020 | Beechem et al. |
| 2021/0403998 | A1 | 12/2021 | Beechem et al. |

FOREIGN PATENT DOCUMENTS

| | | |
|---|---|---|
| WO | WO 97/14028 A2 | 4/1997 |
| WO | WO 99/18434 A1 | 4/1999 |
| WO | WO 00/73777 A1 | 12/2000 |
| WO | WO 01/00875 A2 | 1/2001 |
| WO | WO 2007/000669 A2 | 1/2007 |
| WO | WO 2009/156725 A1 | 12/2009 |
| WO | WO 2010/081114 A2 | 7/2010 |
| WO | WO 2012/106385 A2 | 8/2012 |
| WO | WO 2012/140224 A1 | 10/2012 |
| WO | WO 2013/122996 A1 | 8/2013 |
| WO | WO 2014/060483 A1 | 4/2014 |
| WO | WO 2014/200767 A1 | 12/2014 |
| WO | WO 2015/128272 A2 | 9/2015 |
| WO | WO 2016/162309 A1 | 10/2016 |
| WO | WO 2017/015099 A1 | 1/2017 |
| WO | WO 2018/026873 A1 | 2/2018 |
| WO | WO 2018/091676 A1 | 5/2018 |

OTHER PUBLICATIONS

U.S. Appl. No. 16/596,587, filed Oct. 8, 2019.
U.S. Appl. No. 16/596,596, filed Oct. 8, 2019.
U.S. Appl. No. 17/476,707, filed Sep. 16, 2021.
Agasti, S. S. et al., "Photocleavable DNA Barcode—Antibody Conjugates Allow Sensitive and Multiplexed Protein Analysis in Single Cells," J. Am. Chem. Soc., 134:18499-18502 (2012).

(56) References Cited

OTHER PUBLICATIONS

Alfano, R. R. et al., "Optical Sensing, Imaging, and Manipulation for Biological and Biomedical Applications," SPIE—The International Society for Optical Engineering, Jul. 2000, vol. 4082, Taiwan, 342 pages.

Angelo, M. et al., "Multiplexed ion beam imaging of human breast tumors," Nature Medicine, 20(4):436-442 (2014).

Armani, M. et al., "2D-PCR: a method of mapping DNA in tissue sections," Lab Chip., 9(24):3526-3534 (2009); doi:10.1039/b910807f.

Bailey, R. C. et al., "DNA-Encoded Antibody Libraries: A Unified Platform for Multiplexed Cell Sorting and Detection of Genes and Proteins," J. Am. Chem. Soc., 129:1959-1967 (2007).

Cesano, A. et al., "Abstract 1371: Spatially-resolved, multiplexed digital characterizatio nof protein distribution and abundance in FFPE tissue sections," AACR 107th Annual Meeting, Apr. 16-20, 2016, 5 pages.

Chow, S. et al., "Measurement of MAP Kinase Activation by Flow Cytometry Using Phospho-Specific Antibodies to MEK and ERK: Potential for Pharmacodynamic Monitoring of Signal Transduction Inhibitors," Cytometry (Communications in Clinical Cytometry), 46:72-78 (2001).

Crossetto, N. et al., "Spatially resolved transcriptomics and beyond," Nature Reviews Genetics, 16:57-66 (2015).

Dictionary Definition of "Abundance." Printed on Sep. 22, 2021, 1 page.

Dierck, K. et al., "Quantitative multiplexed profiling of cellular signaling networks using phosphotyrosinespecific DNA-tagged SH2 domains," Nature Methods, 3:737-744 (2006).

"Digital spatial profiling platform allows for spatially-resolved, high-plex quantification of mRNA distribution and abundance on FFPE and fresh frozen tissue sections," Poster #3434, Power Point Presentation, AACR Annual Meeting, Apr. 14-18, 2018, 1 page.

Drummond, E. S. et al., "Proteomic analysis of neurons microdissected from formalinfixed, paraffin-embedded Alzheimer's disease brain tissue," Scientific Reports, 5:15456 (2015), 8 pages, doi: 10.1038/srep15456.

Ferguson, J. A. et al., "High-Density Fiber-Optic DNA Random Microsphere Array," Analytical Chemistry, 72(22):5618-5624 (2000).

Frei, A. P. et al., "Highly multiplexed simultaneous detection of RNAs and proteins in single cells," Nature Methods, 13:269-275 (2016).

Geiss, G. K. et al., "Direct multiplexed measurement of gene expression with color-coded probe pairs," Nature Biotechnology, 26(3):317-326 (2008).

Gullberg, M. et al., "Cytokine detection by antibody-based proximity ligation," PNAS, 101(22):8420-8424 (2004).

Lee, H. et al., "Colour-barcoded magnetic microparticles for multiplexed bioassays," Nature Materials, 9:745-749 (2010).

Lemaire, R. et al., "Tag-Mass: Specific Molecular Imaging of Transcriptome and Proteome by Mass Spectrometry Based on Photocleavable Tag," J Proteome Res., 6(6):2057-2067 (2007); oi:10.1021/pr0700044.

Lind, K. & Kubista, M., "Development and evaluation of three real-time immuno-PCR assemblages for quantification of PSA," Journal of Immunological Methods, 304:107-116 (2005).

"Membrane permeability," last updated Jul. 9, 2020, https://phys.libretexts.org/Courses/University_of_California_Davis/UCD%3A_Biophysics_241_-_Membrane_Biology/04%3A_Membrane-Protein_Interactions/4.01%3A_Membrane_Permeability; 5 pages.

Steemers, F. J. et al., "Screening unlabeled DNA targets with randomly ordered fiber-optic gene arrays," Nature Biotechnology, 18:91-94 (2000).

"Strategies for Detecting mRNA Northern blotting, Nuclease Protection Assays, In Situ hybridization, and RT-PCR," ThermoFisher Scientific. Printed on Sep. 22, 2021, 2 pages.

Thiery-Lavenant, G. et al., "Targeted Multiplex Imaging Mass Spectrometry in Transmission Geometry for Subcellular Spatial Resolution," Journal of the American Society for Mass Spectrometry, 24:609-614 (2013).

Ullal, A. V. et al., "Cancer cell profiling by barcoding allows multiplexed protein analysis in fine needle aspirates," Science Translational Medicine, 6(219):219ra9 (2015), 22 pages. doi: 10.1126/scitranslmed.3007361.

Werner, J. H. et al., Current status of DNA sequencing by single molecule detection, Proc. SPIE 3602, Advances in Fluorescence Sensing Technology IV, pp. 355-366 (1999).

Zinchuk, V. et al., "Quantitative Colocalization Analysis of Multicolor Confocal Immunofluorescence Microscopy Images: Pushing Pixels to Explore Biological Phenomena," The Japan Society of Histochemistry and Cytochemistry, 40(4):101-111 (2007).

Zollinger, D. et al., "Abstract 3434: Digital spatial profiling platform allows for spatially resolved, high-plex quantification of mRNA distribution and abundance on FFPE and fresh frozen tissue sections," AACR Annual Meeting, Apr. 14-18, 2018, 2 pages.

Large Molecules Cross Membranes via Vesicles, printed on Jan. 10, 2022,1 page; https://www.macmillanhighered.com/BrainHoney/Resource/6716/digital_first_content/trunk/test/hillis2e/hillis2e_ch05_5.html#:~:text=Macromolecules%20such%20as%20proteins%2C%20polysaccharides,these%20macromolecules%20in%20specific%20locations.

| Protein Immuno-oncology Panel (30-plex) |
|---|
| AKT |
| B7-H3 |
| Bcl-2 |
| Beta-2-microglobulin |
| Beta-Catenin |
| CD14 |
| CD19 |
| CD3 |
| CD4 |
| CD44 |
| CD45 |
| CD45RO |
| CD56 |
| CD68 |
| CD8A |
| FOXP3 |
| GZMB |
| Histone H3 |
| Ki67 |
| CD20 |
| P-AKT |
| PanCK |
| PD1 |
| PD-L1 |
| S6 |
| STAT3 |
| P-STAT3 |
| VISTA |
| IgG Rabbit isotype control |
| IgG Mouse isotype control |

FIG. 21A

| RNA Immuno-oncology Panel (20-plex) |
| --- |
| CD3E |
| CD3G |
| CD4 |
| CD20 |
| CD40 |
| CD45 |
| CD74 |
| CD79A |
| CTLA4 |
| GAPDH |
| KRT13 |
| PD1 |
| PSA |
| RPS6 |
| Negative probe 1 |
| Negative probe 2 |
| Negative probe 3 |
| Negative probe 4 |
| Negative probe 5 |
| Negative probe 6 |

FIG. 22A

CHEMICAL COMPOSITIONS AND USES THEREOF

BACKGROUND OF THE INVENTION

This application is a continuation of U.S. patent application Ser. No. 16/272,487, filed Feb. 11, 2019. U.S. patent application Ser. No. 16/272,487 claims priority to, and the benefit of, U.S. Provisional Application No. 62/629,180, filed Feb. 12, 2018 and U.S. Provisional Application No. 62/771,212, filed Nov. 26, 2018. The contents of each of the aforementioned patent applications are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Sep. 15, 2021, is named "NATE-037_C02US_SeqList.txt" and is about 50,019 bytes in size.

BACKGROUND OF THE INVENTION

Standard immunohistochemical and in situ hybridization methods allow for simultaneous detection of, at most, six to ten protein or nucleic acid targets, with three to four targets being typical. There exists a need for probes, compositions, methods, and kits for simultaneous, multiplexed detection and quantification of protein and/or nucleic acid expression in a user-defined region of a tissue, user-defined cell, and/or user-defined subcellular structure within a cell. Furthermore, there is a need for such systems to be adaptable for use with existing sequencing technologies that are already available to a large number of end users.

SUMMARY OF THE INVENTION

The present disclosure relates to probes, compositions, methods, and kits for simultaneous, multiplexed, spatial detection and quantification of protein and/or nucleic acid expression in a user-defined region of a tissue, user-defined cell, and/or user-defined subcellular structure within a cell.

The present disclosure provides a method for spatially detecting at least one target analyte in at least one cell from a tissue sample comprising: (1) contacting at least one target analyte in at least one cell in a tissue sample with at least one probe comprising a target binding domain and an identifier oligonucleotide, wherein the identifier oligonucleotide comprises a unique nucleic acid sequence which identifies the target analyte bound to the target binding domain; (2) providing a force to a location of the tissue sample sufficient to release the identifier oligonucleotide; (3) collecting the released identifier oligonucleotide; (4) ligating to the released identifier oligonucleotide at least one nucleic acid adapter, wherein the nucleic acid adapter comprises a nucleic acid sequence which identifies the specific location of the tissue sample from which the identifier oligonucleotide was released, a nucleic acid sequence comprising a unique molecular identifier, a first amplification primer binding site, a second amplification primer binding site and optionally, a constant nucleic acid sequence to minimize ligation bias; (5) amplifying the ligation product produced in step (4); and (6) Identifying the released identifier oligonucleotide by sequencing the amplified products produced in step (5), thereby spatially detecting the at least one target analyte in the at least one cell in a tissue sample.

The present disclosure also provides a method for spatially detecting at least one target analyte in at least one cell from a tissue sample comprising: (1) contacting at least one target analyte in at least one cell in a tissue sample with at least one probe comprising a target binding domain and an identifier oligonucleotide, wherein the identifier oligonucleotide comprises a unique nucleic acid sequence which identifies the target analyte bound to the target binding domain; (2) providing a force to a location of the tissue sample sufficient to release the identifier oligonucleotide; (3) collecting the released identifier oligonucleotide; (4) ligating to the released identifier oligonucleotide at least one nucleic acid adapter, wherein the nucleic acid adapter comprises: a nucleic acid sequence comprising a unique molecular identifier, a first amplification primer binding site, a second amplification primer binding site and optionally, a constant nucleic acid sequence to minimize ligation bias, and wherein at least one of the first or second amplification primer binding sites identifies the specific location of the tissue sample from which the identifier oligonucleotide was released; (5) amplifying the ligation product produced in step (4); and (6) Identifying the released identifier oligonucleotide by sequencing the amplified products produced in step (5), thereby spatially detecting the at least one target analyte in the at least one cell in a tissue sample.

The present disclosure also provides a method for spatially detecting at least one target analyte in at least one cell from a tissue sample comprising: (1) contacting at least one target analyte in at least one cell in a tissue sample with at least one probe comprising a target binding domain and an identifier oligonucleotide, wherein the identifier oligonucleotide comprises a unique nucleic acid sequence which identifies the target analyte bound to the target binding domain; (2) providing a force to a location of the tissue sample sufficient to release the identifier oligonucleotide; (3) collecting the released identifier oligonucleotide; (4) ligating to the released identifier oligonucleotide at least one nucleic acid adapter, wherein the nucleic acid adapter comprises: a nucleic acid sequence comprising a unique molecular identifier, a first amplification primer binding site, a second amplification primer binding site and optionally, a constant nucleic acid sequence to minimize ligation bias; (5) amplifying the extension product produced in step (4) using a first amplification primer capable of binding to the first amplification primer binding site and a second amplification primer capable of binding to the second amplification primer binding site, wherein at least one of the amplification primers comprise a nucleic acid sequence which identifies the specific location of the tissue sample from which the identifier oligonucleotide was released; and (6) Identifying the released identifier oligonucleotide by sequencing the amplified products produced in step (5), thereby spatially detecting the at least one target analyte in the at least one cell in a tissue sample.

The nucleic acid adapter of step (4) can be a partially double-stranded nucleic acid molecule. A partially double-stranded nucleic acid adapter can comprise a double-stranded annealed region, a first single-stranded mismatched region and a second single-stranded mismatched region. The first single-stranded mismatched region and the second single stranded mismatched region can be present on opposing sides of the double-stranded annealed region.

The nucleic acid sequence which identifies the specific location of the tissue sample from which the identifier oligonucleotide was released can be present in the double-stranded annealed region of a partially double-stranded nucleic acid adapter.

The constant nucleic acid sequence to minimize ligation bias can be present in the double-stranded annealed region of a partially double-stranded nucleic acid adapter.

A unique molecular identifier can be present in at least one of the first or second single-stranded mismatched regions of a partially double-stranded nucleic acid adapter.

The first amplification primer binding site can be present in the first single-stranded mismatched region of a partially double-stranded nucleic acid adapter and the second amplification primer binding site can be present in the second single-stranded mismatched region of the same partially double-stranded nucleic acid adapter.

The methods of the present disclosure described in the preceding can further comprise prior to step (4), performing an end repair reaction. The methods can also further comprise prior to step (4), performing a tailing reaction to attach a single nucleotide overhang to the 3' ends of the identifier oligonucleotide. The methods can further comprise, prior to step (4), performing an end repair reaction and a tailing reaction to attach a single nucleotide overhang to the 3' ends of the identifier oligonucleotide. The tailing reaction and the end repair reaction can be performed sequentially or concurrently.

The present disclosure provides a method for spatially detecting at least one target analyte in at least one cell from a tissue sample comprising: (1) contacting at least one target analyte in at least one cell in a tissue sample with at least one probe comprising a target binding domain and an identifier oligonucleotide, wherein the identifier oligonucleotide comprises a first amplification primer binding site, and a unique nucleic acid sequence which identifies the target analyte bound to the target binding domain; (2) providing a force to a location of the tissue sample sufficient to release the identifier oligonucleotide; (3) collecting the released identifier oligonucleotide; (4) ligating to the released identifier oligonucleotide at least one nucleic acid adapter, wherein the nucleic acid adapter comprises a nucleic acid sequence which identifies the specific location of the tissue sample from which the identifier oligonucleotide was released, a nucleic acid sequence comprising a unique molecular identifier, a second amplification primer binding site and optionally, a constant nucleic acid sequence to minimize ligation bias; (5) amplifying the ligation product produced in step (4); and (6) Identifying the released identifier oligonucleotide by sequencing the amplified products produced in step (5), thereby spatially detecting the at least one target analyte in the at least one cell in a tissue sample.

The present disclosure also provides a method for spatially detecting at least one target analyte in at least one cell from a tissue sample comprising: (1) contacting at least one target analyte in at least one cell in a tissue sample with at least one probe comprising a target binding domain and an identifier oligonucleotide, wherein the identifier oligonucleotide comprises: a first amplification primer binding site and a unique nucleic acid sequence which identifies the target analyte bound to the target binding domain; (2) providing a force to a location of the tissue sample sufficient to release the identifier oligonucleotide; (3) collecting the released identifier oligonucleotide; (4) ligating to the released identifier oligonucleotide at least one nucleic acid adapter, wherein the nucleic acid adapter comprises a nucleic acid sequence comprising a unique molecular identifier, a second amplification primer binding site, and optionally, a constant nucleic acid sequence to minimize ligation bias; (5) amplifying the extension product produced in step (4) using a first amplification primer capable of binding to the first amplification primer binding site and a second amplification primer capable of binding to the second amplification primer binding site, wherein at least one of the amplification primers comprise a nucleic acid sequence which identifies the specific location of the tissue sample from which the identifier oligonucleotide was released; and (6) Identifying the released identifier oligonucleotide by sequencing the amplified products produced in step (5), thereby spatially detecting the at least one target analyte in the at least one cell in a tissue sample.

The nucleic acid adapter of step (4) can be a partially double-stranded nucleic acid molecule. A partially double-stranded nucleic acid adapter can comprise a double-stranded annealed region and a single-stranded mismatched region.

The nucleic acid sequence which identifies the specific location of the tissue sample from which the identifier oligonucleotide was released can be present in the double-stranded annealed region of a partially double-stranded nucleic acid adapter.

The constant nucleic acid sequence to minimize ligation bias can be present in the double-stranded annealed region of a partially double-stranded nucleic acid adapter. The constant nucleic acid sequence can also comprise a cleavable moiety. The cleavable moiety can be an enzymatically cleavable moiety. The enzymatically cleavable moiety can be a USER sequence.

A unique molecular identifier can be present in the single-stranded mismatched region of a partially double-stranded nucleic acid adapter.

The second amplification primer binding site can be present in the single-stranded mismatched region of a partially double-stranded nucleic acid adapter.

The present disclosure provides a method for spatially detecting at least one target analyte in at least one cell from a tissue sample comprising: (1) contacting at least one target analyte in at least one cell in a tissue sample with at least one probe comprising a target binding domain and an identifier oligonucleotide, wherein the identifier oligonucleotide comprises a first amplification primer binding site, and a unique nucleic acid sequence which identifies the target analyte bound to the target binding domain; (2) providing a force to a location of the tissue sample sufficient to release the identifier oligonucleotide; (3) collecting the released identifier oligonucleotide; (4) hybridizing to the released identifier oligonucleotide a single stranded nucleic acid template, wherein the nucleic acid template comprises a region complementary to the unique nucleic acid sequence of the identifier oligonucleotide, a nucleic acid sequence comprising a unique molecular identifier, a nucleic acid sequence complementary to a second amplification primer binding site and optionally, an affinity molecule; (5) extending the identifier oligonucleotide of step (4) to form an extension product complementary to the single stranded nucleic acid template, wherein the extension product comprises the identifier oligonucleotide, the nucleic acid sequence complementary to the unique molecular identifier, and the second amplification primer binding site; (6) amplifying the extension product produced in step (5) using a first amplification primer capable of binding to the first amplification primer binding site and a second amplification primer capable of binding to the second amplification primer binding site, wherein at least one of the amplification primers comprise a nucleic acid sequence which identifies the specific location of the tissue sample from which the identifier oligonucleotide was released; (7) Identifying the released identifier oligonucleotide by sequencing the amplified products produced in step (6), thereby spatially detecting the at least one target analyte in the at least one cell in a tissue sample.

The present disclosure provides a method for spatially detecting at least one target analyte in at least one cell from a tissue sample comprising: (1) contacting at least one target analyte in at least one cell in a tissue sample with at least one probe comprising a target binding domain and an identifier oligonucleotide, wherein the identifier oligonucleotide comprises a first amplification primer binding site and a unique nucleic acid sequence which identifies the target analyte bound to the target binding domain; (2) providing a force to a location of the tissue sample sufficient to release the identifier oligonucleotide; (3) collecting the released identifier oligonucleotide; (4) hybridizing to the released identifier oligonucleotide a single stranded nucleic acid template, wherein the nucleic acid template comprises a region complementary to the unique nucleic acid sequence of the identifier oligonucleotide, a nucleic acid sequence which identifies the specific location of the tissue sample from which the identifier oligonucleotide was released, a nucleic acid sequence comprising a unique molecular identifier, a nucleic acid sequence complementary to a second amplification primer binding site and optionally, an affinity molecule; (5) extending the identifier oligonucleotide of step (4) to form an extension product complementary to the single stranded nucleic acid template, wherein the extension product comprises the identifier oligonucleotide, the nucleic acid sequence complementary to the nucleic acid sequence which identifies the specific location of the tissue sample from which the identifier oligonucleotide was released, the nucleic acid sequence complementary to the unique molecular identifier and the second amplification primer binding site; (6) amplifying the extension product produced in step (5); and (7) Identifying the released identifier oligonucleotide by sequencing the amplified products produced in step (6), thereby spatially detecting the at least one target analyte in the at least one cell in a tissue sample.

The single stranded nucleic acid template can further comprise an affinity molecule. In aspects in which the single stranded nucleic acid template comprises an affinity molecule, the methods of the present disclosure described in the preceding can further comprise an affinity purification step between steps (4) and (5).

The present disclosure provides a method for spatially detecting at least one target analyte in at least one cell from a tissue sample comprising: (1) contacting at least one target analyte in at least one cell in a tissue sample with at least one probe comprising a target binding domain and an identifier oligonucleotide, wherein the identifier oligonucleotide comprises a unique nucleic acid sequence which identifies the target analyte bound to the target binding domain; (2) providing a force to a location of the tissue sample sufficient to release the identifier oligonucleotide; (3) collecting the released identifier oligonucleotide; (4) hybridizing to the released identifier oligonucleotide a first nucleic acid probe and a second nucleic acid probe, wherein the first nucleic acid probe comprises a nucleic acid complementary to a portion of the identifier oligonucleotide, a nucleic acid sequence which identifies the specific location of the tissue sample from which the identifier oligonucleotide was released and a first amplification primer binding site, and wherein the second nucleic acid probe comprises a nucleic acid complementary to a portion of the identifier oligonucleotide, a nucleic acid sequence comprising a unique molecular identifier and a second amplification primer binding site, and wherein the first the second nucleic acid probes hybridize to the identifier oligonucleotide such that the first and the second nucleic acid probes are adjacent but not overlapping; (5) performing nick repair such that the hybridized first and second nucleic acid probes are ligated together; (6) amplifying the ligation product produced in step (5); and (7) Identifying the released identifier oligonucleotide by sequencing the amplified products produced in step (6), thereby spatially detecting the at least one target analyte in the at least one cell in a tissue sample.

The present disclosure also provides a method for spatially detecting at least one target analyte in at least one cell from a tissue sample comprising: (1) contacting at least one target analyte in at least one cell in a tissue sample with at least one probe comprising a target binding domain and an identifier oligonucleotide, wherein the identifier oligonucleotide comprises a unique nucleic acid sequence which identifies the target analyte bound to the target binding domain; (2) providing a force to a location of the tissue sample sufficient to release the identifier oligonucleotide; (3) collecting the released identifier oligonucleotide; (4) hybridizing to the released identifier oligonucleotide a first nucleic acid probe and a second nucleic acid probe, wherein the first nucleic acid probe comprises a nucleic acid complementary to a portion of the identifier oligonucleotide and a first amplification primer binding site, and wherein the second nucleic acid probe comprises a nucleic acid complementary to a portion of the identifier oligonucleotide and a second amplification primer binding site, and wherein at least one of the first or second nucleic acid probes comprises a nucleic acid sequence comprising a unique molecular identifier, and wherein at least one of the first or second nucleic acid probes comprises a nucleic acid sequence which identifies the specific location of the tissue sample from which the identifier oligonucleotide was released, and wherein the first and the second nucleic acid probes hybridize to the identifier oligonucleotide such that the first and the second nucleic acid probes are adjacent but not overlapping; (5) performing nick repair such that the hybridized first and second nucleic acid probes are ligated together; (6) amplifying the ligation product produced in step (5); and (7) Identifying the released identifier oligonucleotide by sequencing the amplified products produced in step (6), thereby spatially detecting the at least one target analyte in the at least one cell in a tissue sample.

The present disclosure also provides a method for spatially detecting at least one target analyte in at least one cell from a tissue sample comprising: (1) contacting at least one target analyte in at least one cell in a tissue sample with at least one probe comprising a target binding domain and an identifier oligonucleotide, wherein the identifier oligonucleotide comprises a unique nucleic acid sequence which identifies the target analyte bound to the target binding domain; (2) providing a force to a location of the tissue sample sufficient to release the identifier oligonucleotide; (3) collecting the released identifier oligonucleotide; (4) hybridizing to the released identifier oligonucleotide a first nucleic acid probe and a second nucleic acid probe, wherein the first nucleic acid probe comprises a nucleic acid complementary to a portion of the identifier oligonucleotide, a nucleic acid sequence which identifies the specific location of the tissue sample from which the identifier oligonucleotide was released and a first amplification primer binding site, and wherein the second nucleic acid probe comprises a nucleic acid complementary to a portion of the identifier oligonucleotide, a nucleic acid sequence comprising a unique molecular identifier and a second amplification primer binding site, and wherein the first and the second nucleic acid probes hybridize to the identifier oligonucleotide such that the first and the second nucleic acid probes are not adjacent and are not overlapping; (5) performing a gap extension and nick repair reaction such that the hybridized first and second nucleic acid probes are ligated together; (6) amplifying the ligation product produced in step (5); and (7) Identifying the released identifier oligonucleotide by sequencing the amplified products produced in step (6), thereby spatially detecting the at least one target analyte in the at least one cell in a tissue sample.

The present disclosure also provides a method for spatially detecting at least one target analyte in at least one cell from a tissue sample comprising: (1) contacting at least one target analyte in at least one cell in a tissue sample with at least one probe comprising a target binding domain and an identifier oligonucleotide, wherein the identifier oligonucleotide comprises a unique nucleic acid sequence which identifies the target analyte bound to the target binding domain; (2) providing a force to a location of the tissue sample sufficient to release the identifier oligonucleotide; (3) collecting the released identifier oligonucleotide; (4) hybridizing to the released identifier oligonucleotide a first nucleic acid probe and a second nucleic acid probe, wherein the first nucleic acid probe comprises a nucleic acid complementary to a portion of the identifier oligonucleotide and a first amplification primer binding site, and wherein the second nucleic acid probe comprises a nucleic acid complementary to a portion of the identifier oligonucleotide and a second amplification primer binding site, and wherein at least one of the first or second nucleic acid probes comprises a nucleic acid sequence comprising a unique molecular identifier, and wherein at least one of the first or second nucleic acid probes comprises a nucleic acid sequence which identifies the specific location of the tissue sample from which the identifier oligonucleotide was released, and wherein the first and the second nucleic acid probes hybridize to the identifier oligonucleotide such that the first and the second nucleic acid probes are not adjacent and are not overlapping; (5) performing a gap extension and nick repair reaction such that the hybridized first and second nucleic acid probes are ligated together; (6) amplifying the ligation product produced in step (5); and (7) Identifying the released identifier oligonucleotide by sequencing the amplified products produced in step (6), thereby spatially detecting the at least one target analyte in the at least one cell in a tissue sample.

In aspects in which the nucleic acid sequence which identifies the specific location of the tissue sample from which the identifier oligonucleotide was released is located on the first nucleic acid probe, the nucleic acid sequence which identifies the specific location of the tissue sample from which the identifier oligonucleotide was released can be located 5' to the first amplification primer binding site.

In aspects in which a unique molecular identifier is located on the second nucleic acid probe, the unique molecular identifier can be located 3' to the second amplification primer binding site.

In aspects in which the nucleic acid sequence which identifies the specific location of the tissue sample from which the identifier oligonucleotide was released and a unique molecular identifier are present in the first nucleic acid probe, the nucleic acid sequence which identifies the specific location of the tissue sample from which the identifier oligonucleotide was released and a unique molecular identifier can be located 5' to the first amplification primer binding site.

In aspects in which the nucleic acid sequence which identifies the specific location of the tissue sample from which the identifier oligonucleotide was released and a unique molecular identifier are present in the second nucleic acid probe, the nucleic acid sequence which identifies the specific location of the tissue sample from which the identifier oligonucleotide was released and the unique molecular identifier can be located 3' to the second amplification primer binding site.

In aspects in which a unique molecular identifier is present in the first nucleic acid probe and the nucleic acid sequence which identifies the specific location of the tissue sample from which the identifier oligonucleotide was released is present in the second nucleic acid probe, the unique molecular identifier can be located 5' to the first amplification primer binding site and the nucleic acid sequence which identifies the specific location of the tissue sample from which the identifier oligonucleotide was released can be located 3' to the second amplification binding site.

The present disclosure provides a method for spatially detecting at least one target analyte in at least one cell from a tissue sample comprising: (1) contacting at least one target analyte in at least one cell in a tissue sample with at least one probe comprising a target binding domain and an identifier oligonucleotide, wherein the identifier oligonucleotide comprises a unique nucleic acid sequence which identifies the target analyte bound to the target binding domain; (2) providing a force to a location of the tissue sample sufficient to release the identifier oligonucleotide; (3) collecting the released identifier oligonucleotide; (4) hybridizing to the released identifier oligonucleotide a first nucleic acid probe and a second nucleic acid probe, wherein the first nucleic acid probe comprises a nucleic acid complementary to a portion of the identifier oligonucleotide, a nucleic acid sequence which identifies the specific location of the tissue sample from which the identifier oligonucleotide was released, a first amplification primer binding site, a nucleic acid sequence comprising a first unique molecular identifier and a first flow cell binding site, and wherein the second nucleic acid probe comprises a nucleic acid complementary to a portion of the identifier oligonucleotide, a nucleic acid sequence comprising a second unique molecular identifier, a nucleic acid sequence comprising a third unique molecular identifier and a second flow cell binding site, and wherein the first and the second nucleic acid probes hybridize to the identifier oligonucleotide such that the first and the second nucleic acid probes are adjacent but not overlapping; (5) performing nick repair such that the hybridized first and second nucleic acid probes are ligated together; (6) amplifying the ligation product produced in step (5); and (7) Identifying the released identifier oligonucleotide by sequencing the amplified products produced in step (6), thereby spatially detecting the at least one target analyte in the at least one cell in a tissue sample.

The present disclosure also provides a method for spatially detecting at least one target analyte in at least one cell from a tissue sample comprising: (1) contacting at least one target analyte in at least one cell in a tissue sample with at least one probe comprising a target binding domain and an identifier oligonucleotide, wherein the identifier oligonucleotide comprises a unique nucleic acid sequence which identifies the target analyte bound to the target binding domain; (2) providing a force to a location of the tissue sample sufficient to release the identifier oligonucleotide; (3) collecting the released identifier oligonucleotide; (4) hybridizing to the released identifier oligonucleotide a first nucleic acid probe and a second nucleic acid probe, wherein the first nucleic acid probe comprises a nucleic acid complementary to a portion of the identifier oligonucleotide, a first amplification primer binding site, a nucleic acid sequence comprising a first unique molecular identifier and a first flow cell binding site, and wherein the second nucleic acid probe comprises a nucleic acid complementary to a portion of the identifier oligonucleotide, a nucleic acid sequence comprising a second unique molecular identifier and a second flow cell binding site, and wherein at least one of the first or second nucleic acid probes comprises a nucleic acid sequence comprising a third unique molecular identifier, and wherein at least one of the first or second nucleic acid probes comprises a nucleic acid sequence which identifies the specific location of the tissue sample from which the identifier oligonucleotide was released, and wherein the first and the second nucleic acid probes hybridize to the identifier oligonucleotide such that the first and the second nucleic acid probes are adjacent but not overlapping; (5) performing nick repair such that the hybridized first and second nucleic acid probes are ligated together; (6) amplifying the ligation product produced in step (5); and (7) Identifying the released identifier oligonucleotide by sequencing the amplified products produced in step (6), thereby spatially detecting the at least one target analyte in the at least one cell in a tissue sample.

The present disclosure also provides a method for spatially detecting at least one target analyte in at least one cell from a tissue sample comprising: (1) contacting at least one target analyte in at least one cell in a tissue sample with at least one probe comprising a target binding domain and an identifier oligonucleotide, wherein the identifier oligonucleotide comprises a unique nucleic acid sequence which identifies the target analyte bound to the target binding domain; (2) providing a force to a location of the tissue sample sufficient to release the identifier oligonucleotide; (3) collecting the released identifier oligonucleotide; (4) hybridizing to the released identifier oligonucleotide a first nucleic acid probe and a second nucleic acid probe, wherein the first nucleic acid probe comprises a nucleic acid complementary to the identifier oligonucleotide, a nucleic acid sequence which identifies the specific location of the tissue sample from which the identifier oligonucleotide was released, a first amplification primer binding site, a nucleic acid sequence comprising a first unique molecular identifier and a first flow cell binding site, and wherein the second nucleic acid probe comprises a nucleic acid complementary to the identifier oligonucleotide, a nucleic acid sequence comprising a second unique molecular identifier, a nucleic acid sequence comprising a third unique molecular identifier and a second flow cell binding site, and wherein the first and the second nucleic acid probes hybridize to the identifier oligonucleotide such that the first and the second nucleic acid probes are not adjacent and are not overlapping; (5) performing a gap extension and nick repair reaction such that the hybridized first and second nucleic acid probes are ligated together; (6) amplifying the ligation product produced in step (5); and (7) Identifying the released identifier oligonucleotide by sequencing the amplified products produced in step (6), thereby spatially detecting the at least one target analyte in the at least one cell in a tissue sample.

The present disclosure also provides a method for spatially detecting at least one target analyte in at least one cell from a tissue sample comprising: (1) contacting at least one target analyte in at least one cell in a tissue sample with at least one probe comprising a target binding domain and an identifier oligonucleotide, wherein the identifier oligonucleotide comprises a unique nucleic acid sequence which identifies the target analyte bound to the target binding domain; (2) providing a force to a location of the tissue sample sufficient to release the identifier oligonucleotide; (3) collecting the released identifier oligonucleotide; (4) hybridizing to the released identifier oligonucleotide a first nucleic acid probe and a second nucleic acid probe, wherein the first nucleic acid probe comprises a nucleic acid complementary to the identifier oligonucleotide, a first amplification primer binding site, a nucleic acid sequence comprising a first unique molecular identifier and a first flow cell binding site, and wherein the second nucleic acid probe comprises a nucleic acid complementary to the identifier oligonucleotide, a nucleic acid sequence comprising a second unique molecular identifier and a second flow cell binding site, and wherein at least one of the first or second nucleic acid probes comprises a nucleic acid sequence comprising a third unique molecular identifier, and wherein at least one of the first or second nucleic acid probes comprises a nucleic acid sequence which identifies the specific location of the tissue sample from which the identifier oligonucleotide was released, and wherein the first and the second nucleic acid probes hybridize to the identifier oligonucleotide such that the first and the second nucleic acid probes are not adjacent and are not overlapping; (5) performing a gap extension and nick repair reaction such that the hybridized first and second nucleic acid probes are ligated together; (6) amplifying the ligation product produced in step (5); and (7) Identifying the released identifier oligonucleotide by sequencing the amplified products produced in step (6), thereby spatially detecting the at least one target analyte in the at least one cell in a tissue sample.

In aspects in which the nucleic acid sequence which identifies the specific location of the tissue sample from which the identifier oligonucleotide was released and the first unique molecular identifier are present in the first nucleic acid probe, the nucleic acid sequence which identifies the specific location of the tissue sample from which the identifier oligonucleotide was released and the first unique molecular identifier can be located 5' to the first flow cell binding site.

In aspects in which the second and the third unique molecular identifiers are present in the second nucleic acid probe, the second and the third unique molecular identifiers can be located 3' to the second flow cell binding site.

In some aspects, the first unique molecular identifier can be present in the first nucleic acid probe and can be located 5' to the first flow cell binding site. In other aspects, the second unique molecular identifier can be present in the second nucleic acid probe and can be located 3' to the second flow cell binding site.

In some aspects, the nucleic acid sequence which identifies the specific location of the tissue sample from which the identifier oligonucleotide was released and the third unique molecular identifier can be present in the first nucleic acid probe and can be located 5' to the first flow cell binding site.

In some aspects, the nucleic acid sequence which identifies the specific location of the tissue sample from which the identifier oligonucleotide was released and the third unique molecular identifier can be present in the second nucleic acid probe and can be located 3' to the second flow cell binding site.

In some aspect, the third unique molecular identifier can be present in the first nucleic acid probe and can be located 5' to the first flow cell binding site. In this same aspect, the nucleic acid sequence which identifies the specific location of the tissue sample from which the identifier oligonucleotide was released can be present in the second nucleic acid probe and can be located 3' to the second flow cell binding site.

The present disclosure provides a method for spatially detecting at least one target analyte in at least one cell from a tissue sample comprising: (1) contacting at least one target analyte in at least one cell in a tissue sample with at least one probe comprising a target binding domain and an identifier oligonucleotide, wherein the identifier oligonucleotide comprises a unique nucleic acid sequence which identifies the target analyte bound to the target binding domain, a nucleic acid sequence comprising a unique molecular identifier, a first amplification primer binding site, and a second amplification primer binding site; (2) providing a force to a location of the tissue sample sufficient to release the identifier oligonucleotide; (3) collecting the released identifier oligonucleotide; (4) amplifying the released identifier oligonucleotide using a first amplification primer capable of binding to the first amplification primer binding site and a second amplification primer capable of binding to the second amplification primer binding site, wherein at least one of the amplification primers comprises a nucleic acid sequence which identifies the specific location of the tissue sample from which the identifier oligonucleotide was released; (5) Identifying the released identifier oligonucleotide by sequencing the amplified products produced in step (4), thereby spatially detecting the at least one target analyte in the at least one cell in a tissue sample.

The present disclosure also provides a method for spatially detecting at least one target analyte in at least one cell from a tissue sample comprising: (1) contacting at least one target analyte in at least one cell in a tissue sample with at least one probe comprising a target binding domain and an identifier oligonucleotide, wherein the identifier oligonucleotide comprises a unique nucleic acid sequence which identifies the target analyte bound to the target binding domain, a first amplification primer binding site and a second amplification primer binding site; (2) providing a force to a location of the tissue sample sufficient to release the identifier oligonucleotide; (3) collecting the released identifier oligonucleotide; (4) amplifying the released identifier oligonucleotide using a first amplification primer capable of binding to the first amplification primer binding site and a second amplification primer capable of binding to the second amplification primer binding site, wherein at least one of the amplification primers comprises a nucleic acid sequence which identifies the specific location of the tissue sample from which the identifier oligonucleotide was released, and wherein at least one of the amplification primers comprises a nucleic acid sequence comprising a unique molecular identifier; and (5) Identifying the released identifier oligonucleotide by sequencing the amplified products produced in step (4), thereby spatially detecting the at least one target analyte in the at least one cell in a tissue sample.

The present disclosure provides a method for spatially detecting at least one target analyte in at least one cell from a tissue sample comprising: (1) contacting at least one target analyte in at least one cell in a tissue sample with at least one probe comprising a target binding domain and an identifier oligonucleotide, wherein the identifier oligonucleotide comprises a unique nucleic acid sequence which identifies the target analyte bound to the target binding domain and a capture probe binding site; (2) providing a force to a location of the tissue sample sufficient to release the identifier oligonucleotide; (3) collecting the released identifier oligonucleotide; (4) hybridizing to the released identifier oligonucleotide a capture probe, wherein the capture probe comprises an affinity molecule and a region complementary to the capture probe binding site; and (5) Identifying the released identifier oligonucleotide by sequencing the amplified hybridized product produced in step (4), thereby spatially detecting the at least one target analyte in the at least one cell in a tissue sample.

The present disclosure provides a method for spatially detecting at least one target analyte in at least one cell from a tissue sample comprising: (1) contacting at least one target analyte in at least one cell in a tissue sample with at least one probe comprising a target binding domain and an identifier oligonucleotide, wherein the identifier oligonucleotide comprises a unique nucleic acid sequence which identifies the target analyte bound to the target binding domain, a capture probe binding site and a multiplexing probe binding site; (2) providing a force to a location of the tissue sample sufficient to release the identifier oligonucleotide; (3) collecting the released identifier oligonucleotide; (4) hybridizing to the released identifier oligonucleotide a capture probe and a multiplexing probe, wherein the capture probe comprises an affinity molecule and a region complementary to the capture probe binding site, and wherein the multiplexing probe comprises a nucleic acid sequence which identifies the specific location of the tissue sample from which the identifier oligonucleotide was released and a region complementary to the multiplexing probe binding site; and (5) Identifying the released identifier oligonucleotide by sequencing the hybridized product produced in step (4), thereby spatially detecting the at least one target analyte in the at least one cell in a tissue sample.

The present disclosure provides a method for spatially detecting at least one target analyte in at least one cell from a tissue sample comprising: (1) contacting at least one target analyte in at least one cell in a tissue sample with at least one probe comprising a target binding domain and an identifier oligonucleotide, wherein the identifier oligonucleotide comprises a unique nucleic acid sequence which identifies the target analyte bound to the target binding domain; (2) providing a force to a location of the tissue sample sufficient to release the identifier oligonucleotide; (3) collecting the released identifier oligonucleotide; (4) hybridizing to the released identifier oligonucleotide a first nucleic acid probe and a second nucleic acid probe, wherein the first nucleic acid probe comprises: a nucleic acid complementary to a portion of the identifier oligonucleotide, a nucleic acid sequence comprising a unique molecular identifier, a first amplification primer binding site, and wherein the second nucleic acid probe comprises: a nucleic acid complementary to a portion of the identifier oligonucleotide, and a second amplification primer binding site, and wherein the first and the second nucleic acid probes hybridize to the identifier oligonucleotide such that the first and the second nucleic acid probes are adjacent but not overlapping; (5) ligating the hybridized first and second nucleic acid probes together; (6) amplifying the ligation product produced in step (5); and (7) identifying the released identifier oligonucleotide by sequencing the amplified products produced in step (6), thereby spatially detecting the at least one target analyte in the at least one cell in a tissue sample.

The present disclosure provides a method for spatially detecting at least one target analyte in at least one cell from a tissue sample comprising: (1) contacting at least one target analyte in at least one cell in a tissue sample with at least one probe comprising a target binding domain and an identifier oligonucleotide, wherein the identifier oligonucleotide comprises: a unique nucleic acid sequence which identifies the target analyte bound to the target binding domain, a nucleic acid sequence comprising a unique molecular identifier, a first amplification primer binding site, and a second amplification primer binding site; (2) providing a force to a location of the tissue sample sufficient to release the identifier oligonucleotide; (3) collecting the released identifier oligonucleotide; (4) amplifying the collected identifier oligonucleotide; (5) Identifying the released identifier oligonucleotide by sequencing the amplified products produced in step (4), thereby spatially detecting the at least one target analyte in the at least one cell in a tissue sample.

A In all methods of the present disclosure, the ligation process can be a nick ligation process. The nick ligation process can be a nick repair process.

In all methods of the present disclosure, the sequencing can be an enzyme free sequencing method.

In all methods of the present disclosure, the identifier oligonucleotide can be double-stranded. In aspects in which the identifier oligonucleotide is double-stranded, at least one of the two strands of the identifier oligonucleotide can comprise at least two separate nucleic acid molecules. Alternatively, at least one 3' end of an identifier oligonucleotide can comprise a single nucleotide overhang.

In all methods of the present disclosure, the identifier oligonucleotide can be single-stranded.

In all methods of the present disclosure, the unique nucleic acid sequence which identifies the target analyte bound to a target binding domain can comprise between about 5 nucleotides and about 40 nucleotides preferably about 35 nucleotides, preferably still about 10 nucleotides.

In all methods of the present disclosure, the nucleic acid sequence which identifies the specific location of the tissue sample from which the identifier oligonucleotide was released can comprise between about 6 nucleotides and about 15 nucleotides, preferably about 12 nucleotides, preferably still about 10 nucleotides.

In all methods of the present disclosure, at least one of a first nucleic acid probe or a second nucleic acid probe can comprise an affinity molecule. For example, at least one of a first nucleic acid probe or a second nucleic acid probe can comprise a biotin.

In all methods of the present disclosure, an amplification primer binding site can comprise between about 18 nucleotides and about 40 nucleotides, preferably about 32 nucleotides, preferably still about 25 nucleotides. An amplification primer binding site can comprise an i7 sequence, wherein the i7 sequence comprises the sequence set forth in SEQ ID NO: 1. An amplification primer binding site can comprise an i5 sequence, wherein the i5 sequence comprises the sequence set forth in SEQ ID NO: 2.

In all methods of the present disclosure, an amplification primer can comprise a flow cell adapter sequence, wherein the flow cell adapter sequence is suitable for sequencing. An amplification primer can comprise a P5 flow cell adapter sequence, wherein the P5 flow cell adapter sequence comprises the sequence set forth in SEQ ID NO: 3. An amplification primer can comprise a P7 flow cell adapter sequence, wherein the P7 flow cell adapter sequence comprises the sequence set forth in SEQ ID NO: 4.

In all methods of the present disclosure, a flow cell binding site can comprise a flow cell adapter sequence, wherein the flow cell adapter sequence is suitable for sequencing. A flow cell binding site can comprise a P5 flow cell adapter sequence, wherein the P5 flow cell adapter sequence comprises the sequence set forth in SEQ ID NO: 3. A flow cell binding site can comprise a P7 flow cell adapter sequence, wherein the P7 flow cell adapter sequence comprises the sequence set forth in SEQ ID NO: 4.

In all methods of the present invention, at least one of the amplification primers can comprise an affinity molecule. For example, at least one of the amplification primers cam comprise a biotin.

In all methods of the present disclosure, amplification can comprise performing PCR. Performing PCR can comprise an amplification primer.

An amplification primer can comprise a flow cell binding site. An amplification primer can comprise a nucleic sequence which identifies the specific location of the tissue sample from which an identifier oligonucleotide was released. An amplification primer can comprise a nucleic acid sequence complementary to an amplification primer binding site.

Any of the above aspects can be combined with any other aspect.

Unless otherwise defined, all technical and scientific terms used herein have the same meaning as commonly understood by one of ordinary skill in the art to which this disclosure belongs. In the Specification, the singular forms also include the plural unless the context clearly dictates otherwise; as examples, the terms "a," "an," and "the" are understood to be singular or plural and the term "or" is understood to be inclusive. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Although methods and materials similar or equivalent to those described herein can be used in the practice or testing of the present disclosure, suitable methods and materials are described below. All publications, patent applications, patents, and other references mentioned herein are incorporated by reference in their entirety. The references cited herein are not admitted to be prior art to the claimed invention. In the case of conflict, the present Specification, including definitions, will control. In addition, the materials, methods, and examples are illustrative only and are not intended to be limiting. Other features and advantages of the disclosure will be apparent from the following detailed description and claim.

BRIEF DESCRIPTION OF THE DRAWINGS

The patent or application file contains at least one drawing executed in color. Copies of this patent or patent application publication with color drawings will be provided by the Office upon request and payment of the necessary fee.

The above and further features will be more clearly appreciated from the following detailed description when taken in conjunction with the accompanying drawings.

FIG. 21A, FIG. 21B, FIG. 21C and FIG. 21D show the spatial detection of protein target analytes using the methods of the present disclosure.

FIG. 22A, FIG. 22B, FIG. 22C and FIG. 22D show the spatial detection of RNA target analytes using the methods of the present disclosure.

DETAILED DESCRIPTION OF THE INVENTION

Figure 1:
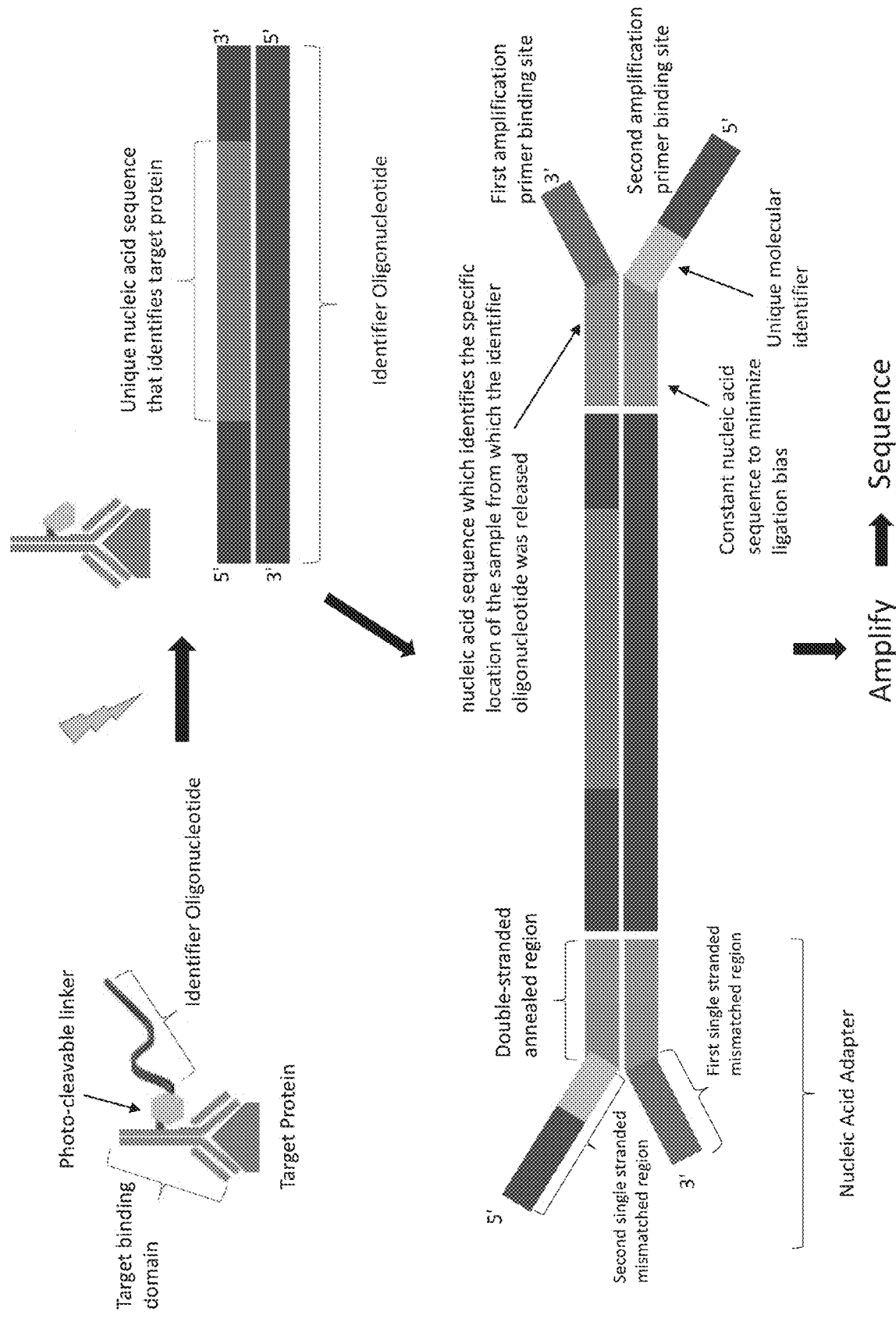
FIG. 1 is a schematic of a two-ended adapter ligation method of the present disclosure.

The present disclosure is based in part on probes, compositions, methods, and kits for simultaneous, multiplexed spatial detection and quantification of protein and/or nucleic acid expression in a user-defined region of a tissue, user-defined cell, and/or user-defined subcellular structure within a cell using existing sequencing methods.

The present disclosure provides a comparison of the identity and abundance of target proteins and/or target nucleic acids present in a first region of interest (e.g., tissue type, a cell (including normal and abnormal cells), and a subcellular structure within a cell) and the identity and abundance of target proteins and/or target nucleic acids present in a second region of interest. There is no pre-defined upper limit to the number of regions of interest and comparisons that can be made; the upper limit relates to the size of the region of interest relative the size of the sample. As examples, when a single cell represents a region of interest, then a section may have hundreds to thousands of regions of interest; however, if a tissue section includes only two cell types, then the section may have only two regions of interest (each including only one cell type).

The present disclosure provides a higher degree of multiplexing than is possible with standard immunohistochemical or in situ hybridization methods. Standard immunohistochemical methods allow for maximal simultaneous detection of six to ten protein targets, with three to four protein targets being more typical. Similarly, in situ hybridization methods are limited to simultaneous detection of fewer than ten nucleic acid targets. The present disclosure provides detection of large combinations of nucleic acid targets and/or protein targets from a defined region of a sample. The present disclosure provides an increase in objective measurements by digital quantification and increased reliability and consistency, thereby enabling comparison of results among multiple centers.

Various compositions and methods of the present disclosure are described in full detail herein.

In one aspect, the present disclosure provides compositions and methods for spatially detecting at least one target analyte in a sample using the probes of the present disclosure in a method herein referred to as a "two-ended adapter ligation method".

A two ended-adapter ligation method of the present disclosure can comprise: (1) contacting at least one target analyte in a sample with at least one probe of the present disclosure. The probes and samples of the present disclosure are described in further detail herein. The at least one target analyte can be a target protein or a target nucleic acid. In the aspect that the at least one target analyte is a target protein, the probe can comprise a target binding domain that is a target protein-binding region that can specifically bind to a target protein of interest. In the aspect that the at least one target analyte is a target nucleic acid, the probe can comprise a target nucleic acid-binding region that can directly or indirectly hybridize to a target nucleic acid of interest. The probe further comprises an identifier oligonucleotide. The identifier oligonucleotide can comprise a unique nucleic acid sequence which identifies the target analyte bound to the target binding domain.

Following contacting the at least on target analyte with the at least one probe, a two-ended adapter ligation method can further comprise: (2) providing a force to a location of the sample sufficient to release the identifier oligonucleotide. In a non-limiting example, in aspects in which the probe comprises a photo-cleavable linker between the identifier oligonucleotide and the target binding domain, a region-of-interest is excited with light of a sufficient wavelength capable of cleaving the photo-cleavable linker.

Following release of the identifier oligonucleotide, a two-ended adapter ligation method can further comprise: (3) collecting the released identifier oligonucleotide. By directing the force only to a specific location in step (2), identifier oligonucleotides are only released from probes within that location and not from probes located outside that location. Thus, identifier oligonucleotides are collected only for probes that are bound to targets within that location, thereby permitting detection of the identities and quantities of the targets (proteins and/or nucleic acids) located only within that location.

Following collection of the released identifier oligonucleotide, a two-ended adapter ligation method can further comprise: (4) ligating to the released identifier oligonucleotide collected in step (3) at least one nucleic acid adapter.

The nucleic acid adapter can comprise a nucleic acid sequence which identifies the specific location of the sample from which the identifier oligonucleotide was released. For example, if the identifier oligonucleotide was released from location of the sample designated "ROI #1", the nucleic acid adapter would comprise a nucleic acid sequence that corresponds to "ROI #1".

The nucleic acid adapter can also comprise a unique molecular identifier.

The nucleic acid adapter can also comprise a first amplification primer binding site. In other aspects, the nucleic acid adapter can also comprise a second amplification primer binding site.

In some aspects, the nucleic acid adapter can also comprise a constant nucleic acid sequence to minimize ligation bias caused by differences in sequences of particular identifier oligonucleotides.

The nucleic acid adapter can be a partially double-stranded nucleic acid molecule. In aspects in which the nucleic acid adapter is partially double-stranded, the nucleic acid adapter comprises a double-stranded annealed region, a first single-stranded mismatched region, and a second single-stranded mismatched region. The first single-stranded mismatched region and the second single stranded mismatched region can be present on opposing sides of the double-stranded annealed region.

In aspects in which the nucleic acid adapter is partially double-stranded and comprises a nucleic acid sequence which identifies the specific location of the sample from which the identifier oligonucleotide was released, the nucleic acid sequence which identifies the specific location of the sample from which the identifier oligonucleotide was released can be present in the double-stranded annealed region of the nucleic acid adapter.

In aspects in which the nucleic acid adapter is partially double-stranded and comprises a constant nucleic acid sequence to minimize ligation bias, the constant nucleic acid sequence to minimize ligation bias can be present in the double-stranded annealed region of the nucleic acid adapter.

In aspects in which the nucleic acid adapter is partially double-stranded and comprises a unique molecular identifier, the unique molecular identifier can be present in at least one of the first or second single-stranded mismatched regions of the nucleic acid adapter.

In aspects in which the nucleic acid adapter is partially double-stranded and comprises a first and a second amplification primer binding site, the first amplification primer binding site can be present in the first single-stranded mismatched region of the nucleic acid adapter and the second amplification primer binding site can be present in the second single-stranded mismatched region of the nucleic acid adapter.

After ligation of the at least one nucleic acid adapter, a two-ended adapter ligation method can further comprise: (5) amplifying the ligation product produced in step (4) using amplification primers that bind to the first and second amplification primer binding sites; and (6) identifying the released oligonucleotide by sequencing the amplified products produced in step (5), thereby spatially detecting the at least one target analyte in the sample.

A two-ended adapter ligation method of the present disclosure can further comprise, prior to step (4), performing an end repair reaction using methods known in the art. The method can also further comprise, prior to step (4), performing a tailing reaction to attach a single nucleotide overhang to the 3' ends of the identifier oligonucleotide using methods known in the art. In aspects, the end repair reaction and the tailing reaction can be performed sequentially or concurrently.

In preferred aspects of a two-ended adapter ligation method, a nucleic acid adapter is ligated to both ends of the released and collected identifier oligonucleotide.

In other aspects of a two-ended adapter ligation method, at least one of the amplification primers used in step (5) to amplify the ligation product produced in step (4) comprises a nucleic acid sequence which identifies the specific location of the tissue sample form which the identifier oligonucleotide was released. For example, if the identifier oligonucleotide was released from location of the sample designated "ROI #1", at least one of the amplification primers would comprise a nucleic acid sequence that corresponds to "ROI #1".

FIG. 1 shows a schematic of a preferred aspect of a two-ended adapter ligation method of the present disclosure. In this aspect, the probe comprises a target binding domain comprising an antibody that binds to a target protein. In the upper left panel, the probe binds to the target protein. In the upper right panel, a UV photo-cleavable linker located between the target binding domain and the identifier oligonucleotide is cleaved, releasing the identifier oligonucleotide. The identifier oligonucleotide comprises a unique nucleic acid sequence which identifies the target protein bound to the target binding domain. In the bottom panel, a nucleic acid adapter is ligated to both ends of the identifier oligonucleotide. In this non-limiting example, the nucleic acid adapter is partially double-stranded and comprises a double-stranded annealed region, a first single-stranded mismatched region, and a second single-stranded mismatched region. Present in the double-stranded annealed region is a constant nucleic acid sequence to minimize ligation bias and a nucleic acid sequence which identifies the specific location of the sample from which the identifier oligonucleotide was released. Present in the first single-stranded mismatched region is a first amplification primer binding site. Present in the second single-stranded mismatched region is a unique molecular identifier and a second amplification primer binding site. Following ligation of the nucleic acid adapters to the identifier oligonucleotide, the product is amplified using amplification primers that bind the first and the second amplification primer binding sites and sequenced to identify the target protein bound by the probe.

In one aspect, the present disclosure provides a composition of an identifier oligonucleotide dually ligated to two nucleic acid adapters for spatially detecting at least one target analyte in a sample. An identifier oligonucleotide dually ligated to two nucleic acid adapters comprises an identifier oligonucleotide, wherein the identifier oligonucleotide comprises a unique nucleic acid sequence which is capable of identifying a target analyte in a sample. Each end of the identifier oligonucleotide is attached to a nucleic acid adapter molecule, wherein the nucleic acid adapter molecule is partially double-stranded and comprises a double-stranded annealed region, a first single-stranded mismatched region and a second single-stranded mismatched region. The first single-stranded mismatched region and the second single stranded mismatched region are present on opposing sides of the double-stranded annealed region. The double-stranded mismatch region comprises a constant nucleic acid sequence to minimize ligation bias and a nucleic acid sequence nucleic acid sequence which is capable of identifying a specific location of a sample. The first single-stranded mismatched region comprises a first amplification primer binding site. The second single-stranded mismatched region comprises a second amplification primer binding site and a nucleic acid sequence comprising a unique molecular identifier. A schematic of an identifier oligonucleotide dually ligated to two nucleic acid adapters is shown in the bottom panel of FIG. 1.

In another aspect, the present disclosure provides compositions and methods for spatially detecting at least one target analyte in a sample using the probes of the present disclosure in a method herein referred to as a "one-ended adapter ligation method".

A one-ended adapter ligation method of the present disclosure can comprise: (1) contacting at least one target analyte in a sample with at least one probe of the present disclosure. The at least one target analyte can be a target protein or a target nucleic acid. In the aspect that the at least one target analyte is a target protein, the probe can comprise a target binding domain that is a target protein-binding region that can specifically bind to a target protein of interest. In the aspect that the at least one target analyte is a target nucleic acid, the probe can comprise a target nucleic acid-binding region that can directly or indirectly hybridize to a target nucleic acid of interest. The probe further comprises an identifier oligonucleotide. The identifier oligonucleotide can comprise a unique nucleic acid sequence which identifies the target analyte bound to the target binding domain. The identifier oligonucleotide can also comprise a first amplification primer binding site. In some aspects, the identifier oligonucleotide also comprises at least one 3' end with a single nucleotide overhang.

Following contacting the at least one target analyte with the at least one probe, a one-ended adapter ligation method can further comprise: (2) providing a force to a location of the sample sufficient to release the identifier oligonucleotide. In a non-limiting example, in aspects in which the probe comprises a photo-cleavable linker between the identifier oligonucleotide and the target binding domain, a region-of-interest (ROI) is excited with light of a sufficient wavelength capable of cleaving the photo-cleavable linker.

Following release of the identifier oligonucleotide, a one-ended adapter ligation method can further comprise: (3) collecting the released identifier oligonucleotide. By directing the force only to a specific location in step (2), identifier oligonucleotides are only released from probes within that location and not from probes located outside that location. Thus, identifier oligonucleotides are collected only for probes that are bound to targets within that location in step (3), thereby permitting detection of the identities and quantities of the targets (proteins and/or nucleic acids) located only within that location.

Following collection of the released identifier oligonucleotide, a one-ended adapter ligation method can further comprise: (4) ligating to the released oligonucleotide collected in step (3) at least one nucleic acid adapter;

The nucleic acid adapter can comprise a nucleic acid sequence which identifies the specific location of the sample from which the identifier oligonucleotide was released. For example, if the identifier oligonucleotide was released from location of the sample designated "ROI #1", the nucleic acid adapter would comprise a nucleic acid sequence that corresponds to "ROI #1". The nucleic acid adapter can also comprise a unique molecular identifier. The nucleic acid adapter can also comprise a second amplification primer binding site.

In some aspects, the nucleic acid adapter can also comprise a constant nucleic acid sequence to minimize ligation bias caused by differences in sequences of particular identifier oligonucleotides. The constant nucleic acid sequence can comprise a cleavable moiety. The cleavable moiety can be enzymatically cleavable. In a non-limiting example, the enzymatically cleavable moiety can be a USER sequence, wherein the USER sequence comprises the sequence GUGUATUG.

The nucleic acid adapter can comprise any combination of the features described above.

The nucleic acid adapter can be a partially double-stranded nucleic acid molecule. In aspects in which the nucleic acid adapter is partially double-stranded, the nucleic acid adapter comprises a double-stranded annealed region and a single-stranded mismatched region.

In aspects in which the nucleic acid adapter is partially double-stranded and comprises a nucleic acid sequence which identifies the specific location of the sample from which the identifier oligonucleotide was released, the nucleic acid sequence which identifies the specific location of the sample from which the identifier oligonucleotide was released can be present in the double-stranded annealed region of the nucleic acid adapter.

In aspects in which the nucleic acid adapter is partially double-stranded and comprises a constant nucleic acid sequence to minimize ligation bias, the constant nucleic acid sequence to minimize ligation bias can be present in the double-stranded annealed region of the nucleic acid adapter.

In aspects in which the nucleic acid adapter is partially double-stranded and comprises a unique molecular identifier, the unique molecular identifier can be present in the single-stranded mismatched region.

In aspects in which the nucleic acid adapter is partially double-stranded and comprises a second amplification primer binding site, the second amplification primer binding site can be present in the single-stranded mismatched region of the nucleic acid adapter.

After ligation of the at least one nucleic acid adapter, a two-ended adapter ligation method can further comprise: (5) amplifying the ligation product produced in step (4); and (6) identifying the released oligonucleotide by sequencing the amplified products produced in step (5), thereby spatially detecting the at least one target analyte in the sample.

In other aspects of a one-ended adapter ligation method of the present disclosure, at least one of the amplification primers used in step (5) to amplify the ligation product produced in step (4) comprises a nucleic acid sequence which identifies the specific location of the tissue sample form which the identifier oligonucleotide was released. For example, if the identifier oligonucleotide was released from location of the sample designated "ROI #1", at least one of the amplification primers would comprise a nucleic acid sequence that corresponds to "ROI #1".

Figure 2:
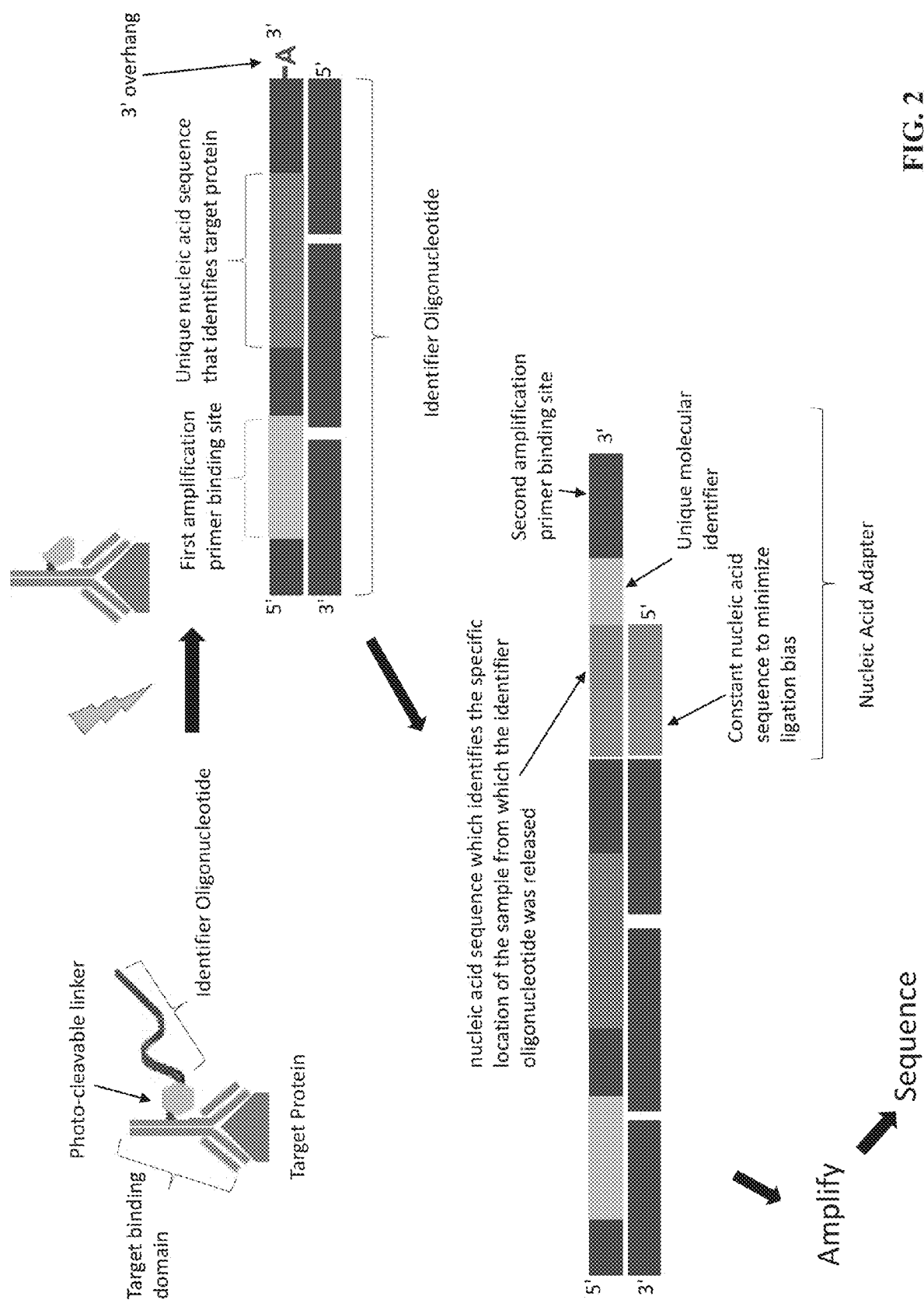
FIG. 2 is a schematic of a one-ended adapter ligation method of the present disclosure.

FIG. 2 shows a schematic of a preferred aspect of a one-ended adapter ligation method of the present disclosure. In this aspect, the probe comprises a target binding domain that is an antibody that binds to a target protein. In the upper left panel, the probe binds to the target protein. In upper right panel, the UV photo-cleavable linker located between the target binding domain and the identifier oligonucleotide is cleaved, releasing the identifier oligonucleotide. The identifier oligonucleotide comprises a unique nucleic acid sequence which identifies the target protein and a first amplification primer binding site. In this non-limiting example, the identifier oligonucleotide is double-stranded with one strand that comprises three separate nucleic acid molecules. The identifier oligonucleotide also comprises one 3' end with a single nucleotide overhang.

In the bottom panel of FIG. 2, a nucleic acid adapter is ligated to the end of the identifier oligonucleotide that comprises the 3' single nucleotide overhang. In this non-limiting example, the nucleic acid adapter is partially double-stranded and comprises a double-stranded annealed region and a single-stranded mismatched region. Present in the double-stranded annealed region is a constant nucleic acid sequence to minimize ligation bias and a nucleic acid sequence which identifies the specific location of the sample from which the identifier oligonucleotide was released. Present in the single-stranded mismatched region is a unique molecular identifier and a second amplification primer binding site. Following ligation of the nucleic acid adapter to the identifier oligonucleotide, the product is amplified using amplification primers that bind to the first and the second amplification primer binding sites and sequenced to identify the target protein bound by the probe.

In one aspect, the present disclosure provides a composition of an identifier oligonucleotide ligated to one nucleic acid adapter for spatially detecting at least one target analyte in a sample.

An identifier oligonucleotide ligated to one nucleic acid adapter comprises an identifier oligonucleotide, wherein the identifier oligonucleotide comprises a unique nucleic acid sequence which is capable of identifying a target analyte in a sample and a first amplification primer binding site. One end of the identifier oligonucleotide is attached to a nucleic acid adapter molecule, wherein the nucleic acid adapter molecule is partially double-stranded and comprises a double-stranded annealed region and a single-stranded mismatched region and a second single-stranded mismatched region. The double-stranded mismatch region comprises a constant nucleic acid sequence to minimize ligation bias and a nucleic acid sequence nucleic acid sequence which is capable of identifying a specific location of a sample. The single-stranded mismatched region comprises a second amplification primer binding site. A schematic of an identifier oligonucleotide ligated to one nucleic acid adapter is shown in the bottom panel of FIG. 2.

In another aspect, the present disclosure provides compositions and methods for spatially detecting at least one target analyte in a sample using the probes of the present disclosure in a method herein referred to as a "templated-primer extension method".

A templated-primer extension method of the present disclosure can comprise: (1) contacting at least one target analyte in a sample with at least one probe of the present disclosure. The at least one target analyte can be a target protein or a target nucleic acid. In the aspect that the at least one target analyte is a target protein, the probe can comprise a target binding domain that is a target protein-binding region that can specifically bind to a target protein of interest. In the aspect that the at least one target analyte is a target nucleic acid, the probe can comprise a target nucleic acid-binding region that can directly or indirectly hybridize to a target nucleic acid of interest. The probe further comprises an identifier oligonucleotide. The identifier oligonucleotide can comprise a unique nucleic acid sequence which identifies the target analyte bound to the target binding domain. The identifier oligonucleotide can also comprise a first amplification primer binding site.

Following contacting the at least one target analyte with the at least one probe, a templated-primer extension method can further comprise: (2) providing a force to a location of the sample sufficient to release the identifier oligonucleotide. In a non-limiting example, in aspects in which the probe comprises a photo-cleavable linker between the identifier oligonucleotide and the target binding domain, a region-of-interest (ROI) is excited with light of a sufficient wavelength capable of cleaving the photo-cleavable linker.

Following release of the identifier oligonucleotide, a templated-primer extension method can further comprise: (3) collecting the released identifier oligonucleotide. By directing the force only to a specific location in step (2), identifier oligonucleotides are only released from probes within that location and not from probes located outside that location. Thus, identifier oligonucleotides are collected only for probes that are bound to targets within that location in step (3), thereby permitting detection of the identities and quantities of the targets (proteins and/or nucleic acids) located only within that location.

Following collection of the released identifier oligonucleotide, a templated-primer extension method can further comprise: (4) hybridizing to the released identifier oligonucleotide collected in step (3) a single stranded nucleic acid template.

The single stranded nucleic acid template can comprise a region complementary to the unique nucleic acid sequence of the identifier oligonucleotide, thereby allowing for the hybridization of the single stranded nucleic acid template and the collected identifier oligonucleotide.

The single stranded nucleic acid template can also comprise a nucleic acid sequence comprising a unique molecular identifier.

The single stranded nucleic acid template can also comprise a nucleic acid sequence which identifies the specific location of the sample from which the identifier oligonucleotide was released.

The single stranded nucleic acid template can also comprise a nucleic acid sequence that is complementary to a second amplification primer binding site.

The single stranded nucleic acid template can comprise any combination of the features described above.

Following hybridization of the identifier oligonucleotide to the single stranded nucleic acid template, a templated-primer extension method can further comprise: (5) extending the identifier oligonucleotide of step (4) to form an extension produce complementary to the single stranded nucleic acid template, wherein the extension product comprises the identifier oligonucleotide and the sequence complementary to the single stranded nucleic acid template;

(6) amplifying the extension product of step (6) using amplification primers that hybridize to the first and second amplification primer binding sites; and (7) identifying the released identifier oligonucleotide by sequencing the amplified products produced in step (6), thereby spatially detecting the at least one target analyte in the sample.

In some aspects, the single stranded nucleic acid template can comprise an affinity molecule. In aspects in which the single stranded nucleic acid template comprises an affinity molecule, a templated-primer extension method can further comprise an affinity purification step between steps (4) and (5).

Figure 3:
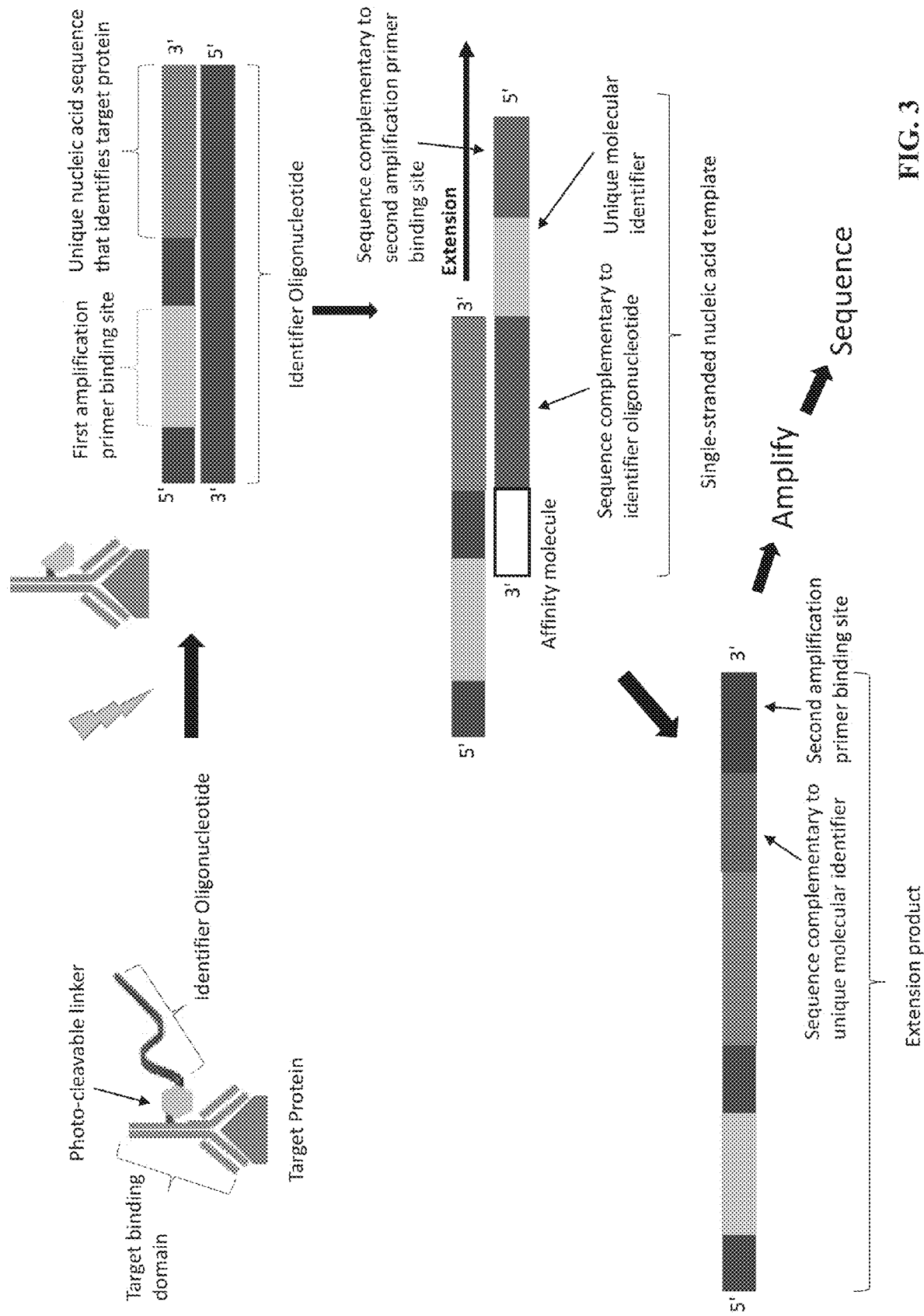
FIG. 3 is a schematic of a templated-primer extension method of the present disclosure.

FIG. 3 shows a schematic of a preferred aspect of a templated-primer extension method of the present disclosure. In this aspect, the probe comprises a target binding domain that is an antibody that binds to a target protein. In the upper left panel, the probe binds to the target protein. In upper right panel, the UV photo-cleavable linker located between the target binding domain and the identifier oligonucleotide is cleaved, releasing the identifier oligonucleotide. The identifier oligonucleotide comprises a unique nucleic acid sequence which identifies the target protein and a first amplification primer binding site. In the lower right panel, the identifier oligonucleotide is hybridized to a single stranded nucleic acid template. In this non-limiting example, the single-stranded nucleic acid template comprises an affinity molecule, a nucleic acid sequence complementary to the unique nucleic acid sequence of the identifier oligonucleotide, a first unique molecular identifier, and a sequence complementary to a second amplification primer biding site. The identifier oligonucleotide is extended to form an extension product complementary to the single stranded nucleic acid template. As shown in the lower left panel, the extension product comprises the identifier oligonucleotide, the nucleic acid sequence complementary to the first unique molecular identifier, and the second amplification primer binding site. Following the extension reaction, the primer extension product is amplified using amplification primers that bind to the first and the second amplification primer binding sites. In this non-limiting example, one of the amplification primers comprises a nucleic acid sequence which identifies the specific location of the sample from which the identifier oligonucleotide was released. The amplified product is then sequenced to identify the target protein bound by the probe.

Figure 4:
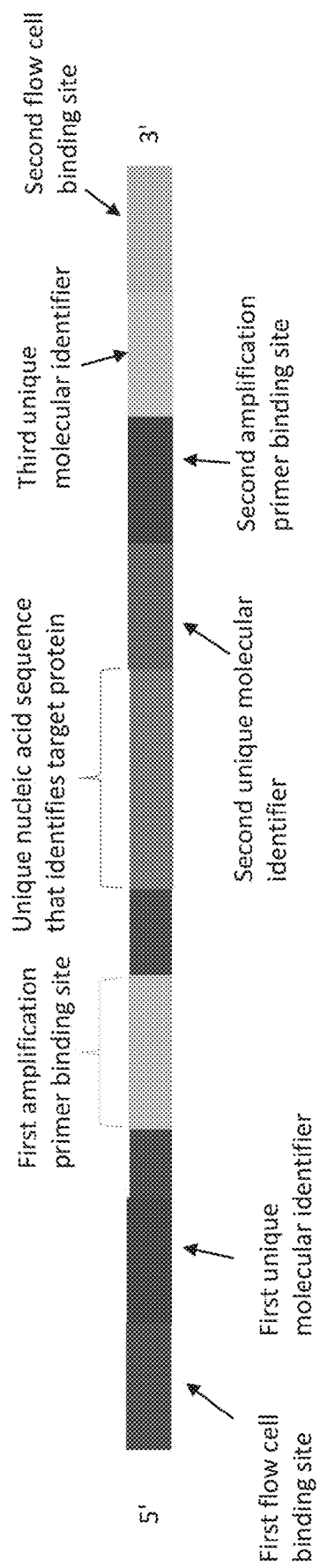
FIG. 4 is a schematic of a template-extended identifier oligonucleotide of the present disclosure.

In one aspect, the present disclosure provides a composition of a template-extended identifier oligonucleotide for spatially detecting at least one target analyte in a sample. The template-extended identifier oligonucleotide comprises a first flow cell adapter sequence suitable for sequencing, followed by a first unique molecular identifier, followed by an identifier oligonucleotide, followed by a second unique molecular identifier, followed by a second amplification primer binding site, followed by a third unique molecular identifier, followed by a second flow cell adapter sequence suitable for sequencing. The identifier oligonucleotide comprises a first amplification primer binding site and a unique nucleic acid sequence which is capable of identifying a target analyte in a sample. A schematic of a template-extended identifier oligonucleotide is shown in the bottom panel of FIG. 4.

In another aspect, the present disclosure provides compositions and methods for spatially detecting at least one target analyte in a sample using the probes of the present disclosure in a method herein referred to as a "short probe hybridization method".

A short probe hybridization method of the present disclosure can comprise: (1) contacting at least one target analyte in a sample with at least one probe of the present disclosure. The at least one target analyte can be a target protein or a target nucleic acid. In the aspect that the at least one target analyte is a target protein, the probe can comprise a target binding domain that is a target protein-binding region that can specifically bind to a target protein of interest. In the aspect that the at least one target analyte is a target nucleic acid, the probe can comprise a target nucleic acid-binding region that can directly or indirectly hybridize to a target nucleic acid of interest. The probe further comprises an identifier oligonucleotide. The identifier oligonucleotide can comprise a unique nucleic acid sequence which identifies the target analyte bound to the target binding domain.

Following contacting the at least one target analyte with the at least one probe, a short probe hybridization method can further comprise: (2) providing a force to a location of the sample sufficient to release the identifier oligonucleotide. In a non-limiting example, in aspects in which the probe comprises a photo-cleavable linker between the identifier oligonucleotide and the target binding domain, a region-of-interest (ROI) is excited with light of a sufficient wavelength capable of cleaving the photo-cleavable linker.

Following release of the identifier oligonucleotide, a short probe hybridization method can further comprise: (3) collecting the released identifier oligonucleotide. By directing the force only to a specific location in step (2), identifier oligonucleotides are only released from probes within that location and not from probes located outside that location. Thus, identifier oligonucleotides are collected only for probes that are bound to targets within that location in step (3), thereby permitting detection of the identities and quantities of the targets (proteins and/or nucleic acids) located only within that location.

Following collection of the released identifier oligonucleotide, a short probe hybridization method can further comprise: (4) hybridizing to the release identifier oligonucleotide a first nucleic acid probe and a second nucleic acid probe.

The first or the second nucleic acid probe can comprise a nucleic acid sequence complementary to a portion of the identifier oligonucleotide. The first or the second nucleic acid probe can also comprise a nucleic acid sequence which identifies the specific location of the sample from which the identifier oligonucleotide was released. The first or the second nucleic acid probe can also comprise a nucleic acid sequence comprising unique molecular identifier. The first nucleic acid probe can comprise a first amplification primer binding site. The second nucleic acid probe can comprise a second amplification primer binding site.

The first or the second nucleic acid probe can comprise any combination of the features described above. In a preferred aspect depicted in FIG. 5, the first nucleic acid probe comprises a first amplification primer binding site, a nucleic acid sequence which identifies the specific location of the sample from which the identifier oligonucleotide was released and a nucleic acid sequence complementary to the identifier oligonucleotide. In the same preferred aspect, the second nucleic acid probe comprises a second amplification primer binding site, a nucleic acid sequence comprising a unique molecular identifier and a nucleic acid sequence complementary to a portion of the identifier oligonucleotide. In this preferred aspect, the nucleic acid sequence which identifies the specific location of the sample from which the identifier oligonucleotide was released is located 5' to the first amplification primer binding site and the unique molecular identifier is located 3' to the second amplification primer binding site.

Figure 6:
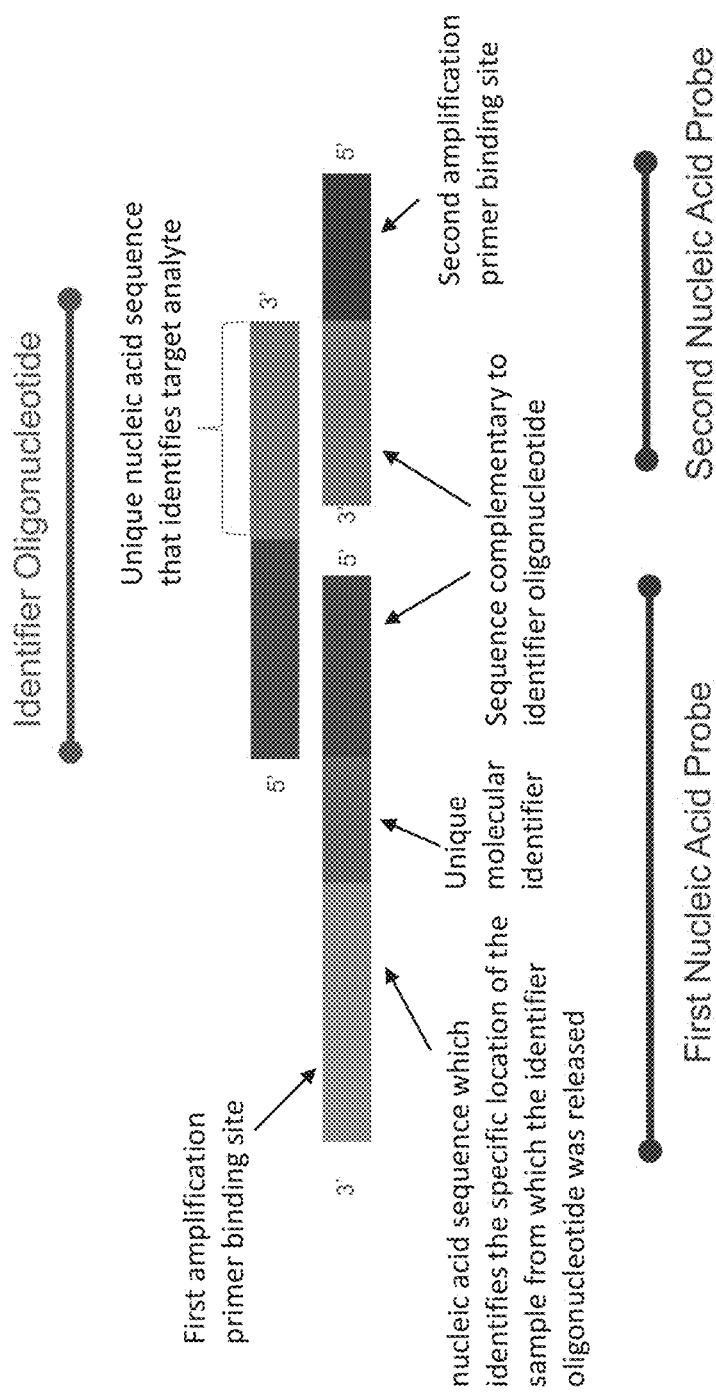
FIG. 6 is a schematic of a short probe hybridization method of the present disclosure.

In another preferred aspect depicted in FIG. 6, the first nucleic acid probe comprises a first amplification primer binding site, a nucleic acid sequence which identifies the specific location of the sample from which the identifier oligonucleotide was released, a nucleic acid sequence comprising a unique molecular identifier and a nucleic acid sequence complementary to a portion of the identifier oligonucleotide. In this same preferred aspect, the second nucleic acid probe comprises a second amplification primer binding site and a nucleic acid sequence complementary to the identifier oligonucleotide. In this preferred aspect, the nucleic acid sequence which identifies the specific location of the sample from which the identifier oligonucleotide was released and the unique molecular identifier are located 5' to the first amplification primer binding site.

Figure 7:
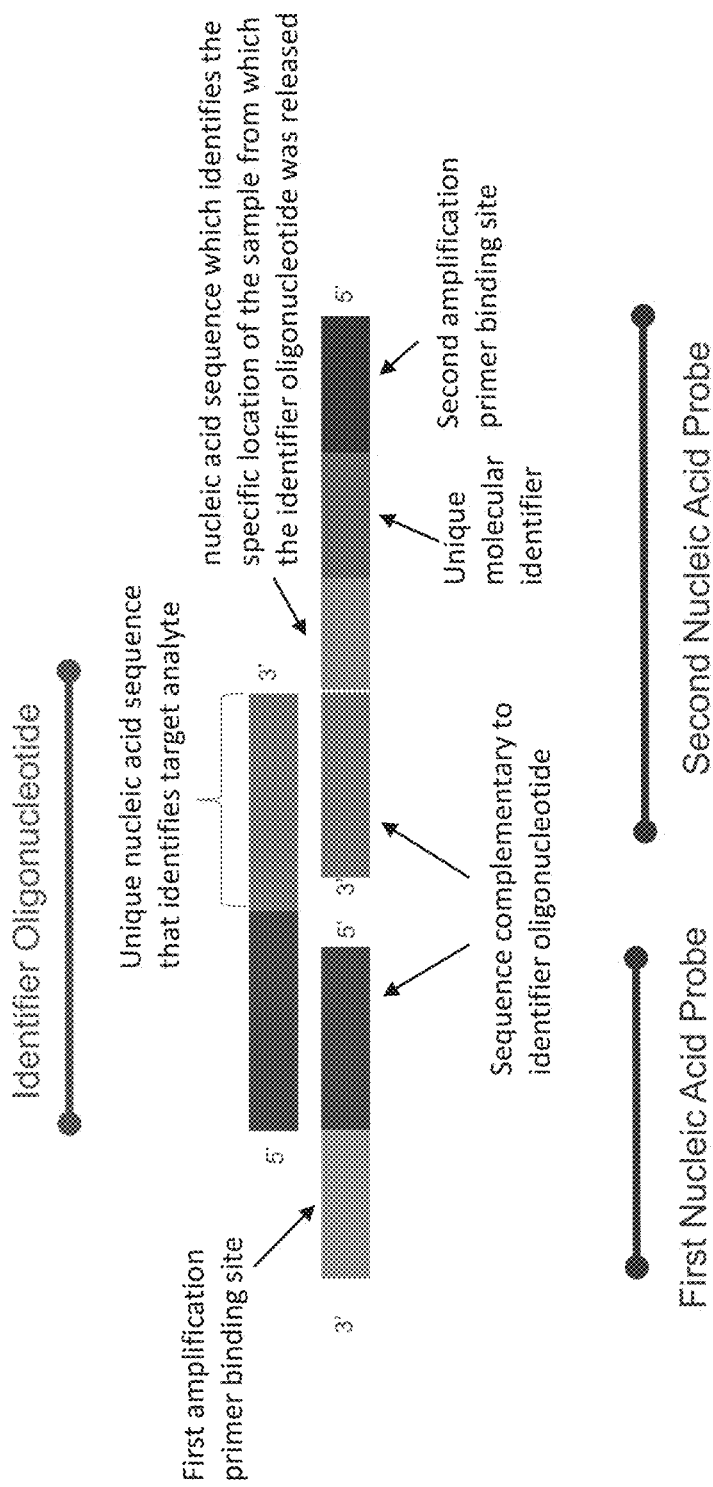
FIG. 7 is a schematic of a short probe hybridization method of the present disclosure.

In another preferred aspect depicted in FIG. 7, the first nucleic acid probe comprises a first amplification primer binding site and a nucleic acid sequence complementary to a portion of the identifier oligonucleotide. In this same preferred aspect, the second nucleic acid probe comprises a second amplification primer binding site, a nucleic acid sequence which identifies the specific location of the sample from which the identifier oligonucleotide was released, a nucleic acid sequence comprising a unique molecular identifier and a nucleic acid sequence complementary to the identifier oligonucleotide. In this preferred aspect, the nucleic acid sequence which identifies the specific location of the sample from which the identifier oligonucleotide was released and the unique molecular identifier are located 3' to the second amplification primer binding site.

Figure 15:
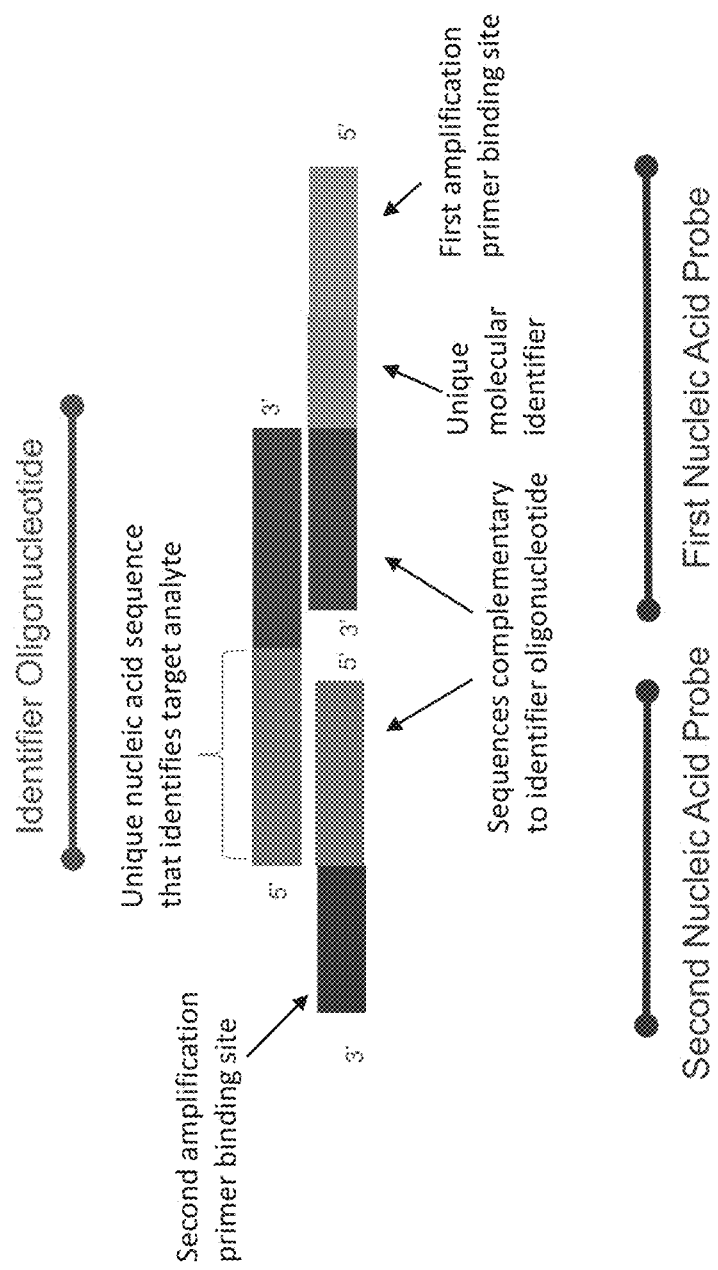
FIG. 15 is a schematic of an identifier oligonucleotide-short nucleic acid probe complex of the present disclosure.

In another preferred aspect depicted in FIG. 15, the first nucleic acid probe comprises a first amplification primer binding site, a nucleic acid sequence comprising a unique molecular identifier and a nucleic acid sequence complementary to a portion of the identifier oligonucleotide. In the same preferred aspect, the second nucleic acid probe comprises a second amplification primer binding site and a nucleic acid sequence complementary to a portion of the identifier oligonucleotide. In this preferred aspect, the nucleic acid sequence comprising a unique molecular identifier is located 3' to the first amplification binding site.

Figure 17:
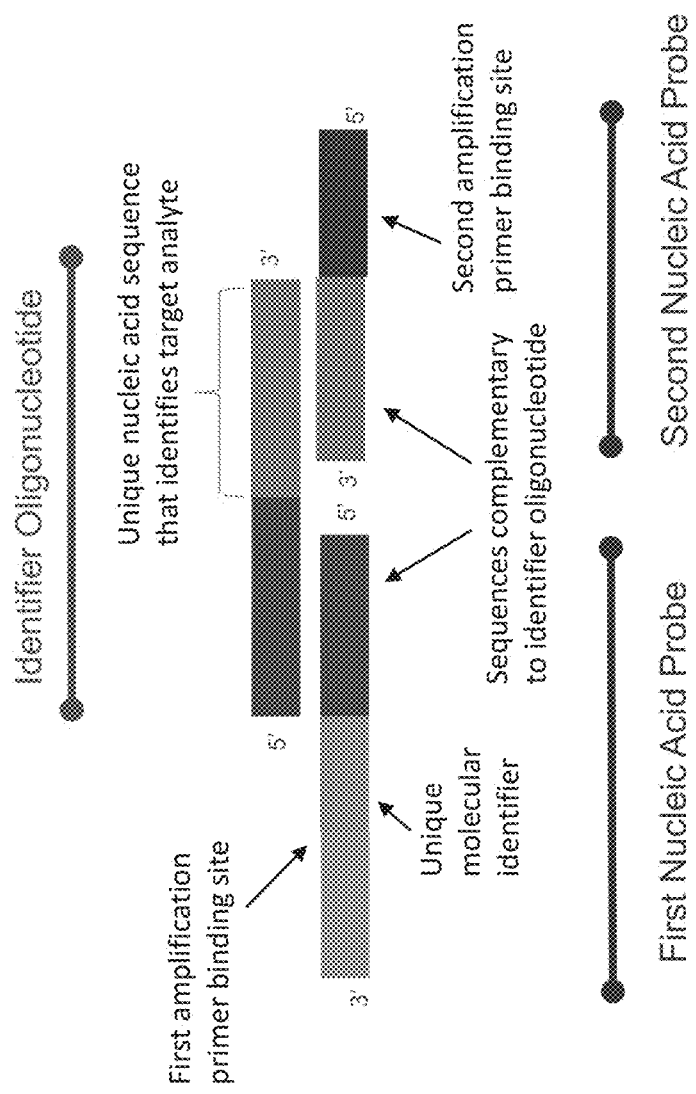
FIG. 17 is a schematic of an identifier oligonucleotide-short nucleic acid probe complex of the present disclosure.

In another preferred aspect depicted in FIG. 17, the first nucleic acid probe comprises a first amplification primer binding site, a nucleic acid sequence comprising a unique molecular identifier and a nucleic acid sequence complementary to a portion of the identifier oligonucleotide. In the same preferred aspect, the second nucleic acid probe comprises a second amplification primer binding site and a nucleic acid sequence complementary to a portion of the identifier oligonucleotide. In this preferred aspect, the nucleic acid sequence comprising a unique molecular identifier is located 5' to the first amplification binding site.

The first nucleic acid probe and the second nucleic acid probe can hybridize to the identifier oligonucleotide such that the first and the second nucleic acid probes are adjacent and are not overlapping. Alternatively, the first nucleic acid probe and the second nucleic acid probe can hybridize to the identifier oligonucleotide such that the first and the second nucleic acid probes are not adjacent and are not overlapping.

Following hybridization of the first and the second nucleic acid probe to the identifier oligonucleotide, a short probe hybridization method can further comprise: (5) in the aspect in which the first and the second nucleic acid probe hybridize to the identifier oligonucleotide such that the first and the second nucleic acid probes are adjacent and are not overlapping, ligating the first and the second nucleic acid probes together, for example, by performing a nick repair reaction. Alternatively, in the aspect in which the first and the second nucleic acid probe hybridize to the identifier oligonucleotide such that the first and the second nucleic acid probes are not adjacent and are not overlapping, the method comprises ligating the first and the second nucleic acid probes together, for example, by performing a gap extension reaction and a nick repair reaction, such that the first and the second nucleic acid probes are ligated together.

Following ligation of the first and the second nucleic acid probe, a short probe hybridization method can further comprise: (6) amplifying the ligation product produced in step (5) using amplification primers that hybridize to the first and second amplification primer binding sites; and (7) identifying the released identifier oligonucleotide by sequencing the amplified products produced in step (6), thereby spatially detecting the at least one target analyte in the sample.

Figure 5:
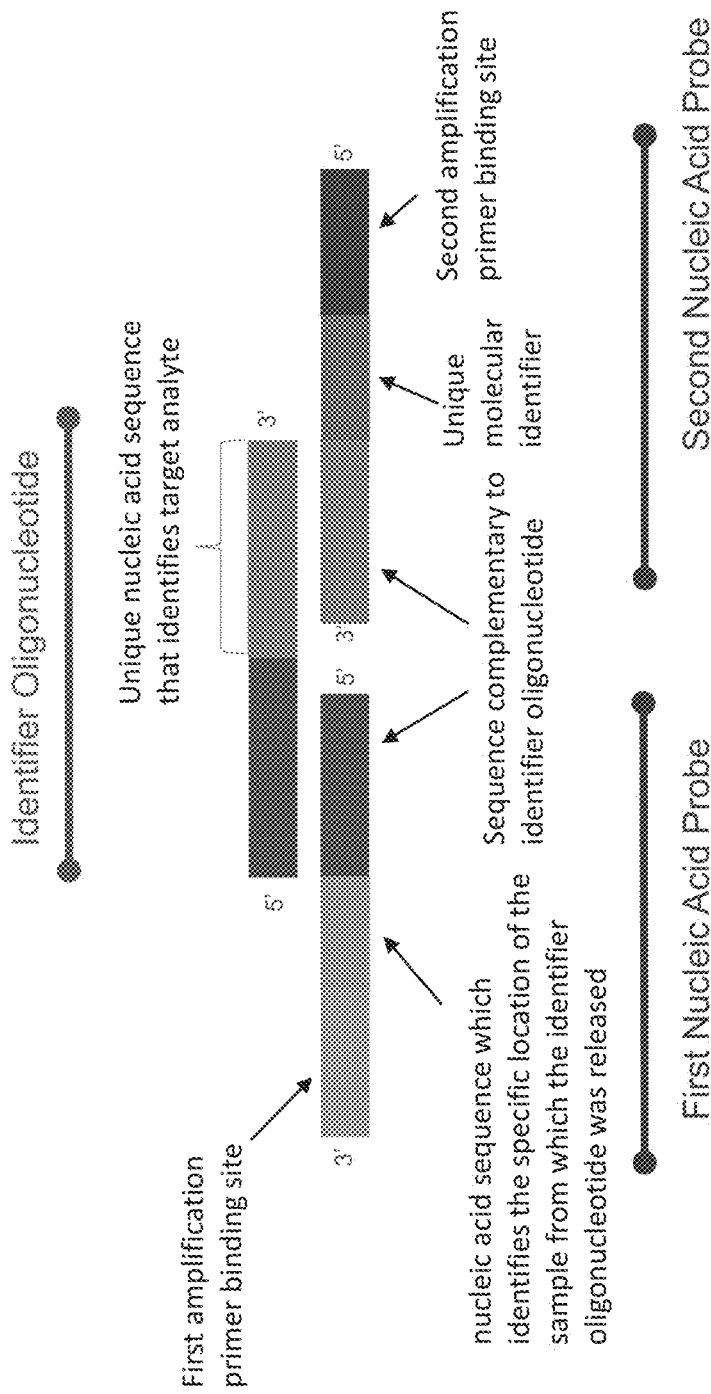
FIG. 5 is a schematic of a short probe hybridization method of the present disclosure.

In one aspect, the present disclosure provides a composition of an identifier oligonucleotide-short nucleic acid probe complex for spatially detecting at least one target analyte in a sample. An identifier oligonucleotide-short nucleic acid probe complex comprises an identifier oligonucleotide hybridized to a first nucleic acid probe and a second nucleic acid probe. The identifier oligonucleotide comprises a unique nucleic acid sequence capable of identifying a target analyte in a sample. The first nucleic acid probe comprises a first amplification primer binding site, followed by a unique nucleic acid sequence capable of identifying a specific location in a sample, followed by a region complementary to the identifier oligonucleotide. The second nucleic acid probe comprises a second amplification primer binding site, followed by a nucleic acid sequence comprising a unique molecular identifier, followed by a region complementary to the identifier oligonucleotide. A schematic of an identifier oligonucleotide-short nucleic acid probe complex is depicted in FIG. 5.

In one aspect, the present disclosure provides a composition of an identifier oligonucleotide-short nucleic acid probe complex for spatially detecting at least one target analyte in a sample. An identifier oligonucleotide-short nucleic acid probe complex comprises an identifier oligonucleotide hybridized to a first nucleic acid probe and a second nucleic acid probe. The identifier oligonucleotide comprises a unique nucleic acid sequence capable of identifying a target analyte in a sample. The first nucleic acid probe comprises a first amplification primer binding site, followed by a nucleic acid sequence comprising a unique molecular identifier, followed by a region complementary to the identifier oligonucleotide, wherein the nucleic acid sequence comprising a unique molecular identifier is located 3' to the first amplification primer binding site. The second nucleic acid probe comprises a second amplification primer binding site followed by a region complementary to the identifier oligonucleotide. A schematic of an identifier oligonucleotide-short nucleic acid probe complex is depicted in FIG. 15.

In one aspect, the present disclosure provides a composition of an identifier oligonucleotide-short nucleic acid probe complex for spatially detecting at least one target analyte in a sample. An identifier oligonucleotide-short nucleic acid probe complex comprises an identifier oligonucleotide hybridized to a first nucleic acid probe and a second nucleic acid probe. The identifier oligonucleotide comprises a unique nucleic acid sequence capable of identifying a target analyte in a sample. The first nucleic acid probe comprises a first amplification primer binding site, followed by a nucleic acid sequence comprising a unique molecular identifier, followed by a region complementary to the identifier oligonucleotide, wherein the nucleic acid sequence comprising a unique molecular identifier is located 5' to the first amplification primer binding site. The second nucleic acid probe comprises a second amplification primer binding site followed by a region complementary to the identifier oligonucleotide. A schematic of an identifier oligonucleotide-short nucleic acid probe complex is depicted in FIG. 17.

Figure 16:
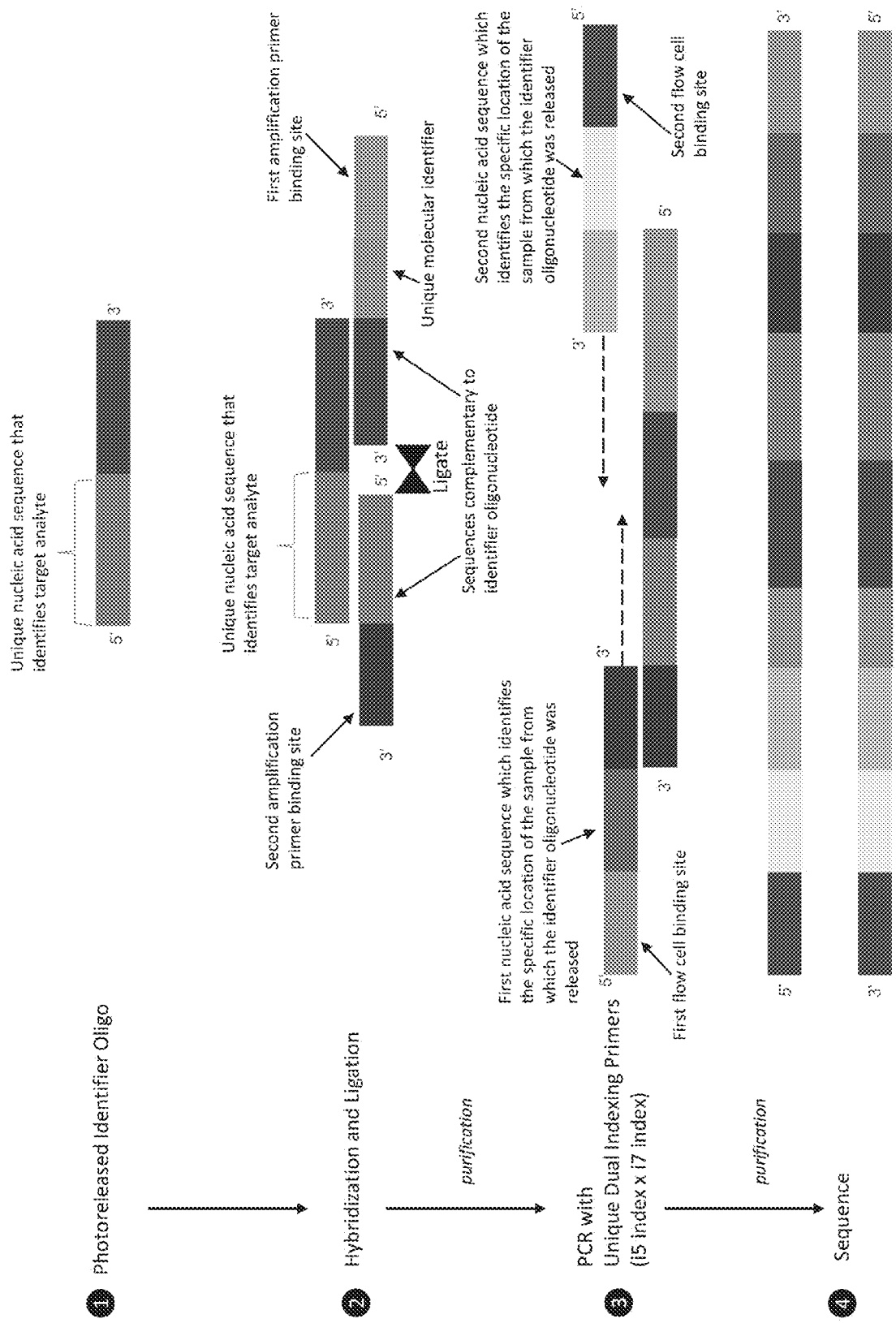
FIG. 16 is a schematic of a short probe hybridization method of the present disclosure.

FIG. 16 shows a schematic overview of an exemplary short probe hybridization method of the present disclosure. First at least one target analyte in a sample is contacted with at least one probe of the present disclosure. The at least one target analyte can be a target protein or a target nucleic acid. In the aspect that the at least one target analyte is a target protein, the probe can comprise a target binding domain that is a target protein-binding region that can specifically bind to a target protein of interest. In the aspect that the at least one target analyte is a target nucleic acid, the probe can comprise a target nucleic acid-binding region that can directly or indirectly hybridize to a target nucleic acid of interest. The probe further comprises an identifier oligonucleotide. The identifier oligonucleotide can comprise a unique nucleic acid sequence which identifies the target analyte bound to the target domain.

Following contacting the at least one target analyte with the at least one probe, a force is then provided to a location of the sample sufficient to release the identifier oligonucleotide. The identifier oligonucleotide is collected following release, as shown in the top panel of FIG. 16.

As shown in the second panel from the top of FIG. 16, the released identifier oligonucleotide is then hybridized to a first nucleic acid probe and a second nucleic acid probe. In this non-limiting example, the first nucleic acid probe comprises a first amplification primer binding site, a nucleic acid sequence comprising a unique molecular identifier and a nucleic acid sequence complementary to a portion of the identifier oligonucleotide. The nucleic acid sequence comprising the unique molecular identifier is located 3' to the first amplification primer binding site. The second nucleic acid probe comprises a second amplification primer binding site and a nucleic acid sequence complementary to a portion of the identifier oligonucleotide. In this non-limiting example, the first and the second nucleic acid probe hybridize to the identifier oligonucleotide such that the first and the second nucleic acid probes are adjacent and are not overlapping. Following hybridization to the identifier oligonucleotide, the first and second probe are ligated together, for example, by performing a nick repair reaction.

Following ligation of the first and second nucleic acid probes, the ligation product is amplified via PCR using amplification primers that hybridize to the first and second amplification primer binding sites. As shown in the second panel from the bottom of FIG. 16, the amplification primer that hybridizes to the second amplification primer binding site comprises a first flow cell binding site, a first nucleic acid sequence which identifies the specific location of the sample from which the identifier oligonucleotide was released and a nucleic acid sequence complementary to the second amplification primer binding site. The amplification primer that hybridizes to the first amplification primer binding site comprises a second flow cell binding site, a second nucleic acid sequence which identifies the specific location from which the identifier oligonucleotide was released and a nucleic acid sequence complementary to the first amplification primer binding site. The PCR product shown in the bottom panel of FIG. 16 is then sequenced to identify the released oligonucleotide, thereby spatially detecting the at least one target analyte in the sample.

Figure 18:
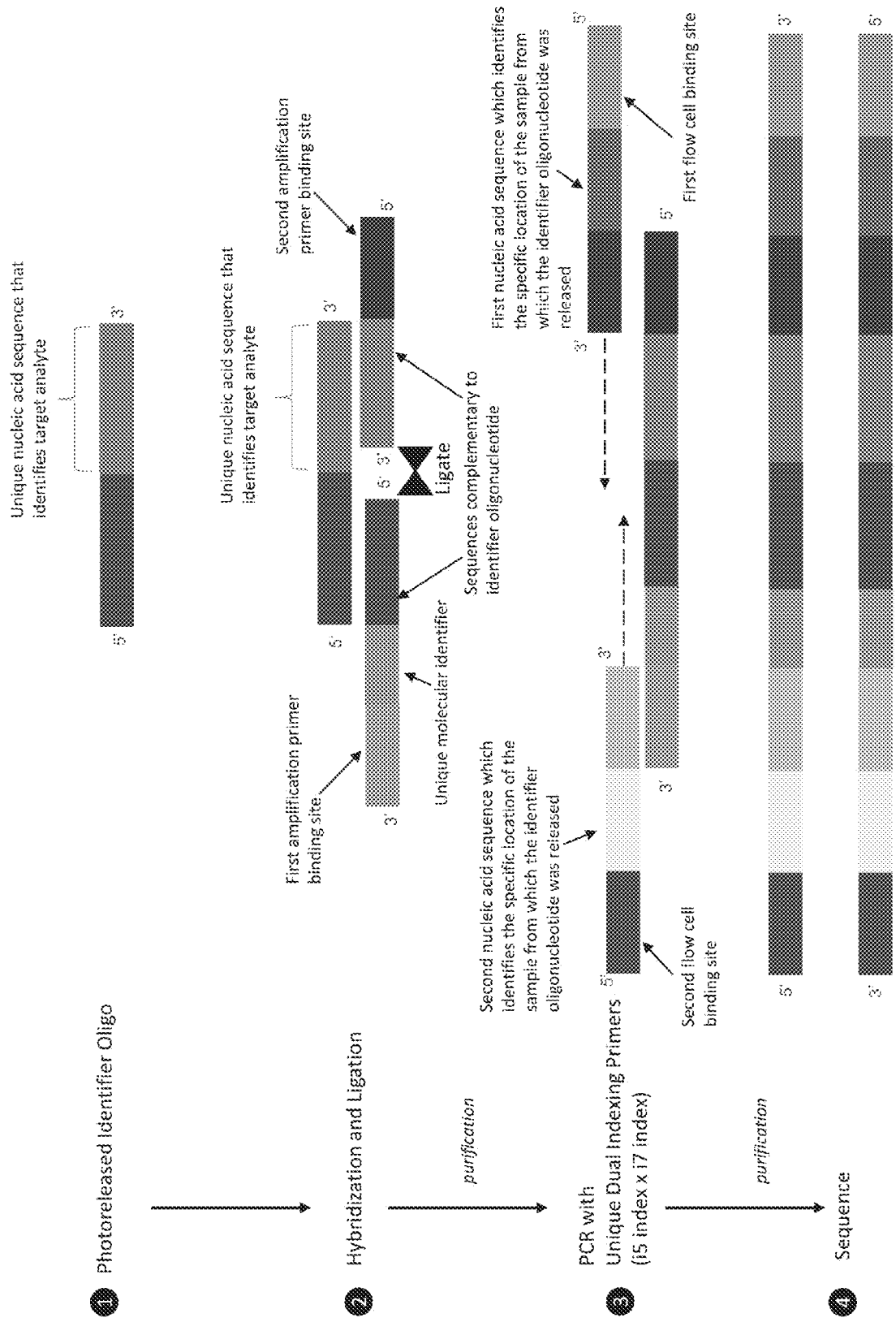
FIG. 18 is a schematic of a short probe hybridization method of the present disclosure.

FIG. 18 shows a schematic overview of an exemplary short probe hybridization method of the present disclosure. First, at least one target analyte in a sample is contacted with at least one probe of the present disclosure. The at least one target analyte can be a target protein or a target nucleic acid. In the aspect that the at least one target analyte is a target protein, the probe can comprise a target binding domain that is a target protein-binding region that can specifically bind to a target protein of interest. In the aspect that the at least one target analyte is a target nucleic acid, the probe can comprise a target nucleic acid-binding region that can directly or indirectly hybridize to a target nucleic acid of interest. The probe further comprises an identifier oligonucleotide. The identifier oligonucleotide can comprise a unique nucleic acid sequence which identifies the target analyte bound to the target domain.

Following contacting the at least one target analyte with the at least one probe, a force is then provided to a location of the sample sufficient to release the identifier oligonucleotide. The identifier oligonucleotide is collected following release, as shown in the top panel of FIG. 18.

As shown in the second panel from the top of FIG. 18, the released identifier oligonucleotide is then hybridized to a first nucleic acid probe and a second nucleic acid probe. In this non-limiting example, the first nucleic acid probe comprises a first amplification primer binding site, a nucleic acid sequence comprising a unique molecular identifier and a nucleic acid sequence complementary to a portion of the identifier oligonucleotide. The nucleic acid sequence comprising the unique molecular identifier is located 5' to the first amplification primer binding site. The second nucleic acid probe comprises a second amplification primer binding site and a nucleic acid sequence complementary to a portion of the identifier oligonucleotide. In this non-limiting example, the first and the second nucleic acid probe hybridize to the identifier oligonucleotide such that the first and the second nucleic acid probes are adjacent and are not overlapping. Following hybridization to the identifier oligonucleotide, the first and second probe are ligated together, for example, by performing a nick repair reaction.

Following ligation of the first and second nucleic acid probes, the ligation product is amplified via PCR using amplification primers that hybridize to the first and second amplification primer binding sites. As shown in the second panel from the bottom of FIG. 18, the amplification primer that hybridizes to the second amplification primer binding site comprises a first flow cell binding site, a first nucleic acid sequence which identifies the specific location of the sample from which the identifier oligonucleotide was released and a nucleic acid sequence complementary to the second amplification primer binding site. The amplification primer that hybridizes to the first amplification primer binding site comprises a second flow cell binding site, a second nucleic acid sequence which identifies the specific location from which the identifier oligonucleotide was released and a nucleic acid sequence complementary to the first amplification primer binding site. The PCR product shown in the bottom panel FIG. 18 is then sequenced to identify the released oligonucleotide, thereby spatially detecting the at least one target analyte in the sample.

In another aspect, the present disclosure provides compositions and methods for spatially detecting at least one target analyte in a sample using the probes of the present disclosure in a method herein referred to as a "long probe hybridization method".

A long probe hybridization method of the present disclosure can comprise: (1) contacting at least one target analyte in a sample with at least one probe of the present disclosure. The at least one target analyte can be a target protein or a target nucleic acid. In the aspect that the at least one target analyte is a target protein, the probe can comprise a target binding domain that is a target protein-binding region that can specifically bind to a target protein of interest. In the aspect that the at least one target analyte is a target nucleic acid, the probe can comprise a target nucleic acid-binding region that can directly or indirectly hybridize to a target nucleic acid of interest. The probe further comprises an identifier oligonucleotide. The identifier oligonucleotide can comprise a unique nucleic acid sequence which identifies the target analyte bound to the target binding domain.

Following contacting the at least one target analyte with the at least one probe, a long probe hybridization method can further comprise: (2) providing a force to a location of the sample sufficient to release the identifier oligonucleotide. In a non-limiting example, in aspects in which the probe comprises a photo-cleavable linker between the identifier oligonucleotide and the target binding domain, a region-of-interest (ROI) is excited with light of a sufficient wavelength capable of cleaving the photo-cleavable linker.

Following release of the identifier oligonucleotide, a long probe hybridization method can further comprise: (3) collecting the released identifier oligonucleotide. By directing the force only to a specific location in step (2), identifier oligonucleotides are only released from probes within that location and not from probes located outside that location. Thus, identifier oligonucleotides are collected only for probes that are bound to targets within that location in step (3), thereby permitting detection of the identities and quantities of the targets (proteins and/or nucleic acids) located only within that location.

Following collection of the released identifier oligonucleotide(s), a long probe hybridization method can further comprise: (4) hybridizing to the released identifier oligonucleotide a first nucleic acid probe and a second nucleic acid probe.

The first or the second nucleic acid probe can comprise a nucleic acid sequence complementary to a portion of the identifier oligonucleotide. The first or the second nucleic acid probe can also comprise a nucleic acid sequence which identifies the specific location of the sample from which the identifier oligonucleotide was released.

The first or the second nucleic acid probe can also comprise a first unique molecular identifier. The first or the second nucleic acid probe can also comprise a second unique molecular identifier. The first or the second nucleic acid probe can also comprise a third unique molecular identifier.

The first nucleic acid probe can comprise a first amplification primer binding site.

The first nucleic acid probe can also comprise a first flow cell binding site. The second nucleic acid probe can comprise a second flow cell binding site.

The first and the second nucleic acid probes can comprise any combination of the features described above. In a preferred aspect depicted in FIG. 8, the first nucleic acid probe comprises a first flow cell binding site, a first unique molecular identifier, a first amplification primer binding site, a nucleic acid sequence which identifies the specific location of the sample from which the identifier oligonucleotide was released and a nucleic acid sequence complementary to the identifier oligonucleotide. In the same preferred aspect, the second nucleic acid probe comprises a second flow cell binding site, a second unique molecular identifier, a third unique molecular identifier and a nucleic acid sequence complementary to the identifier oligonucleotide. In this preferred aspect, the nucleic acid sequence which identifies the specific location of the sample from which the identifier oligonucleotide was released and the first unique molecular identifier are located 5' to the first flow cell binding site and the second and the third unique molecular identifiers are located 3' to the second flow cell binding site.

Figure 9:
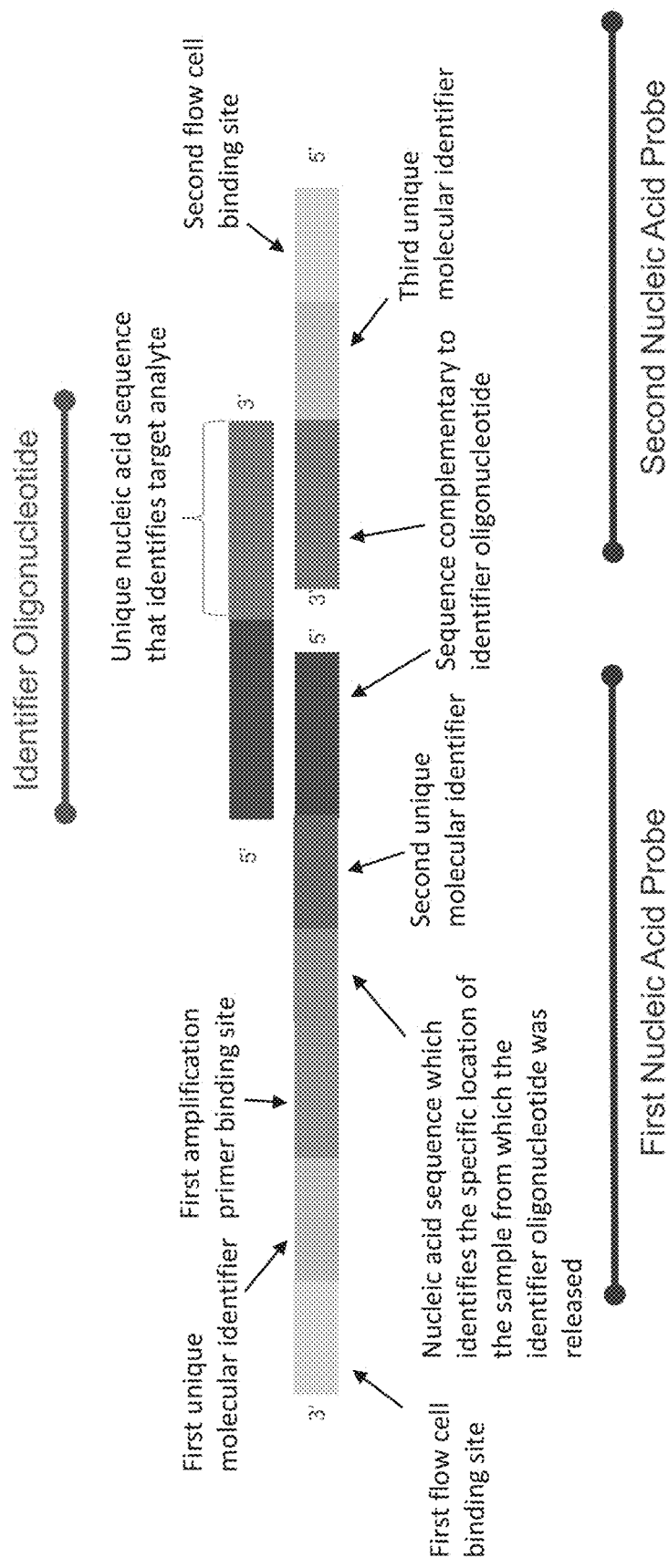
FIG. 9 is a schematic of a long probe hybridization method of the present disclosure.

In another preferred aspect depicted in FIG. 9, the first nucleic acid probe comprises a first flow cell binding site, a first unique molecular identifier, a second unique molecular identifier, a first amplification primer binding site, a nucleic acid sequence which identifies the specific location of the sample from which the identifier oligonucleotide was released and a nucleic acid sequence complementary to the identifier oligonucleotide. In the same preferred aspect, the second nucleic acid probe comprises a second flow cell binding site, a third unique molecular identifier and a nucleic acid sequence complementary to the identifier oligonucleotide. In this preferred aspect, the first unique molecular identifier, the second unique molecular identifier and the nucleic acid sequence which identifies the specific location of the sample from which the identifier oligonucleotide was released are located 5' to the first flow cell binding site and the third unique molecular identifier is located 3' to the second flow cell binding site.

Figure 10:
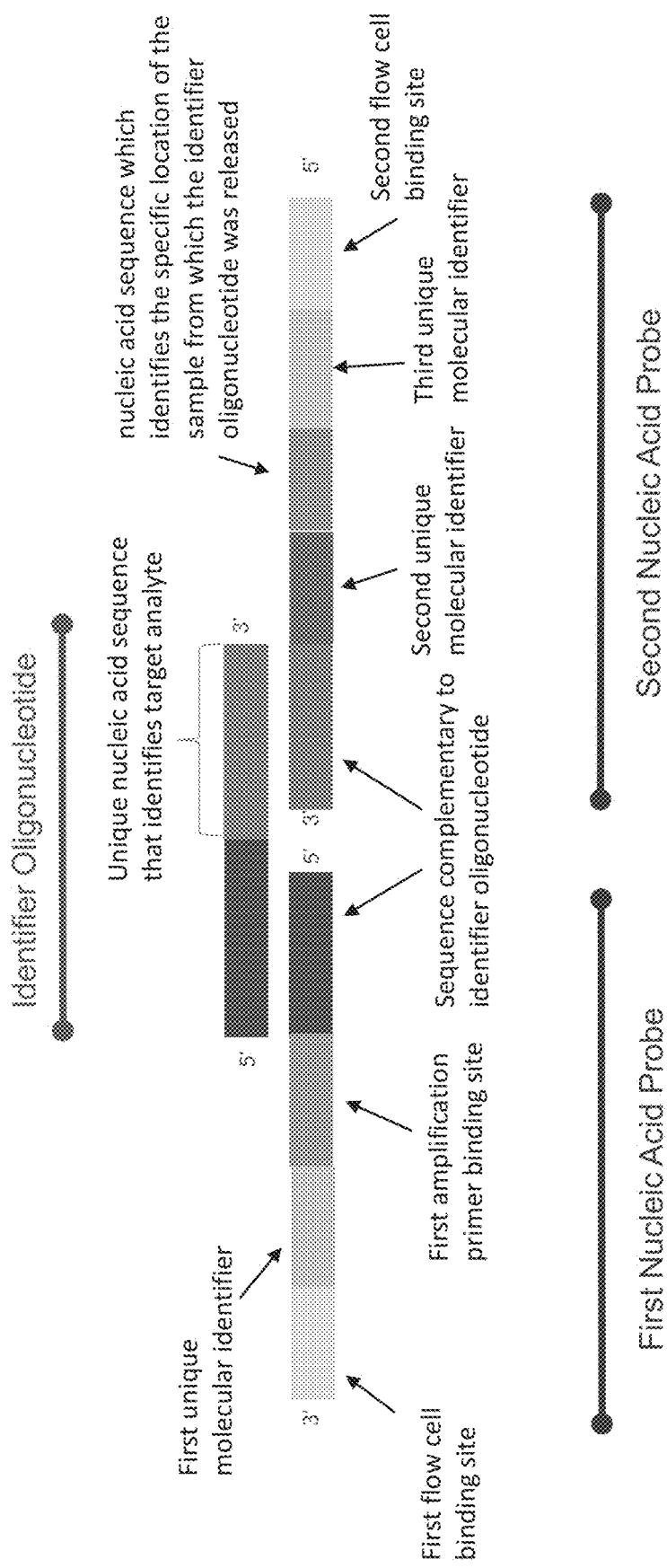
FIG. 10 is a schematic of a long probe hybridization method of the present disclosure.

In another preferred aspect depicted in FIG. 10, the first nucleic acid probe comprises a first flow cell binding site, a first unique molecular identifier, a first amplification primer binding site and a nucleic acid sequence complementary to the identifier oligonucleotide. In this same preferred aspect, the second nucleic acid probe comprises a second flow cell binding site, a second unique molecular identifier, a third unique molecular identifier, a nucleic acid sequence which identifies the specific location of the sample from which the identifier oligonucleotide was released and a nucleic acid sequence complementary to the identifier oligonucleotide. In this preferred aspect, the first unique molecular identifier is located 5' to the first flow cell binding site and the second unique molecular identifier, the third unique molecular identifier, and the nucleic acid sequence which identifies the specific location of the sample form which the identifier oligonucleotide was released are located 3' to the second amplification primer binding site.

The first nucleic acid probe and the second nucleic acid probe can hybridize to the identifier oligonucleotide such that the first and the second nucleic acid probes are adjacent and are not overlapping. Alternatively, the first nucleic acid probe and the second nucleic acid probe can hybridize to the identifier oligonucleotide such that the first and the second nucleic acid probes are not adjacent and are not overlapping.

Following hybridization of the first and the second nucleic acid probe to the identifier oligonucleotide, a long probe hybridization method can further comprise: (5) in the aspect in which the first and the second nucleic acid probe hybridize to the identifier oligonucleotide such that the first and the second nucleic acid probes are adjacent and are not overlapping, performing a nick repair reaction such that the first and the second nucleic acid probes are ligated together. Alternatively, in the aspect in which the first and the second nucleic acid probe hybridize to the identifier oligonucleotide such that the first and the second nucleic acid probes are not adjacent and are not overlapping, the method comprises performing a gap extension and a nick repair reaction such that the first and the second nucleic acid probes are ligated together.

The name method can further comprise: (6) amplifying the ligation product produced in step (5) using amplification primers that hybridize to the first and second amplification primer binding sites; and (7) identifying the released identifier oligonucleotide by sequencing the amplified products produced in step (6), thereby spatially detecting the at least one target analyte in the sample.

Figure 8:
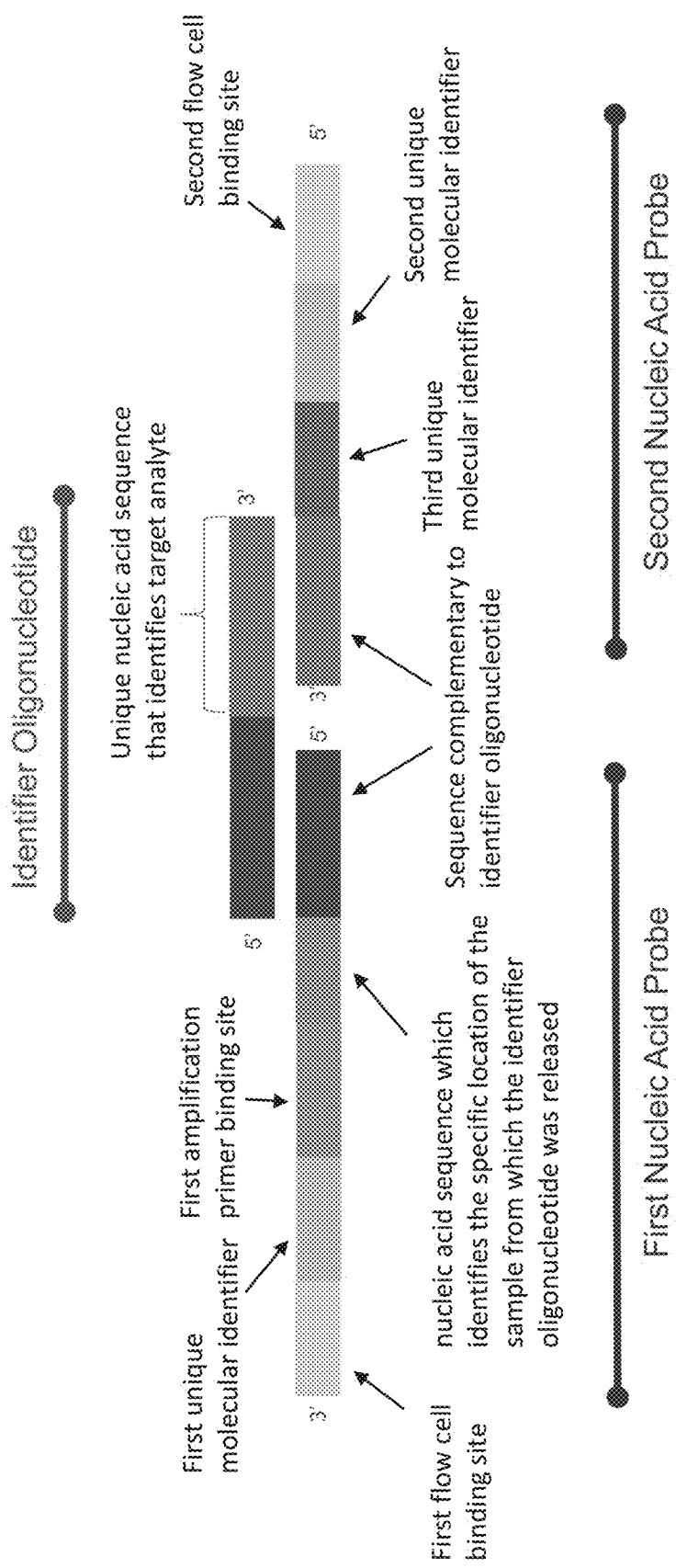
FIG. 8 is a schematic of a long probe hybridization method of the present disclosure.

In one aspect, the present disclosure provides a composition of an identifier oligonucleotide-long nucleic acid probe complex for spatially detecting at least one target analyte in a sample. An identifier oligonucleotide-long nucleic acid probe complex comprises an identifier oligonucleotide hybridized to a first nucleic acid probe and a second nucleic acid probe. The identifier oligonucleotide comprises a unique nucleic acid sequence capable of identifying a target analyte in a sample. The first nucleic acid probe comprises a first flow cell binding site suitable for sequencing, followed by a first unique molecular identifier, followed by a first amplification primer binding site, followed by a unique nucleic acid sequence capable of identifying a specific location in a sample, followed by a region complementary to the identifier oligonucleotide. The second nucleic acid probe comprises a second flow cell binding site, followed by a second unique molecular identifier, followed by a third unique molecular identifier, followed by a region complementary to the identifier oligonucleotide. A schematic of an identifier oligonucleotide-short nucleic acid probe complex is depicted in FIG. 8.

In another aspect, the present disclosure provides compositions and methods for spatially detecting at least one target analyte in a sample using the probes of the present disclosure in a method herein referred to as a "direct PCR method".

A direct PCR method of the present disclosure can comprise: (1) contacting at least one target analyte in a sample with at least one probe of the present disclosure. The at least one target analyte can be a target protein or a target nucleic acid. In the aspect that the at least one target analyte is a target protein, the probe can comprise a target binding domain that is a target protein-binding region that can specifically bind to a target protein of interest. In the aspect that the at least one target analyte is a target nucleic acid, the probe can comprise a target nucleic acid-binding region that can directly or indirectly hybridize to a target nucleic acid of interest. The probe further comprises an identifier oligonucleotide. The identifier oligonucleotide can comprise a unique nucleic acid sequence which identifies the target analyte bound to the target binding domain. The identifier oligonucleotide can also comprise a first amplification primer binding site, a second amplification primer binding site, or a unique molecular identifier. The identifier oligonucleotide can comprise any combination of these features. Any of these features can also be flanked by regions comprising constant nucleic acid sequences of about 1 nucleotide to about 10 nucleotides.

Following contacting the at least one analyte with the at least one probe, a direct PCR method further comprises: (2) providing a force to a location of the sample sufficient to release the identifier oligonucleotide. In a non-limiting example, in aspects in which the probe comprises a photo-cleavable linker between the identifier oligonucleotide and the target binding domain, a region-of-interest (ROI) is excited with light of a sufficient wavelength capable of cleaving the photo-cleavable linker.

A direct PCR method can further comprise: (3) collecting the released identifier oligonucleotide. By directing the force only to a specific location in step (2), identifier oligonucleotides are only released from probes within that location and not from probes located outside that location. Thus, identifier oligonucleotides are collected only for probes that are bound to targets within that location in step (3), thereby permitting detection of the identities and quantities of the targets (proteins and/or nucleic acids) located only within that location.

Following release of the identifier oligonucleotide, a direct PCR method can further comprise: (4) amplifying the released identifier oligonucleotide using a first amplification primer capable of binding to the first amplification primer binding site and a second amplification primer capable of binding to the second amplification primer binding site. In some aspects, at least one of the amplification primers comprises a nucleic acid sequence which identifies the specific location of the sample from which the identifier oligonucleotide was released. For example, if the identifier oligonucleotide was released from location of the sample designated "ROI #1", at least one of the amplification primers would comprise a nucleic acid sequence that corresponds to "ROI #1". In still other aspects, at least one of the amplification primers comprises a unique molecular identifier.

Following amplification, a direct PCR method of the present disclosure can further comprise: (5) identifying the released oligonucleotide by sequencing the amplified products produced in step (5), thereby spatially detecting the at least one target analyte in the sample.

Figure 11:
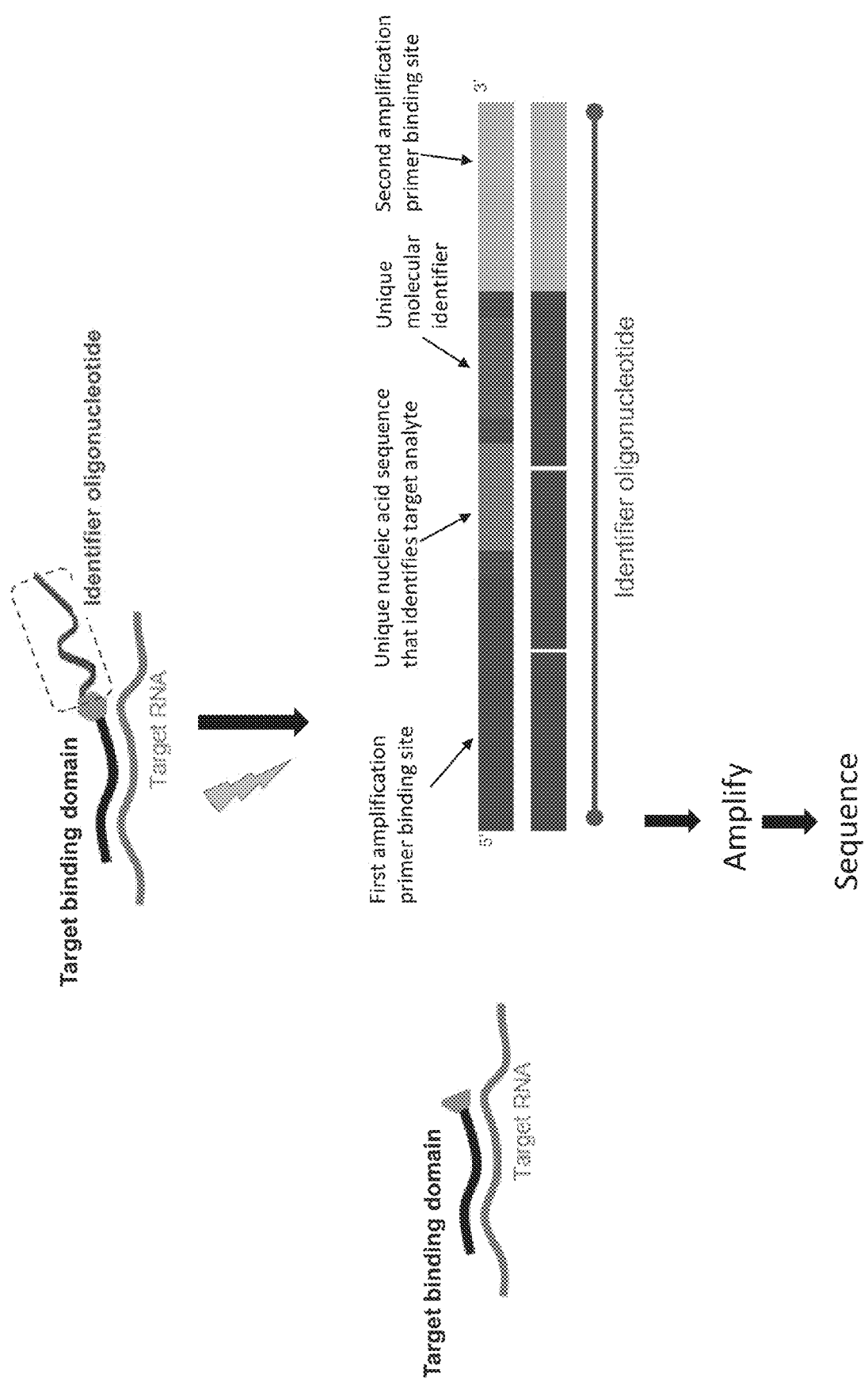
FIG. 11 is a schematic of a direct-PCR method of the present disclosure.

FIG. 11 shows a schematic of a preferred aspect of a direct PCR method of the present disclosure. In this aspect, the probe comprises a target binding domain comprising a nucleic acid sequence that is complementary to a target nucleic acid. In the upper panel, the probe hybridizes to the target nucleic acid. In the lower panel, a UV photo-cleavable linker located between the target binding domain and the identifier oligonucleotide is cleaved, releasing the identifier oligonucleotide. The identifier oligonucleotide comprises a first amplification primer binding site, a second amplification primer binding site, a unique molecular identifier, and a unique nucleic acid sequence which identifies the target analyte bound to the target binding domain. Located between these four features are constant spacer regions that are 3 nucleotides in length. The identifier oligonucleotide is double-stranded and comprises a strand that comprises 3 separate nucleic acid molecules. After release, the identifier oligonucleotide is amplified using a first amplification primer that hybridizes to the first amplification primer binding site and comprises a nucleic acid sequence which identifies the specific location of the sample from which the identifier oligonucleotide was released and a second amplification primer that hybridizes to the second amplification primer binding site. The amplified product is then sequenced to identify the target nucleic acid bound by the probe.

Figure 19:
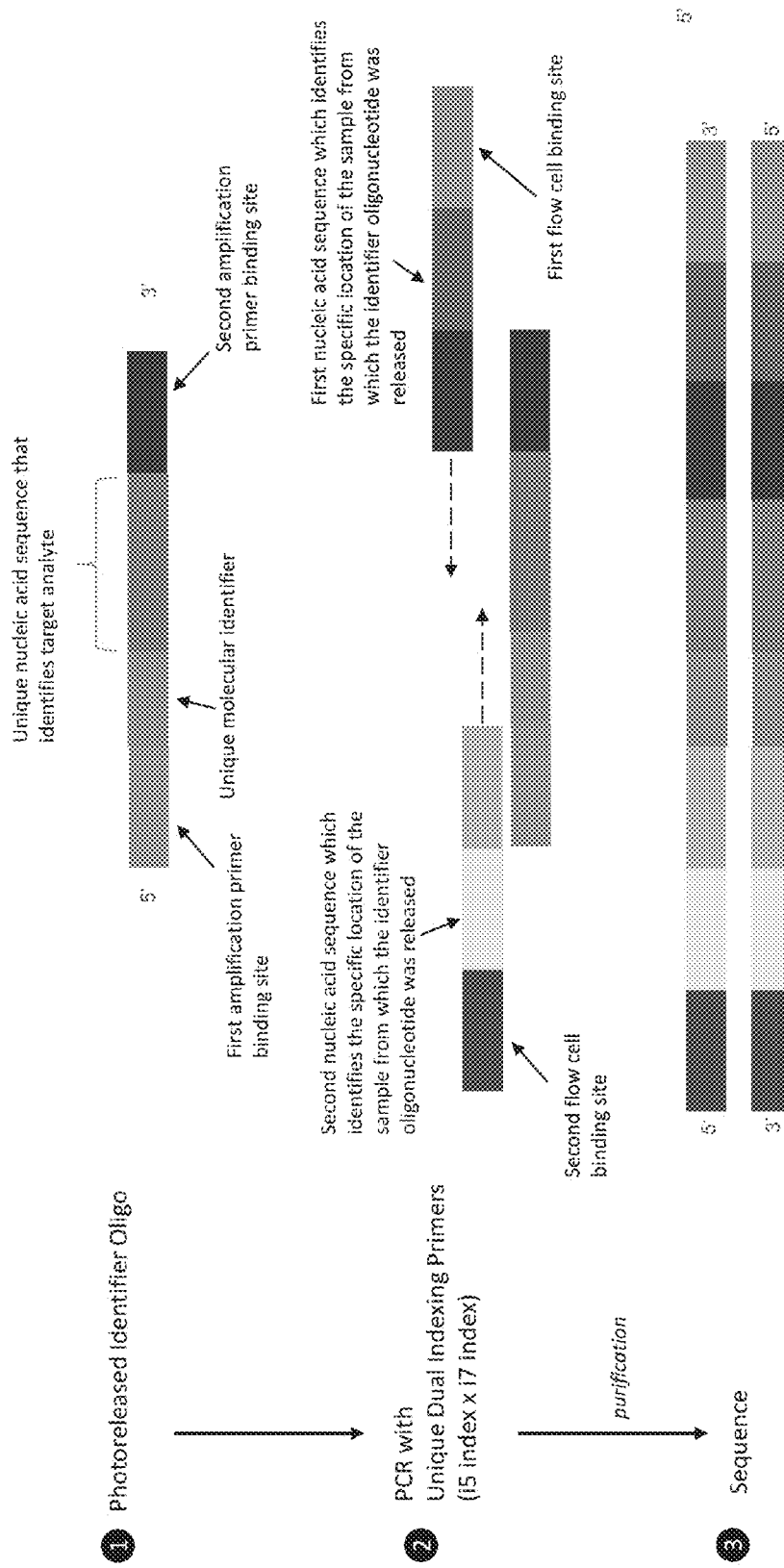
FIG. 19 is a schematic of a direct-PCR method of the present disclosure.

FIG. 19 shows a schematic of a preferred aspect of a direct PCR method of the present disclosure. In this aspect, the identifier oligonucleotide comprises a first amplification primer binding site, a nucleic acid sequence comprising a unique molecular identifier, a unique nucleic acid sequence which identifies the target analyte bound to the target binding domain and a second amplification primer binding site, as shown in the top panel of FIG. 19. The identifier oligonucleotide is amplified using amplification primers that hybridize to the first and second amplification primer binding sites. As shown in the middle panel of FIG. 19, the amplification primer that hybridizes to the second amplification primer binding site comprises a first flow cell binding site, a first nucleic acid sequence which identifies the specific location of the sample from which the identifier oligonucleotide was released and a nucleic acid sequence complementary to the second amplification primer binding site. The amplification primer that hybridizes to the first amplification primer binding site comprises a second flow cell binding site, a second nucleic acid sequence which identifies the specific location of the sample from which the identifier oligonucleotide was released and a nucleic acid sequence complementary to the first amplification primer binding site. The PCR product shown in the bottom panel of FIG. 19 is sequenced to identify the released oligonucleotide, thereby spatially detecting the at least one target analyte in the sample.

In one aspect, the present disclosure provides a composition of a direct-PCR compatible identifier oligonucleotide for spatially detecting at least one target analyte in a sample. A direct-PCR compatible identifier oligonucleotide comprises a first amplification primer binding site, followed a unique nucleic acid sequence which is capable of identifying a target analyte in a sample, followed by a unique molecular identifier, followed by a second amplification primer binding site. A schematic of a direct-PCR compatible identifier oligonucleotide is depicted in the lower panel of FIG. 11.

In one aspect, the present disclosure provides a composition of a direct-PCR compatible identifier oligonucleotide for spatially detecting at least one target analyte in a sample. A direct-PCR compatible identifier oligonucleotide comprises a first amplification primer binding site, followed a nucleic acid sequence comprising a unique molecular identifier, followed by a unique nucleic acid sequence which is capable of identifying a target analyte in a sample, followed by a second amplification primer binding site. A schematic of a direct-PCR compatible identifier oligonucleotide is shown in the top panel of FIG. 19.

Figure 27:
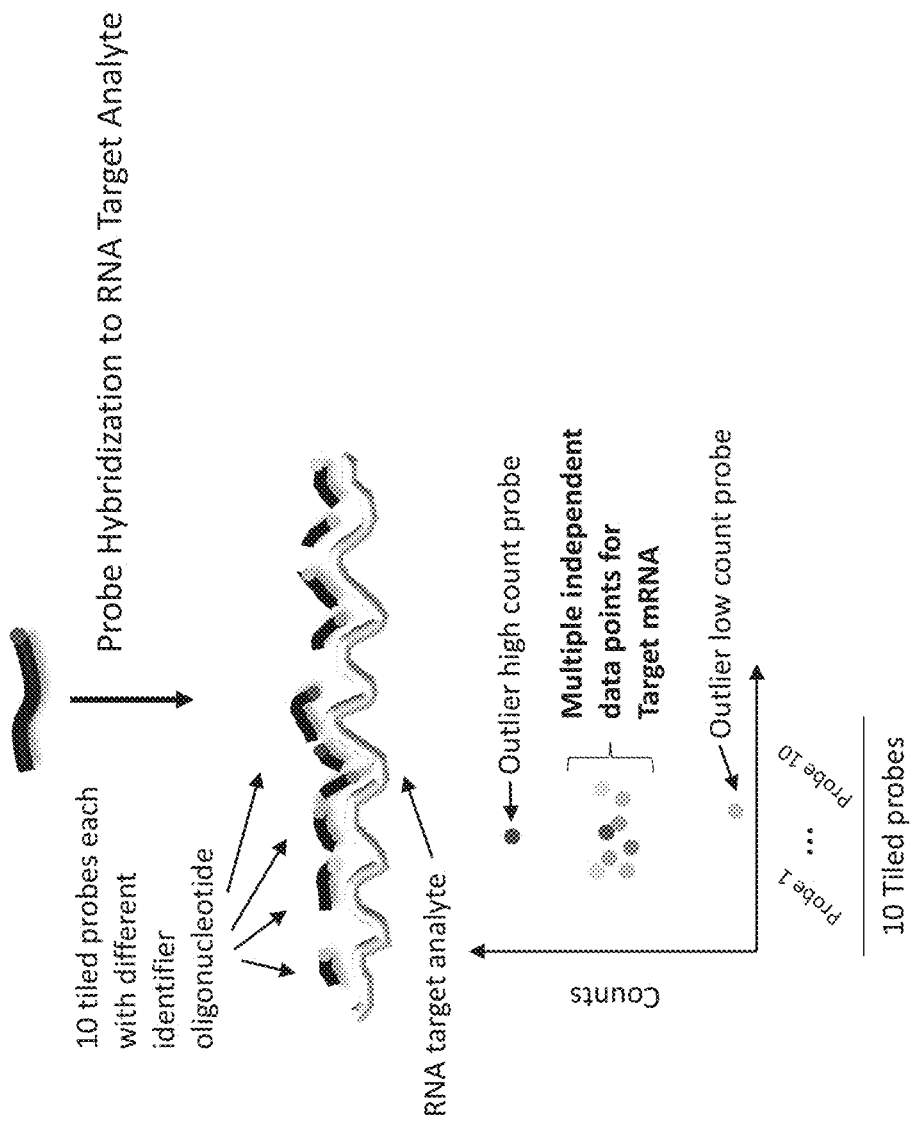
FIG. 27 shows the use of probe tiling in the methods of the present disclosure.

In some aspects of the methods of the present disclosure at least one, or at least two, or at least three, or at least four, or at least five, or at least six, or at least seven, or at least eight, or at least nine, or at least ten, or at least eleven, or at least twelve, or at least thirteen, or at least fourteen, or at least fifteen, or at least sixteen, or at least seventeen, or at least eighteen, or at least nineteen, or at least twenty, or at least thirty, or at least forty, or at least fifty, or at least sixty, or at least seventy, or at least eighty, or at least ninety, or at least one hundred probes can been to a single target analyte. As used herein, the term "tiling" is used to describe when more than one probe of the present disclosure is bound to a target analyte. The top panel of FIG. 27 shows the tiling of probes onto a target RNA. Tiling multiple probes onto a target analyte means that each target analyte will be individually detected multiple times, increasing the overall accuracy of the measurement. In a non-limiting example, as shown in the bottom panel of FIG. 27, in the case where 10 probes are tiled onto a single target RNA, one of the probes may be incorrectly detected too many times (outlier high count probe), while another probe may be incorrectly detected too few times (outlier low count probe). However, the other 8 probes may be detected at a similar level, indicating that the two outliers should be discarded during analysis and the signals from the 8 probes used to generate a more accurate measurement of the abundance of the target RNA.

The present disclosure provides compositions and methods for spatially detecting at least one target analyte in a sample using the probes of the present disclosure in a method herein referred to as an "enzyme free method".

An enzyme free method of the present disclosure can comprise: (1) contacting at least one target analyte in a sample with at least one probe of the present disclosure. The at least one target analyte can be a target protein or a target nucleic acid. In the aspect that the at least one target analyte is a target protein, the probe can comprise a target binding domain that is a target protein-binding region that can specifically bind to a target protein of interest. In the aspect that the at least one target analyte is a target nucleic acid, the probe can comprise a target nucleic acid-binding region that can directly or indirectly hybridize to a target nucleic acid of interest. The probe further comprises an identifier oligonucleotide. An identifier oligonucleotide can comprise a unique nucleic acid sequence which identifies the target analyte bound to the target binding domain. An identifier oligonucleotide can also comprise a capture probe binding site.

Following contacting at least one target analyte with at least one probe, an enzyme free method can further comprise: (2) providing a force to a location of the sample sufficient to release the identifier oligonucleotide. In a non-limiting example, in aspects in which the probe comprises a photo-cleavable linker between the identifier oligonucleotide and the target binding domain, a region-of-interest (ROI) is excited with light of a sufficient wavelength capable of cleaving the photo-cleavable linker.

Following release of an identifier oligonucleotide, an enzyme free method can further comprise: (3) collecting the released identifier oligonucleotide. By directing the force only to a specific location in step (2), identifier oligonucleotides are only released from probes within that location and not from probes located outside that location. Thus, identifier oligonucleotides are collected only for probes that are bound to targets within that location in step (3), thereby permitting detection of the identities and quantities of the targets (proteins and/or nucleic acids) located only within that location.

Following collection of a released identifier oligonucleotide, an enzyme free method can further comprise: (4) hybridizing to a released identifier oligonucleotide a capture probe.

A capture probe can comprise a region complementary to the capture probe binding site. A capture probe can also comprise an affinity molecule.

Following hybridization of a capture probe, an enzyme free method can further comprise: (5) Identifying a released identifier oligonucleotide by sequencing the hybridized product produced in step (4), thereby spatially detecting the at least one target analyte in the at least one cell in a tissue sample.

A hybridized product produced in step (4) can be sequenced using an enzyme free method of sequencing. Enzyme-free methods of sequencing have been described in, e.g., US2014946386 and U.S. Ser. No. 15/819,151 (U.S. Pat. No. 10,415,080), each of which is incorporated herein by reference in its entirety.

Figure 12:
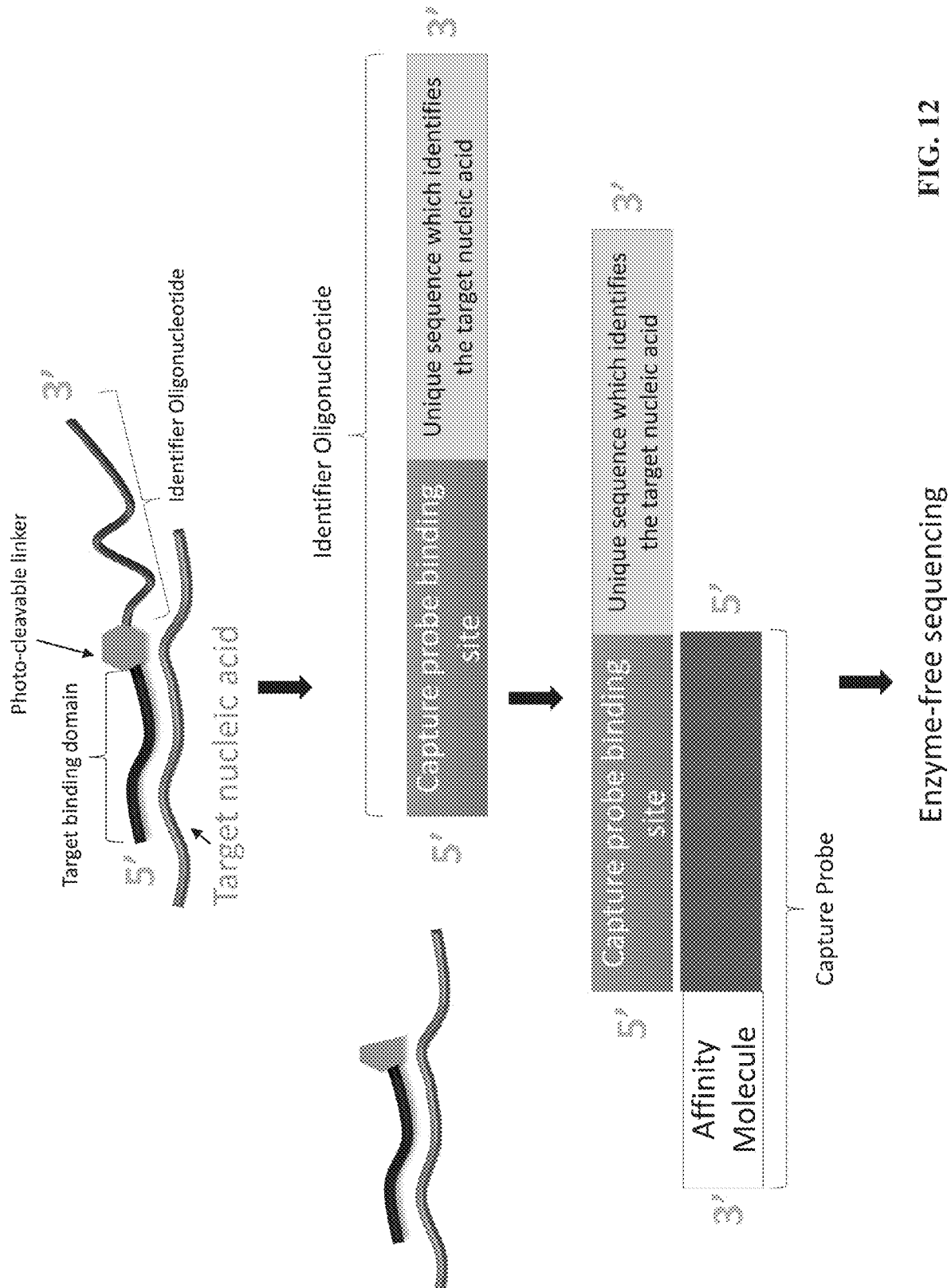
FIG. 12 is a schematic of an enzyme free method of the present disclosure.

FIG. 12 shows a schematic of a preferred aspect of an enzyme free method of the present disclosure. In this aspect, the probe comprises a target binding domain comprising a nucleic acid sequence that is complementary to a target nucleic acid. In the top panel, the probe hybridizes to the target nucleic acid. In the middle panel, a UV photo-cleavable linker located between the target binding domain and the identifier oligonucleotide is cleaved, releasing the identifier oligonucleotide. The identifier oligonucleotide comprises a unique nucleic acid sequence which identifies the target nucleic acid bound to the target binding domain and a capture probe binding site. After release, the identifier oligonucleotide is hybridized to a capture probe, as depicted in the bottom panel. The capture probe comprises a nucleic acid sequence complementary to the capture probe binding site and an affinity molecule. The hybridized product is then sequenced using enzyme free sequencing methods to identify the target nucleic acid bound by the probe.

In one aspect, the present disclosure provides a composition of a hybridized identifier oligonucleotide-capture probe complex for spatially detecting at least one target analyte in a sample. A hybridized identifier oligonucleotide-capture probe complex comprises an identifier oligonucleotide hybridized to a capture probe. An identifier oligonucleotide comprises a unique nucleic acid sequence capable of identifying a specific a target analyte in a sample and a capture probe binding site. A capture probe comprises an affinity molecule and a region complementary to the capture probe binding site. A schematic of a hybridized identifier oligonucleotide-capture probe complex is depicted in the bottom of panel FIG. 12.

The present disclosure provides compositions and methods for spatially detecting at least one target analyte in a sample using the probes of the present disclosure in a method herein referred to as a "multiplexed enzyme free method".

A multiplexed enzyme free method of the present disclosure can comprise: (1) contacting at least one target analyte in a sample with at least one probe of the present disclosure. The at least one target analyte can be a target protein or a target nucleic acid. In the aspect that the at least one target analyte is a target protein, the probe can comprise a target binding domain that is a target protein-binding region that can specifically bind to a target protein of interest. In the aspect that the at least one target analyte is a target nucleic acid, the probe can comprise a target nucleic acid-binding region that can directly or indirectly hybridize to a target nucleic acid of interest. The probe further comprises an identifier oligonucleotide. The identifier oligonucleotide can comprise a unique nucleic acid sequence which identifies the target analyte bound to the target binding domain. The identifier oligonucleotide can also comprise a capture probe binding site. The identifier oligonucleotide can also comprise a multiplexing probe binding site.

Following contacting the at least one target analyte with the at least one probe, a multiplexed enzyme free method can further comprise: (2) providing a force to a location of the sample sufficient to release the identifier oligonucleotide. In a non-limiting example, in aspects in which the probe comprises a photo-cleavable linker between the identifier oligonucleotide and the target binding domain, a region-of-interest (ROI) is excited with light of a sufficient wavelength capable of cleaving the photo-cleavable linker.

Following release of the identifier oligonucleotide, a multiplexed enzyme free method can further comprise: (3) collecting the released identifier oligonucleotide. By directing the force only to a specific location in step (2), identifier oligonucleotides are only released from probes within that location and not from probes located outside that location. Thus, identifier oligonucleotides are collected only for probes that are bound to targets within that location in step (3), thereby permitting detection of the identities and quantities of the targets (proteins and/or nucleic acids) located only within that location.

Following collection of the released identifier oligonucleotide, a multiplexed enzyme free method can further comprise: (4) hybridizing to the released identifier oligonucleotide a capture probe and a multiplexing probe.

A capture probe can comprise a region complementary to the capture probe binding site. A capture probe can also comprise an affinity molecule.

A multiplexing probe can comprise a region complementary to the multiplexing probe binding site. A multiplexing probe can also comprise a nucleic acid sequence which identifies the specific location of the sample from which the identifier oligonucleotide was released and a region complementary to the multiplexing probe binding site.

Following hybridization of a capture probe and a multiplexing probe, a multiplexed enzyme free method can further comprise: (5) Identifying the released identifier oligonucleotide by sequencing the hybridized product produced in step (4), thereby spatially detecting the at least one target analyte in the at least one cell in a tissue sample.

A hybridized product produced in step (4) can be sequenced using an enzyme free method of sequencing. Enzyme-free methods of sequencing have been described in, e.g., US2014946386 and U.S. Ser. No. 15/819,151, each of which is incorporated herein by reference in its entirety.

Figure 13:
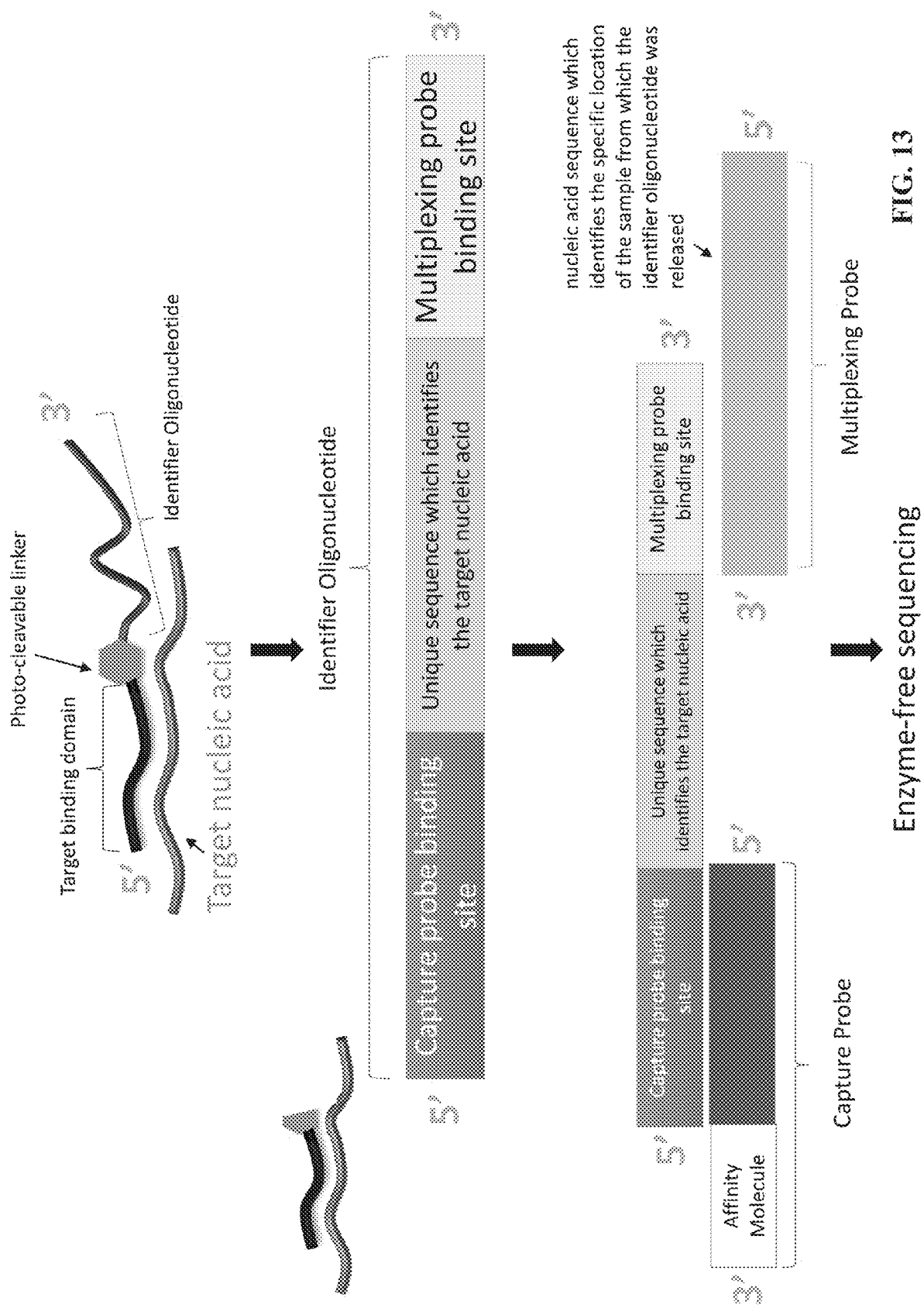
FIG. 13 is a schematic of a multiplexed enzyme free method of the present disclosure.

FIG. 13 shows a schematic of a preferred aspect of a multiplexed enzyme free method of the present disclosure. In this aspect, the probe comprises a target binding domain comprising a nucleic acid sequence that is complementary to a target nucleic acid. In the top panel, the probe hybridizes to the target nucleic acid. In the middle panel, a UV photo-cleavable linker located between the target binding domain and the identifier oligonucleotide is cleaved, releasing the identifier oligonucleotide. The identifier oligonucleotide comprises a unique nucleic acid sequence which identifies the target analyte bound to the target binding domain, a capture probe binding site, and a multiplexing probe binding site, as shown in the middle panel. After release, the identifier oligonucleotide is hybridized to a capture probe and a multiplexing probe as shown in the lower panel. The capture probe comprises a nucleic acid sequence complementary to the capture probe binding site and an affinity molecule. The multiplexing probe comprises a nucleic acid sequence complementary to the multiplexing probe binding site and a nucleic acid sequence which identifies the specific location of a sample from which the identifier oligonucleotide was released. The hybridized product is then sequenced using enzyme free sequencing methods to identify the target nucleic acid bound by the probe.

In one aspect, the present disclosure provides a composition of a hybridized identifier oligonucleotide-capture probe-multiplex probe complex for spatially detecting at least one target analyte in a sample. A hybridized identifier oligonucleotide-capture probe-multiplex probe complex comprises an identifier oligonucleotide hybridized to a capture probe and a multiplexing probe. The identifier oligonucleotide comprises a unique nucleic acid sequence capable of identifying a specific a target analyte in a sample, a capture probe binding site and a multiplexing probe binding site. The capture probe comprises an affinity molecule and a region complementary to the capture probe binding site. The multiplexing probe comprises a nucleic acid sequence which identifies the specific location of a sample from which the identifier oligonucleotide was released and a region complementary to the multiplexing probe binding site. A schematic of a hybridized identifier oligonucleotide-capture probe-multiplex probe complex is depicted in the bottom panel of FIG. 13.

Figure 20:
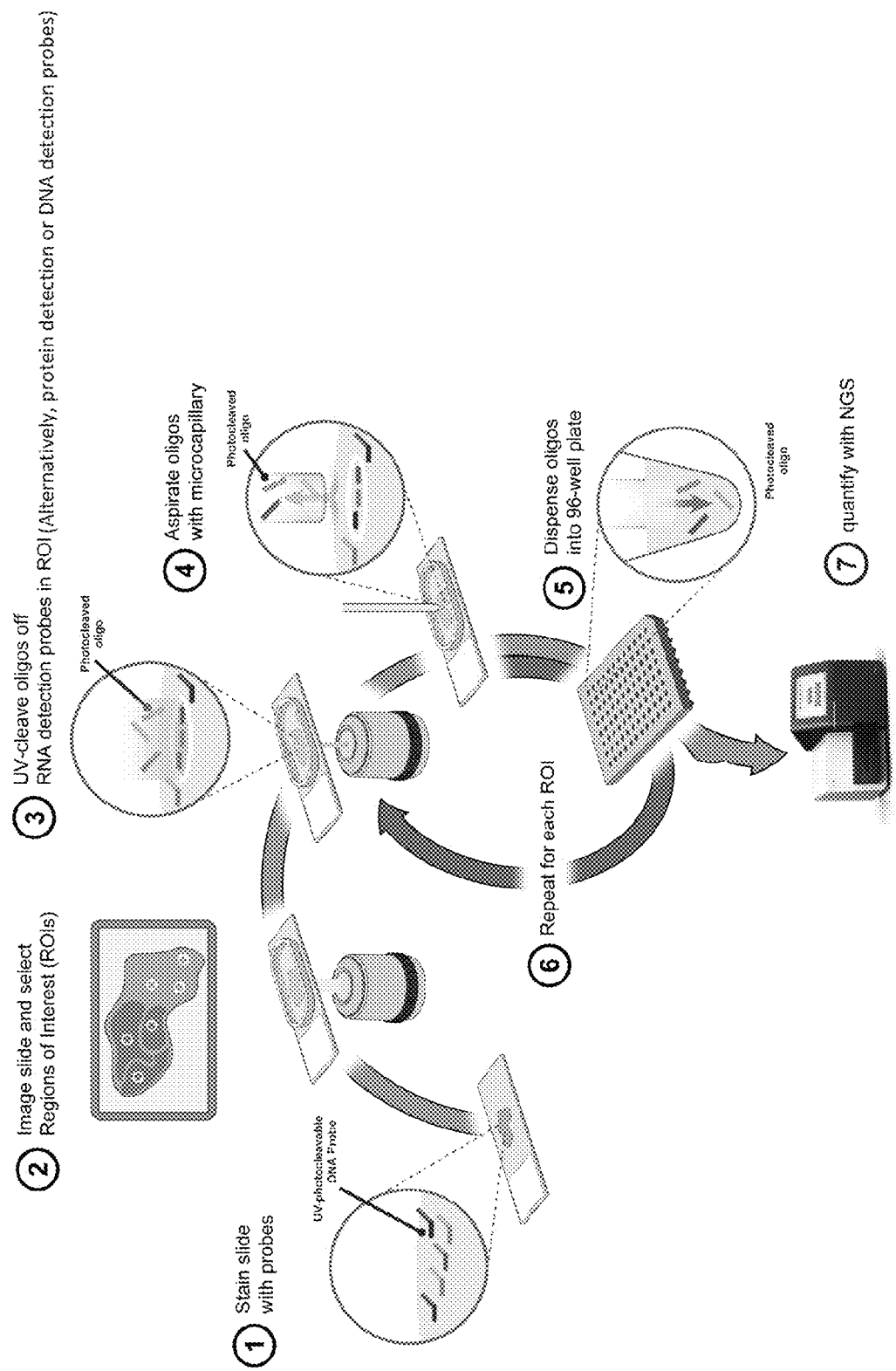
FIG. 20 is a schematic overview of the methods of the present disclosure.
Figure 21B:
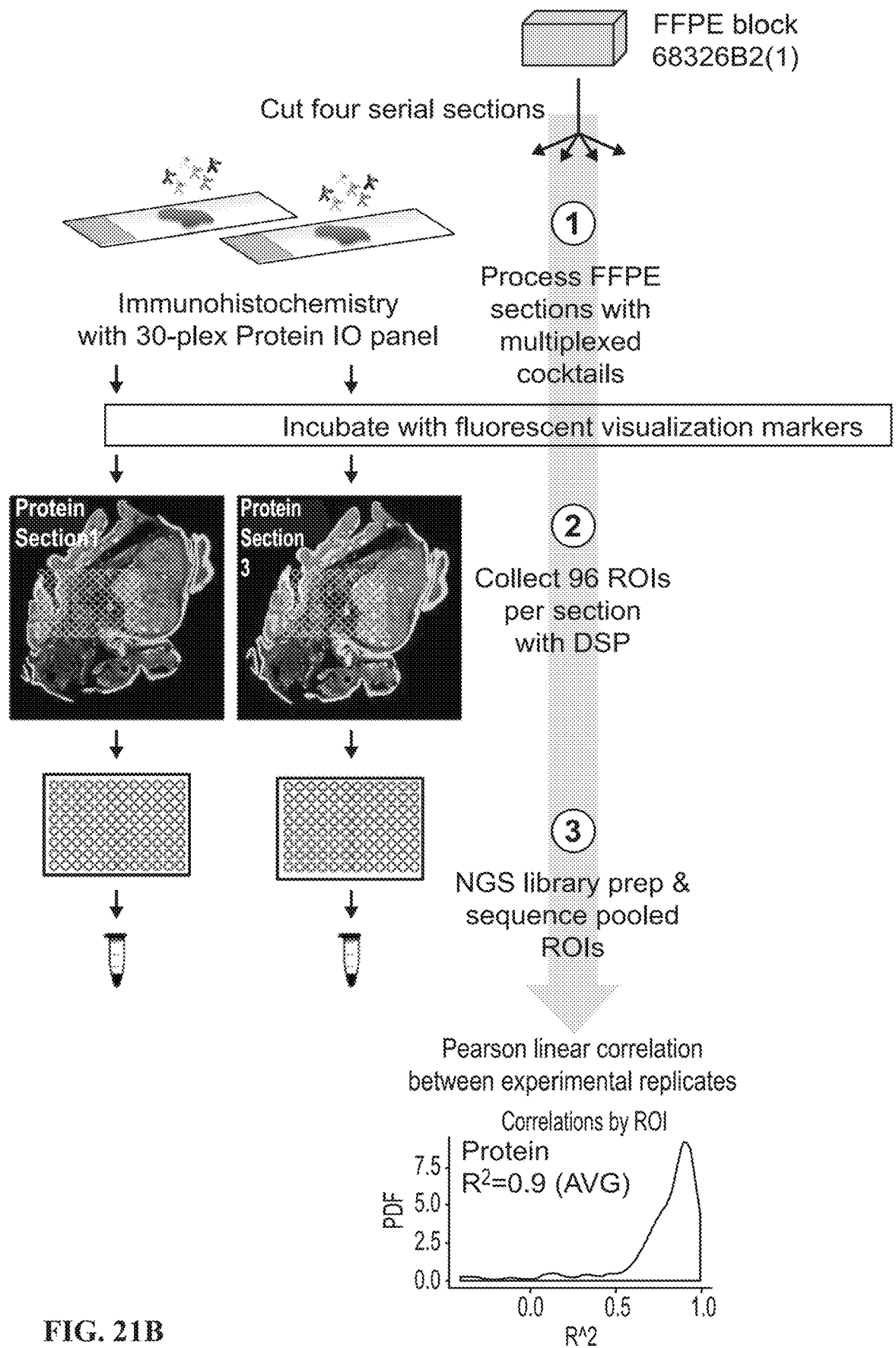
Figure 21C:
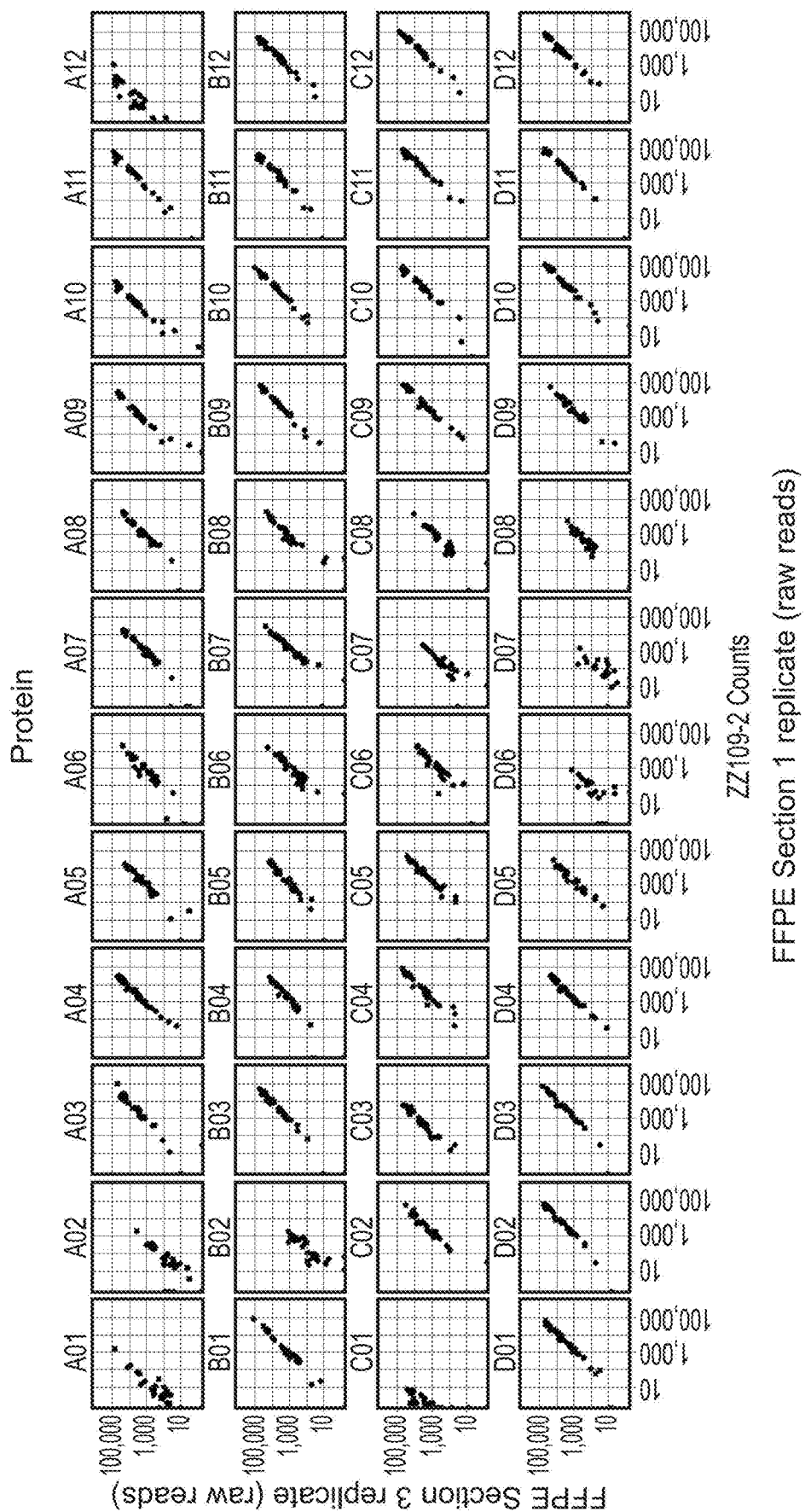
Figure 21D:
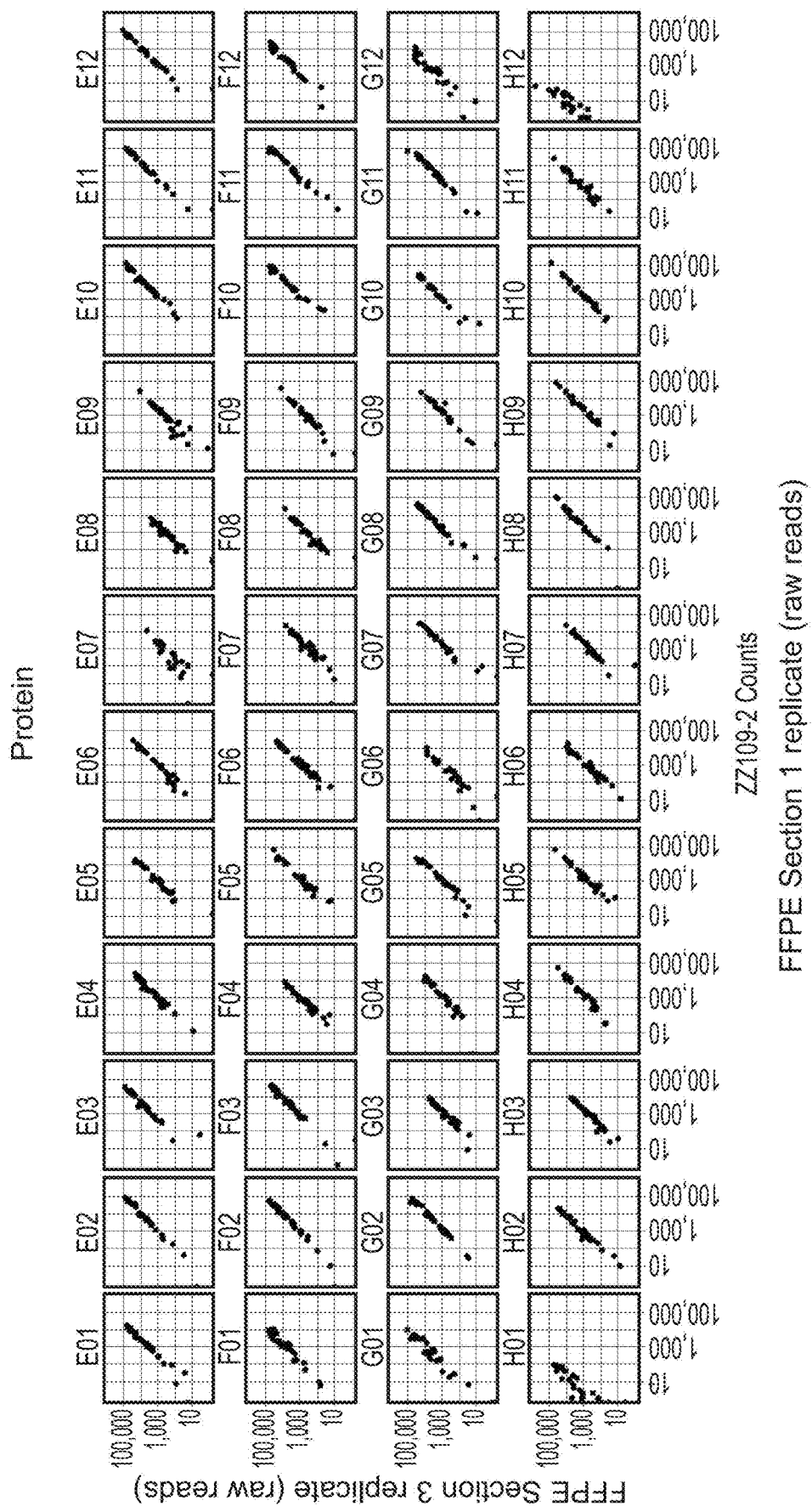
Figure 22B:
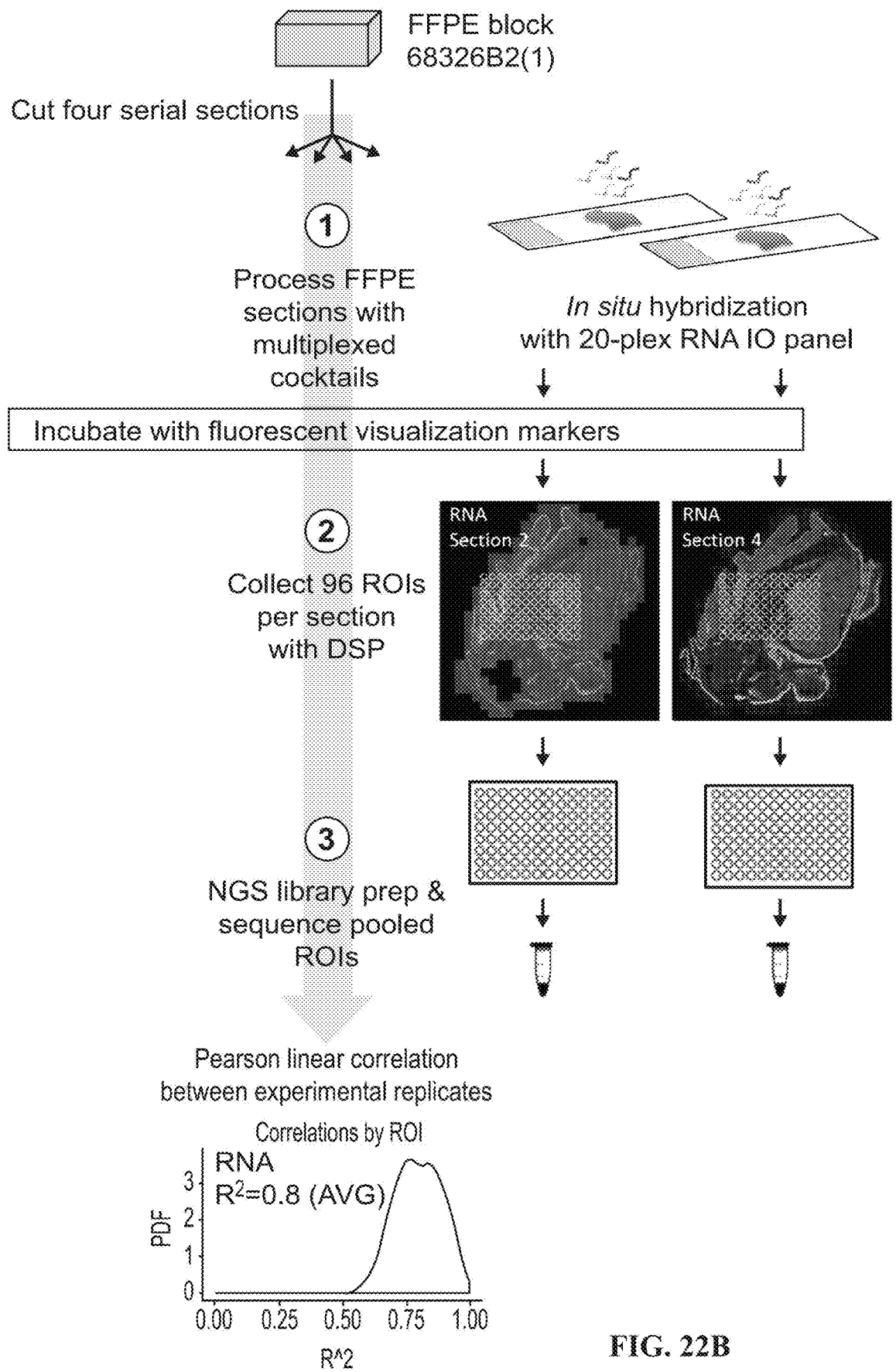
Figure 22C:
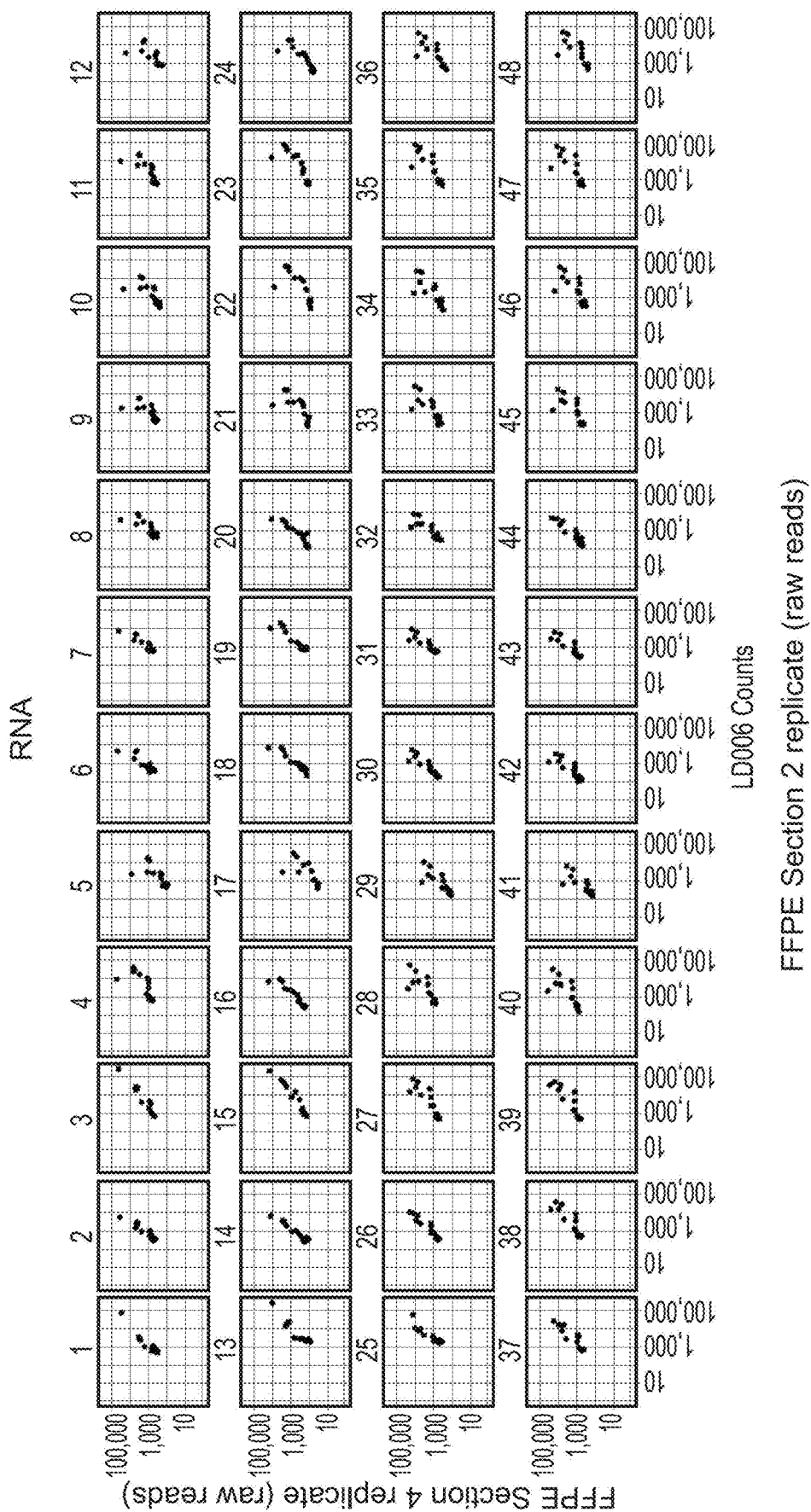
Figure 22D:
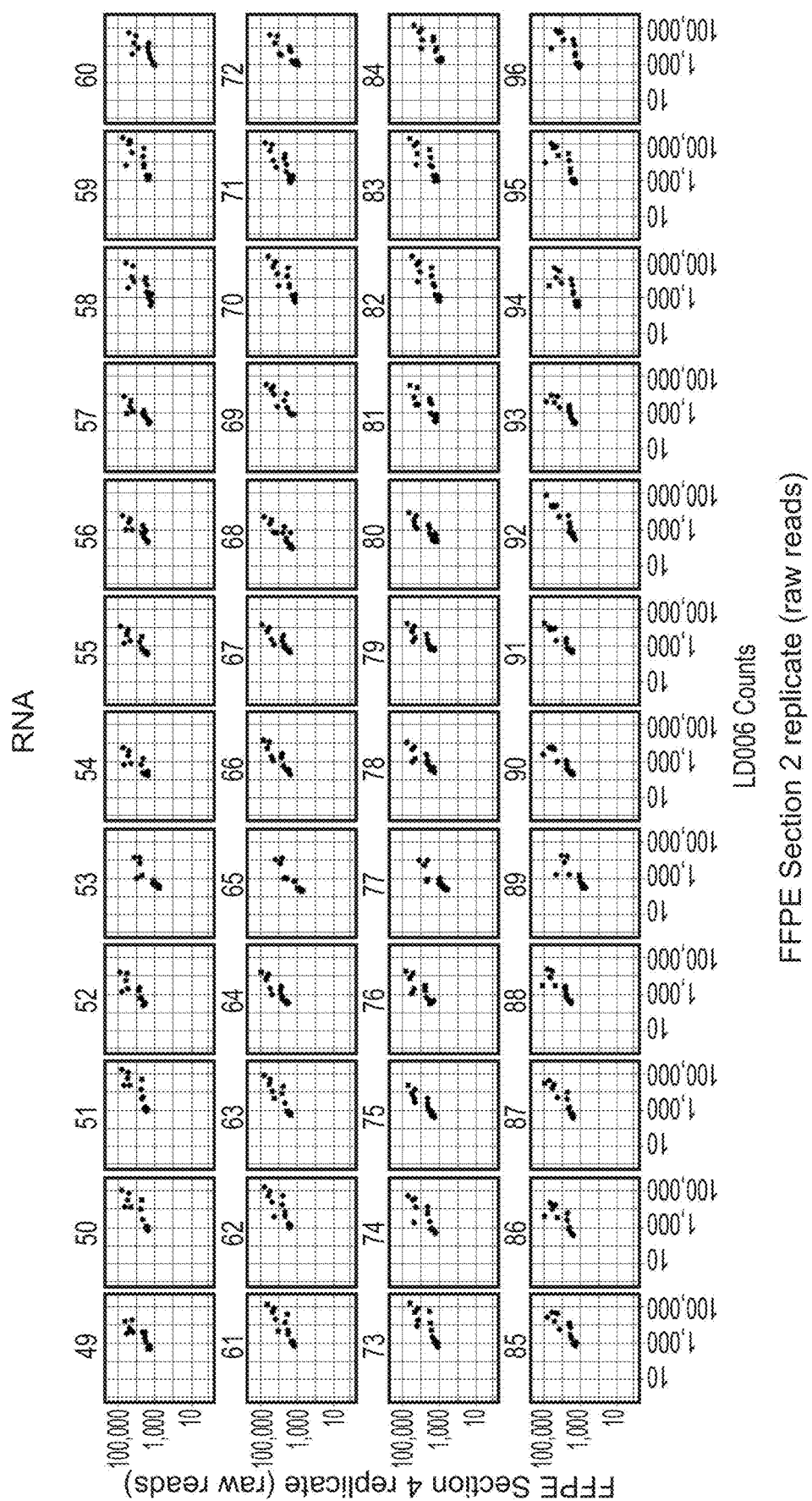

FIG. 20 is an exemplary schematic of overview of the methods of the present disclosure. First, a sample on a microscope slide is contacted with a plurality of probes of the present disclosure (step 1 in FIG. 20). The slide is then imaged and particular regions of interest (ROIs) are selected (step 2 in FIG. 20). A specific ROI is then illuminated by UV light to release identifier oligonucleotides from probes bound within the ROI. The released identifier oligonucleotides are then collected via aspiration with a microcapillary. Following aspiration, the identifier oligonucleotides are transferred to a particular well within a 96 well plate. Steps 4 and 5 are then repeated for each ROI identified in step 2. After all ROIs have been illuminated and all released identifier oligonucleotides collected, the identifier oligonucleotides are sequenced using next generation sequencing methods to spatially detect at least one target analyte in the sample.

As described in the preceding, the present disclosure provides probes for the compositions and methods of spatially detecting at least one target analyte in a sample. The present disclosure provides probes comprising a target binding domain and an identifier oligonucleotide. The target binding domain is a region of the probe that specifically binds to at least one target analyte in a sample.

Probes of the present disclosure can be used for spatially detecting a target nucleic acid. In this aspect, the target binding domain can be a target nucleic acid-binding region. The target nucleic acid-binding region is preferably at least 15 nucleotides in length, and more preferably is at least 20 nucleotides in length. In specific aspects, the target nucleic acid-binding region is approximately 10 to 500, 20 to 400, 25, 30 to 300, 35, 40 to 200, or 50 to 100 nucleotides in length. Probes and methods for binding and identifying a target nucleic acid have been described in, e.g., US2003/0013091, US2007/0166708, US2010/0015607, US2010/0261026, US2010/0262374, US2010/0112710, US2010/0047924, and US2014/0371088, each of which is incorporated herein by reference in its entirety.

Figure 14:
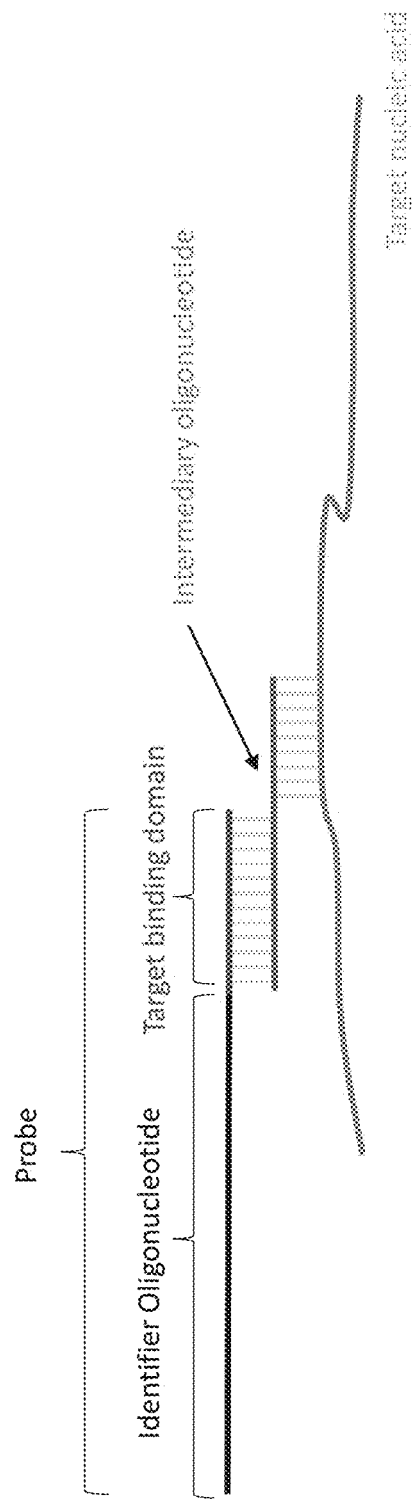
FIG. 14 is a schematic of a probe of the present disclosure indirectly binding to a target nucleic acid.

The target nucleic acid-binding region can directly hybridize to a target nucleic acid present in a sample. Alternatively, the probes of the present disclosure can indirectly hybridize to a target nucleic acid present in a sample (via an intermediary oligonucleotide). FIG. 14 illustrates a probe (or composition) of this aspect. The probe includes a target nucleic-acid binding domain which binds to a synthetic oligonucleotide (the intermediary oligonucleotide) that in turn binds to a target nucleic acid in a biological sample. It could be said that the intermediary oligonucleotide is a probe, as defined herein, since it comprises a nucleic acid backbone and is capable of binding a target nucleic acid. In these aspects, a probe's target nucleic acid-binding region hybridizes to a region of an intermediary oligonucleotide (i.e., a synthetic oligonucleotide) which is different from the target nucleic acid present in a sample. Thus, the probe's target binding region is independent of the ultimate target nucleic acid in the sample. This allows economical and rapid flexibility in an assay design, as the target (present in a sample)-specific components of the assay are included in inexpensive and widely-available synthetic DNA oligonucleotides rather than the more expensive probes. Such synthetic oligonucleotides are simply designed by including a region that hybridizes to the target nucleic acid present in a sample and a region that hybridizes to a probe. Therefore, a single set of indirectly-binding probes can be used to detect an infinite variety of target nucleic acids (present in a sample) in different experiments simply by replacing the target-specific (synthetic) oligonucleotide portion of the assay.

A target nucleic acid may be DNA or RNA and preferably messenger RNA (mRNA) or miRNA.

Probes of the present disclosure can be used for detecting a target protein. In this aspect, the target binding domain can be a target protein-binding region. A target protein-binding region includes molecules or assembles that are designed to bind to at least one target protein, at least one target protein surrogate, or both and can, under appropriate conditions, form a molecular complex comprising the probe and the target protein. The target-protein binding region can include an antibody, a peptide, an aptamer, or a peptoid. The antibody can be obtained from a variety of sources, including but not limited to polyclonal antibody, monoclonal antibody, monospecific antibody, recombinantly expressed antibody, humanized antibody, plantibodies, and the like. The terms protein, polypeptide, peptide, and amino acid sequence are used interchangeably herein to refer to polymers of amino acids of any length. The polymer may be linear or branched, it may comprise modified amino acids, and it may be interrupted by non-amino acids or synthetic amino acids. The terms also encompass an amino acid polymer that has been modified, for example, by disulfide bond formation, glycosylation, lipidation, acetylation, phosphorylation, or any other manipulation, such as conjugation with a labeling component. As used herein the term amino acid refers to either natural and/or unnatural or synthetic amino acids, including but not limited to glycine and both the D or L optical isomers, and amino acid analogs and peptidomimetics. Probes and methods for binding and identifying a target protein have been described, e.g., in US2011/0086774, the contents of which is incorporated herein by reference in its entirety.

An identifier oligonucleotide is a nucleic acid molecule that identifies the target analyte bound to the target binding domain. The identifier oligonucleotide comprises a unique nucleic acid sequence that identifies the target analyte bound to the target binding domain of the probe. In a non-limiting example, a probe with a target binding domain that binds to the protein P53 comprises an identifier oligonucleotide with a unique nucleic acid sequence that corresponds to P53, while a probe with a target binding domain that binds to the protein P97 comprises an identifier oligonucleotide with a unique nucleic acid sequence that corresponds to P97.

An identifier oligonucleotide can be DNA, RNA, or a combination of DNA and RNA.

In some aspects, an identifier oligonucleotide can comprise at least one amplification primer binding site. An amplification primer binding site is a nucleic acid sequence capable of binding to an amplification primer. An amplification primer can be used to amplify the nucleic molecule to which it is bound using methods known in the art, including, but not limited to, polymerase chain reaction (PCR).

In some aspects, an identifier oligonucleotide can comprise at least one unique molecular identifier.

An identifier oligonucleotide can be a single-stranded, a double-stranded, or a partially double-stranded nucleic acid molecule. In the aspects in which an identifier oligonucleotide is double-stranded or partially double-stranded, at least one of the two strands can comprise at least two separate nucleic acid molecules which, without being bound by theory, allows for denaturing of the identifier oligonucleotide at lower temperatures.

An identifier oligonucleotide can also comprise at least one 3' end that comprises a single nucleotide overhang.

An identifier oligonucleotide can also comprise a capture probe binding site. A capture probe binding site is a nucleic acid sequence to which a capture probe can bind.

A capture probe of the present disclosure can comprise a nucleic acid sequence complementary to a capture probe binding site. A capture probe can also comprise an affinity molecule.

An identifier oligonucleotide can also comprise a multiplexing probe binding site. A multiplexing probe binding site is a nucleic acid sequence to which a multiplexing probe can bind.

A multiplexing probe of the present disclosure can comprise a nucleic acid sequence complementary to a multiplexing probe binding site. A multiplexing probe can also comprise a nucleic acid sequence which identifies the specific location of the tissue sample from which an identifier oligonucleotide was released.

A probe of the present disclosure can include a region which permits the release of an identifier oligonucleotide following the application of a suitable force. In one non-limited example, the region is a cleavable motif (e.g., a restriction enzyme site or cleavable linker). The cleavable motif allows release of an identifier oligonucleotide from a bound target nucleic acid or protein and the identifier oligonucleotide can then be collected and detected. The region which permits the release of an identifier oligonucleotide can be positioned between the target-binding domain and the identifier oligonucleotide, allowing for the release of the identifier oligonucleotide from the target binding domain. An identifier oligonucleotide is said to be releasable when it can be separated (i.e., cleaved and released) from the remainder of the probe. Examples of cleavable motives include but are not limited to photo-cleavable linkers. Photo-cleavable linkers can be cleaved by light provided by a suitable coherent light source (e.g., a laser and a UV light source) or a suitable incoherent light source (e.g., an arc-lamp and a light-emitting diode (LED)).

In some aspects, the identifier oligonucleotide is collected from a solution proximal to, e.g., at least immediately above or surrounding, the point at which the identifier oligonucleotide is released or the at least one cell. The proximal solution may be collected by aspirating, e.g., via a pipette, a capillary tube, a microarray pin, a flow cell comprising holes, or another suitable aspirating system known in the art or any combination thereof. The capillary tube may comprise an optical device capable of transmitting a light force, e.g., UV light, to the at least one cell. The pipette or a microarray pin may be attached to an array comprising a plurality of pipettes or microarray pins. The proximal solution may comprise an anionic polymer, e.g., dextran sulfate, and/or salmon sperm DNA and/or the collected signal oligonucleotide may be added to a solution comprising an anionic polymer, e.g., dextran sulfate, and/or salmon sperm DNA. Other non-specific blocking agents known in the art in addition to or instead of salmon sperm DNA may be used.

In some aspects, the identifier oligonucleotide is collected from a tissue, at least one cell or proximal to the point at which the identifier oligonucleotide is released via liquid laminar, turbulent, or transitional flow. The flow may be via a channel, e.g., having 25 to 500 m depth between the tissue and a fluidic device or impermeable barrier placed over the tissue.

In aspects where the target-binding domain of a probe is an antibody, the probe can be prepared using a cysteine bioconjugation method that is stable, site-specific to, preferably, the antibody's hinge-region heavy-chain. This preparation method provides relatively controllable identifier oligonucleotides to antibody stoichiometric ratios. A probe can comprise a plurality (i.e., more than one, e.g., 2, 3, 4, 5, or more) identifier oligonucleotides per antibody. Generally, "heavier" probes, which comprise 3 or 4 identifier oligonucleotides per antibody, are significantly less sensitive than antibodies lacking an identifier oligonucleotide or "lighter" probes, which comprise 1 or 2 identifier oligonucleotides per antibody.

In aspects, probes are provided to a sample at concentrations typically less than that used for immunohistochemistry (IHC) or for in situ hybridization (ISH). Alternately, the concentration may be significantly less than that used for IHC or ISH. For example, the probe concentration may be 2 fold less, 5 fold less, 10 fold less, 20 fold less, 25 fold less, 30 fold less, 50 fold less, 60 fold less, 70 fold less, 80 fold less, 90 fold less, 100 fold less, 200 fold less, 300 fold less, 400 fold less, 500 fold less, 600 fold less, 700 fold less, 800 fold less, 900 fold less, 1000 fold less, 2000 fold less, or less and any number in between. In aspects, probes are provided at a concentration of 100 nM, 70 nM, 60 nM, 50 nM, 40 nM, 30 nM, 20 nM, 10 nM, 9 nM, 8 nM, 7 nM, 6 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, 0.1 nM, 0.09 nM, 0.08 nM, 0.07 nM, 0.06 nM, 0.05 nM, 0.04 nM, 0.03 nM, 0.02 nM, 0.01 nM, and less and any concentration in between.

Background noise, during protein detection, can be reduced by performing a negative purification of the intact probe molecule. This can be done by conducting an affinity purification of the antibody or photo-cleavable linker after collection of eluate from a region of interest. Normally, released signal oligonucleotides will not be pulled out of solution. A protein-G or -O mechanism in a pipet tip, tube, or plate can be employed for this step. Such devices and reagents commercially available.

Background noise, during nucleic acid detection, can be reduced by performing a negative purification of the intact probe molecule. This can be done by conducting an affinity purification of the target binding domain or photo-cleavable linker after collection of eluate from a region of interest. Normally, released signal oligonucleotides will not be pulled out of solution. To assist in the negative purification, a universal purification sequence may be included in a probe, e.g., in the target binding domain.

Protein-targeting probes and nucleic acid-targeting probes may be applied simultaneously as long as conditions allow for binding of both a protein target and a nucleic acid target. Alternately, protein-targeting probes and nucleic acid-targeting probes may be applied sequentially when conditions allowing for binding of both a protein target and a nucleic acid target are not possible.

A set of probes is synonymous with a composition of probes. A set of probes includes at least one species of probes, i.e., directed to one target. A set of probes preferably includes at least two, e.g., 3, 4, 5, 6, 7, 8, 9, 10, 11, 12, 13, 14, 15, 16, 17, 18, 19 20, 30, 40, 50, 60, 70, 80, 90, 100, 200, 300, 400, 500, 600, 700, 800, 900, 1000 or more species of probes. A probe set may include one or multiple copies of each species of probe.

A first set of probes only may be applied to a sample. Alternatively, a second set (or higher number) of probes may be later applied to the sample. The first set and second (or higher number) may target only nucleic acids, only proteins, or a combination thereof.

In the present disclosure, two or more targets (i.e., proteins, nucleic acids, or a combination thereof) are detected; 3, 4, 5, 6, 7, 8, 9, 10, 11, 12, 13, 14, 15, 16, 17, 18, 19 20, 30, 40, 50, 60, 70, 80, 90, 100, 200, 300, 400, 500, 600, 700, 800, 900, 1000 or more targets, and any number there between, are detected.

A set of probes may be pre-defined based upon the cell type or tissue type to be targeted. For example, if the tissue is a breast cancer, then the set of probes will include probes directed to proteins relevant to breast cancer cells (e.g., Her2, EGFR, and PR) and/or probes directed to proteins relevant to normal breast tissues. Additionally, the set of probes may be pre-defined based upon developmental status of a cell or tissue to be targeted. Alternately, the set of probes may be pre-defined based upon subcellular localizations of interest, e.g., nucleus, cytoplasm, and membrane. For example, antibodies directed to Foxp3, Histone H3, or P-S6 label the nucleus, antibodies directed to CD3, CD4, PD-1, or CD45RO label the cytoplasm, and antibodies directed to PD-L1 label membranes.

A probe may be chemically synthesized or may be produced biologically using a vector into which a nucleic acid encoding the probe has been cloned.

Any probe or set of probes described herein may be used in methods and kits of the present disclosure.

For the herein-described probes, association of a unique nucleic acid sequence to a specific target nucleic acid or target protein is not fixed.

As described in the preceding, probes of the present disclosure can be used to detect a target nucleic acid or target protein present in any sample, e.g., a biological sample. As will be appreciated by those in the art, the sample may comprise any number of things, including, but not limited to: cells (including both primary cells and cultured cell lines) and tissues (including cultured or explanted). In aspects, a tissue sample (fixed or unfixed) is embedded, serially sectioned, and immobilized onto a microscope slide. As is well known, a pair of serial sections will include at least one cell that is present in both serial sections. Structures and cell types, located on a first serial section will have a similar location on an adjacent serial section. The sample can be cultured cells or dissociated cells (fixed or unfixed) that have been immobilized onto a slide. A sample can be a formalin-fixed paraffin-embedded (FFPE) tissue sample.

In aspects, a tissue sample is a biopsied tumor or a portion thereof, i.e., a clinically-relevant tissue sample. For example, the tumor may be from a breast cancer. The sample may be an excised lymph node.

The sample can be obtained from virtually any organism including multicellular organisms, e.g., of the plant, fungus, and animal kingdoms; preferably, the sample is obtained from an animal, e.g., a mammal. Human samples are particularly preferred.

In some aspects, the probes, compositions, methods, and kits described herein are used in the diagnosis of a condition. As used herein the term diagnose or diagnosis of a condition includes predicting or diagnosing the condition, determining predisposition to the condition, monitoring treatment of the condition, diagnosing a therapeutic response of the disease, and prognosis of the condition, condition progression, and response to particular treatment of the condition. For example, a tissue sample can be assayed according to any of the probes, methods, or kits described herein to determine the presence and/or quantity of markers of a disease or malignant cell type in the sample (relative to the non-diseased condition), thereby diagnosing or staging a disease or a cancer.

In general, samples attached to a slide can be first imaged using fluorescence (e.g., fluorescent antibodies or fluorescent stains (e.g., DAPI)) to identify morphology, regions of interest, cell types of interest, and single cells and then expression of proteins and/or nucleic acids can be digitally counted from the sample on the same slide.

Compositions and kits of the present disclosure can include probes and other reagents, for example, buffers and other reagents known in the art to facilitate binding of a protein and/or a nucleic acid in a sample, i.e., for performing hybridization reactions.

A kit also will include instructions for using the components of the kit, including, but not limited to, information necessary to hybridize labeled oligonucleotides to a probe, to hybridize a probe to a target-specific oligonucleotide, to hybridize a target-specific oligonucleotide to a target nucleic acid and/or to hybridize a probe to target protein.

A region of interest may be a tissue type present in a sample, a cell type, a cell, or a subcellular structure within a cell.

Together, a comparison of the identity and abundance of the target proteins and/or target nucleic acids present in a first region of interest (e.g., tissue type, a cell type (including normal and abnormal cells), and a subcellular structure within a cell) and the identity and abundance of the target proteins and/or target nucleic acids present in second region of interest or more regions of interest can be made using the methods of the present disclosure.

As described in the preceding, the products produced by the methods of the present disclosure can be used for nucleic acid amplification. In a preferred aspect, the nucleic acid amplification can be solid-phase nucleic acid amplification. Thus, in further aspects the invention provides a method of solid-phase nucleic acid amplification of template polynucleotide molecules which comprises: preparing a library of template polynucleotide molecules which have common sequences at their 5' and 3' ends using the methods of the present disclosure and carrying out a solid-phase nucleic acid amplification reaction wherein said template polynucleotide molecules are amplified. Compositions and methods for nucleic acid amplification and sequencing have been described in, e.g., U.S. Pat. No. 9,376,678, which is incorporated herein by reference in its entirety.

The term "solid-phase amplification" as used herein refers to any nucleic acid amplification reaction carried out on or in association with a solid support such that all or a portion of the amplified products are immobilized on the solid support as they are formed. In particular, the term encompasses solid-phase polymerase chain reaction (solid-phase PCR), which is a reaction analogous to standard solution phase PCR, except that one or both of the forward and reverse amplification primers is/are immobilized on the solid support.

Although the invention encompasses "solid-phase" amplification methods in which only one amplification primer is immobilized (the other primer usually being present in free solution), it is preferred for the solid support to be provided with both the forward and the reverse primers immobilized. In practice, there will be a "plurality" of identical forward primers and/or a "plurality" of identical reverse primers immobilized on the solid support, since the PCR process requires an excess of primers to sustain amplification. References herein to forward and reverse primers are to be interpreted accordingly as encompassing a "plurality" of such primers unless the context indicates otherwise.

As will be appreciated by the skilled reader, any given PCR reaction requires at least one type of forward primer and at least one type of reverse primer specific for the template to be amplified. However, in certain aspects the forward and reverse primers may comprise template-specific portions of identical sequence, and may have entirely identical nucleotide sequence and structure (including any non-nucleotide modifications). In other words, it is possible to carry out solid-phase amplification using only one type of primer, and such single-primer methods are encompassed within the scope of the invention. Other aspects may use forward and reverse primers which contain identical template-specific sequences but which differ in some other structural features. For example one type of primer may contain a non-nucleotide modification which is not present in the other.

In other aspects of the invention the forward and reverse primers may contain template-specific portions of different sequence.

Amplification primers for solid-phase PCR are preferably immobilized by covalent attachment to the solid support at or near the 5' end of the primer, leaving the template-specific portion of the primer free for annealing to its cognate template and the 3' hydroxyl group free for primer extension. Any suitable covalent attachment means known in the art may be used for this purpose. The chosen attachment chemistry will depend on the nature of the solid support, and any derivatization or functionalization applied to it. The primer itself may include a moiety, which may be a non-nucleotide chemical modification, to facilitate attachment. In one particularly preferred aspect the primer may include a sulphur-containing nucleophile, such as phosphorothioate or thiophosphate, at the 5' end. In the case of solid-supported polyacrylamide hydrogels (as described below), this nucleophile will bind to a "C" group present in the hydrogel. The most preferred means of attaching primers and templates to a solid support is via 5' phosphorothioate attachment to a hydrogel comprised of polymerised acrylamide and N-(5-bromoacetamidylpentyl)acrylamide (BRAPA).

The terms "cluster" and "colony" are used interchangeably herein to refer to a discrete site on a solid support comprised of a plurality of identical immobilized nucleic acid strands and a plurality of identical immobilized complementary nucleic acid strands. The term "clustered array" refers to an array formed from such clusters or colonies. In this context the term "array" is not to be understood as requiring an ordered arrangement of clusters.

The invention also encompasses methods of sequencing the amplified nucleic acids generated by solid-phase amplification. Thus, the invention provides a method of nucleic acid sequencing comprising amplifying a library of nucleic acid templates by the methods of the present disclosure described above, using solid-phase amplification as described above to amplify this library on a solid support, and carrying out a nucleic acid sequencing reaction to determine the sequence of the whole or a part of at least one amplified nucleic acid strand produced in the solid-phase amplification reaction.

Sequencing, as referred to herein, can be carried out using any suitable "sequencing-by-synthesis" technique, wherein nucleotides are added successively to a free 3' hydroxyl group, resulting in synthesis of a polynucleotide chain in the 5' to 3' direction. The nature of the nucleotide added is preferably determined after each nucleotide addition.

The initiation point for the sequencing reaction may be provided by annealing of a sequencing primer to a product of the whole genome or solid-phase amplification reaction. In this connection, one or both of the adapters added during formation of the template library may include a nucleotide sequence which permits annealing of a sequencing primer to amplified products derived by whole genome or solid-phase amplification of the template library.

The products of solid-phase amplification reactions wherein both forward and reverse amplification primers are covalently immobilized on the solid surface are so-called "bridged" structures formed by annealing of pairs of immobilized polynucleotide strands and immobilized complementary strands, both strands being attached to the solid support at the 5' end. Arrays comprised of such bridged structures provide inefficient templates for nucleic acid sequencing, since hybridization of a conventional sequencing primer to one of the immobilized strands is not favored compared to annealing of this strand to its immobilized complementary strand under standard conditions for hybridization.

In order to provide more suitable templates for nucleic acid sequencing it is preferred to remove substantially all or at least a portion of one of the immobilized strands in the "bridged" structure in order to generate a template which is at least partially single-stranded. The portion of the template which is single-stranded will thus be available for hybridization to a sequencing primer. The process of removing all or a portion of one immobilized strand in a "bridged" double-stranded nucleic acid structure may be referred to herein as "linearization".

Bridged template structures may be linearized by cleavage of one or both strands with a restriction endonuclease or by cleavage of one strand with a nicking endonuclease. Other methods of cleavage can be used as an alternative to restriction enzymes or nicking enzymes, including inter alia chemical cleavage (e.g. cleavage of a diol linkage with periodate), cleavage of abasic sites by cleavage with endonuclease, or by exposure to heat or alkali, cleavage of ribonucleotides incorporated into amplification products otherwise comprised of deoxyribonucleotides, photochemical cleavage or cleavage of a peptide linker.

It will be appreciated that a linearization step may not be essential if the solid-phase amplification reaction is performed with only one primer covalently immobilized and the other in free solution.

In order to generate a linearized template suitable for sequencing it is necessary to remove "unequal" amounts of the complementary strands in the bridged structure formed by amplification so as to leave behind a linearized template for sequencing which is fully or partially single stranded. Most preferably one strand of the bridged structure is substantially or completely removed.

Following the cleavage step, regardless of the method used for cleavage, the product of the cleavage reaction may be subjected to denaturing conditions in order to remove the portion(s) of the cleaved strand(s) that are not attached to the solid support. Suitable denaturing conditions will be apparent to the skilled reader with reference to standard molecular biology protocols.

Denaturation (and subsequent re-annealing of the cleaved strands) results in the production of a sequencing template which is partially or substantially single-stranded. A sequencing reaction may then be initiated by hybridization of a sequencing primer to the single-stranded portion of the template.

Thus, the nucleic acid sequencing reaction may comprise hybridizing a sequencing primer to a single-stranded region of a linearized amplification product, sequentially incorporating one or more nucleotides into a polynucleotide strand complementary to the region of amplified template strand to be sequenced, identifying the base present in one or more of the incorporated nucleotide(s) and thereby determining the sequence of a region of the template strand.

One preferred sequencing method which can be used in accordance with the invention relies on the use of modified nucleotides that can act as chain terminators. Once the modified nucleotide has been incorporated into the growing polynucleotide chain complementary to the region of the template being sequenced there is no free 3'-OH group available to direct further sequence extension and therefore the polymerase cannot add further nucleotides. Once the nature of the base incorporated into the growing chain has been determined, the 3' block may be removed to allow addition of the next successive nucleotide. By ordering the products derived using these modified nucleotides it is possible to deduce the DNA sequence of the DNA template. Such reactions can be done in a single experiment if each of the modified nucleotides has attached a different label, known to correspond to the particular base, to facilitate discrimination between the bases added at each incorporation step. Alternatively, a separate reaction may be carried out containing each of the modified nucleotides separately.

The modified nucleotides may carry a label to facilitate their detection. Preferably this is a fluorescent label. Each nucleotide type may carry a different fluorescent label. However the detectable label need not be a fluorescent label. Any label can be used which allows the detection of an incorporated nucleotide.

One method for detecting fluorescently labelled nucleotides comprises using laser light of a wavelength specific for the labelled nucleotides, or the use of other suitable sources of illumination. The fluorescence from the label on the nucleotide may be detected by a CCD camera or other suitable detection means.

The invention is not intended to be limited to use of the sequencing method outlined above, as essentially any sequencing methodology which relies on successive incorporation of nucleotides into a polynucleotide chain can be used. Suitable alternative techniques include, for example, Pyrosequencing, FISSEQ (fluorescent in situ sequencing), MPSS (massively parallel signature sequencing) and sequencing by ligation-based methods.

In methods of the present disclosure, the unique nucleic acid sequence present in the identifier oligonucleotide of a probe which identifies the target analyte bound to the target binding domain of the probe can comprise between about 5 nucleotides and about 50 nucleotides. Preferably, the sequence comprises between about 20 nucleotides and about 40 nucleotides. Even more preferably, the sequence comprises about 35 nucleotides. In some preferred aspects, the sequence comprises 10 nucleotides.

In methods of the present disclosure, the nucleic acid sequence which identifies the specific location of the tissue sample from which the identifier oligonucleotide was released comprises between about 6 nucleotides and about 15 nucleotides. Preferably, the sequence comprises about 12 nucleotides.

In methods of the present disclosure, an amplification primer binding sites comprises between about 18 nucleotides and about 40 nucleotides. Preferably, an amplification primer binding sites comprises about 32 nucleotides.

In some aspects of the methods of the present disclosure, an amplification primer binding site can comprise an i7 sequence, wherein the i7 sequence comprises the sequence set forth in SEQ ID NO: 1.

In some aspects of the methods of the present disclosure, an amplification primer binding site can comprise an i5 sequence, wherein the i5 sequence comprises the sequence set forth in SEQ ID NO: 2.

In some aspects of the methods of the present disclosure, an amplification primer can comprise a flow cell adapter sequence, wherein the flow cell adapter sequence is suitable for sequencing. Preferably, at least one amplification primer used in the methods of the present disclosure comprises a P5 flow cell adapter sequence, wherein the P5 flow cell adapter sequence comprises the sequence set forth in SEQ ID NO: 3. Preferably still, at least one amplification primer used in the methods of the present disclosure comprises a P7 flow cell adapter sequence, wherein the P7 flow cell adapter sequence comprises the sequence set forth in SEQ ID NO: 4.

In methods of the present disclosure, a unique molecular identifier can comprise between about 6 nucleotides and about 30 nucleotides. Preferably, a unique molecular identifier can comprise about 15 nucleotides. The terms unique molecular identifier and random molecular tags are used interchangeably herein. Using methods known in that art, unique molecular identifiers are random sequences that can be used to correct for biases in amplification prior to sequencing.

In methods of the present disclosure, a constant nucleic acid sequence to minimize ligation bias comprises between about 1 nucleotide and about 15 nucleotides. Preferably, the constant sequence comprises about 8 nucleotides.

In some aspects, a flow cell binding site can comprise between about 15 to about 40 nucleotides. A flow cell binding site can comprise about 29 nucleotides. A flow cell binding site can comprise about 24 nucleotides.

In some aspects, a target binding domain can comprise between about 10 to about 70 nucleotides. A target binding domain can comprise between about 30 to about 55 nucleotides. A target binding domain can comprise between about 35 to about 50 nucleotides.

In some aspects, a unique nucleic acid sequence which identifies the target analyte bound to the target binding domain can comprise between about 20 to about 40. A unique nucleic acid sequence which identifies the target analyte bound to the target binding domain can comprise about 25 nucleotides, or about 35 nucleotides, or about 12 nucleotides.

In some aspects, an amplification primer binding site can comprise between about 20 to about 50 nucleotides. An amplification primer binding site can comprise about 33 nucleotides, or about 34 nucleotides.

In some aspects, a nucleic acid sequence which identifies the specific location of the tissue sample from which the identifier oligonucleotide was released can comprise between about 1 to about 20 nucleotides. A nucleic acid sequence which identifies the specific location of the tissue sample from which the identifier oligonucleotide was released can comprise about 8 nucleotides.

In some aspects, a nucleic acid sequence comprising a unique molecular identifier can comprise between about 5 to about 20 nucleotides. A nucleic acid sequence comprising a unique molecular identifier can comprise about 14 nucleotides.

As used herein, the terms "region of interest" and "ROI" are used in their broadest sense to refer to a specific location within a sample that is to be analyzed using the methods of the present disclosure.

As used herein, the term "adjacent" can mean within about 1 nucleotide, or within about 2 nucleotides, or within about 3 nucleotides, or within about 4 nucleotides, or within about 5 nucleotides, or within about 6 nucleotides, or within about 7 nucleotides, or within about 8 nucleotides, or within about 9 nucleotides, or within about 10 nucleotides, or within about 11 nucleotides, or within about 12 nucleotides, or within about 13 nucleotides, or within about 14 nucleotides, or within about 15 nucleotides, or within about 16 nucleotides, or within about 17 nucleotides, or within about 18 nucleotides, or within about 19 nucleotides, or within about 20 nucleotides, or within about 21 nucleotides, or within about 22 nucleotides, or within about 23 nucleotides, or within about 24 nucleotides, or within about 25 nucleotides, or within about 26 nucleotides, or within about 27 nucleotides, or within about 28 nucleotides, or within about 29 nucleotides, or within about 30 nucleotides, or within about 40 nucleotides, or within about nucleotides, or within about 50 nucleotides, or within about 60 nucleotides, or within about 70 nucleotides, or within about 80 nucleotides, or within about 90 nucleotides, or within about 100 nucleotides.

As used herein, the term "spatially detecting" is used in its broadest sense to refer to the identification of the presence of a specific target analyte within a specific region of interest in a sample. Spatially detecting can comprise quantifying the amount of a specific target analyte present within a specific region of interest in a sample. Spatially detecting can further comprise quantifying the relative amount of a first target analyte within a specific region of interest in a sample as compared to the amount of at least a second target analyte within a specific region of interest in a sample. Spatially detecting can also comprise quantifying the relative amount of a specific target analyte within a first region of interest in a sample compared to the amount of the same target analyte in at least a second region of interest in the same sample or different sample.

In some aspects of the methods and compositions of the present disclosure, a target analyte can be any molecule within a sample that is to be spatially detected. Target analytes include, but are not limited to, nucleic acid molecules and protein molecules. When the target analyte is a protein, the protein can be referred to as a target protein. When the target analyte is a nucleic acid, the nucleic acid can be referred to as a target nucleic acid. Target nucleic acids can include, but are not limited to, mRNA molecules, micro RNA (miRNA) molecules, tRNA molecules, rRNA molecules, gDNA or any other nucleic acid present within a sample.

In some aspects of the methods and compositions of the present disclosure, the term target binding domain is used in its broadest sense to refer to a portion of a probe of the present disclosure that binds to, either directly or indirectly, a target analyte located in a sample. A target binding domain can comprise nucleic acid, protein, at least one antibody, an aptamer, or any combination thereof. A target binding domain can comprise DNA, RNA or any combination thereof. A target binding domain can comprise any number of modified nucleotides and/or nucleic acid analogues.

In the aspect that the target analyte to be spatially detected is a target protein, a target binding domain can be a protein-target binding domain. A protein-target binding domain can comprise an antibody or antibody fragment that binds to the target protein.

In the aspect that the target analyte to be spatially detected is a target nucleic acid, a target binding domain can be a target nucleic acid-binding region. A target nucleic acid-binding region can comprise a nucleic acid that is complementary to the target nucleic acid to be spatially detected. A target nucleic acid-binding region can comprise a nucleic acid that hybridizes to the target nucleic acid to be detected.

As used herein, the term "hybridize" is used in its broadest sense to mean the formation of a stable nucleic acid duplex. In one aspect, "stable duplex" means that a duplex structure is not destroyed by a stringent wash under conditions such as, for example, a temperature of either about 5° C. below or about 5° C. above the Tm of a strand of the duplex and low monovalent salt concentration, e.g., less than 0.2 M, or less than 0.1 M or salt concentrations known to those of skill in the art. A duplex can be "perfectly matched", such that the polynucleotide and/or oligonucleotide strands making up the duplex form a double stranded structure with one another such that every nucleotide in each strand undergoes Watson-Crick base pairing with a nucleotide in the other strand. The term "duplex" comprises, but is not limited to, the pairing of nucleoside analogs, such as deoxyinosine, nucleosides with 2-aminopurine bases, PNAs, and the like, that can be employed. A duplex can comprise at least one mismatch, wherein the term "mismatch" means that a pair of nucleotides in the duplex fail to undergo Watson-Crick bonding.

As used herein, the term "hybridization conditions," will typically include salt concentrations of less than about 1 M, more usually less than about 500 mM and even more usually less than about 200 mM. Hybridization temperatures can be as low as 5° C., but are typically greater than 22° C., more typically greater than about 30° C., and often in excess of about 37° C. Hybridizations are usually performed under stringent conditions, e.g., conditions under which a probe will specifically hybridize to its target analyte. Stringent conditions are sequence-dependent and are different in different circumstances. Longer fragments can require higher hybridization temperatures for specific hybridization. As other factors can affect the stringency of hybridization, including base composition and length of the complementary strands, presence of organic solvents and extent of base mismatching, the combination of parameters is more important than the absolute measure of any one alone. Certain hybridization conditions will promote the formation of a duplex between the entire length of a target binding domain and the target analyte. Other hybridization conditions will promote the formation of a duplex only along certain portions of the target binding domain.

In some aspects of the methods and compositions of the present disclosure, a probe can comprise a target binding domain directly, or indirectly linked to an identifier oligonucleotide. In the context of a probe, an identifier oligonucleotide is a polynucleotide that comprises a nucleic acid sequence that identifies the target analyte bound to the target binding domain of that probe. That is to say, the identifier oligonucleotide comprises a specific nucleic acid sequence that is a priori assigned to the specific target analyte bound to the target binding to which the identifier oligonucleotide is attached. In a non-limiting example, a probe designated as "probe X" designed to spatially detect "target analyte X" comprises a target binding domain designated "target binding domain X" linked to an identifier oligonucleotide designated "identifier oligonucleotide X". Target binding domain X binds to target analyte X and identifier oligonucleotide X comprises a nucleic acid sequence, designated as "nucleic acid sequence X", which corresponds to target analyte X Thus, if a skilled artisan practicing the methods of the present disclosure were to collect identifier oligonucleotides released from a region of interest in sample and obtain nucleic acid sequence X after sequencing, the skilled artisan would understand that to indicate that target analyte X was present in that region of interest. The amount, or number of sequencing reads, of nucleic acid sequence X can be used to determine the quantify, in absolute or relative terms, the amount of target analyte X within the region of interest.

As used herein, the term "amplification primer binding site" is used in its broadest sense to refer to a nucleic acid sequence that is complementary to, or at least partially complementary to at least one amplification primer, wherein the amplification primer is a short single-stranded or partially single-stranded oligonucleotide that is sufficient to prime DNA and/or RNA synthesis, for example, by PCR.

In some aspects of the methods and compositions of the present disclosure, a target binding domain can be linked to an identifier oligonucleotide by a cleavable linker. Suitable cleavable linkers include, but are not limited to, chemically cleavable linkers (e.g. a linker that is cleaved when exposed to a particular chemical, combination of chemicals or reaction conditions), a photo-cleavable linker (e.g. a linker that is cleaved when exposed to light of a sufficient wavelength or light comprising a sufficient range of wavelengths), or an enzymatically cleavable linker (e.g. a linker that is cleaved by a specific enzyme or class of enzymes). Thus, as used herein the phrase "providing a force to a location of the sample sufficient to release an identifier oligonucleotide" is used in its broadest sense to describe changing the conditions within a certain region of interest in a sample such that, for any probe bound to a target analyte within that region of interest, the linker between the target binding domain of the probe and the identifier oligonucleotide of the probe is cleaved, thereby separating the identifier oligonucleotide from the target binding domain so that the identifier oligonucleotide can be subsequently collected from solution. For example, in aspects wherein a probe comprises a chemically cleavable linker between the target binding domain and the identifier oligonucleotide, providing a force to a location of the sample sufficient to release an identifier oligonucleotide can comprise exposing that location of the sample to the specific chemical, combination of chemicals or reaction conditions that catalyze the cleavage of the linker. In another non-limiting example, in aspects wherein a probe comprises a photo-cleavable linker between the target binding domain and the identifier oligonucleotide, providing a force to a location of the sample sufficient to release an identifier oligonucleotide can comprise exposing/exciting that location of the sample with light of a sufficient wavelength capable of cleaving the photo-cleavable linker. In another non-limiting example, in aspects wherein a probe comprises an enzymatically cleavable linker between the target binding domain and the identifier oligonucleotide, providing a force to a location of the sample sufficient to release an identifier oligonucleotide can comprise exposing that location of the sample to an amount of enzyme sufficient to catalyze the cleavage of the linker.

Providing a force to a location of the sample sufficient to release an identifier oligonucleotide can result in at least about 10%, or at least about 20%, or at least about 30%, or at least about 40%, or at least about 50%, or at least about 60%, or at least about 70%, or at least about 80%, or at least about 85%, or at least about 90%, or at least about 95%, or at least about 99% of probes bound to target analytes within that location of the sample to undergo cleavage of the linker connecting the target binding domain and the identifier oligonucleotide.

As would be appreciated by one skilled in the art, the term "unique molecular identifier" or "UMI" refer to short nucleic acid sequences that are used to quantify and reduce quantitative bias caused by nucleic acid amplification prior to sequencing reactions.

In some aspects of the methods and compositions of the present disclosure, an affinity moiety can comprise biotin, avidin, streptavidin, nucleic acid, or any combination thereof.

In some aspects of the methods and compositions of the present disclosure, a probe can comprise at least at least about 5, about 10, at least about 15, at least about 20, at least about 25, at least about 30, at least about 35 at least about 40, at least about 45, at least about 50, at least about 55, at least about 60, at least about 65, at least about 70, at least about 75, at least about 80, at least about 85, at least about 90, at least about 95, at least about 100, at least about 110, at least about 120, at least about 130, at least about 140, at least about 150, at least about 160, at least about 170, at least about 180, at least about 190 or at least about 200 nucleotides.

In some aspects of the methods and compositions of the present disclosure, a target binding domain can comprise at least at least about 5, about 10, at least about 15, at least about 20, at least about 25, at least about 30, at least about 35 at least about 40, at least about 45, at least about 50, at least about 55, at least about 60, at least about 65, at least about 70, at least about 75, at least about 80, at least about 85, at least about 90, at least about 95, at least about 100, at least about 110, at least about 120, at least about 130, at least about 140, at least about 150, at least about 160, at least about 170, at least about 180, at least about 190 or at least about 200 nucleotides.

In some aspects of the methods and compositions of the present disclosure, an identifier oligonucleotide can comprise at least about 5, at least about 10, at least about 15, at least about 20, at least about 25, at least about 30, at least about 35 at least about 40, at least about 45, at least about 50, at least about 55, at least about 60, at least about 65, at least about 70, at least about 75, at least about 80, at least about 85, at least about 90, at least about 95, at least about 100, at least about 110, at least about 120, at least about 130, at least about 140, at least about 150, at least about 160, at least about 170, at least about 180, at least about 190 or at least about 200 nucleotides.

In some aspects of the methods and compositions of the present disclosure, an amplification primer can comprise at least about 5, at least about 10, at least about 15, at least about 20, at least about 25, at least about 30, at least about 35 at least about 40, at least about 45, at least about 50, at least about 55, at least about 60, at least about 65, at least about 70, at least about 75, at least about 80, at least about 85, at least about 90, at least about 95, at least about 100, at least about 110, at least about 120, at least about 130, at least about 140, at least about 150, at least about 160, at least about 170, at least about 180, at least about 190 or at least about 200 nucleotides.

In some aspects of the methods and compositions of the present disclosure, a nucleic acid probe can comprise at least about 5, at least about 10, at least about 15, at least about 20, at least about 25, at least about 30, at least about 35 at least about 40, at least about 45, at least about 50, at least about 55, at least about 60, at least about 65, at least about 70, at least about 75, at least about 80, at least about 85, at least about 90, at least about 95, at least about 100, at least about 110, at least about 120, at least about 130, at least about 140, at least about 150, at least about 160, at least about 170, at least about 180, at least about 190 or at least about 200 nucleotides.

In some aspects of the methods and compositions of the present disclosure, a nucleic acid complementary to a portion of a identifier oligonucleotide can comprise at least about 5, at least about 10, at least about 15, at least about 20, at least about 25, at least about 30, at least about 35 at least about 40, at least about 45, at least about 50, at least about 55, at least about 60, at least about 65, at least about 70, at least about 75, at least about 80, at least about 85, at least about 90, at least about 95 or at least about 100 nucleotides.

In some aspects of the methods and compositions of the present disclosure, a nucleic acid sequence comprising a molecular identifier can comprise at least about 5, or at least about 10 nucleotides, or at least about 15, or at least about 20, or at least about 25, or at least about 30, or at least about 35, or at least about 40, or at least about 45, or at least about 50 nucleotides.

In some aspects of the methods and compositions of the present disclosure, an amplification primer binding site can comprise at least about 5, at least about 10, at least about 15, at least about 20, at least about 25, at least about 30, at least about 35, at least about 40, at least about 45, at least about 50, at least about 55, at least about 60, at least about 65 or at least about 70 nucleotides.

In some aspects of the methods and compositions of the present disclosure, a flow cell adapter sequence suitable for sequencing can comprise at least about 5, at least about 10, at least about 15, at least about 20, at least about 25, at least about 30, at least about 35 at least about 40, at least about 45, at least about 50, at least about 55, at least about 60, at least about 65, at least about 70, at least about 75, at least about 80, at least about 85, at least about 90, at least about 95 or at least about 100 nucleotides.

In some aspects of the methods and compositions of the present disclosure, a flow cell binding site can comprise at least about 5, at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 90, at least about 95 or at least about 100 nucleotides.

In some aspects of the methods and compositions of the present disclosure, a nucleic acid sequence which identifies the specific location of the tissue sample from which an identifier oligonucleotide was released can comprise at least about 5, or at least about 10 nucleotides, or at least about 15, or at least about 20, or at least about 25, or at least about 30, or at least about 35, or at least about 40, or at least about 45, or at least about 50 nucleotides.

In some aspects of the methods and compositions of the present disclosure, a unique nucleic acid sequence which identifies the target analyte bound to a target binding domain can comprise at least about 5, at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 90, at least about 95 or at least about 100 nucleotides.

In some aspects of the methods and compositions of the present disclosure, a probe, a target binding domain, an identifier oligonucleotide, an amplification primer, a nucleic acid probe, a nucleic acid complementary to a portion of a identifier oligonucleotide, a nucleic acid sequence comprising a molecular identifier, an amplification primer binding site, a flow cell adapter sequence, a flow cell binding site, a nucleic acid sequence which identifies the specific location of the tissue sample from which an identifier oligonucleotide was released, a unique nucleic acid sequence which identifies the target analyte bound to a target binding domain or any combination thereof can comprise at least one natural base, can comprise no natural bases, can comprise at least one modified nucleotide or nucleic acid analog, can comprise no modified nucleotides or nucleic acid analogs, can comprise at least one universal base, can comprise no universal bases, can comprise at least one degenerate base or can comprise no degenerate bases.

In some aspects of the methods and compositions of the present disclosure, a probe, a target binding domain, an identifier oligonucleotide, an amplification primer, a nucleic acid probe, a nucleic acid complementary to a portion of a identifier oligonucleotide, a nucleic acid sequence comprising a molecular identifier, an amplification primer binding site, a flow cell adapter sequence, a flow cell binding site, a nucleic acid sequence which identifies the specific location of the tissue sample from which an identifier oligonucleotide was released, a unique nucleic acid sequence which identifies the target analyte bound to a target binding domain or any combination thereof can comprise any combination natural bases (e.g. 0, 1, 2, 3, 4, 5, 6, 7, 8, 9, 10, or more natural bases), modified nucleotides or nucleic acid analogs (e.g. 0, 1, 2, 3, 4, 5, 6, 7, 8, 9, 10, or more modified or analog nucleotides), universal bases (e.g. 0, 1, 2, 3, 4, 5, 6, 7, 8, 9, 10, or more universal bases), or degenerate bases (e.g. 0, 1, 2, 3, 4, 5, 6, 7, 8, 9, 10, or more degenerative bases). When present in a combination, the natural bases, modified nucleotides or nucleic acid analogs, universal bases and degenerate bases can be arranged in any order.

The terms "modified nucleotides" or "nucleic acid analogues" include, but are not limited to, locked nucleic acids (LNA), bridged nucleic acids (BNA), propyne-modified nucleic acids, zip nucleic acids (ZNA®), isoguanine and isocytosine. Preferably, the modified nucleotides or nucleic acid analogues are locked nucleic acids (LNAs).

The term "locked nucleic acids (LNA)" as used herein includes, but is not limited to, a modified RNA nucleotide in which the ribose moiety comprises a methylene bridge connecting the 2' oxygen and the 4' carbon. This methylene bridge locks the ribose in the 3'-endo confirmation, also known as the north confirmation, that is found in A-form RNA duplexes. The term inaccessible RNA can be used interchangeably with LNA. The term "bridged nucleic acids (BNA)" as used herein includes, but is not limited to, modified RNA molecules that comprise a five-membered or six-membered bridged structure with a fixed 3'-endo confirmation, also known as the north confirmation. The bridged structure connects the 2' oxygen of the ribose to the 4' carbon of the ribose. Various different bridge structures are possible containing carbon, nitrogen, and hydrogen atoms. The term "propyne-modified nucleic acids" as used herein includes, but is not limited to, pyrimidines, namely cytosine and thymine/uracil, that comprise a propyne modification at the C5 position of the nucleic acid base. The term "zip nucleic acids) (ZNA®)" as used herein includes, but is not limited to, oligonucleotides that are conjugated with cationic spermine moieties.

The term "universal base" as used herein includes, but is not limited to, a nucleotide base does not follow Watson-Crick base pair rules but rather can bind to any of the four canonical bases (A, T/U, C, G) located on the target nucleic acid. The term "degenerate base" as used herein includes, but is not limited to, a nucleotide base that does not follow Watson-Crick base pair rules but rather can bind to at least two of the four canonical bases A, T/U, C, G), but not all four. A degenerate base can also be termed a Wobble base; these terms are used interchangeably herein.

As used in this Specification and the appended claims, the singular forms "a," "an" and "the" include plural referents unless the context clearly dictates otherwise.

Unless specifically stated or obvious from context, as used herein, the term "or" is understood to be inclusive and covers both "or" and "and".

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Unless defined otherwise, all technical and scientific terms used herein have the same meaning as commonly understood by one of ordinary skill in the art to which the invention pertains. Although other probes, compositions, methods, and kits similar, or equivalent, to those described herein can be used in the practice of the present disclosure, the preferred materials and methods are described herein. It is to be understood that the terminology used herein is for the purpose of describing particular aspects only, and is not intended to be limiting.

EXAMPLES

Example 1—Two-Ended Adapter Ligation Method for 96 Multiplexed Samples

In this example, a two-ended adapter ligation method of the present disclosure was used to sequence identifier oligonucleotides collected from 96 multiplexed samples. The nucleic acid adapters used in this experiment were partially double-stranded. The nucleic acid adapters comprised a first strand and a second strand. The first strand comprised a 5' phosphate moiety for ligation. The first strand also comprised a constant nucleic acid sequence to minimize ligation bias (GCGTAGTG), a nucleic acid sequence comprising a unique molecular identifier, a unique nucleic acid sequence which identifies the specific location of the sample from which the identifier oligonucleotide was released and a first amplification primer binding site (SEQ ID NO: 2). The second strand comprised a single overhanging thymine nucleotide at the 3' end, a sequence complementary to the constant nucleic acid sequence to minimize ligation bias present in the first strand, a sequence complementary to the unique nucleic acid sequence which identifies the specific location of the sample from which the identifier oligonucleotide was released present in the first strand and a second amplification primer binding site (SEQ ID NO: 1).

To form the partially double stranded nucleic acid adapters, first strand oligonucleotides and second strand oligonucleotides were combined in equimolar proportion for a final total oligonucleotide concentration of 28 µM in buffer comprising 50 mM NaCl. The oligonucleotide mixture was heated at 95° C. for 2 minutes and cooled at ambient temperature for 30 minutes, thereby annealing the first stand and second strand oligonucleotides together to form the partially double-stranded nucleic acid adapters. Annealed nucleic acid adaptors were diluted to final concentration ranging between 0.02 µM to 0.002 µM in a solution of 10 mM Tris pH 8 and 0.05% Tween20.

Collected identifier oligonucleotides were end repaired and A-tailed using NEBNext Ultra II DNA Library Prep Kit for Illumina (New England Biolabs) with a modified protocol. End repair/A-tail master mix was prepared by combining the following: 627.8 µL of PCR-grade H2O, 143.9 µL of NEBNext Ultra II End Prep Reaction Buffer, and 61.7 µL of NEBNext Ultra II End Prep Enzyme Mix. 8.3 µL of end repair/A-tail master mix was added to 4 µL of each sample of identifier oligonucleotides. The reaction was incubated for 30 minutes at 20° C. with a heated lid of >75° C., followed by a second incubation for 30 minutes at 65° C. The repaired/A-tailed identifier oligonucleotide mixtures were then stored at 4° C.

Following end repair and A-tailing, the nucleic acid adaptors were ligated to the repaired/A-tailed identifier oligonucleotides by adding 6.4 µL of NEBNext Ultra II Ligation Master Mix, 0.2 µL of NEBNext Ligation Enhancer, and 1 µL of the nucleic acid adapter dilution to each repaired/A-tailed identifier oligonucleotide mixture. These reactions were incubated for 15 minutes at 20° C. with the heated lid off and subsequently quenched with 1 µL 0.5M EDTA. All of the reactions were then pooled into a single 15 mL conical tube to form a pooled adapter-ligated sample.

The pooled adaptor-ligated sample was purified using diluted Agencourt AMPure XP magnetic beads (Beckman Coulter Genomics Inc.), which were prepared by combining 350 of AMPure XP beads and 3.15 mL of AMPure XP buffer (2.5M NaCl, 20% PEG8000). AMPure XP bead cleanup was performed with 3.5 mL of diluted AMPure XP beads and eluted in 200 of a buffer comprising 10 mM Tris pH 8 and 0.05% Tween20. AMPure XP bead cleanup was then repeated with 400 µL of AMPure XP beads and eluted in 20 µL of a buffer comprising 10 mM Tris pH 8 and 0.05% Tween20 to obtain purified adapter-ligated samples.

Following AMPure XP cleanup, PCR reactions with purified adaptor-ligated sample were prepared to amplify the adapter-ligated identifier oligonucleotides. To 6 µL of the purified adapter-ligated sample, 10 µL of NEBNext Ultra II Q5 Master Mix, 0.2 µL of 100 µM forward and reverse primers, and 3.6 µL of PCR-grade H2O was added. The forward primers comprised a flow cell adapter sequence suitable for sequencing, a unique molecular identifier and a nucleic acid sequence complementary to the first amplification primer binding site located on the first strand of the nucleic acid adapter. Table 1 provides the sequences of the forward primers used.

TABLE 1

Forward primers for two-ended adapter ligation

| Primer Sequence | SEQ ID NO |
|---|---|
| AATGATACGGCGACCACCGAGATCTACACG CTCAGATATAGCCTACACTCTTTAAGACGA CGTCGCTATGGCCTCTCC | 5 |
| AATGATACGGCGACCACCGAGATCTACACG CTCAGAATAGAGGCACACTCTTTAAGACGA CGTCGCTATGGCCTCTCC | 6 |
| AATGATACGGCGACCACCGAGATCTACACG CTCAGACCTATCCTACACTCTTTAAGACGA CGTCGCTATGGCCTCTCC | 7 |
| AATGATACGGCGACCACCGAGATCTACACG CTCAGAGGCTCTGAACACTCTTTAAGACGA CGTCGCTATGGCCTCTCC | 8 |
| AATGATACGGCGACCACCGAGATCTACACG CTCAGAAGGCGAAGACACTCTTTAAGACGA CGTCGCTATGGCCTCTCC | 9 |

TABLE 1-continued

Forward primers for two-ended adapter ligation

| Primer Sequence | SEQ ID NO |
|---|---|
| AATGATACGGCGACCACCGAGATCTACACG CTCAGATAATCTTAACACTCTTTAAGACGA CGTCGCTATGGCCTCTCC | 10 |
| AATGATACGGCGACCACCGAGATCTACACG CTCAGACAGGACGTACACTCTTTAAGACGA CGTCGCTATGGCCTCTCC | 11 |
| AATGATACGGCGACCACCGAGATCTACACG CTCAGAGTACTGACACACTCTTTAAGACGA CGTCGCTATGGCCTCTCC | 12 |

The reverse primers comprised a flow cell adapter sequence suitable for sequencing, a unique molecular identifier and a nucleic acid sequence complementary to the second amplification primer binding site located on the second strand of the nucleic acid adapter. Table 2 provides the sequences of the reverse primers used.

TABLE 2

Reverse primers for two-ended adapter ligation

| Primer Sequence | SEQ ID NO |
|---|---|
| CAAGCAGAAGACGGCATACGAGATCGAGTA ATGTGACTGGAGTTCAGACGTGTGCTCTTC CGATCT | 13 |
| CAAGCAGAAGACGGCATACGAGATTCTCCG GAGTGACTGGAGTTCAGACGTGTGCTCTTC CGATCT | 14 |
| CAAGCAGAAGACGGCATACGAGATAATGAG CGGTGACTGGAGTTCAGACGTGTGCTCTTC CGATCT | 15 |
| CAAGCAGAAGACGGCATACGAGATGGAATC TCGTGACTGGAGTTCAGACGTGTGCTCTTC CGATCT | 16 |
| CAAGCAGAAGACGGCATACGAGATTTCTGA ATGTGACTGGAGTTCAGACGTGTGCTCTTC CGATCT | 17 |
| CAAGCAGAAGACGGCATACGAGATACGAAT TCGTGACTGGAGTTCAGACGTGTGCTCTTC CGATCT | 18 |
| CAAGCAGAAGACGGCATACGAGATAGCTTC AGGTGACTGGAGTTCAGACGTGTGCTCTTC CGATCT | 19 |
| CAAGCAGAAGACGGCATACGAGATGCGCAT TAGTGACTGGAGTTCAGACGTGTGCTCTTC CGATCT | 20 |
| CAAGCAGAAGACGGCATACGAGATCATAGC CGGTGACTGGAGTTCAGACGTGTGCTCTTC CGATCT | 21 |
| CAAGCAGAAGACGGCATACGAGATTTCGCG GAGTGACTGGAGTTCAGACGTGTGCTCTTC CGATCT | 22 |
| CAAGCAGAAGACGGCATACGAGATGCGCGA GAGTGACTGGAGTTCAGACGTGTGCTCTTC CGATCT | 23 |

TABLE 2-continued

Reverse primers for two-ended adapter ligation

| Primer Sequence | SEQ ID NO |
|---|---|
| CAAGCAGAAGACGGCATACGAGATCTATCG CTGTGACTGGAGTTCAGACGTGTGCTCTTC CGATCT | 24 |

The optimal number of PCR cycles was determined empirically with triplicate PCR reactions. Alternately, the optimal number of PCR cycles could have been determined using real-time/qPCR. The PCR program used comprised the following steps:
(1) 30 seconds at 98° C.
(2) 10 seconds at 98° C.
(3) 1 minute at 65° C.
(4) Repeating steps (2) and (3) nine times
(5) 5 minutes at 65° C.

The amplified products were purified using 18 µL of AMPure XP beads and eluting with 20 µL of a buffer comprising 10 mM Tris pH 8 and 0.05% Tween20.

The amplified products were assessed using a High Sensitivity DNA chip on 2100 Bioanalyzer (Agilent Genomics) and KAPA Library Quantification Kit for Illumina Platforms (Kapa Biosystems). The amplified products were also diluted to 15 pM for sequencing on a MiSeq (Illumina) according to manufacturer's instructions (MiSeq Reagent Kit v3 2×75 bp) with a custom spike-in primer comprising the nucleotide sequence (SEQ ID NO: 25)
ACACTCTTTAAGACGACGTCGCTATGGCCTCTCC.

Example 2—One-Ended Adapter Ligation Method for 96 Multiplexed Samples

In this example, a one-ended adapter ligation method of the present disclosure was used to sequence identifier oligonucleotides collected from 96 multiplexed samples. The nucleic acid adapters used in this experiment were partially double-stranded. The nucleic acid adapters comprised a first strand and a second strand. The first strand comprised a 5' phosphate moiety for ligation. The first strand also comprised a constant nucleic acid sequence to minimize ligation bias (CACTACGC), a nucleic acid sequence comprising a unique molecular identifier, a unique nucleic acid sequence which identifies the specific location of the sample from which the identifier oligonucleotide was released and a first amplification primer binding site (SEQ ID NO: 1). The second strand comprised a single overhanging thymine nucleotide at the 3' end, a sequence complementary to the constant nucleic acid sequence to minimize ligation bias present in the first strand and a sequence complementary to the unique nucleic acid sequence which identifies the specific location of the sample from which the identifier oligonucleotide was released present in the first strand.

To form the partially double stranded nucleic acid adapters, first strand oligonucleotides and second strand oligonucleotides were combined in equimolar proportion for a final total oligonucleotide concentration of 28 µM in 50 mM NaCl. The oligonucleotide mixture was heated to 95° C. for 2 minutes and cooled at ambient temperature for 30 minutes, thereby annealing the first stand and second strand oligonucleotides together to form the partially double-stranded nucleic acid adapters. Annealed nucleic acid adaptors were diluted to a final concentration ranging between 0.02 μM to 0.002 μM in a solution of 10 mM Tris pH 8 and 0.05% Tween20.

Nucleic acid adapters were ligated to the collected identifier oligonucleotides by addition of 10 μL of 2× rapid ligation buffer (Enzymatics), 1 μL of T4 DNA Rapid Ligase (Enzymatics), and 1 μL of annealed nucleic acid adapter dilutions to each sample of collected identifier oligonucleotides. Samples were incubated for 15 minutes at 20° C. with the heated lid off and subsequently quenched with 1 μL 0.5M EDTA. All of the reactions were then pooled into a single 15 mL conical tube to form a pooled adapter-ligated sample.

The pooled adaptor-ligated sample was purified using diluted Agencourt AMPure XP magnetic beads (Beckman Coulter Genomics Inc.), which were prepared by combining 350 of AMPure XP beads and 3.15 mL of AMPure XP buffer (2.5M NaCl, 20% PEG8000). AMPure XP bead cleanup was performed with 3.5 mL of diluted AMPure XP beads and eluted in 200 of a buffer comprising 10 mM Tris pH 8 and 0.05% Tween20. AMPure XP bead cleanup was then repeated with 400 μL of AMPure XP beads and eluted in 20 μL of a buffer comprising 10 mM Tris pH 8 and 0.05% Tween20 to obtain purified adapter-ligated samples.

Following AMPure XP cleanup, PCR reactions with purified adaptor-ligated sample were prepared to amplify the adapter-ligated identifier oligonucleotides. To 6 μL of the purified adapter-ligated sample, 10 μL of NEBNext Ultra II Q5 Master Mix, 0.2 μL of 100 μM forward and reverse primers, and 3.6 μL of PCR-grade H₂O was added. The forward primers comprised a flow cell adapter sequence suitable for sequencing, a unique molecular identifier and a nucleic acid sequence complementary to the first amplification primer binding site located on the first strand of the nucleic acid adapter. Table 3 provides the sequences of the forward primers used.

TABLE 3

Forward primers for two-ended adapter ligation

| Primer Sequence | SEQ ID NO |
|---|---|
| AATGATACGGCGACCACCGAGATCTACACG CTCAGATATAGCCTACACTCTTTAAGACGA CGTCGCTATGGCCTCTCC | 5 |
| AATGATACGGCGACCACCGAGATCTACACG CTCAGAATAGAGGCACACTCTTTAAGACGA CGTCGCTATGGCCTCTCC | 6 |
| AATGATACGGCGACCACCGAGATCTACACG CTCAGACCTATCCTACACTCTTTAAGACGA CGTCGCTATGGCCTCTCC | 7 |
| AATGATACGGCGACCACCGAGATCTACACG CTCAGAGGCTCTGAACACTCTTTAAGACGA CGTCGCTATGGCCTCTCC | 8 |
| AATGATACGGCGACCACCGAGATCTACACG CTCAGAAGGCGAAGACACTCTTTAAGACGA CGTCGCTATGGCCTCTCC | 9 |
| AATGATACGGCGACCACCGAGATCTACACG CTCAGATAATCTTAACACTCTTTAAGACGA CGTCGCTATGGCCTCTCC | 10 |

TABLE 3-continued

Forward primers for two-ended adapter ligation

| Primer Sequence | SEQ ID NO |
|---|---|
| AATGATACGGCGACCACCGAGATCTACACG CTCAGACAGGACGTACACTCTTTAAGACGA CGTCGCTATGGCCTCTCC | 11 |
| AATGATACGGCGACCACCGAGATCTACACG CTCAGAGTACTGACACACTCTTTAAGACGA CGTCGCTATGGCCTCTCC | 12 |

The reverse primers comprised a flow cell adapter sequence suitable for sequencing, a unique molecular identifier and a nucleic acid sequence complementary to the second amplification primer binding site located on the second strand of the nucleic acid adapter. Table 4 provides the sequences of the reverse primers used.

TABLE 4

Reverse primers for two-ended adapter ligation

| Primer Sequence | SEQ ID NO |
|---|---|
| CAAGCAGAAGACGGCATACGAGATCGAGTA ATGTGACTGGAGTTCAGACGTGTGCTCTTC CGATCT | 13 |
| CAAGCAGAAGACGGCATACGAGATTCTCCG GAGTGACTGGAGTTCAGACGTGTGCTCTTC CGATCT | 14 |
| CAAGCAGAAGACGGCATACGAGATAATGAG CGGTGACTGGAGTTCAGACGTGTGCTCTTC CGATCT | 15 |
| CAAGCAGAAGACGGCATACGAGATGGAATC TCGTGACTGGAGTTCAGACGTGT GCTCTT CCGATCT | 16 |
| CAAGCAGAAGACGGCATACGAGATTTCTGA ATGTGACTGGAGTTCAGACGTGTGCTCTTC CGATCT | 17 |
| CAAGCAGAAGACGGCATACGAGATACGAAT TCGTGACTGGAGTTCAGACGTGTGCTCTTC CGATCT | 18 |
| CAAGCAGAAGACGGCATACGAGATAGCTTC AGGTGACTGGAGTTCAGACGTGTGCTCTTC CGATCT | 19 |
| CAAGCAGAAGACGGCATACGAGATGCGCAT TAGTGACTGGAGTTCAGACGTGTGCTCTTC CGATCT | 20 |
| CAAGCAGAAGACGGCATACGAGATCATAGC CGGTGACTGGAGTTCAGACGTGTGCTCTTC CGATCT | 21 |
| CAAGCAGAAGACGGCATACGAGATTTCGCG GAGTGACTGGAGTTCAGACGTGTGCTCTTC CGATCT | 22 |
| CAAGCAGAAGACGGCATACGAGATGCGCGA GAGTGACTGGAGTTCAGACGTGTGCTCTTC CGATCT | 23 |
| CAAGCAGAAGACGGCATACGAGATCTATCG CTGTGACTGGAGTTCAGACGTGTGCTCTTC CGATCT | 24 |

The optimal number of PCR cycles was determined empirically with triplicate PCR reactions. Alternately, the optimal number of PCR cycles could have been determined using real-time/qPCR. The PCR program used comprised the following steps:

(1) 30 seconds at 98° C.
(2) 10 seconds at 98° C.
(3) 1 minute at 65° C.
(4) Repeating steps (2) and (3) nine times
(5) 5 minutes at 65° C.

The amplified products were purified using 18 μL of AMPure XP beads and eluting with 20 μL of a buffer comprising 10 mM Tris pH 8 and 0.05% Tween20.

The amplified products were assessed using a High Sensitivity DNA chip on 2100 Bioanalyzer (Agilent Genomics) and KAPA Library Quantification Kit for Illumina Platforms (Kapa Biosystems). The amplified products were also diluted to 15 pM for sequencing on a MiSeq (Illumina) according to manufacturer's instructions (MiSeq Reagent Kit v3 2×75 bp) with a custom spike-in primer comprising the nucleotide sequence

ACACTCTTTAAGACGACGTCGCTATGGCCTCTCC. (SEQ ID NO: 25)

Example 3—Templated-Primer Extension Method for 96 Multiplexed Samples

In this example, a templated-primer extension method of the present disclosure was used to sequence identifier oligonucleotides collected from 96 multiplexed samples. The single stranded nucleic acid templates used in this example comprised a 3' biotin moiety, a region complementary to the unique nucleic acid sequences present in the collected identifier oligonucleotides, a nucleic acid sequence comprising a unique molecular identifier and a second amplification primer binding sequence (GTGACTGGAGTTCAGACGTGTGCTCTTCCGATCT, SEQ ID NO: 26). Table 5 provides the sequences of the single-stranded nucleic acid templates used in this example.

TABLE 5

| Single stranded nucleic acid templates for templated-primer extension method | |
|---|---|
| Single-stranded nucleic acid templates | SEQ ID NO |
| GTGACTGGAGTTCAGACGTGTGCTCTTCCG ATCTNNNNNNNNNNNNNNNNNTTGAAGCACAC CGTTTTCTTTCTTCTTTCACGG | 27 |
| GTGACTGGAGTTCAGACGTGTGCTCTTCCG ATCTNNNNNNNNNNNNNNNNNACCCACAGGTT ATACGGGATTATCCGGTTATCCA | 28 |
| GTGACTGGAGTTCAGACGTGTGCTCTTCCG ATCTNNNNNNNNNNNNNNNNNCGACACCGAGT TCGACCGTTATGTTGGTAGGATC | 29 |
| GTGACTGGAGTTCAGACGTGTGCTCTTCCG ATCTNNNNNNNNNNNNNNNNNCGGTGTGTAAG CGTAACGATGTTGGTGTCGCTCT | 30 |
| GTGACTGGAGTTCAGACGTGTGCTCTTCCG ATCTNNNNNNNNNNNNNNNNNCAGACACTGCG ACAACTCACGATCATGACACAGA | 31 |

TABLE 5-continued

| Single stranded nucleic acid templates for templated-primer extension method | |
|---|---|
| Single-stranded nucleic acid templates | SEQ ID NO |
| GTGACTGGAGTTCAGACGTGTGCTCTTCCG ATCTNNNNNNNNNNNNNNNNNATATTCTGTAC TCAGTGCCTATCCACCTAATAGG | 32 |
| GTGACTGGAGTTCAGACGTGTGCTCTTCCG ATCTNNNNNNNNNNNNNNNNNTTCAGTTATAA TGTGTCCAGCAGAAGCAGGAATT | 33 |
| GTGACTGGAGTTCAGACGTGTGCTCTTCCG ATCTNNNNNNNNNNNNNNNNNGTCCnTGTTGG GCGGACCGTAATGAGGAATTTG | 34 |
| GTGACTGGAGTTCAGACGTGTGCTCTTCCG ATCTNNNNNNNNNNNNNNNNNGATGAGACTTC TACATGTCCGATGTTTTTGTGCT | 35 |
| GTGACTGGAGTTCAGACGTGTGCTCTTCCG ATCTNNNNNNNNNNNNNNNNNACTCACACATA GTACTGACACGTAAGATAGGATG | 36 |
| GTGACTGGAGTTCAGACGTGTGCTCTTCCG ATCTNNNNNNNNNNNNNNNNNTTACCCTATCT CGTCTATGTACGTCAGGCTGAAT | 37 |
| GTGACTGGAGTTCAGACGTGTGCTCTTCCG ATCTNNNNNNNNNNNNNNNNNATCAACGTAGG GTAAGGTCATATTTTTACCTTAC | 38 |
| GTGACTGGAGTTCAGACGTGTGCTCTTCCG ATCTNNNNNNNNNNNNNNNNNTTCCCTCTTTC TCCGCTTATGGATGAAAGGACAG | 39 |
| GTGACTGGAGTTCAGACGTGTGCTCTTCCG ATCTNNNNNNNNNNNNNNNNNCCTGCACAGTG AGTTTCTTTCACTCTAACTCTCT | 40 |
| GTGACTGGAGTTCAGACGTGTGCTCTTCCG ATCTNNNNNNNNNNNNNNNNNTGTCGCTCTAG TGTGACTTTTCCACCTCGCATCT | 41 |
| GTGACTGGAGTTCAGACGTGTGCTCTTCCG ATCTNNNNNNNNNNNNNNNNNATATCTTTCTC GGGTAAAGATTAGGCGTCCGATA | 42 |
| GTGACTGGAGTTCAGACGTGTGCTCTTCCG ATCTNNNNNNNNNNNNNNNNNCGATTAGCCGT AGACGCAACTCATTGCCGAAGAT | 43 |
| GTGACTGGAGTTCAGACGTGTGCTCTTCCG ATCTNNNNNNNNNNNNNNNNNTGTGAGCATTT CAGTACGAGTGATGCAGATAAAC | 44 |
| GTGACTGGAGTTCAGACGTGTGCTCTTCCG ATCTNNNNNNNNNNNNNNNNNTATAGTTACCA AGTACTATGGGTTGGTGGAAGCC | 45 |
| GTGACTGGAGTTCAGACGTGTGCTCTTCCG ATCTNNNNNNNNNNNNNNNNNCCAATTATACT GTCTGTTATGTTCTCGGATAAGC | 46 |
| GTGACTGGAGTTCAGACGTGTGCTCTTCCG ATCTNNNNNNNNNNNNNNNNNTCAGGTGCTTG TAGGCTCATGATAGGGTAATGC | 47 |
| GTGACTGGAGTTCAGACGTGTGCTCTTCCG ATCTNNNNNNNNNNNNNNNNNCTCTGCTGTAA TCTCAGCTCCACTTGTTTCTAAG | 48 |
| GTGACTGGAGTTCAGACGTGTGCTCTTCCG ATCTNNNNNNNNNNNNNNNNNGTGCATATTGC AGCTGAGCCAGCTCAATTTGAAG | 49 |

TABLE 5-continued

Single stranded nucleic acid templates for templated-primer extension method

| Single-stranded nucleic acid templates | SEQ ID NO |
|---|---|
| GTGACTGGAGTTCAGACGTGTGCTCTTCCG ATCTNNNNNNNNNNNNNNNNNCCGTTGATTTA CGCAACAGCGGCTTATATAGCTC | 50 |
| GTGACTGGAGTTCAGACGTGTGCTCTTCCG ATCTNNNNNNNNNNNNNNNNNCATCATCGACA GTTCGCAGCCCTATAACATGATA | 51 |
| GTGACTGGAGTTCAGACGTGTGCTCTTCCG ATCTNNNNNNNNNNNNNNNNNATCGCAGGATG GTACAGCATCATACATGATGAGC | 52 |
| GTGACTGGAGTTCAGACGTGTGCTCTTCCG ATCTNNNNNNNNNNNNNNNNNCTGATAAGTCG TAGGAATGTCGCTTAATACGGAT | 53 |
| GTGACTGGAGTTCAGACGTGTGCTCTTCCG ATCTNNNNNNNNNNNNNNNNNATGGCGGTTTC GGGTCCTGCACTATTCCTAATAA | 54 |
| GTGACTGGAGTTCAGACGTGTGCTCTTCCG ATCTNNNNNNNNNNNNNNNNNCCAGTACGGGT ACTAATAAGTGTCATATCTATTG | 55 |
| GTGACTGGAGTTCAGACGTGTGCTCTTCCG ATCTNNNNNNNNNNNNNNNNNTGTTGGAGAGG TTAGAGGTGAGGAGGCGAAGATA | 56 |

Single stranded nucleic acid templates were ordered from Integrated DNA Technologies, Inc. and quantified using a NanoDrop 1000 spectrophotometer (Thermo Fisher Scientific). Individual single stranded nucleic acid templates were normalized to a standard concentration and then pooled to be equimolar. The pool of single stranded nucleic acid templates was diluted to 0.83 nM in a buffer comprising 10 mM Tris pH 8 and 0.05% Tween20.

The collected identifier oligonucleotides were hybridized to the single stranded nucleic acid templates and extended by addition of 10 µL of NEBNext Ultra II Q5 Master Mix (New England Biolabs), 4 µL of the diluted single stranded nucleic acid template pool and 4 µL of $H_2O$ to 2 µL of each sample of identifier oligonucleotides. The following PCR program was used to extend the identifier oligonucleotides:

(1) 30 seconds at 98° C., 10×
(2) 1 minutes at 98° C.,
(3) 1 minutes at 68° C.
(4) 1 minutes at 72° C.
(5) Repeating steps (2)-(4) ten times
(6) 2 minutes at 72° C.

The extension products were stored at 4° C. Magnetic streptavidin beads (MyOne Streptavidin C1 beads, Thermo Fisher Scientific) were washed in 1× Binding and Washing Buffer (5 mM Tris-HCl, 0.5 mM EDTA, 1M NaCl), and 5 µL of streptavidin beads were added to each extension product sample. The extension product samples were incubated with the beads on an orbital mixer for a minimum of 15 minutes. Following incubation, the samples were heated to 95° C. for 3 minutes and transferred to a magnetic plate. Supernatant was extracted immediately after sufficient bead pelleting to yield the purified extension product samples.

The purified extension product samples were amplified by adding to 7.5 µL of each purified extension product sample, 12.5 µL of NEBNext Ultra II Q5 Master Mix, 0.25 µL of 100 forward primer, 1 µL of 25 µM reverse primer and 3.8 µL of PCR-grade $H_2O$. The forward primer comprised a flow cell adapter sequence suitable for sequencing, a unique molecular identifier and a nucleic acid sequence complementary to the first amplification primer binding site located on the identifier oligonucleotide. Table 6 provides the sequences of the forward primers used in this example.

TABLE 6

Forward primers for templated-primer extension method

| Primer Sequence | SEQ ID NO |
|---|---|
| AATGATACGGCGACCACCGAGATCTACACG CTCAGATATAGCCTACACTCTTTAAGACGA CGTCGCTATGGCCTCTCC | 5 |
| AATGATACGGCGACCACCGAGATCTACACG CTCAGAATAGAGGCACACTCTTTAAGACGA CGTCGCTATGGCCTCTCC | 6 |
| AATGATACGGCGACCACCGAGATCTACACG CTCAGACCTATCCTACACTCTTTAAGACGA CGTCGCTATGGCCTCTCC | 7 |
| AATGATACGGCGACCACCGAGATCTACACG CTCAGAGGCTCTGAACACTCTTTAAGACGA CGTCGCTATGGCCTCTCC | 8 |
| AATGATACGGCGACCACCGAGATCTACACG CTCAGAAGGCGAAGACACTCTTTAAGACGA CGTCGCTATGGCCTCTCC | 9 |
| AATGATACGGCGACCACCGAGATCTACACG CTCAGATAATCTTAACACTCTTTAAGACGA CGTCGCTATGGCCTCTCC | 10 |
| AATGATACGGCGACCACCGAGATCTACACG CTCAGACAGGACGTACACTCTTTAAGACGA CGTCGCTATGGCCTCTCC | 11 |
| AATGATACGGCGACCACCGAGATCTACACG CTCAGAGTACTGACACACTCTTTAAGACGA CGTCGCTATGGCCTCTCC | 12 |

The reverse primers comprised a flow cell adapter sequence suitable for sequencing, a unique molecular identifier and a nucleic acid sequence complementary to the second amplification primer binding site located single-stranded nucleic acid template. Table 7 provides the sequences of the reverse primers used.

TABLE 7

Reverse primers for templated-primer extension method

| Primer Sequence | SEQ ID NO |
|---|---|
| CAAGCAGAAGACGGCATACGAGATGTCGGT AAGTGACTGGAGTTCAGACGTGTGCTCTTC CGATCT | 57 |
| CAAGCAGAAGACGGCATACGAGATAGGTCA CTGTGACTGGAGTTCAGACGTGTGCTCTTC CGATCT | 58 |
| CAAGCAGAAGACGGCATACGAGATGAATCC GAGTGACTGGAGTTCAGACGTGTGCTCTTC CGATCT | 59 |
| CAAGCAGAAGACGGCATACGAGATGTACCT TGGTGACTGGAGTTCAGACGTGTGCTCTTC CGATCT | 60 |

TABLE 7-continued

Reverse primers for templated-primer extension method

| Primer Sequence | SEQ ID NO |
|---|---|
| CAAGCAGAAGACGGCATACGAGATCATGAGGAGTGACTGGAGTTCAGACGTGTGCTCTTCCGATCT | 61 |
| CAAGCAGAAGACGGCATACGAGATTGACTGACGTGACTGGAGTTCAGACGTGTGCTCTTCCGATCT | 62 |
| CAAGCAGAAGACGGCATACGAGATCGTATTCGGTGACTGGAGTTCAGACGTGTGCTCTTCCGATCT | 63 |
| CAAGCAGAAGACGGCATACGAGATCTCCTAGAGTGACTGGAGTTCAGACGTGTGCTCTTCCGATCT | 64 |
| CAAGCAGAAGACGGCATACGAGATTAGTTGCGGTGACTGGAGTTCAGACGTGTGCTCTTCCGATCT | 65 |
| CAAGCAGAAGACGGCATACGAGATGAGATACGGTGACTGGAGTTCAGACGTGTGCTCTTCCGATCT | 66 |
| CAAGCAGAAGACGGCATACGAGATAGGTGTACGTGACTGGAGTTCAGACGTGTGCTCTTCCGATCT | 67 |
| CAAGCAGAAGACGGCATACGAGATTAATGCCGGTGACTGGAGTTCAGACGTGTGCTCTTCCGATCT | 68 |
| CAAGCAGAAGACGGCATACGAGATTCAGACGAGTGACTGGAGTTCAGACGTGTGCTCTTCCGATCT | 69 |
| CAAGCAGAAGACGGCATACGAGATGATAGGCTGTGACTGGAGTTCAGACGTGTGCTCTTCCGATCT | 70 |
| CAAGCAGAAGACGGCATACGAGATTGGTACAGGTGACTGGAGTTCAGACGTGTGCTCTTCCGATCT | 71 |
| CAAGCAGAAGACGGCATACGAGATCAAGGTCTGTGACTGGAGTTCAGACGTGTGCTCTTCCGATCT | 72 |
| CAAGCAGAAGACGGCATACGAGATGCTATCCTGTGACTGGAGTTCAGACGTGTGCTCTTCCGATCT | 73 |
| CAAGCAGAAGACGGCATACGAGATATGGAAGGGTGACTGGAGTTCAGACGTGTGCTCTTCCGATCT | 74 |
| CAAGCAGAAGACGGCATACGAGATTCAAGGACGTGACTGGAGTTCAGACGTGTGCTCTTCCGATCT | 75 |
| CAAGCAGAAGACGGCATACGAGATGTTACGCAGTGACTGGAGTTCAGACGTGTGCTCTTCCGATCT | 76 |
| CAAGCAGAAGACGGCATACGAGATAGTCTGTGGTGACTGGAGTTCAGACGTGTGCTCTTCCGATCT | 77 |
| CAAGCAGAAGACGGCATACGAGATGCACGTAAGTGACTGGAGTTCAGACGTGTGCTCTTCCGATCT | 78 |
| CAAGCAGAAGACGGCATACGAGATAACCTTGGGTGACTGGAGTTCAGACGTGTGCTCTTCCGATCT | 79 |
| CAAGCAGAAGACGGCATACGAGATATTGCGTGGTGACTGGAGTTCAGACGTGTGCTCTTCCGATCT | 80 |
| CAAGCAGAAGACGGCATACGAGATACCTGGAAGTGACTGGAGTTCAGACGTGTGCTCTTCCGATCT | 81 |
| CAAGCAGAAGACGGCATACGAGATGGAGATGAGTGACTGGAGTTCAGACGTGTGCTCTTCCGATCT | 82 |
| CAAGCAGAAGACGGCATACGAGATGTACTCTCGTGACTGGAGTTCAGACGTGTGCTCTTCCGATCT | 83 |
| CAAGCAGAAGACGGCATACGAGATGTAACGACGTGACTGGAGTTCAGACGTGTGCTCTTCCGATCT | 84 |
| CAAGCAGAAGACGGCATACGAGATATTCCTCCGTGACTGGAGTTCAGACGTGTGCTCTTCCGATCT | 85 |
| CAAGCAGAAGACGGCATACGAGATGTGTTCCTGTGACTGGAGTTCAGACGTGTGCTCTTCCGATCT | 86 |
| CAAGCAGAAGACGGCATACGAGATAAGCACTGGTGACTGGAGTTCAGACGTGTGCTCTTCCGATCT | 87 |
| CAAGCAGAAGACGGCATACGAGATCTAGCAAGGTGACTGGAGTTCAGACGTGTGCTCTTCCGATCT | 88 |
| CAAGCAGAAGACGGCATACGAGATTGCTTCCAGTGACTGGAGTTCAGACGTGTGCTCTTCCGATCT | 89 |
| CAAGCAGAAGACGGCATACGAGATGCTTAGCTGTGACTGGAGTTCAGACGTGTGctcttCCGATCT | 90 |
| CAAGCAGAAGACGGCATACGAGATAACCGTTCGTGACTGGAGTTCAGACGTGTGCTCTTCCGATCT | 91 |
| CAAGCAGAAGACGGCATACGAGATGACATTCCGTGACTGGAGTTCAGACGTGTGCTCTTCCGATCT | 92 |
| CAAGCAGAAGACGGCATACGAGATAGACCGTAGTGACTGGAGTTCAGACGTGTGCTCTTCCGATCT | 93 |
| CAAGCAGAAGACGGCATACGAGATGATACTGGGTGACTGGAGTTCAGACGTGTGCTCTTCCGATCT | 94 |
| CAAGCAGAAGACGGCATACGAGATTGCGTAGAGTGACTGGAGTTCAGACGTGTGCTCTTCCGATCT | 95 |
| CAAGCAGAAGACGGCATACGAGATTCGGTTACGTGACTGGAGTTCAGACGTGTGCTCTTCCGATCT | 96 |

TABLE 7-continued

Reverse primers for templated-primer extension method

| Primer Sequence | SEQ ID NO |
|---|---|
| CAAGCAGAAGACGGCATACGAGATATGACG TCGTGACTGGAGTTCAGACGTGTGCTCTTC CGATCT | 97 |
| CAAGCAGAAGACGGCATACGAGATGCTGTA AGGTGACTGGAGTTCAGACGTGTGCTCTTC CGATCT | 98 |
| CAAGCAGAAGACGGCATACGAGATGCAATG GAGTGACTGGAGTTCAGACGTGTGCTCTTC CGATCT | 99 |
| CAAGCAGAAGACGGCATACGAGATATCTCG CTGTGACTGGAGTTCAGACGTGTGCTCTTC CGATCT | 100 |
| CAAGCAGAAGACGGCATACGAGATGGCTAT TGGTGACTGGAGTTCAGACGTGTGCTCTTC CGATCT | 101 |
| CAAGCAGAAGACGGCATACGAGATGGTGTC TTGTGACTGGAGTTCAGACGTGTGCTCTTC CGATCT | 102 |
| CAAGCAGAAGACGGCATACGAGATTCAACT GGGTGACTGGAGTTCAGACGTGTGCTCTTC CGATCT | 103 |
| CAAGCAGAAGACGGCATACGAGATCTTCAC CAGTGACTGGAGTTCAGACGTGTGCTCTTC CGATCT | 104 |
| CAAGCAGAAGACGGCATACGAGATACGGTC TTGTGACTGGAGTTCAGACGTGTGCTCTTC CGATCT | 105 |
| CAAGCAGAAGACGGCATACGAGATTCTCGC AAGTGACTGGAGTTCAGACGTGTGCTCTTC CGATCT | 106 |
| CAAGCAGAAGACGGCATACGAGATGGAATT GCGTGACTGGAGTTCAGACGTGTGCTCTTC CGATCT | 107 |
| CAAGCAGAAGACGGCATACGAGATACGGAT TCGTGACTGGAGTTCAGACGTGTGCTCTTC CGATCT | 108 |
| CAAGCAGAAGACGGCATACGAGATTTAAGC GGGTGACTGGAGTTCAGACGTGTGCTCTTC CGATCT | 109 |
| CAAGCAGAAGACGGCATACGAGATTGCAGG TAGTGACTGGAGTTCAGACGTGTGCTCTTC CGATCT | 110 |
| CAAGCAGAAGACGGCATACGAGATCAATCG ACGTGACTGGAGTTCAGACGTGTGCTCTTC CGATCT | 111 |
| CAAGCAGAAGACGGCATACGAGATGTGCCA TAGTGACTGGAGTTCAGACGTGTGCTCTTC CGATCT | 112 |
| CAAGCAGAAGACGGCATACGAGATTGTTCG AGGTGACTGGAGTTCAGACGTGTGCTCTTC CGATCT | 113 |
| CAAGCAGAAGACGGCATACGAGATTGGAGT TGGTGACTGGAGTTCAGACGTGTGCTCTTC CGATCT | 114 |
| CAAGCAGAAGACGGCATACGAGATACGATG ACGTGACTGGAGTTCAGACGTGTGCTCTTC CGATCT | 115 |
| CAAGCAGAAGACGGCATACGAGATTGATGT CCGTGACTGGAGTTCAGACGTGTGCTCTTC CGATCT | 116 |
| CAAGCAGAAGACGGCATACGAGATTGAACC TGGTGACTGGAGTTCAGACGTGTGCTCTTC CGATCT | 117 |
| CAAGCAGAAGACGGCATACGAGATCTTCGT TCGTGACTGGAGTTCAGACGTGTGCTCTTC CGATCT | 118 |
| CAAGCAGAAGACGGCATACGAGATCTTCTG AGGTGACTGGAGTTCAGACGTGTGCTCTTC CGATCT | 119 |
| CAAGCAGAAGACGGCATACGAGATTGCTCA TGGTGACTGGAGTTCAGACGTGTGctcttC CGATCT | 120 |
| CAAGCAGAAGACGGCATACGAGATAGTTCG TCGTGACTGGAGTTCAGACGTGTGCTCTTC CGATCT | 121 |
| CAAGCAGAAGACGGCATACGAGATTAGCGT CTGTGACTGGAGTTCAGACGTGTGCTCTTC CGATCT | 122 |
| CAAGCAGAAGACGGCATACGAGATGGCGTT ATGTGACTGGAGTTCAGACGTGTGCTCTTC CGATCT | 123 |
| CAAGCAGAAGACGGCATACGAGATGGTGAT TCGTGACTGGAGTTCAGACGTGTGCTCTTC CGATCT | 124 |
| CAAGCAGAAGACGGCATACGAGATAACTTG CCGTGACTGGAGTTCAGACGTGTGCTCTTC CGATCT | 125 |
| CAAGCAGAAGACGGCATACGAGATGCAAGA TCGTGACTGGAGTTCAGACGTGTGCTCTTC CGATCT | 126 |
| CAAGCAGAAGACGGCATACGAGATTCGCAT TGGTGACTGGAGTTCAGACGTGTGCTCTTC CGATCT | 127 |
| CAAGCAGAAGACGGCATACGAGATTGTACA CCGTGACTGGAGTTCAGACGTGTGCTCTTC CGATCT | 128 |
| CAAGCAGAAGACGGCATACGAGATAGCTCC TAGTGAC'TGGAGTTCAGACGTGTGCTCTT CCGATCT | 129 |
| CAAGCAGAAGACGGCATACGAGATGCAATT CGGTGACTGGAGTTCAGACGTGTGCTCTTC CGATCT | 130 |
| CAAGCAGAAGACGGCATACGAGATCTTAGG ACGTGACTGGAGTTCAGACGTGTGCTCTTC CGATCT | 131 |
| CAAGCAGAAGACGGCATACGAGATGTCCTA AGGTGACTGGAGTTCAGACGTGTGCTCTTC CGATCT | 132 |

TABLE 7-continued

Reverse primers for templated-primer extension method

| Primer Sequence | SEQ ID NO |
|---|---|
| CAAGCAGAAGACGGCATACGAGATAACGTGGAGTGACTGGAGTTCAGACGTGTGCTCTTCCGATCT | 133 |
| CAAGCAGAAGACGGCATACGAGATCTGTGTTGGTGACTGGAGTTCAGACGTGTGCTCTTCCGATCT | 134 |
| CAAGCAGAAGACGGCATACGAGATGTTAAGGCGTGACTGGAGTTCAGACGTGTGCTCTTCCGATCT | 135 |
| CAAGCAGAAGACGGCATACGAGATCACCTTACGTGACTGGAGTTCAGACGTGTGCTCTTCCGATCT | 136 |
| CAAGCAGAAGACGGCATACGAGATTGGTAGCTGTGACTGGAGTTCAGACGTGTGCTCTTCCGATCT | 137 |
| CAAGCAGAAGACGGCATACGAGATCAGTGAAGGTGACTGGAGTTCAGACGTGTGCTCTTCCGATCT | 138 |
| CAAGCAGAAGACGGCATACGAGATGTTCAACCGTGACTGGAGTTCAGACGTGTGCTCTTCCGATCT | 139 |
| CAAGCAGAAGACGGCATACGAGATTGGCTATCGTGACTGGAGTTCAGACGTGTGCTCTTCCGATCT | 140 |
| CAAGCAGAAGACGGCATACGAGATCTGGAGTAGTGACTGGAGTTCAGACGTGTGCTCTTCCGATCT | 141 |
| CAAGCAGAAGACGGCATACGAGATTCTCTTCCGTGACTGGAGTTCAGACGTGTGCTCTTCCGATCT | 142 |
| CAAGCAGAAGACGGCATACGAGATTCTAACGCGTGACTGGAGTTCAGACGTGTGCTCTTCCGATCT | 143 |
| CAAGCAGAAGACGGCATACGAGATGGTCAGATGTGACTGGAGTTCAGACGTGTGCTCTTCCGATCT | 144 |
| CAAGCAGAAGACGGCATACGAGATCTCTGGTTGTGACTGGAGTTCAGACGTGTGCtctttCCGATCT | 145 |
| CAAGCAGAAGACGGCATACGAGATTGTGGTACGTGACTGGAGTTCAGACGTGTGCTCTTCCGATCT | 146 |
| CAAGCAGAAGACGGCATACGAGATCCTATACCGTGACTGGAGTTCAGACGTGTGCTCTTCCGATCT | 147 |
| CAAGCAGAAGACGGCATACGAGATTTCTCTCGGTGACTGGAGTTCAGACGTGTGCTCTTCCGATCT | 148 |
| CAAGCAGAAGACGGCATACGAGATGTATGCTGGTGACTGGAGTTCAGACGTGTGCTCTTCCGATCT | 149 |
| CAAGCAGAAGACGGCATACGAGATAAGTCGAGGTGACTGGAGTTCAGACGTGTGCTCTTCCGATCT | 150 |
| CAAGCAGAAGACGGCATACGAGATAACCGAAGGTGACTGGAGTTCAGACGTGTGCTCTTCCGATCT | 151 |
| CAAGCAGAAGACGGCATACGAGATTGTTGTGGGTGACTGGAGTTCAGACGTGTGCTCTTCCGATCT | 152 |

The PCR program used to amplify the purified extension products comprised the following steps:
(1) 30 seconds at 98° C.
(2) 10 seconds at 98° C.
(3) 30 seconds at 65° C.
(4) 30 seconds at 72° C.
(5) Repeat steps (2)-(4) eighteen times
(6) 2 minutes at 72° C.

The amplified extension products were stored at 4° C. 4 μL of each PCR reaction were combined into four pools, for 24 samples per pool.

The pooled PCR reactions were purified using diluted Agencourt AMPure XP magnetic beads (Beckman Coulter Genomics Inc.), which were prepared by combining 100 μL of AMPure XP beads and 400 μL of AMPure XP buffer (2.5M NaCl, 20% PEG8000). Purification was performed with 76.8 μL of diluted AMPure XP beads and eluted in 20 μL of a buffer comprising 10 mM Tris pH 8 and 0.05% Tween20. Beads were retained and cleanup process was repeated with 24 μL of AMPure XP buffer and eluted in 20 μL of buffer comprising 10 mM Tris pH 8 and 0.05% Tween20.

The purified PCR products were assessed using a High Sensitivity DNA chip on 2100 Bioanalyzer (Agilent Genomics) and KAPA Library Quantification Kit for Illumina Platforms (Kapa Biosystems). The purified PCR products were also diluted to 15 pM for sequencing on a MiSeq (Illumina) according to manufacturer's instructions (MiSeq Reagent Kit v3 2×75 bp) with a custom spike-in primer comprising the nucleotide sequence ACACTCTTTAAGACGACGTCGCTATGGCCTCTCC (SEQ ID NO: 25).

Example 4—Long Probe Hybridization Method for 96 Multiplexed Samples

In this example, a long probe hybridization method of the present disclosure was used to sequence identifier oligonucleotides collected from 96 multiplexed samples. In this example, the first nucleic acid probe comprises a 5' phosphate moiety, a nucleic acid sequence complementary to a portion of the identifier oligonucleotide, a first amplification primer binding site comprising an i7 sequence (SEQ ID NO: 1), unique nucleic acid sequence which identifies the specific location of the sample from which the identifier oligonucleotide was released and a P7 flow cell adapter sequence (SEQ ID NO: 4). The second nucleic acid probe comprises a nucleic acid sequence complementary to a portion of the identifier oligonucleotide, a nucleic acid sequence comprising a unique molecular identifier, a second amplification primer binding site comprising and i5 sequence (SEQ ID NO: 2) and a P5 flow cell adapter sequence (SEQ ID NO: 3).

The first and second nucleic acid probes were ordered from Integrated DNA Technologies, Inc. and quantified using a NanoDrop 1000 spectrophotometer (Thermo Fisher Scientific). Individual nucleic acid probes were normalized to a standard concentration, pooled to be equimolar, and diluted to 0.83 nM in a buffer comprising 10 mM Tris pH 8 and 0.05% Tween20. The nucleic acid probes and the identifier oligonucleotides were hybridized by combining 0.5 µL of diluted nucleic acid probe pool with 2 µL of a mixture of identifier oligonucleotides collected from a sample solution in a buffer comprising 50 mM NaCl. This mixture was heated for 2 minutes at 95° C. and cooled for 30 minutes at ambient temperature to yield an annealed identifier oligonucleotide-nucleic acid probe mixture.

In the case in which the first and the second nucleic acid probes hybridized to the identifier oligonucleotide such that the first and the second nucleic acid probes were not adjacent and were not overlapping, a gap extension reaction was performed. To 2.5 µL of each annealed identifier oligonucleotide-nucleic acid probe mixture, 3.8 µL of NEBNext Ultra II Q5 Master mix and 1.3 µL of PCR-grade $H_2O$ was added. The mixture was then subjected to the following Gap extension temperature cycle:
(1) 30 seconds at 98° C.
(2) 1 minute at 98° C.
(3) 1 minute at 68° C.
(4) 1 minute at 72° C.,
(5) Repeat steps (2)-(4) ten times
(6) 2 minutes at 72° C.

The gap extension products were then stored at 4° C. The first and second nucleic acid probes were then ligated together by adding to 1 µL of the gap extension product, 10 µL of 2× rapid ligation buffer (Enzymatics), 1 µL of T4 DNA Rapid Ligase (Enzymatics), and 8 µL of PCR-grade $H_2O$. These ligation reactions were incubated for 15 minutes 20° C., subsequently quenched with 1 µL 0.5M EDTA, and pooled into a single 15 mL conical tube.

In the case in which the first and the second nucleic acid probes hybridized to the identifier oligonucleotide such that the first and the second nucleic acid probes were adjacent and were not overlapping, nick repair ligation reaction was performed. To 2.5 µL of each annealed identifier oligonucleotide-nucleic acid probe mixture, 10 µL of 2× rapid ligation buffer (Enzymatics), 1 µL of T4 DNA Rapid Ligase (Enzymatics), and 1 µL of PCR-grade $H_2O$ was added. These ligation reactions were incubated for 15 minutes at 20° C., subsequently quenched with 1 µL of 0.5M EDTA, and pooled into a single 15 mL conical tube.

The pools of quenched ligation reactions were then purified using diluted Agencourt AMPure XP magnetic beads (Beckman Coulter Genomics Inc.), which were prepared by combining 350 µL of AMPure XP beads and 3.15 mL of AMPure XP buffer (2.5M NaCl, 20% PEG8000). The purification was performed with 3.5 mL of diluted AMPure XP beads and eluted in 200 µL of a buffer comprising 10 mM Tris pH 8 and 0.05% Tween20. The AMPure XP bead cleanup was then repeated with 400 µL of AMPure XP beads and eluted in 20 µL of a buffer comprising 10 mM Tris pH 8 and 0.05% Tween20.

To amplify the purified ligation products, PCR reactions with purified ligation products and primers were prepared. To 6 µL of purified ligation product, 10 µL of NEBNext Ultra II Q5 Master Mix, 0.2 µL of 100 µM forward primer (CAAGCAGAAGACGGCATACGA, SEQ ID NO: 153) and reverse primer (AATGATACGGCGACCACCGA, SEQ ID NO: 154) and 3.6 of PCR-grade $H_2O$ was added. The PCR program used to amplify the purified extension products comprised the following steps:
(1) 30 seconds at 98° C.
(2) 10 seconds at 98° C.
(3) 30 seconds at 65° C.
(4) 30 seconds at 72° C.
(5) Repeat steps (2)-(4) eighteen times
(6) 2 minutes at 72° C.

The amplified products were stored at 4° C. 4 µL of each PCR reaction were combined into six pools, for 16 samples per pool. The amplified products were further purified using an AMPure XP bead cleanup with 64 µL of AMPure XP beads and eluting with 20 µL of a buffer comprising 10 mM Tris pH 8 and 0.05% Tween20.

The purified amplified products were assessed using a High Sensitivity DNA chip on 2100 Bioanalyzer (Agilent Genomics) and KAPA Library Quantification Kit for Illumina Platforms (Kapa Biosystems). The purified amplified products were also diluted to 15 pM for sequencing on a MiSeq (Illumina) according to manufacturer's instructions (MiSeq Reagent Kit v3 2×75 bp) with either standard sequencing primers or a custom spike-in Read1 primer (SEQ ID NO: 25).

Example 5—Short Probe Hybridization Method for 96 Multiplexed Samples

In this example, a short probe hybridization method of the present disclosure was used to sequence identifier oligonucleotides collected from 96 multiplexed samples. In this example, the first nucleic acid probe comprises a 5' phosphate moiety, a nucleic acid sequence complementary to a portion of the identifier oligonucleotide, a first amplification primer binding site comprising an i7 sequence (SEQ ID NO: 1) and a unique nucleic acid sequence which identifies the specific location of the sample from which the identifier oligonucleotide was released. The second nucleic acid probe comprises a nucleic acid sequence complementary to a portion of the identifier oligonucleotide, a nucleic acid sequence comprising a unique molecular identifier and a second amplification primer binding site comprising an i5 sequence (SEQ ID NO: 2).

The first and second nucleic acid probes were ordered from Integrated DNA Technologies, Inc. and quantified using a NanoDrop 1000 spectrophotometer (Thermo Fisher Scientific). Individual nucleic acid probes were normalized to a standard concentration, pooled to be equimolar, and diluted to 0.83 nM in a buffer comprising 10 mM Tris pH 8 and 0.05% Tween20. The nucleic acid probes and the identifier oligonucleotides were hybridized by combining 0.5 µL of diluted nucleic acid probe pool with 2 µL of a mixture of identifier oligonucleotides collected from a sample solution in a buffer comprising 50 mM NaCl. This mixture was heated for 2 minutes at 95° C. and cooled for 30 minutes at ambient temperature to yield an annealed identifier oligonucleotide-nucleic acid probe mixture.

In the case in which the first and the second nucleic acid probes hybridized to the identifier oligonucleotide such that the first and the second nucleic acid probes were not adjacent and were not overlapping, a gap extension reaction was performed. To 2.5 µL of each annealed identifier oligonucleotide-nucleic acid probe mixture, 3.8 µL of NEBNext Ultra II Q5 Master mix and 1.3 µL of PCR-grade $H_2O$ was added. The mixture was then subjected to the following Gap extension temperature cycle:
(1) 30 seconds at 98° C.
(2) 1 minute at 98° C.

(3) 1 minute at 68° C.
(4) 1 minute at 72° C.,
(5) Repeat steps (2)-(4) ten times
(6) 2 minutes at 72° C.

The gap extension products were then stored at 4° C. The first and second nucleic acid probes were then ligated together by adding to 1 μL of the gap extension product, 10 μL of 2× rapid ligation buffer (Enzymatics), 1 μL of T4 DNA Rapid Ligase (Enzymatics), and 8 μL of PCR-grade H$_2$O. These ligation reactions were incubated 15 min 20° C., quenched with 1 μL 0.5M EDTA, and pooled into a single 15 mL conical tube.

In the case in which the first and the second nucleic acid probes hybridized to the identifier oligonucleotide such that the first and the second nucleic acid probes were adjacent and were not overlapping, nick repair ligation reaction was performed. To 2.5 μL of each annealed identifier oligonucleotide-nucleic acid probe mixture, 10 μL of 2× rapid ligation buffer (Enzymatics), 1 μL of T4 DNA Rapid Ligase (Enzymatics), and 1 μL of PCR-grade H$_2$O was added. These ligation reactions were incubated for 15 minutes at 20° C., subsequently quenched with 1 μL of 0.5M EDTA, and pooled into a single 15 mL conical tube.

The pools of quenched ligation reactions were then purified using diluted Agencourt AMPure XP magnetic beads (Beckman Coulter Genomics Inc.), which were prepared by combining 350 μL of AMPure XP beads and 3.15 mL of AMPure XP buffer (2.5M NaCl, 20% PEG8000). The purification was performed with 3.5 mL of diluted AMPure XP beads and eluted in 200 μL of a buffer comprising 10 mM Tris pH 8 and 0.05% Tween20. The AMPure XP bead cleanup was then repeated with 400 μL of AMPure XP beads and eluted in 20 μL of a buffer comprising 10 mM Tris pH 8 and 0.05% Tween20.

To amplify the purified ligation products, PCR reactions with purified ligation products and primers were prepared. To 6 μL of purified ligation product, 10 μL of NEBNext Ultra II Q5 Master Mix, 0.2 μL of 100 μM forward primer and reverse primer and 3.6 μL of PCR-grade H$_2$O was added. The forward primers comprised a flow cell adapter sequence suitable for sequencing, a unique molecular identifier and a nucleic acid sequence complementary to the first amplification primer binding site located on the first strand of the nucleic acid adapter. Table 8 provides the sequences of the forward primers used.

TABLE 8

Forward primers for short probe hybridization method

| Primer Sequence | SEQ ID NO |
| --- | --- |
| CAAGCAGAAGACGGCATACGAGATCGAGTA ATGTGACTGGAGTTCAGACGTGTGCTCTTC CGATCT | 13 |
| CAAGCAGAAGACGGCATACGAGATTCTCCG GAGTGACTGGAGTTCAGACGTGTGCTCTTC CGATCT | 14 |
| CAAGCAGAAGACGGCATACGAGATAATGAG CGGTGACTGGAGTTCAGACGTGTGCTCTTC CGATCT | 15 |
| CAAGCAGAAGACGGCATACGAGATGGAATC TCGTGACTGGAGTTCAGACGTGTGCTCTTC CGATCT | 16 |

TABLE 8-continued

Forward primers for short probe hybridization method

| Primer Sequence | SEQ ID NO |
| --- | --- |
| CAAGCAGAAGACGGCATACGAGATTTCTGA ATGTGACTGGAGTTCAGACGTGTGCTCTTC CGATCT | 17 |
| CAAGCAGAAGACGGCATACGAGATACGAAT TCGTGACTGGAGTTCAGACGTGTGCTCTTC CGATCT | 18 |
| CAAGCAGAAGACGGCATACGAGATAGCTTC AGGTGACTGGAGTTCAGACGTGTGCTCTTC CGATCT | 19 |
| CAAGCAGAAGACGGCATACGAGATGCGCAT TAGTGACTGGAGTTCAGACGTGTGCTCTTC CGATCT | 20 |
| CAAGCAGAAGACGGCATACGAGATCATAGC CGGTGACTGGAGTTCAGACGTGTGCTCTTC CGATCT | 21 |
| CAAGCAGAAGACGGCATACGAGATTTCGCG GAGTGACTGGAGTTCAGACGTGTGCTCTTC CGATCT | 22 |
| CAAGCAGAAGACGGCATACGAGATGCGCGA GAGTGACTGGAGTTCAGACGTGTGCTCTTC CGATCT | 23 |
| CAAGCAGAAGACGGCATACGAGATCTATCG CTGTGACTGGAGTTCAGACGTGTGCTCTTC CGATCT | 24 |

The reverse primers comprised a flow cell adapter sequence suitable for sequencing, a unique molecular identifier and a nucleic acid sequence complementary to the second amplification primer binding site located on the second strand of the nucleic acid adapter. Table 9 provides the sequences of the reverse primers used.

TABLE 9

Reverse primers for short probe hybridization method

| Primer Sequence | SEQ ID NO |
| --- | --- |
| AATGATACGGCGACCACCGAGATCTACACT ATAGCCTACACTCTTTCCCTACACGACGCT CTTCCGATCT | 155 |
| AATGATACGGCGACCACCGAGATCTACACA TAGAGGCACACTCTTTCCCTACACGACGCT CTTCCGATCT | 156 |
| AATGATACGGCGACCACCGAGATCTACACC CTATCCTACACTCTTTCCCTACACGACGCT CTTCCGATCT | 157 |
| AATGATACGGCGACCACCGAGATCTACACG GCTCTGAACACTCTTTCCCTACACGACGCT CTTCCGATCT | 158 |
| AATGATACGGCGACCACCGAGATCTACACA GGCGAAGACACTCTTTCCCTACACGACGCT CTTCCGATCT | 159 |
| AATGATACGGCGACCACCGAGATCTACACT AATCTTAACACTCTTTCCCTACACGACGCT CTTCCGATCT | 160 |

TABLE 9-continued

Reverse primers for short
probe hybridization method

| Primer Sequence | SEQ ID NO |
|---|---|
| AATGATACGGCGACCACCGAGATCTACACC AGGACGTACACTCTTTCCCTACACGACGCT CTTCCGATCT | 161 |
| AATGATACGGCGACCACCGAGATCTACACG TACTGACACACTCTTTCCCTACACGACGCT CTTCCGATCT | 162 |

The PCR program used to amplify the purified extension products comprised the following steps:
(1) 30 seconds at 98° C.
(2) 10 seconds at 98° C.
(3) 30 seconds at 65° C.
(4) 30 seconds at 72° C.
(5) Repeat steps (2)-(4) eighteen times
(6) 2 minutes at 72° C.

The amplified products were stored at 4° C. 4 µL of each PCR reaction were combined into six pools, for 16 samples per pool. The amplified products were further purified using an AMPure XP bead cleanup with 64 µL of AMPure XP beads and eluting with 20 µL of a buffer comprising 10 mM Tris pH 8 and 0.05% Tween20.

The purified amplified products were assessed using a High Sensitivity DNA chip on 2100 Bioanalyzer (Agilent Genomics) and KAPA Library Quantification Kit for Illumina Platforms (Kapa Biosystems). The purified amplified products were also diluted to 15 pM for sequencing on a MiSeq (Illumina) according to manufacturer's instructions (MiSeq Reagent Kit v3 2×75 bp) with either standard sequencing primers or a custom spike-in Read1 primer (SEQ ID NO: 25).

Example 6—Direct PCR Method for 96 Multiplexed Samples

In this example, a direct PCR method of the present disclosure was used to sequence identifier oligonucleotides collected from 96 multiplexed samples. In this example, 8 species of forward amplification primers and 12 species of reverse amplification primers were used. The forward primers comprised a P5 flow cell adapter (SEQ ID NO: 3), a nucleic acid sequence comprising a unique molecular identifier and a region complementary to a first amplification primer binding site present on the identifier oligonucleotide. Table 10 provides the sequences of the forward amplification primers used.

TABLE 10

Forward amplification primers
for direct PCR method

| Primer Sequence | SEQ ID NO |
|---|---|
| AATGATACGGCGACCACCGAGATCTACACG CTCAGATATAGCCTACACTCTTTAAGACGA CGTCGCTATGGCCTCTCC | 5 |
| AATGATACGGCGACCACCGAGATCTACACG CTCAGAATAGAGGCACACTCTTTAAGACGA CGTCGCTATGGCCTCTCC | 6 |

TABLE 10-continued

Forward amplification primers
for direct PCR method

| Primer Sequence | SEQ ID NO |
|---|---|
| AATGATACGGCGACCACCGAGATCTACACG CTCAGACCTATCCTACACTCTTTAAGACGA CGTCGCTATGGCCTCTCC | 7 |
| AATGATACGGCGACCACCGAGATCTACACG CTCAGAGGCTCTGAACACTCTTTAAGACGA CGTCGCTATGGCCTCTCC | 8 |
| AATGATACGGCGACCACCGAGATCTACACG CTCAGAAGGCGAAGACACTCTTTAAGACGA CGTCGCTATGGCCTCTCC | 9 |
| AATGATACGGCGACCACCGAGATCTACACG CTCAGATAATCTTAACACTCTTTAAGACGA CGTCGCTATGGCCTCTCC | 10 |
| AATGATACGGCGACCACCGAGATCTACACG CTCAGACAGGACGTACACTCTTTAAGACGA CGTCGCTATGGCCTCTCC | 11 |
| AATGATACGGCGACCACCGAGATCTACACG CTCAGAGTACTGACACACTCTTTAAGACGA CGTCGCTATGGCCTCTCC | 12 |

The reverse primers comprised a P7 flow cell adapter (SEQ ID NO: 4), a nucleic acid sequence comprising a unique molecular identifier and a region complementary to a second amplification primer binding site present on the identifier oligonucleotide. Table 11 provides the sequences of the reverse amplification primers used.

TABLE 11

Reverse amplification primers
for direct PCR method

| Primer Sequence | SEQ ID NO |
|---|---|
| CAAGCAGAAGACGGCATACGAGATCGTGAT GTGACTGGAGTTCAGACGTGTGCTCTTCCG ATCTNNNNNNNNNNNNNNNNNNAACGGACAGGAT GCAGCAAAAT | 163 |
| CAAGCAGAAGACGGCATACGAGATACATCG GTGACTGGAGTTCAGACGTGTGCTCTTCCG ATCTNNNNNNNNNNNNNNNNNNAACGGACAGGAT GCAGCAAAAT | 164 |
| CAAGCAGAAGACGGCATACGAGATGCCTAA GTGACTGGAGTTCAGACGTGTGCTCTTCCG ATCTNNNNNNNNNNNNNNNNNNAACGGACAGGAT GCAGCAAAAT | 165 |
| CAAGCAGAAGACGGCATACGAGATTGGTCA GTGACTGGAGTTCAGACGTGTGCTCTTCCG ATCTNNNNNNNNNNNNNNNNNNAACGGACAGGAT GCAGCAAAAT | 166 |
| CAAGCAGAAGACGGCATACGAGATCACTGT GTGACTGGAGTTCAGACGTGTGCTCTTCCG ATCTNNNNNNNNNNNNNNNNNNAACGGACAGGAT GCAGCAAAAT | 167 |
| CAAGCAGAAGACGGCATACGAGATATTGGC GTGACTGGAGTTCAGACGTGTGCTCTTCCG ATCTNNNNNNNNNNNNNNNNNNAACGGACAGGAT GCAGCAAAAT | 168 |

TABLE 11-continued

Reverse amplification primers
for direct PCR method

| Primer Sequence | SEQ ID NO |
|---|---|
| CAAGCAGAAGACGGCATACGAGATGATCTG GTGACTGGAGTTCAGACGTGTGCTCTTCCG ATCTNNNNNNNNNNNNNNNAACGGACAGGAT GCAGCAAAAT | 169 |
| CAAGCAGAAGACGGCATACGAGATTCAAGT GTGACTGGAGTTCAGACGTGTGCTCTTCCG ATCTNNNNNNNNNNNNNNNAACGGACAGGAT GCAGCAAAAT | 170 |
| CAAGCAGAAGACGGCATACGAGATCTGATC GTGACTGGAGTTCAGACGTGTGCTCTTCCG ATCTNNNNNNNNNNNNNNNAACGGACAGGAT GCAGCAAAAT | 171 |
| CAAGCAGAAGACGGCATACGAGATAAGCTA GTGACTGGAGTTCAGACGTGTGCTCTTCCG ATCTNNNNNNNNNNNNNNNAACGGACAGGAT GCAGCAAAAT | 172 |
| CAAGCAGAAGACGGCATACGAGATGTAGCC GTGACTGGAGTTCAGACGTGTGCTCTTCCG ATCTNNNNNNNNNNNNNNNAACGGACAGGAT GCAGCAAAAT | 173 |
| CAAGCAGAAGACGGCATACGAGATTACAAG GTGACTGGAGTTCAGACGTGTGCTCTTCCG ATCTNNNNNNNNNNNNNNNAACGGACAGGAT GCAGCAAAAT | 174 |

In the case of 8 forward amplification primers and 12 reverse amplification primers, when the unique molecular identifiers from a pair of forward and reverse primers are combined, a total of 96 unique combinations can be obtained, allowing for the multiplexing of 96 samples.

To amplify the collected identifier oligonucleotides for sequencing, PCR reactions with collected identifier oligonucleotides and forward and reverse amplification primers were prepared on a 96-well plate with 2 µL of each identifier oligonucleotide sample, 10 µL of NEBNext Ultra II Q5 Master Mix, 2 µL of 10 µM forward amplification primer, 2 µL of reverse amplification primer, and 4 µL of PCR-grade H$_2$O. Each well in the 96-well plate contained an identifier oligonucleotide sample and a unique combination of forward and reverse amplification primers. The PCR program used comprised the following steps:
(1) 30 seconds at 98° C.
(2) 10 seconds at 98° C.
(3) 30 seconds at 65° C.
(4) 30 seconds at 72° C.
(5) Repeat steps (2)-(4) six to ten times
(6) 2 minutes at 72° C.

The amplified products were stored at 4° C. 10 µL of each PCR reaction was combined into a single 15 mL conical tube.

The pooled PCR reactions were purified using diluted Agencourt AMPure XP magnetic beads (Beckman Coulter Genomics Inc.), which were prepared by combining 115.2 µL of AMPure XP beads and 1036.8 µL of AMPure XP buffer (2.5M NaCl, 20% PEG8000). Purification was performed with 1152 µL of diluted AMPure XP beads and eluted in 60 µL of a buffer comprising 10 mM Tris pH 8. The purification process was repeated with 60 µL of AMPure XP beads and eluted in 70 µL of a buffer comprising 10 mM Tris pH 8.

Following AMPure XP cleanup, PCR reactions with universal primers were prepared with 9 µL of pooled direct PCR product, 15 µL of NEBNext Ultra II Q5 Master Mix, 3 µL of 10 universal P7 primer (SEQ ID NO: 153) and 2 µL of 10 µM universal P5 primer (SEQ ID NO: 154). The PCR program used was:
(1) 30 seconds at 98° C.,
(2) 10 seconds at 98° C.
(3) 30 seconds at 65° C.
(4) 30 seconds at 72° C.
(5) Repeat steps (2)-(4) 15 to 24 times
(6) 2 minutes at 72° C.

Two rounds of AMPure XP bead cleanup was performed. The first round was performed with 30 µL of beads and eluted with 20 µL of a buffer comprising 10 mM Tris pH 8 and the second round was performed with 20 µL beads and eluted with 11 µL of a buffer comprising 10 mM Tris pH 8.

These purified PCR products were assessed using a High Sensitivity DNA chip on 2100 Bioanalyzer (Agilent Genomics). The purified PCR products were also diluted for sequencing on a MiSeq (Illumina) according to manufacturer's instructions (MiSeq Reagent Kit v3 2×75 bp) with a custom spike-in primer (SEQ ID NO: 25).

Example 7—Spatially Detecting Target Analytes in a FFPE Sample

The methods of the present invention were used to spatially detect a plurality of different target analytes, including target proteins and target RNAs, in a sample of inflamed human tonsil tissue FFPE section.

In one experiment, 30 different target proteins were spatially detected using the methods of the present disclosure in two serial sections cut from the inflamed human tonsil tissue FFPE section. The 30 target proteins are put forth in Table 12. The 30 target proteins included IgG Rabbit isotype and IgG Mouse isotype as negative controls, as these target proteins should not have been present in the inflamed human tonsil sample and therefore should not have been detected.

TABLE 12

| Target Proteins | |
|---|---|
| Target Protein | Target Protein |
| AKT | FOXP3 |
| B7-H3 | GZMB |
| Bcl-2 | Histone H3 |
| Beta-2-microglobulin | Ki67 |
| Beta-catenin | CD20 |
| CD14 | P-AKT |
| CD19 | PanCK |
| CD3 | PD1 |
| CD4 | PD-L1 |
| CD44 | S6 |
| CD45 | STAT3 |
| CD45RO | P-STAT3 |
| CD56 | VISTA |
| CD68 | IgG Rabbit isotype (negative control) |
| CD8A | IgG Mouse isotype (control) |

To spatially detect the 30 target proteins, 30 different probes of the present disclosure were used. Each probe comprised a target binding domain comprising an antibody that specifically binds to one of the 30 target proteins in Table 12. The two serial sections were contacted with a plurality of the 30 different probes. Ninety-six regions of interest (ROI) were then identified. For each ROI, the ROI was illuminated with UV light to release the identifier oligonucleotides from the probes bound within the ROI. The released identifier oligonucleotides were then collected and identified using a short probe hybridization method of the present disclosure, thereby spatially detecting the 30 target proteins in the two serial sections. As shown in FIGS. 21A-21D, the number of reads per target protein in each ROI for the two serial sections were well correlated, demonstrating that the method yields reproducible results.

In a second experiment, 20 different target RNAs were spatially detected using the methods of the present disclosure in two different serial sections cut from the inflamed human tonsil tissue FFPE section. The 20 different target RNAs are put forth in Table 13. The 20 target RNAs included 6 negative controls (Negative Probe) that should not have been detected in the sample.

TABLE 13

| Target RNAs | | |
|---|---|---|
| Target RNA | Target RNA | Target RNA |
| CD3E | CD40 | CTLA4 |
| CD3G | CD45 | GAPDH |
| CD4 | CD74 | KRT13 |
| CD20 | CD79A | PD1 |
| PSA | RP56 | Negative Probe #1 |
| Negative Probe #2 | Negative Probe #3 | Negative Probe #4 |
| Negative Probe #5 | Negative Probe #6 | |

To spatially detect the 20 Target RNAs, 20 different probes of the present disclosure were used. Each probe comprised a target binding domain comprising a nucleic acid sequence complementary to at least one portion of one of the 20 target RNAs. The two serial sections were contacted with a plurality of the 20 different probes. Ninety-six regions of interest (ROI) were then identified. For each ROI, the ROI was illuminated with UV light to release the identifier oligonucleotides from the probes bound within the ROI. The released identifier oligonucleotides were then collected and identified using a direct PCR method of the present disclosure, thereby spatially detecting the 20 target RNAs in the two serial sections. As shown in FIGS. 22A-22D, the number of reads per target RNA in each ROI for the two serial sections were well correlated, demonstrating that the method yields reproducible results.

Figure 23:
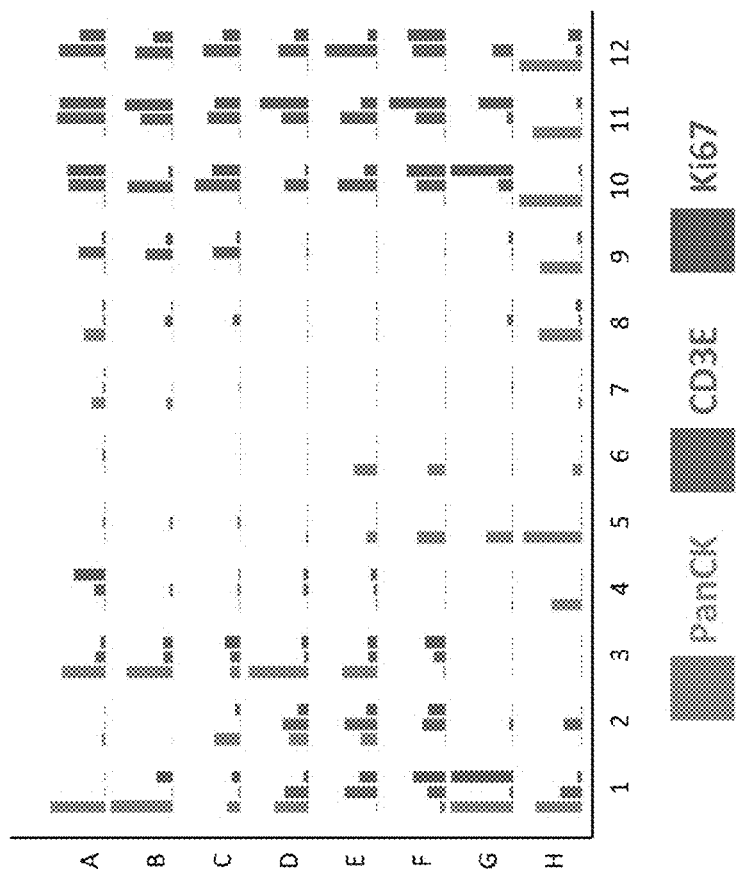
FIG. 23 shows the spatial detection of protein target analytes using the methods of the present disclosure.
Figure 23:
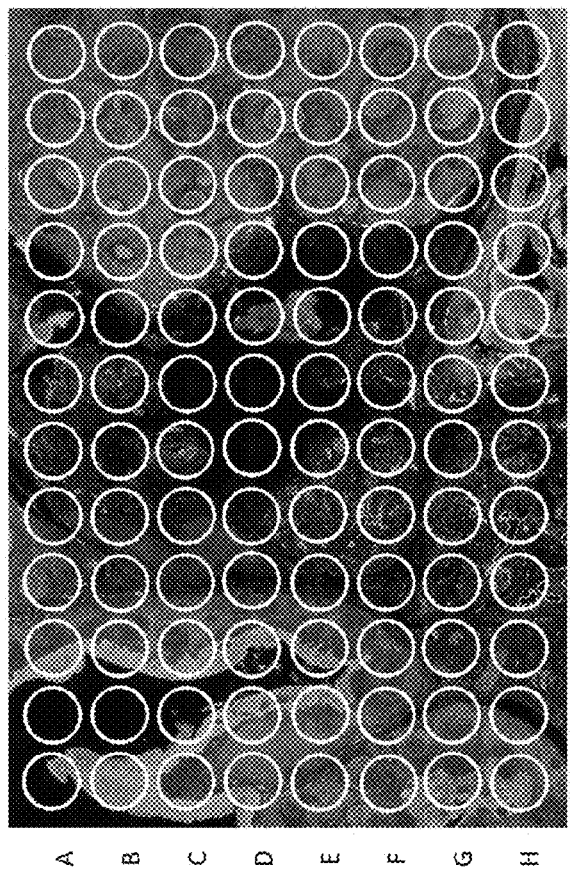

Example 8—Spatially Detecting Target Proteins in a Fluorescently Stained FFPE Sample In another experiment, a 5 μm FFPE section of inflamed human tonsil tissue was stained with 4 fluorescent visualization markers: (1) CD3E, a T-cell marker; (2) PanCK, an epithelial cell marker; (3) Ki-67, a proliferation marker; and (4) SYTO83, a DNA stain, as shown in the left panel of FIG. 23. The stained FFPE section was then contacted with the probes directed against 30 target proteins, as described in Example 7. As shown in the left panel FIG. 23, 96 regions of interest (ROIs) were selected. Each ROI was a circle with a 500 μm diameter. For each ROI, the ROI was illuminated with UV light to release the identifier oligonucleotides from the probes bound within the ROI. The released identifier oligonucleotides were then collected and identified using a short probe hybridization method of the present disclosure, thereby spatially detecting the 30 target proteins in the FFPE section. As shown in the right panel of FIG. 23, PanCK, CD3E and Ki67 were spatially detected in ROIs that correlated with their fluorescent visualization markers. Thus, the results generated by the methods of the present disclosure correlate with the results generated using established immunohistochemical method.

Example 9—Spatially Detecting Target RNAs in a FFPE Sample

Figure 24:
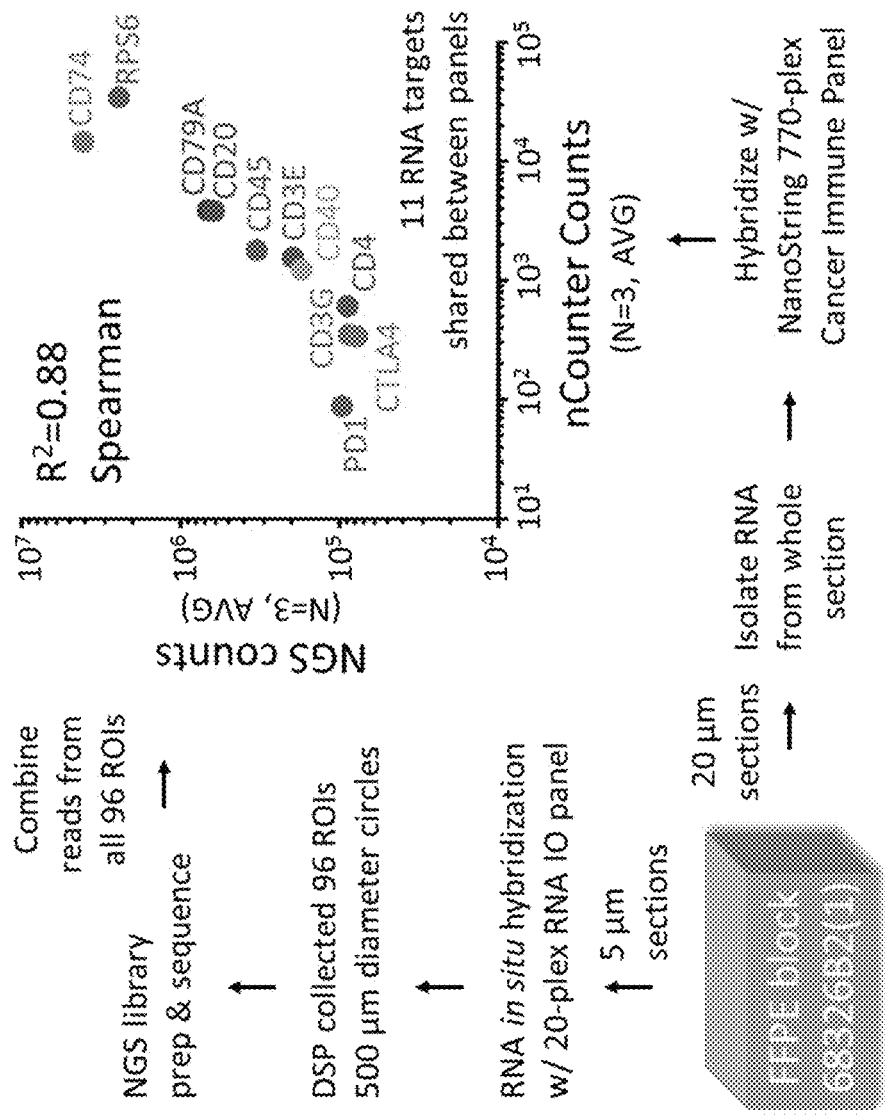
FIG. 24 shows the spatial detection of RNA target analytes using the methods of the present disclosure.

In another experiment, a 5 μm section from an inflamed human tonsil tissue FFPE block was contacted with probes directed against 20 target RNAs, as described in Example 7. 96 regions of interest (ROIs) were then selected. Each ROI was a circle with a 500 μm diameter. For each ROI, the ROI was illuminated with UV light to release the identifier oligonucleotides from the probes bound within the ROI. The released identifier oligonucleotides were then collected and identified using a direct PCR method of the present disclosure, thereby spatially detecting the 20 target RNAs in the two serial sections. The total RNA from a 20 μm section from the same inflamed human tonsil tissue FFPE block was then isolated. The total RNA was analyzed using the NanoString nCounter® system. FIG. 24 shows that the average number of counts for 11 different RNA targets recorded using the methods of the present disclosure were well correlated with the average number of counts for the same 11 different RNA targets recorded using the nCounter® system. Thus, the results generated using the methods of the present disclosure correlate with the results generated using established direct detection methods.

Example 10—Spatially Detecting Target RNAs in Specific Sub-Regions of an ROI

Figure 25:
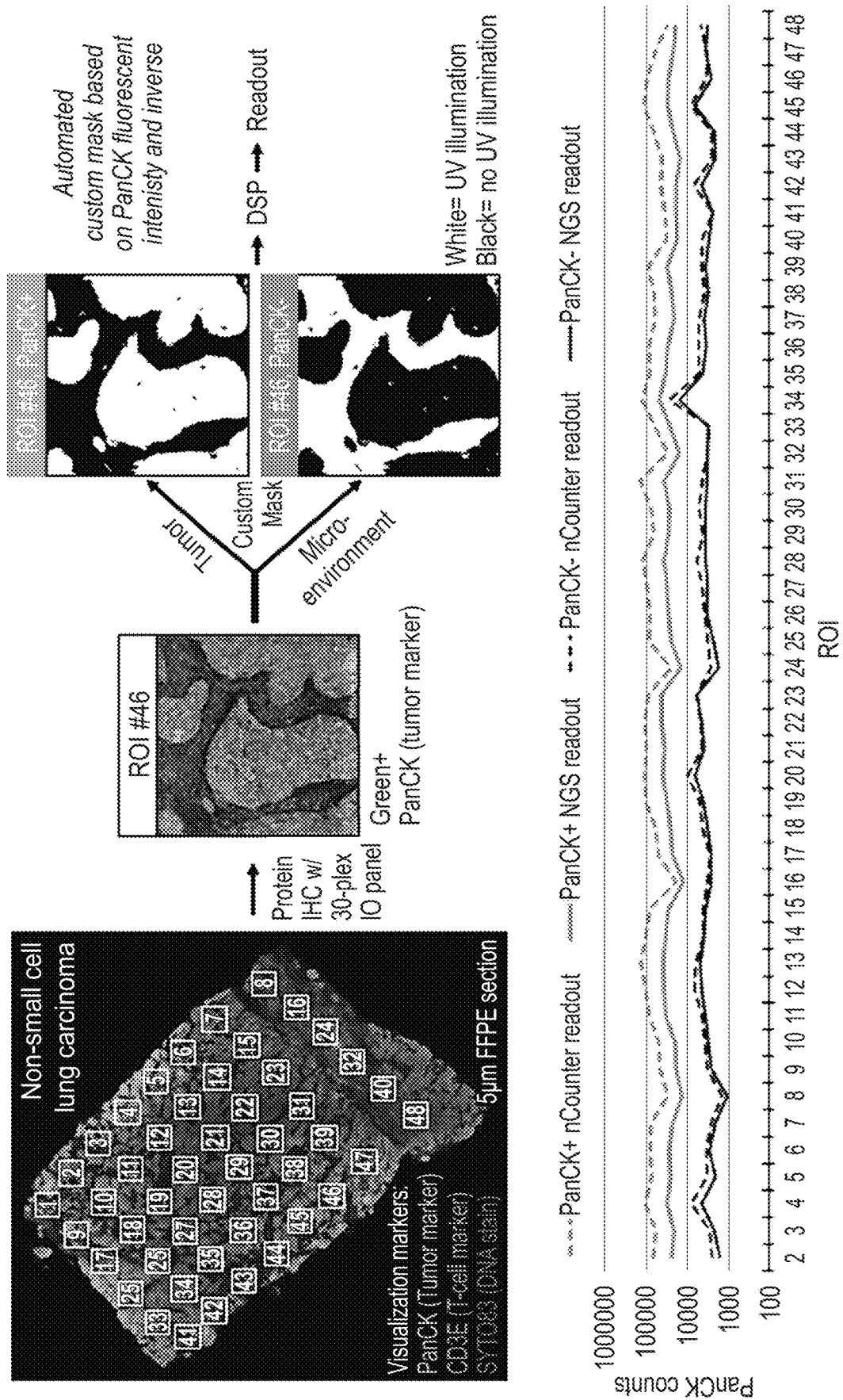
FIG. 25 shows the spatial detection of protein target analytes using the methods of the present disclosure.

In another experiment, a 5 μm section from an inflamed human tonsil tissue FFPE block was contacted with probes directed against 30 target proteins, as described in Example 7. The same 5 μm section was also stained with 4 fluorescent visualization markers: (1) CD3E, a T-cell marker; (2) PanCK, an epithelial cell marker; (3) Ki-67, a proliferation marker; and (4) SYTO83, a DNA stain. As shown in FIG. 25, 48 regions of interest (ROIs) were identified. For each ROI, two sub-regions were then identified based on the fluorescent staining. Areas of an ROI that were fluorescently stained positive for PanCK (PanCK+) were designated a "tumor" sub-region and the areas of an ROI that lacked PanCK fluorescent staining were designated a "micro-environment" sub-region, as shown in FIG. 25. For each ROI, the tumor sub-region and the micro-environment sub-region were separately illuminated with UV light to release the identifier oligonucleotides from the probes bound within each sub-region by creating a custom mask based on the intensity of PanCK fluorescent staining. The released identifier oligonucleotides were also separately collected. The collected identifier oligonucleotides were then analyzed using the short-probe hybridization method of the present disclosure and the NanoString nCounter® system. As shown in the bottom panel of FIG. 25, the results using the NanoString nCounter® system and the short-probe hybridization method of the present disclosure were well correlated. Furthermore, in the tumor sub-regions, PanCK was detected at a significantly higher level as compared to the micro-environment sub-regions. Thus, the spatial detection results provided by the methods of the present disclosure are consistent with established fluorescent immunohistochemical methods and allows for the spatial detection within highly specific regions of a sample.

Example 11—96-Plex Human Immuno-Oncology Panel

A 96-plex human immuno-oncology panel was designed for use in the direct-PCR methods of the present invention. The panel comprised a plurality of probes that could be used to spatially detect 96 different human target RNAs using the direct-PCR methods of the present disclosure. The 96 target RNAs are shown in Table 14.

TABLE 14

Target RNAs
Target

AKT1
ARG1
B2M
BATF3
BCL2
BCL2L1
CCL5
CCND1
CD14
CD27
CD274
CD276
CD3E
CD4
CD40
CD40LG
CD44
CD47
CD68
CD74
CD86
CD8A
CEACAM1
CEACAM6
CEACAM8
CMKLR1
CSF1R
CTLA4
CTNNB1
CXCL10
CXCL9
CSCR6
DKK2
EPCAM
FAS
FASLG
FOXP3
GZMB
H3F3A
HAVCR2
HIF1A
HLA_DQA1
HLA_DRB
HLA_E
ICAM1
ICOSLG
IDO1
IFNAR1
IFNG
IFNGR1
IL10
IL12B
IL15
IL1B
IL6
ITGAM
ITGAV
ITGAX
ITGB2
ITGB8
KRT1
KRT10
KRT14
KRT17
KRT18

TABLE 14-continued

Target RNAs
Target

KRT19
KRT6A
KRT7
LAG3
LY6E
MKI67
MS4A1
NCAM1
NKG7
NT5E
PDCD1
PDCD1LG2
PECAM1
PMEL
PSMB10
PTEN
PRTPRC
RPS6
S100B
SOD2
SOX10
STAT1
STAT2
STAT3
TBX21
TIGIT
TNF
TNFRSF9
TNFSF4
VEGFA
VSIR

Figure 26:
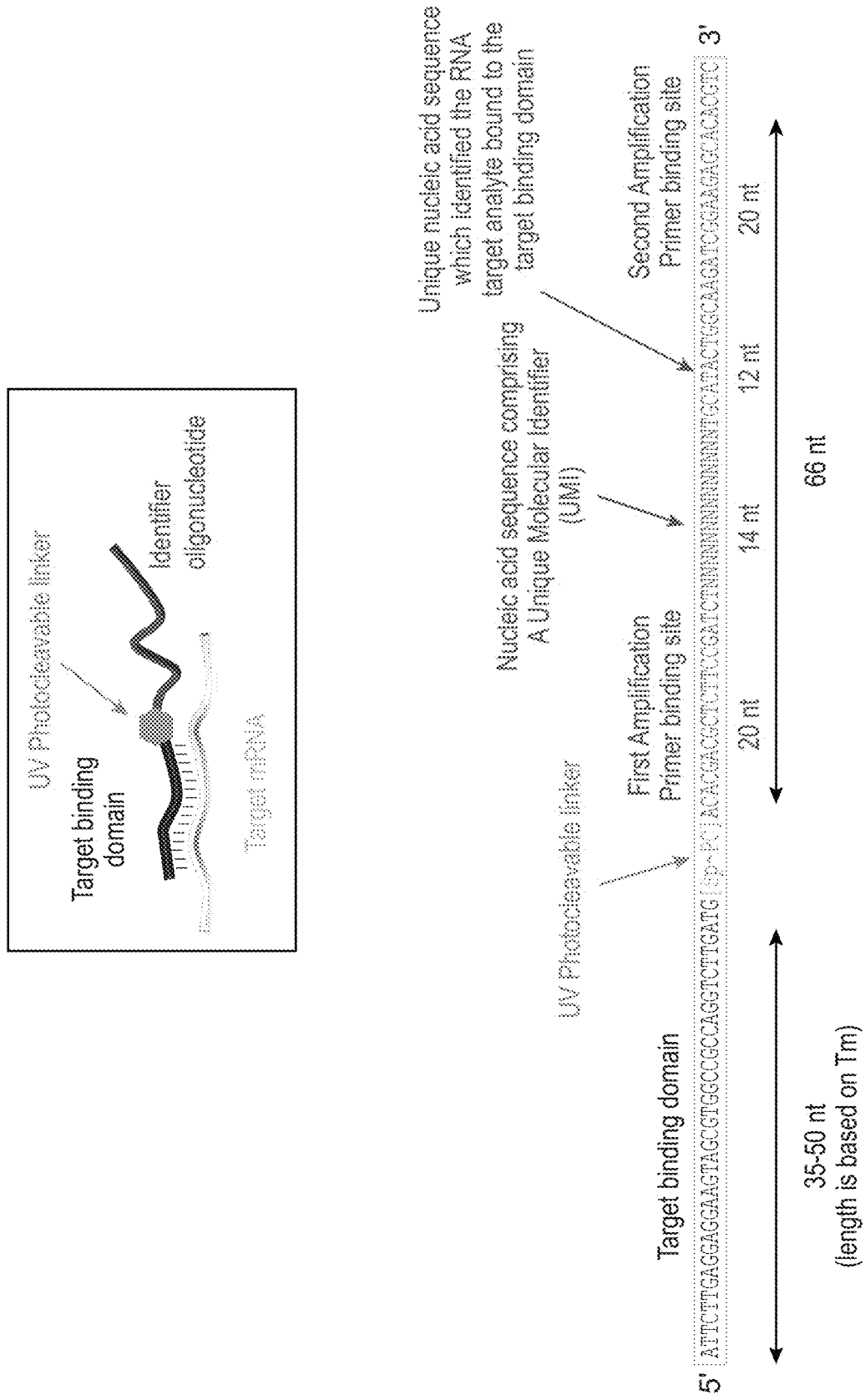
FIG. 26 is a schematic of a probe of the present disclosure. The nucleic acid sequence shown in FIG. 26 corresponds to SEQ ID NO: 175.

In total, the panel comprised 928 different probes. Each of the probes comprised an identifier oligonucleotide comprising a first amplification primer binding site, a nucleic acid sequence comprising a unique molecular identifier, a unique nucleic acid sequence which identified the target RNA bound to the target binding domain and a second amplification primer binding site. FIG. 26 shows a schematic of the probes used in the panel. For each of the 96 target RNAs, there was at least one probe within the 928 probe set comprising a target binding domain that directly or indirectly hybridized to that target RNA. For most of the 96 target RNAs, there were 10 different probes that directly or indirectly hybridized to the specific target RNA. These 10 different probes directly or indirectly hybridized to different locations on the target RNA to create a "tiling" effect, as shown in the top panel of FIG. 27. Tiling multiple probes onto a target RNA means that each target RNA will be individually detected multiple times, increasing the overall accuracy of the measurement. For example, as shown in the bottom panel of FIG. 27, in the case where 10 probes are tiled onto a single target RNA, one of the probes may be incorrectly detected too many times (outlier high count probe), while another probe may be incorrectly detected too few times (outlier low count probe). However, the other 8 probes may be detected at a similar level, indicating that the two outliers should be discarded during analysis and the signals from the 8 probes used to generate a more accurate measurement of the abundance of the target RNA.

The set of 928 probes also comprised 80 negative control probes. Each of the 80 negative control probes comprised a target binding domain comprising a scrambled, non-specific nucleic acid sequence that was designed using guidelines from the External RNA Controls Consortium such that the target binding domain should not be complementary to RNA molecules present within a human sample. Thus, these 80 negative control probes should not be detected during analysis.

The 96-plex human immune-oncology panel was used to analyze a tissue microarray. The tissue microarray comprised FFPE samples of 22 common human cell lines, including normal and cancerous cell types. Some of the cell lines are shown in Table 15.

TABLE 15

Cell lines

| Cell Line | Cell Line | Cell Line | Cell Line |
|---|---|---|---|
| CCRF-CEM | DAUDI | H596 | H2228 |
| HT29 | HUT78 | HUH7 | JURKAT |
| M14 | MDA-MB-468 | MOLT4 | RAJI |
| SKBR3 | SUDHL1 | SUDHL4 | |

Figure 28:
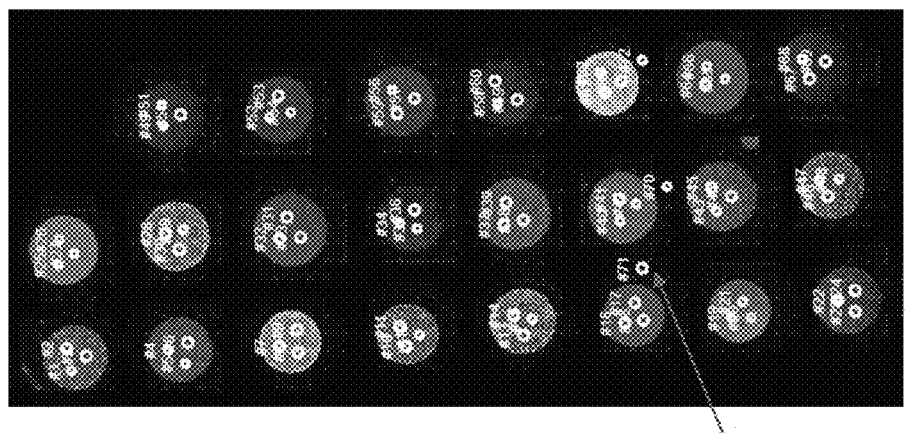
FIG. 28 shows the regions of interest selected on a tissue microarray.

The tissue microarray also comprised one mouse cell line (3T3) as a negative control. Each of the FFPE samples on the microarray was contacted with a plurality of the 928 different probes in the imunno-onocology panel. As shown in FIG. 28, for each of the FFPE samples, at least three circular regions of interest (ROIs) with a diameter of 300 µm were selected. As a negative control, ROIs were also selected on regions of the microarray that did not comprise a FFPE sample (glass negative control). For each ROI, the ROI was illuminated with UV light to release the identifier oligonucleotides from the probes bound within the ROI. The released identifier oligonucleotides were then collected and identified using a direct PCR method of the present disclosure thereby spatially detecting the 96 target RNAs in each of the FFPE samples on the tissue microarray.

Figure 29:
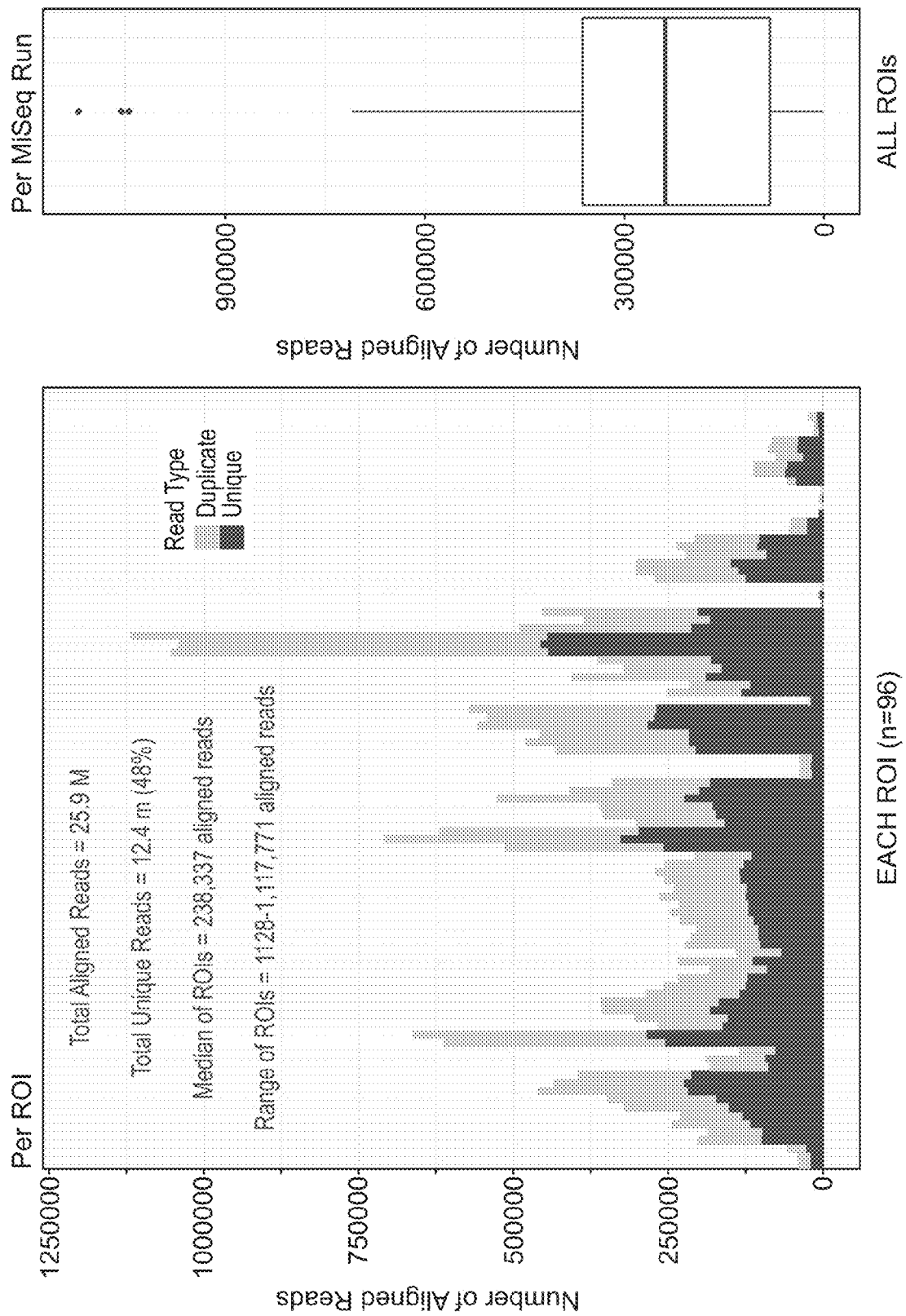
FIG. 29 is a series of graphs showing the read depth achieved using the methods of the present disclosure.
Figure 30:
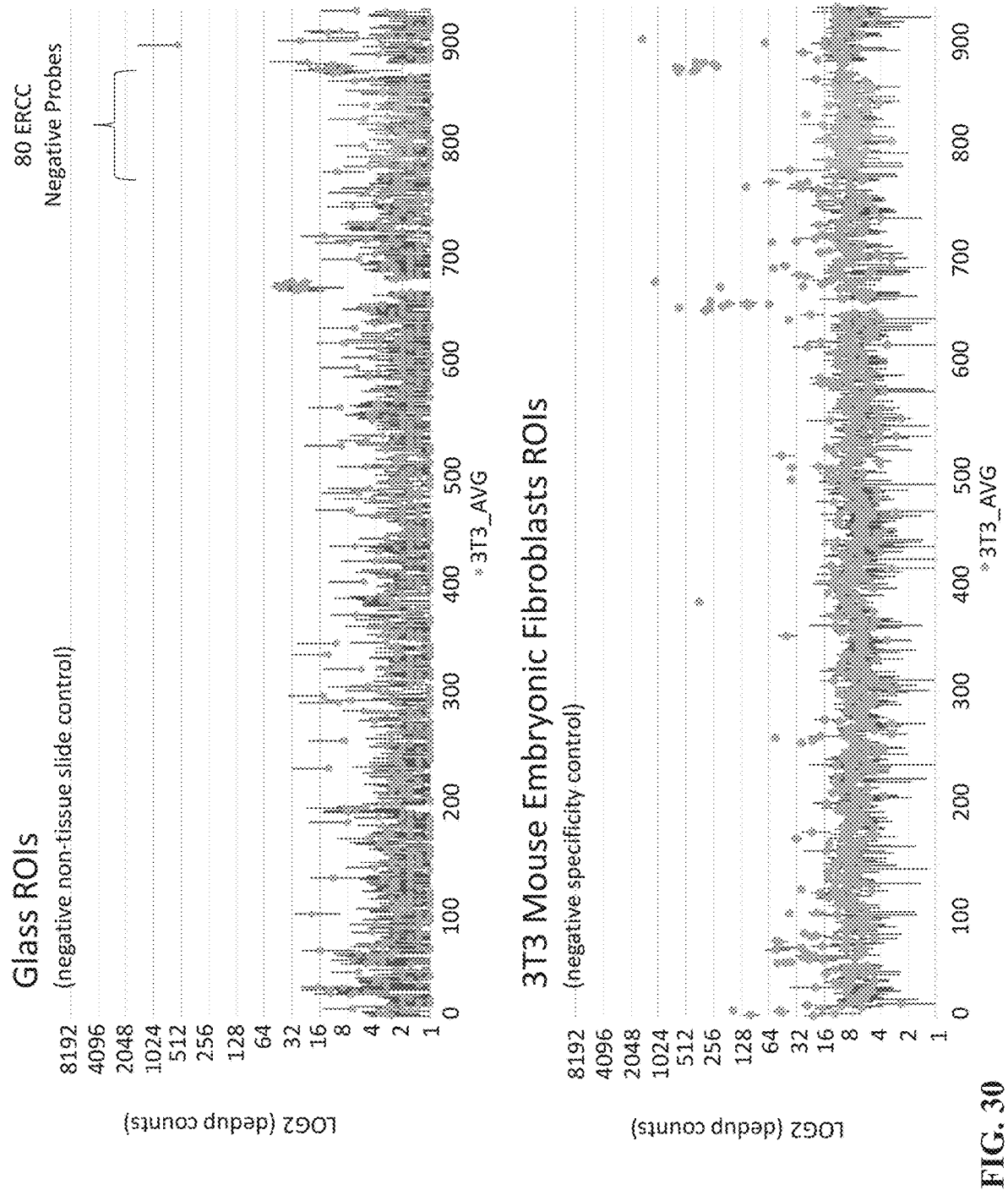
FIG. 30 is a series of graphs showing the spatial detection of RNA target analytes in negative control samples using the methods of the present disclosure.
Figure 31:
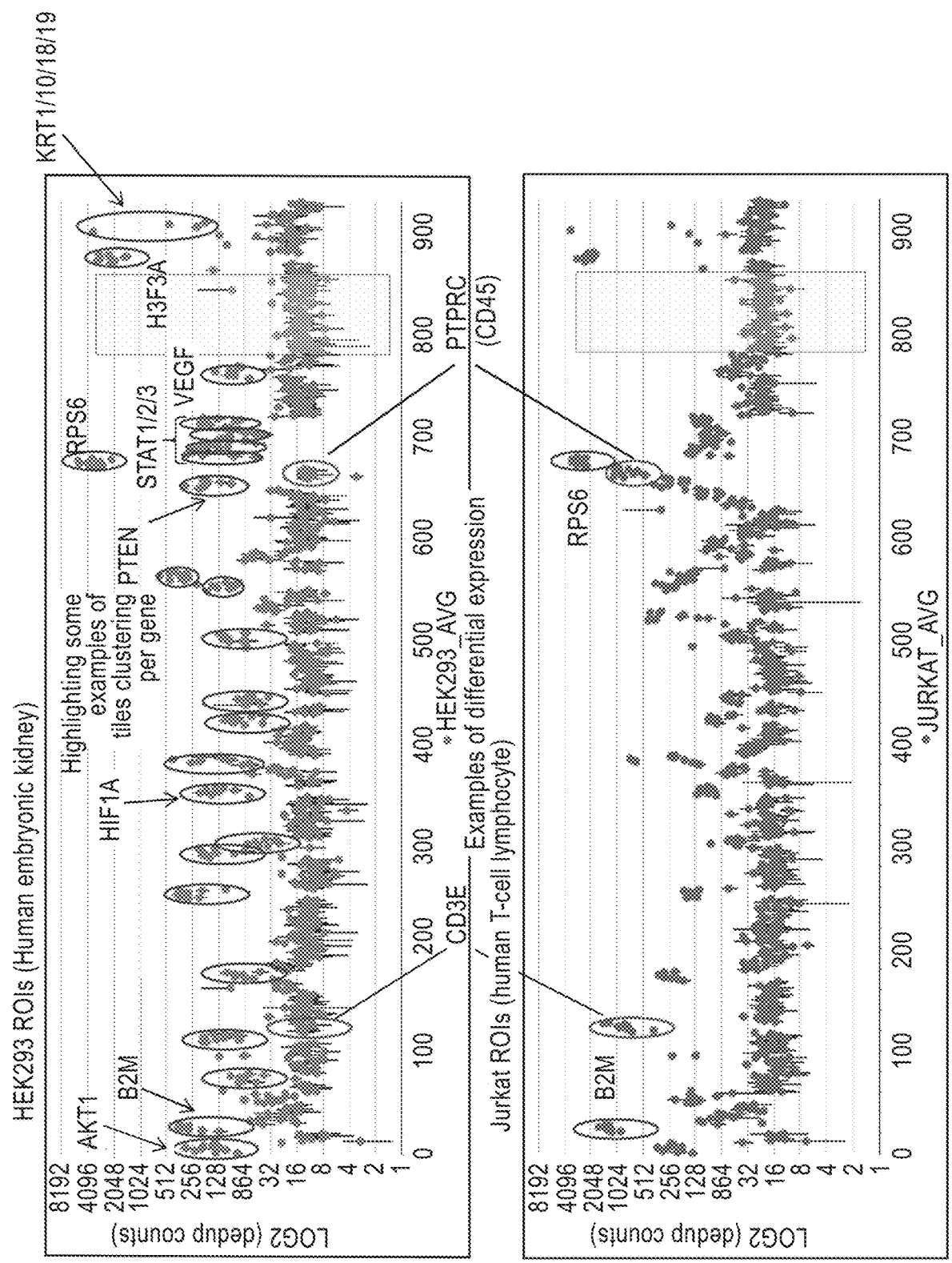
FIG. 31 is a series of graphs showing the spatial detection of RNA target analytes in a HEK293 sample (top panel) and a Jurkat cell sample (bottom panel) using the methods of the present disclosure.
Figure 32:
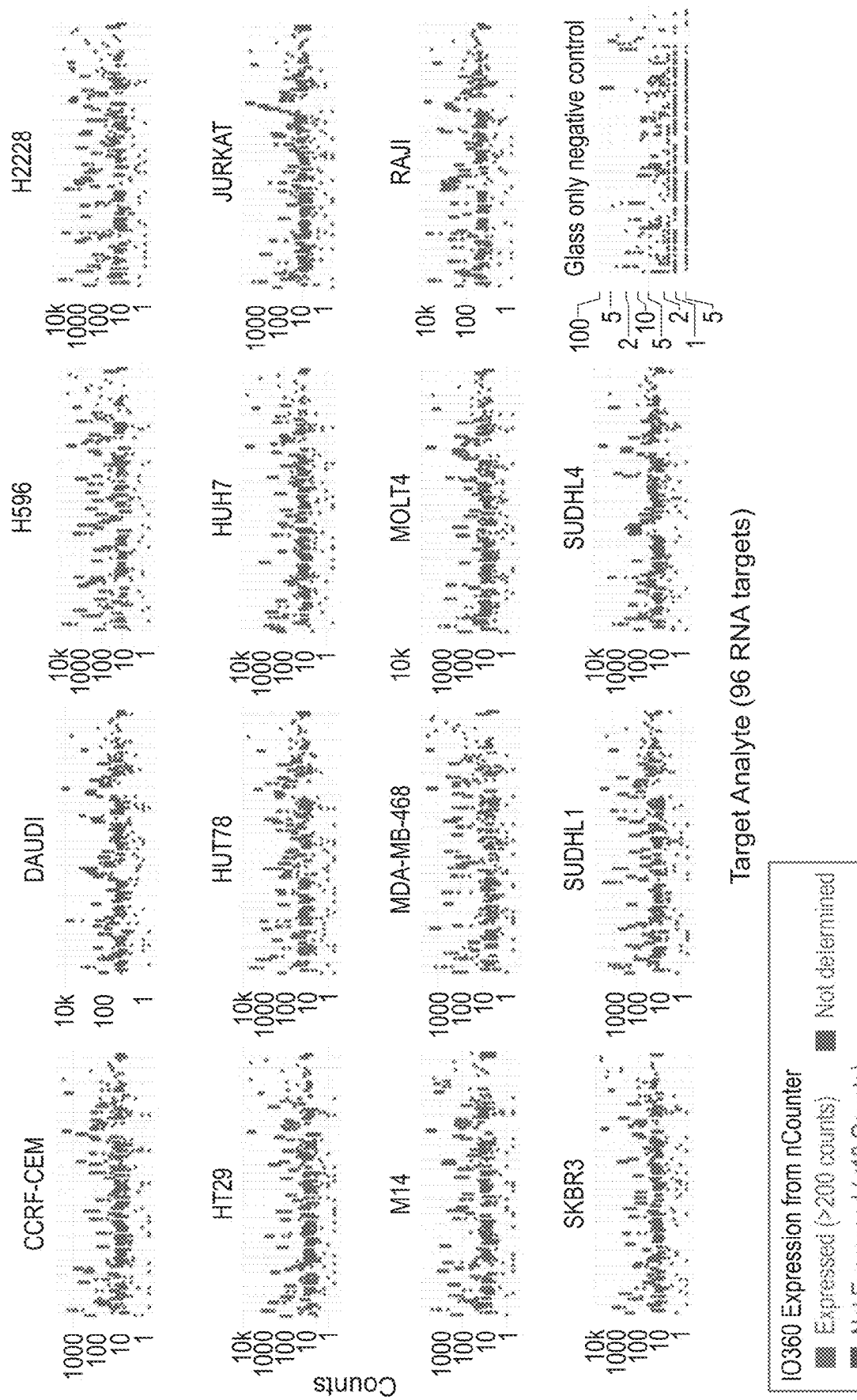
FIG. 32 is a series of graphs showing the spatial detection of RNA target analytes in sixteen FFPE samples using the methods of the present disclosure.
Figure 33:
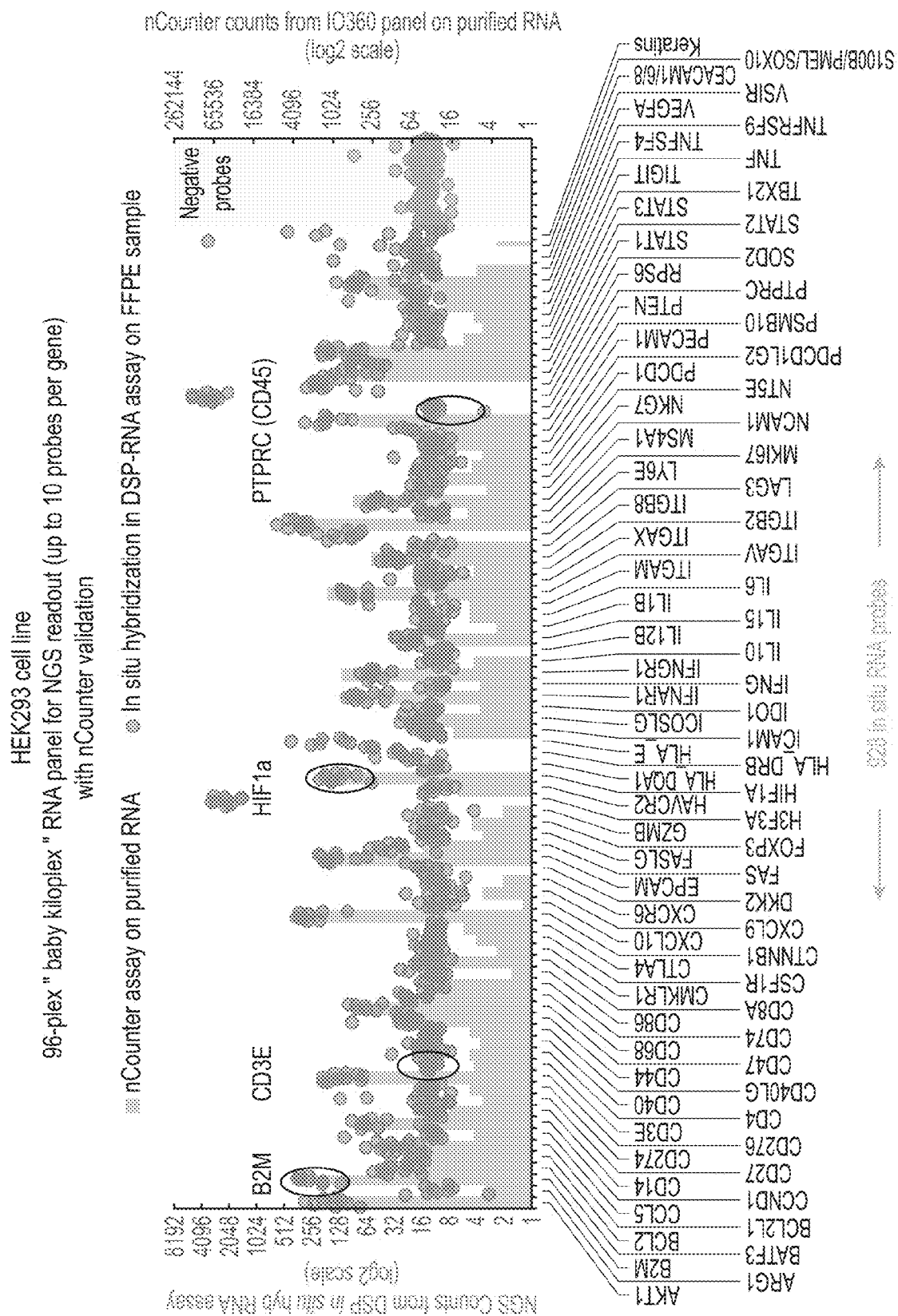
FIG. 33 is a graph showing the spatial detection of RNA target analytes in a HEK293 sample using the methods of the present disclosure.
Figure 34:
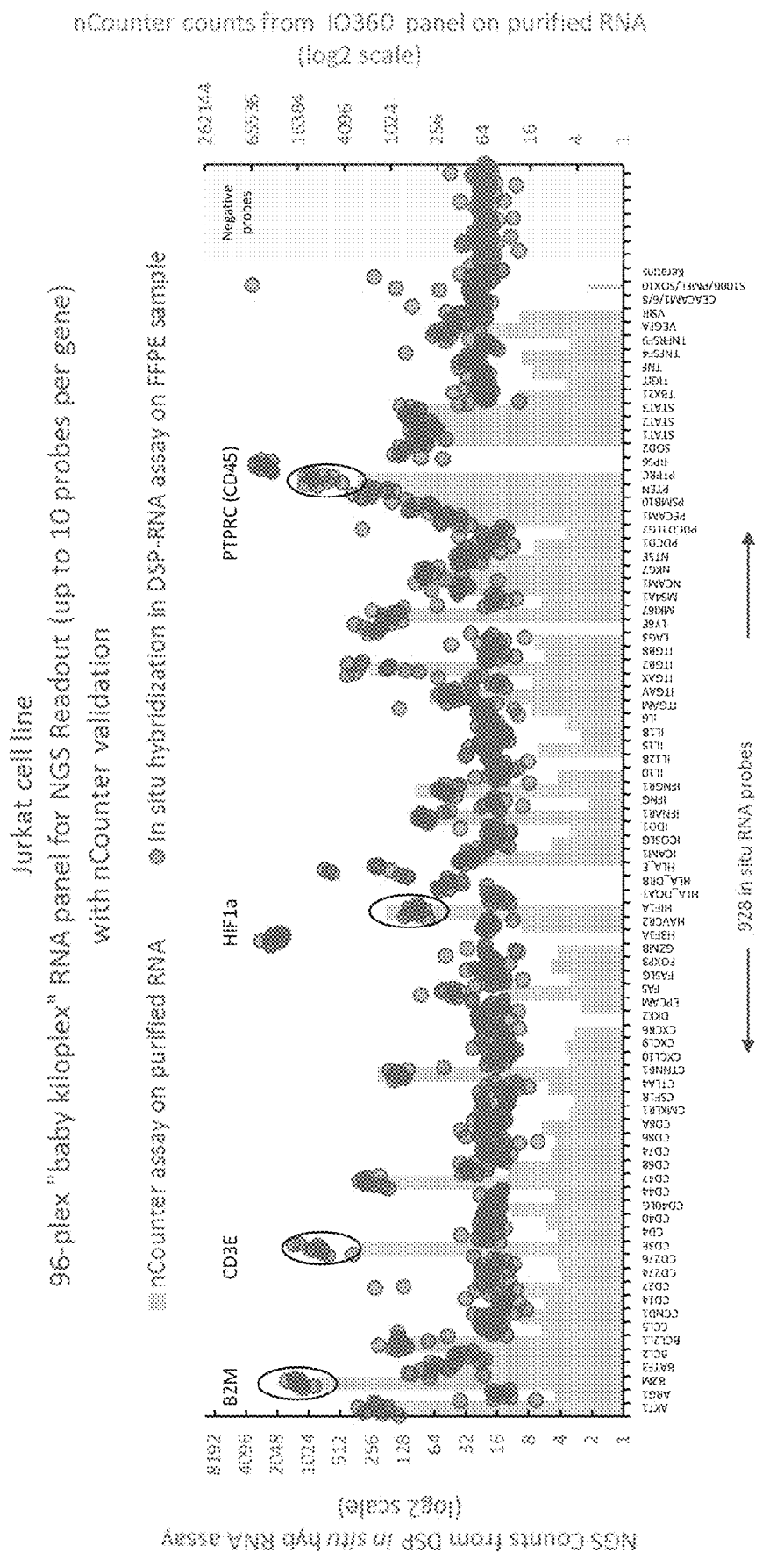
FIG. 34 is a graph showing the spatial detection of RNA target analytes in a Jurkat cell sample using the methods of the present disclosure.

FIG. 29 shows that a sufficient read depth was achieved using a MiSeq v3 flowcell. The top panel of FIG. 30 shows that none of the target RNAs were spatially detected for the glass negative control ROIs. Likewise, the bottom panel of FIG. 30 shows that nearly none of the target RNAs were detected in the negative control mouse 3T3 FFPE sample. Conversely, as shown in FIGS. 31, 33 and 34, specific target RNAs were successfully detected in the HEK293 (human embryonic kidney) FFPE sample and the Jurkat (human T-cell lymphocyte) FFPE sample. FIGS. 31, 33 and 34 show that clusters of "tiled" probes were detected for particular target RNAs, including AKT1, B2M, CD3E, HIF1A, PTEN, RPS6, STAT1, STAT2, STAT3, VEGF, PTPRC (CD45), and KRT1/10/18/19. These results indicated that there are certain target RNAs that are differentially transcribed in the two different cells lines. The results of this experiment were also verified using the NanoString nCounter system to identify the collected identifier oligonucleotides. As shown in FIG. 27, the results using the direct-PCR method of the present disclosure were consistent with the results obtained using the NanoString nCounter system.

What is claimed is:

1. A method comprising:
   a) collecting a plurality of oligonucleotides from a first location of a tissue sample under conditions that release the plurality of oligonucleotides from the first location of the tissue sample;
   b) collecting a plurality of oligonucleotides from a second location of the tissue sample under conditions that release the plurality of oligonucleotides from the second location of the tissue sample;
   c) synthesizing a first plurality of DNA products by performing a synthesis reaction that uses the plurality of oligonucleotides collected in step (a) as templates and incorporates at least one nucleic acid sequence that identifies the first location of the tissue sample into each of the first plurality of DNA products;
   d) synthesizing a second plurality of DNA products by performing a synthesis reaction that uses the plurality of oligonucleotides collected in step (b) as templates and incorporates at least one nucleic acid sequence that identifies the second location of the tissue sample into each of the second plurality of DNA products; and
   e) identifying the first plurality of DNA products and the second plurality of DNA products synthesized in step (c) and step (d) by sequencing the first plurality of DNA products and the second plurality of DNA products, thereby spatially detecting the plurality of oligonucleotides collected from the first location of the tissue sample and the plurality of oligonucleotides collected from the second location of the tissue sample.

2. The method of claim 1, wherein the tissue sample is immobilized onto a microscope slide.

3. The method of claim 2, wherein the microscope slide comprises a plurality of primers immobilized on the microscope slide.

4. The method of claim 3, wherein the plurality of primers is immobilized on the microscope slide at their 5' ends.

5. The method of claim 4, wherein each of step (c) and step (d) comprises performing a solid-phase amplification reaction, wherein the solid-phase amplification reaction is carried out on the microscope slide using the plurality of primers immobilized on the microscope slide.

6. The method of claim 1, wherein the sequencing step is performed using a next generation sequencing reaction.

7. The method of claim 1, further comprises amplifying a library using the first plurality of DNA products and the second plurality of DNA products as templates.

8. The method of claim 1, wherein the at least one nucleic acid sequence that identifies the first location of the tissue sample comprise at least one unique molecular identifier.

9. The method of claim 1, wherein the at least one nucleic acid sequence that identifies the second location of the tissue sample comprise at least one unique molecular identifier.

10. The method of claim 1, wherein the first plurality of DNA products further comprises at least one amplification primer binding site.

11. The method of claim 1, wherein the second plurality of DNA products further comprises at least one amplification primer binding site.

12. The method of claim 1, wherein steps (a) and (b) are performed simultaneously.

13. The method of claim 1, wherein steps (c) and (d) are performed simultaneously.

* * * * *

SEQUENCE LISTING

```
<160> NUMBER OF SEQ ID NOS: 175

<210> SEQ ID NO 1
<211> LENGTH: 34
<212> TYPE: DNA
<213> ORGANISM: Artificial Sequence
<220> FEATURE:
<223> OTHER INFORMATION: i7 sequence

<400> SEQUENCE: 1
agatcggaag agcacacgtc tgaactccag tcac                         34

<210> SEQ ID NO 2
<211> LENGTH: 30
<212> TYPE: DNA
<213> ORGANISM: Artificial Sequence
<220> FEATURE:
<223> OTHER INFORMATION: i5 sequence

<400> SEQUENCE: 2
acactctttc cctacacgac gctcttccga                              30

<210> SEQ ID NO 3
<211> LENGTH: 29
<212> TYPE: DNA
<213> ORGANISM: Artificial Sequence
<220> FEATURE:
<223> OTHER INFORMATION: P5 flow cell adapter

<400> SEQUENCE: 3
aatgatacgg cgaccaccga gatctacac                               29

<210> SEQ ID NO 4
<211> LENGTH: 24
<212> TYPE: DNA
<213> ORGANISM: Artificial Sequence
<220> FEATURE:
<223> OTHER INFORMATION: P7 flow cell adapter
```

<400> SEQUENCE: 4
atctcgtatg ccgtcttctg cttg					24

<210> SEQ ID NO 5
<211> LENGTH: 78
<212> TYPE: DNA
<213> ORGANISM: Artificial Sequence
<220> FEATURE:
<223> OTHER INFORMATION: DSP_NGS_i501 Primer

<400> SEQUENCE: 5
aatgatacgg cgaccaccga gatctacacg ctcagatata gcctacactc tttaagacga		60 cgtcgctatg gcctctcc						78

<210> SEQ ID NO 6
<211> LENGTH: 78
<212> TYPE: DNA
<213> ORGANISM: Artificial Sequence
<220> FEATURE:
<223> OTHER INFORMATION: DSP_NGS_i502 Primer

<400> SEQUENCE: 6
aatgatacgg cgaccaccga gatctacacg ctcagaatag aggcacactc tttaagacga		60 cgtcgctatg gcctctcc						78

<210> SEQ ID NO 7
<211> LENGTH: 78
<212> TYPE: DNA
<213> ORGANISM: Artificial Sequence
<220> FEATURE:
<223> OTHER INFORMATION: DSP_NGS_i503 Primer

<400> SEQUENCE: 7
aatgatacgg cgaccaccga gatctacacg ctcagaccta tcctacactc tttaagacga		60 cgtcgctatg gcctctcc						78

<210> SEQ ID NO 8
<211> LENGTH: 78
<212> TYPE: DNA
<213> ORGANISM: Artificial Sequence
<220> FEATURE:
<223> OTHER INFORMATION: DSP_NGS_i504 Primer

<400> SEQUENCE: 8
aatgatacgg cgaccaccga gatctacacg ctcagaggct ctgaacactc tttaagacga		60 cgtcgctatg gcctctcc						78

<210> SEQ ID NO 9
<211> LENGTH: 78
<212> TYPE: DNA
<213> ORGANISM: Artificial Sequence
<220> FEATURE:
<223> OTHER INFORMATION: DSP_NGS_i505 Primer

<400> SEQUENCE: 9
aatgatacgg cgaccaccga gatctacacg ctcagaaggc gaagacactc tttaagacga		60 cgtcgctatg gcctctcc						78

<210> SEQ ID NO 10
<211> LENGTH: 78
<212> TYPE: DNA
<213> ORGANISM: Artificial Sequence

```
<220> FEATURE:
<223> OTHER INFORMATION: DSP_NGS_i506 Primer

<400> SEQUENCE: 10
aatgatacgg cgaccaccga gatctacacg ctcagataat cttaacactc tttaagacga      60
cgtcgctatg gcctctcc                                                    78

<210> SEQ ID NO 11
<211> LENGTH: 78
<212> TYPE: DNA
<213> ORGANISM: Artificial Sequence
<220> FEATURE:
<223> OTHER INFORMATION: DSP_NGS_i507 Primer

<400> SEQUENCE: 11
aatgatacgg cgaccaccga gatctacacg ctcagacagg acgtacactc tttaagacga      60
cgtcgctatg gcctctcc                                                    78

<210> SEQ ID NO 12
<211> LENGTH: 78
<212> TYPE: DNA
<213> ORGANISM: Artificial Sequence
<220> FEATURE:
<223> OTHER INFORMATION: DSP_NGS_i508 Primer

<400> SEQUENCE: 12
aatgatacgg cgaccaccga gatctacacg ctcagagtac tgacacactc tttaagacga      60
cgtcgctatg gcctctcc                                                    78

<210> SEQ ID NO 13
<211> LENGTH: 66
<212> TYPE: DNA
<213> ORGANISM: Artificial Sequence
<220> FEATURE:
<223> OTHER INFORMATION: NEBNext i701 Primer

<400> SEQUENCE: 13
caagcagaag acggcatacg agatcgagta atgtgactgg agttcagacg tgtgctcttc      60
cgatct                                                                 66

<210> SEQ ID NO 14
<211> LENGTH: 66
<212> TYPE: DNA
<213> ORGANISM: Artificial Sequence
<220> FEATURE:
<223> OTHER INFORMATION: NEBNext i702 Primer

<400> SEQUENCE: 14
caagcagaag acggcatacg agattctccg gagtgactgg agttcagacg tgtgctcttc      60
cgatct                                                                 66

<210> SEQ ID NO 15
<211> LENGTH: 66
<212> TYPE: DNA
<213> ORGANISM: Artificial Sequence
<220> FEATURE:
<223> OTHER INFORMATION: NEBNext i703 Primer

<400> SEQUENCE: 15
caagcagaag acggcatacg agataatgag cggtgactgg agttcagacg tgtgctcttc      60
cgatct                                                                 66
```

```
<210> SEQ ID NO 16
<211> LENGTH: 66
<212> TYPE: DNA
<213> ORGANISM: Artificial Sequence
<220> FEATURE:
<223> OTHER INFORMATION: NEBNext i704 Primer

<400> SEQUENCE: 16
caagcagaag acggcatacg agatggaatc tcgtgactgg agttcagacg tgtgctcttc      60
cgatct                                                                66

<210> SEQ ID NO 17
<211> LENGTH: 66
<212> TYPE: DNA
<213> ORGANISM: Artificial Sequence
<220> FEATURE:
<223> OTHER INFORMATION: NEBNext i705 Primer

<400> SEQUENCE: 17
caagcagaag acggcatacg agatttctga atgtgactgg agttcagacg tgtgctcttc      60
cgatct                                                                66

<210> SEQ ID NO 18
<211> LENGTH: 66
<212> TYPE: DNA
<213> ORGANISM: Artificial Sequence
<220> FEATURE:
<223> OTHER INFORMATION: NEBNext i706 Primer

<400> SEQUENCE: 18
caagcagaag acggcatacg agatacgaat tcgtgactgg agttcagacg tgtgctcttc      60
cgatct                                                                66

<210> SEQ ID NO 19
<211> LENGTH: 66
<212> TYPE: DNA
<213> ORGANISM: Artificial Sequence
<220> FEATURE:
<223> OTHER INFORMATION: NEBNext i707 Primer

<400> SEQUENCE: 19
caagcagaag acggcatacg agatagcttc aggtgactgg agttcagacg tgtgctcttc      60
cgatct                                                                66

<210> SEQ ID NO 20
<211> LENGTH: 66
<212> TYPE: DNA
<213> ORGANISM: Artificial Sequence
<220> FEATURE:
<223> OTHER INFORMATION: NEBNext i708 Primer

<400> SEQUENCE: 20
caagcagaag acggcatacg agatgcgcat tagtgactgg agttcagacg tgtgctcttc      60
cgatct                                                                66

<210> SEQ ID NO 21
<211> LENGTH: 66
<212> TYPE: DNA
<213> ORGANISM: Artificial Sequence
<220> FEATURE:
<223> OTHER INFORMATION: NEBNext i709 Primer

<400> SEQUENCE: 21
```
caagcagaag acggcatacg agatcatagc cggtgactgg agttcagacg tgtgctcttc    60
cgatct                                                              66

<210> SEQ ID NO 22
<211> LENGTH: 66
<212> TYPE: DNA
<213> ORGANISM: Artificial Sequence
<220> FEATURE:
<223> OTHER INFORMATION: NEBNext i710 Primer

<400> SEQUENCE: 22
caagcagaag acggcatacg agatttcgcg gagtgactgg agttcagacg tgtgctcttc    60
cgatct                                                              66

<210> SEQ ID NO 23
<211> LENGTH: 66
<212> TYPE: DNA
<213> ORGANISM: Artificial Sequence
<220> FEATURE:
<223> OTHER INFORMATION: NEBNext i711 Primer

<400> SEQUENCE: 23
caagcagaag acggcatacg agatgcgcga gagtgactgg agttcagacg tgtgctcttc    60
cgatct                                                              66

<210> SEQ ID NO 24
<211> LENGTH: 66
<212> TYPE: DNA
<213> ORGANISM: Artificial Sequence
<220> FEATURE:
<223> OTHER INFORMATION: NEBNext i712 Primer

<400> SEQUENCE: 24
caagcagaag acggcatacg agatctatcg ctgtgactgg agttcagacg tgtgctcttc    60
cgatct                                                              66

<210> SEQ ID NO 25
<211> LENGTH: 34
<212> TYPE: DNA
<213> ORGANISM: Artificial Sequence
<220> FEATURE:
<223> OTHER INFORMATION: Spike-in primer

<400> SEQUENCE: 25
acactcttta agacgacgtc gctatggcct ctcc                               34

<210> SEQ ID NO 26
<211> LENGTH: 34
<212> TYPE: DNA
<213> ORGANISM: Artificial Sequence
<220> FEATURE:
<223> OTHER INFORMATION: Amplification primer binding site

<400> SEQUENCE: 26
gtgactggag ttcagacgtg tgctcttccg atct                               34

<210> SEQ ID NO 27
<211> LENGTH: 83
<212> TYPE: DNA
<213> ORGANISM: Artificial Sequence
<220> FEATURE:
<223> OTHER INFORMATION: P01_PriExtUMI15_tpt
<220> FEATURE:

-continued

<221> NAME/KEY: misc_feature
<222> LOCATION: (35)..(49)
<223> OTHER INFORMATION: n is a, c, g, or t

<400> SEQUENCE: 27
gtgactggag ttcagacgtg tgctcttccg atctnnnnnn nnnnnnnnnt tgaagcacac      60 cgttttctt tcttctttca cgg                                              83

<210> SEQ ID NO 28
<211> LENGTH: 83
<212> TYPE: DNA
<213> ORGANISM: Artificial Sequence
<220> FEATURE:
<223> OTHER INFORMATION: P03_PriExtUMI15_tpt
<220> FEATURE:
<221> NAME/KEY: misc_feature
<222> LOCATION: (35)..(49)
<223> OTHER INFORMATION: n is a, c, g, or t

<400> SEQUENCE: 28
gtgactggag ttcagacgtg tgctcttccg atctnnnnnn nnnnnnnna cccacaggtt      60 atacgggatt atccggttat cca                                             83

<210> SEQ ID NO 29
<211> LENGTH: 83
<212> TYPE: DNA
<213> ORGANISM: Artificial Sequence
<220> FEATURE:
<223> OTHER INFORMATION: P04_PriExtUMI15_tpt
<220> FEATURE:
<221> NAME/KEY: misc_feature
<222> LOCATION: (35)..(49)
<223> OTHER INFORMATION: n is a, c, g, or t

<400> SEQUENCE: 29
gtgactggag ttcagacgtg tgctcttccg atctnnnnnn nnnnnnnnc gacaccgagt      60 tcgaccgtta tgttggtagg atc                                             83

<210> SEQ ID NO 30
<211> LENGTH: 83
<212> TYPE: DNA
<213> ORGANISM: Artificial Sequence
<220> FEATURE:
<223> OTHER INFORMATION: P05_PriExtUMI15_tpt
<220> FEATURE:
<221> NAME/KEY: misc_feature
<222> LOCATION: (35)..(49)
<223> OTHER INFORMATION: n is a, c, g, or t

<400> SEQUENCE: 30
gtgactggag ttcagacgtg tgctcttccg atctnnnnnn nnnnnnnnc ggtgtgtaag      60 cgtaacgatg ttggtgtcgc tct                                             83

<210> SEQ ID NO 31
<211> LENGTH: 83
<212> TYPE: DNA
<213> ORGANISM: Artificial Sequence
<220> FEATURE:
<223> OTHER INFORMATION: P06_PriExtUMI15_tpt
<220> FEATURE:
<221> NAME/KEY: misc_feature
<222> LOCATION: (35)..(49)
<223> OTHER INFORMATION: n is a, c, g, or t

<400> SEQUENCE: 31
gtgactggag ttcagacgtg tgctcttccg atctnnnnnn nnnnnnnnc agacactgcg      60 acaactcacg atcatgacac aga          83

<210> SEQ ID NO 32
<211> LENGTH: 83
<212> TYPE: DNA
<213> ORGANISM: Artificial Sequence
<220> FEATURE:
<223> OTHER INFORMATION: P07_PriExtUMI15_tpt
<220> FEATURE:
<221> NAME/KEY: misc_feature
<222> LOCATION: (35)..(49)
<223> OTHER INFORMATION: n is a, c, g, or t

<400> SEQUENCE: 32
gtgactggag ttcagacgtg tgctcttccg atctnnnnnn nnnnnnnnna tattctgtac     60
tcagtgccta tccacctaat agg          83

<210> SEQ ID NO 33
<211> LENGTH: 83
<212> TYPE: DNA
<213> ORGANISM: Artificial Sequence
<220> FEATURE:
<223> OTHER INFORMATION: P09_PriExtUMI15_tpt
<220> FEATURE:
<221> NAME/KEY: misc_feature
<222> LOCATION: (35)..(49)
<223> OTHER INFORMATION: n is a, c, g, or t

<400> SEQUENCE: 33
gtgactggag ttcagacgtg tgctcttccg atctnnnnnn nnnnnnnnnt tcagttataa     60
tgtgtccagc agaagcagga att          83

<210> SEQ ID NO 34
<211> LENGTH: 83
<212> TYPE: DNA
<213> ORGANISM: Artificial Sequence
<220> FEATURE:
<223> OTHER INFORMATION: P11_PriExtUMI15_tpt
<220> FEATURE:
<221> NAME/KEY: misc_feature
<222> LOCATION: (35)..(49)
<223> OTHER INFORMATION: n is a, c, g, or t

<400> SEQUENCE: 34
gtgactggag ttcagacgtg tgctcttccg atctnnnnnn nnnnnnnnng tcctttgttg     60
ggcggaccgt aatgaggaat ttg          83

<210> SEQ ID NO 35
<211> LENGTH: 83
<212> TYPE: DNA
<213> ORGANISM: Artificial Sequence
<220> FEATURE:
<223> OTHER INFORMATION: P13_PriExtUMI15_tpt
<220> FEATURE:
<221> NAME/KEY: misc_feature
<222> LOCATION: (35)..(49)
<223> OTHER INFORMATION: n is a, c, g, or t

<400> SEQUENCE: 35
gtgactggag ttcagacgtg tgctcttccg atctnnnnnn nnnnnnnng atgagacttc     60 tacatgtccg atgttttgt gct          83

<210> SEQ ID NO 36
<211> LENGTH: 83
<212> TYPE: DNA

```
<213> ORGANISM: Artificial Sequence
<220> FEATURE:
<223> OTHER INFORMATION: P15_PriExtUMI15_tpt
<220> FEATURE:
<221> NAME/KEY: misc_feature
<222> LOCATION: (35)..(49)
<223> OTHER INFORMATION: n is a, c, g, or t

<400> SEQUENCE: 36
gtgactggag ttcagacgtg tgctcttccg atctnnnnnn nnnnnnnnna ctcacacata    60
gtactgacac gtaagatagg atg                                            83

<210> SEQ ID NO 37
<211> LENGTH: 83
<212> TYPE: DNA
<213> ORGANISM: Artificial Sequence
<220> FEATURE:
<223> OTHER INFORMATION: P16_PriExtUMI15_tpt
<220> FEATURE:
<221> NAME/KEY: misc_feature
<222> LOCATION: (35)..(49)
<223> OTHER INFORMATION: n is a, c, g, or t

<400> SEQUENCE: 37
gtgactggag ttcagacgtg tgctcttccg atctnnnnnn nnnnnnnnnt taccctatct    60
cgtctatgta cgtcaggctg aat                                            83

<210> SEQ ID NO 38
<211> LENGTH: 83
<212> TYPE: DNA
<213> ORGANISM: Artificial Sequence
<220> FEATURE:
<223> OTHER INFORMATION: P17_PriExtUMI15_tpt
<220> FEATURE:
<221> NAME/KEY: misc_feature
<222> LOCATION: (35)..(49)
<223> OTHER INFORMATION: n is a, c, g, or t

<400> SEQUENCE: 38
gtgactggag ttcagacgtg tgctcttccg atctnnnnnn nnnnnnnnna tcaacgtagg    60
gtaaggtcat atttttacct tac                                            83

<210> SEQ ID NO 39
<211> LENGTH: 83
<212> TYPE: DNA
<213> ORGANISM: Artificial Sequence
<220> FEATURE:
<223> OTHER INFORMATION: P18_PriExtUMI15_tpt
<220> FEATURE:
<221> NAME/KEY: misc_feature
<222> LOCATION: (35)..(49)
<223> OTHER INFORMATION: n is a, c, g, or t

<400> SEQUENCE: 39
gtgactggag ttcagacgtg tgctcttccg atctnnnnnn nnnnnnnnnt tccctctttc    60
tccgcttatg gatgaaagga cag                                            83

<210> SEQ ID NO 40
<211> LENGTH: 83
<212> TYPE: DNA
<213> ORGANISM: Artificial Sequence
<220> FEATURE:
<223> OTHER INFORMATION: P19_PriExtUMI15_tpt
<220> FEATURE:
<221> NAME/KEY: misc_feature
<222> LOCATION: (35)..(49)
<223> OTHER INFORMATION: n is a, c, g, or t
```

```
<400> SEQUENCE: 40
gtgactggag ttcagacgtg tgctcttccg atctnnnnnn nnnnnnnnnc ctgcacagtg    60
agtttctttc actctaactc tct                                           83

<210> SEQ ID NO 41
<211> LENGTH: 83
<212> TYPE: DNA
<213> ORGANISM: Artificial Sequence
<220> FEATURE:
<223> OTHER INFORMATION: P20_PriExtUMI15_tpt
<220> FEATURE:
<221> NAME/KEY: misc_feature
<222> LOCATION: (35)..(49)
<223> OTHER INFORMATION: n is a, c, g, or t

<400> SEQUENCE: 41
gtgactggag ttcagacgtg tgctcttccg atctnnnnnn nnnnnnnnnt gtcgctctag    60
tgtgactttt ccacctcgca tct                                           83

<210> SEQ ID NO 42
<211> LENGTH: 83
<212> TYPE: DNA
<213> ORGANISM: Artificial Sequence
<220> FEATURE:
<223> OTHER INFORMATION: P21_PriExtUMI15_tpt
<220> FEATURE:
<221> NAME/KEY: misc_feature
<222> LOCATION: (35)..(49)
<223> OTHER INFORMATION: n is a, c, g, or t

<400> SEQUENCE: 42
gtgactggag ttcagacgtg tgctcttccg atctnnnnnn nnnnnnnna tatctttctc    60 gggtaaagat taggcgtccg ata                                           83

<210> SEQ ID NO 43
<211> LENGTH: 83
<212> TYPE: DNA
<213> ORGANISM: Artificial Sequence
<220> FEATURE:
<223> OTHER INFORMATION: P23_PriExtUMI15_tpt
<220> FEATURE:
<221> NAME/KEY: misc_feature
<222> LOCATION: (35)..(49)
<223> OTHER INFORMATION: n is a, c, g, or t

<400> SEQUENCE: 43
gtgactggag ttcagacgtg tgctcttccg atctnnnnnn nnnnnnnnnc gattagccgt    60
agacgcaact cattgccgaa gat                                           83

<210> SEQ ID NO 44
<211> LENGTH: 83
<212> TYPE: DNA
<213> ORGANISM: Artificial Sequence
<220> FEATURE:
<223> OTHER INFORMATION: P24_PriExtUMI15_tpt
<220> FEATURE:
<221> NAME/KEY: misc_feature
<222> LOCATION: (35)..(49)
<223> OTHER INFORMATION: n is a, c, g, or t

<400> SEQUENCE: 44
gtgactggag ttcagacgtg tgctcttccg atctnnnnnn nnnnnnnnnt gtgagcattt    60
cagtacgagt gatgcagata aac                                           83
```

<210> SEQ ID NO 45
<211> LENGTH: 83
<212> TYPE: DNA
<213> ORGANISM: Artificial Sequence
<220> FEATURE:
<223> OTHER INFORMATION: P25_PriExtUMI15_tpt
<220> FEATURE:
<221> NAME/KEY: misc_feature
<222> LOCATION: (35)..(49)
<223> OTHER INFORMATION: n is a, c, g, or t

<400> SEQUENCE: 45
gtgactggag ttcagacgtg tgctcttccg atctnnnnnn nnnnnnnnnt atagttacca    60
agtactatgg gttggtggaa gcc                                           83

<210> SEQ ID NO 46
<211> LENGTH: 83
<212> TYPE: DNA
<213> ORGANISM: Artificial Sequence
<220> FEATURE:
<223> OTHER INFORMATION: P26_PriExtUMI15_tpt
<220> FEATURE:
<221> NAME/KEY: misc_feature
<222> LOCATION: (35)..(49)
<223> OTHER INFORMATION: n is a, c, g, or t

<400> SEQUENCE: 46
gtgactggag ttcagacgtg tgctcttccg atctnnnnnn nnnnnnnnnc caattatact    60
gtctgttatg ttctcggata agc                                           83

<210> SEQ ID NO 47
<211> LENGTH: 83
<212> TYPE: DNA
<213> ORGANISM: Artificial Sequence
<220> FEATURE:
<223> OTHER INFORMATION: P27_PriExtUMI15_tpt
<220> FEATURE:
<221> NAME/KEY: misc_feature
<222> LOCATION: (35)..(49)
<223> OTHER INFORMATION: n is a, c, g, or t

<400> SEQUENCE: 47
gtgactggag ttcagacgtg tgctcttccg atctnnnnnn nnnnnnnnnt caggtgcttg    60
taggctcatg atagggtaa tgc                                            83

<210> SEQ ID NO 48
<211> LENGTH: 83
<212> TYPE: DNA
<213> ORGANISM: Artificial Sequence
<220> FEATURE:
<223> OTHER INFORMATION: P28_PriExtUMI15_tpt
<220> FEATURE:
<221> NAME/KEY: misc_feature
<222> LOCATION: (35)..(49)
<223> OTHER INFORMATION: n is a, c, g, or t

<400> SEQUENCE: 48
gtgactggag ttcagacgtg tgctcttccg atctnnnnnn nnnnnnnnnc tctgctgtaa    60
tctcagctcc acttgtttct aag                                           83

<210> SEQ ID NO 49
<211> LENGTH: 83
<212> TYPE: DNA
<213> ORGANISM: Artificial Sequence
<220> FEATURE:
<223> OTHER INFORMATION: P29_PriExtUMI15_tpt
<220> FEATURE:
<221> NAME/KEY: misc_feature
<222> LOCATION: (35)..(49)
<223> OTHER INFORMATION: n is a, c, g, or t

<400> SEQUENCE: 49
gtgactggag ttcagacgtg tgctcttccg atctnnnnnn nnnnnnnnng tgcatattgc    60
agctgagcca gctcaatttg aag    83

<210> SEQ ID NO 50
<211> LENGTH: 83
<212> TYPE: DNA
<213> ORGANISM: Artificial Sequence
<220> FEATURE:
<223> OTHER INFORMATION: P30_PriExtUMI15_tpt
<220> FEATURE:
<221> NAME/KEY: misc_feature
<222> LOCATION: (35)..(49)
<223> OTHER INFORMATION: n is a, c, g, or t

<400> SEQUENCE: 50
gtgactggag ttcagacgtg tgctcttccg atctnnnnnn nnnnnnnnnc cgttgattta    60
cgcaacagcg gcttatatag ctc    83

<210> SEQ ID NO 51
<211> LENGTH: 83
<212> TYPE: DNA
<213> ORGANISM: Artificial Sequence
<220> FEATURE:
<223> OTHER INFORMATION: P31_PriExtUMI15_tpt
<220> FEATURE:
<221> NAME/KEY: misc_feature
<222> LOCATION: (35)..(49)
<223> OTHER INFORMATION: n is a, c, g, or t

<400> SEQUENCE: 51
gtgactggag ttcagacgtg tgctcttccg atctnnnnnn nnnnnnnnnc atcatcgaca    60
gttcgcagcc ctataacatg ata    83

<210> SEQ ID NO 52
<211> LENGTH: 83
<212> TYPE: DNA
<213> ORGANISM: Artificial Sequence
<220> FEATURE:
<223> OTHER INFORMATION: P32_PriExtUMI15_tpt
<220> FEATURE:
<221> NAME/KEY: misc_feature
<222> LOCATION: (35)..(49)
<223> OTHER INFORMATION: n is a, c, g, or t

<400> SEQUENCE: 52
gtgactggag ttcagacgtg tgctcttccg atctnnnnnn nnnnnnnnna tcgcaggatg    60
gtacagcatc atacatgatg agc    83

<210> SEQ ID NO 53
<211> LENGTH: 83
<212> TYPE: DNA
<213> ORGANISM: Artificial Sequence
<220> FEATURE:
<223> OTHER INFORMATION: P33_PriExtUMI15_tpt
<220> FEATURE:
<221> NAME/KEY: misc_feature
<222> LOCATION: (35)..(49)
<223> OTHER INFORMATION: n is a, c, g, or t

<400> SEQUENCE: 53

```
gtgactggag ttcagacgtg tgctcttccg atctnnnnnn nnnnnnnnna tcgcaggatg    60
gtacagcatc atacatgatg agc                                           83
```

<210> SEQ ID NO 54
<211> LENGTH: 83
<212> TYPE: DNA
<213> ORGANISM: Artificial Sequence
<220> FEATURE:
<223> OTHER INFORMATION: P34_PriExtUMI15_tpt
<220> FEATURE:
<221> NAME/KEY: misc_feature
<222> LOCATION: (35)..(49)
<223> OTHER INFORMATION: n is a, c, g, or t

<400> SEQUENCE: 54

```
gtgactggag ttcagacgtg tgctcttccg atctnnnnnn nnnnnnnnna tggcggtttc    60
gggtcctgca ctattcctaa taa                                           83
```

<210> SEQ ID NO 55
<211> LENGTH: 83
<212> TYPE: DNA
<213> ORGANISM: Artificial Sequence
<220> FEATURE:
<223> OTHER INFORMATION: P35_PriExtUMI15_tpt
<220> FEATURE:
<221> NAME/KEY: misc_feature
<222> LOCATION: (35)..(49)
<223> OTHER INFORMATION: n is a, c, g, or t

<400> SEQUENCE: 55

```
gtgactggag ttcagacgtg tgctcttccg atctnnnnnn nnnnnnnnnc cagtacgggt    60
actaataagt gtcatatcta ttg                                           83
```

<210> SEQ ID NO 56
<211> LENGTH: 83
<212> TYPE: DNA
<213> ORGANISM: Artificial Sequence
<220> FEATURE:
<223> OTHER INFORMATION: P36_PriExtUMI15_tpt
<220> FEATURE:
<221> NAME/KEY: misc_feature
<222> LOCATION: (35)..(49)
<223> OTHER INFORMATION: n is a, c, g, or t

<400> SEQUENCE: 56

```
gtgactggag ttcagacgtg tgctcttccg atctnnnnnn nnnnnnnnnt gttggagagg    60
ttagaggtga ggaggcgaag ata                                           83
```

<210> SEQ ID NO 57
<211> LENGTH: 66
<212> TYPE: DNA
<213> ORGANISM: Artificial Sequence
<220> FEATURE:
<223> OTHER INFORMATION: Reverse primer

<400> SEQUENCE: 57

```
caagcagaag acggcatacg agatgtcggt aagtgactgg agttcagacg tgtgctcttc    60
cgatct                                                              66
```

<210> SEQ ID NO 58
<211> LENGTH: 66
<212> TYPE: DNA
<213> ORGANISM: Artificial Sequence
<220> FEATURE:
<223> OTHER INFORMATION: Reverse primer

```
<400> SEQUENCE: 58
caagcagaag acggcatacg agataggtca ctgtgactgg agttcagacg tgtgctcttc      60
cgatct                                                                66

<210> SEQ ID NO 59
<211> LENGTH: 66
<212> TYPE: DNA
<213> ORGANISM: Artificial Sequence
<220> FEATURE:
<223> OTHER INFORMATION: Reverse primer

<400> SEQUENCE: 59
caagcagaag acggcatacg agatgaatcc gagtgactgg agttcagacg tgtgctcttc      60
cgatct                                                                66

<210> SEQ ID NO 60
<211> LENGTH: 66
<212> TYPE: DNA
<213> ORGANISM: Artificial Sequence
<220> FEATURE:
<223> OTHER INFORMATION: Reverse primer

<400> SEQUENCE: 60
caagcagaag acggcatacg agatgtacct tggtgactgg agttcagacg tgtgctcttc      60
cgatct                                                                66

<210> SEQ ID NO 61
<211> LENGTH: 66
<212> TYPE: DNA
<213> ORGANISM: Artificial Sequence
<220> FEATURE:
<223> OTHER INFORMATION: Reverse primer

<400> SEQUENCE: 61
caagcagaag acggcatacg agatcatgag gagtgactgg agttcagacg tgtgctcttc      60
cgatct                                                                66

<210> SEQ ID NO 62
<211> LENGTH: 66
<212> TYPE: DNA
<213> ORGANISM: Artificial Sequence
<220> FEATURE:
<223> OTHER INFORMATION: Reverse primer

<400> SEQUENCE: 62
caagcagaag acggcatacg agattgactg acgtgactgg agttcagacg tgtgctcttc      60
cgatct                                                                66

<210> SEQ ID NO 63
<211> LENGTH: 66
<212> TYPE: DNA
<213> ORGANISM: Artificial Sequence
<220> FEATURE:
<223> OTHER INFORMATION: Reverse primer

<400> SEQUENCE: 63
caagcagaag acggcatacg agatcgtatt cggtgactgg agttcagacg tgtgctcttc      60
cgatct                                                                66

<210> SEQ ID NO 64
```

```
<211> LENGTH: 66
<212> TYPE: DNA
<213> ORGANISM: Artificial Sequence
<220> FEATURE:
<223> OTHER INFORMATION: Reverse primer

<400> SEQUENCE: 64
caagcagaag acggcatacg agatctccta gagtgactgg agttcagacg tgtgctcttc     60
cgatct                                                                66

<210> SEQ ID NO 65
<211> LENGTH: 66
<212> TYPE: DNA
<213> ORGANISM: Artificial Sequence
<220> FEATURE:
<223> OTHER INFORMATION: Reverse primer

<400> SEQUENCE: 65
caagcagaag acggcatacg agattagttg cggtgactgg agttcagacg tgtgctcttc     60
cgatct                                                                66

<210> SEQ ID NO 66
<211> LENGTH: 66
<212> TYPE: DNA
<213> ORGANISM: Artificial Sequence
<220> FEATURE:
<223> OTHER INFORMATION: Reverse primer

<400> SEQUENCE: 66
caagcagaag acggcatacg agatgagata cggtgactgg agttcagacg tgtgctcttc     60
cgatct                                                                66

<210> SEQ ID NO 67
<211> LENGTH: 66
<212> TYPE: DNA
<213> ORGANISM: Artificial Sequence
<220> FEATURE:
<223> OTHER INFORMATION: Reverse primer

<400> SEQUENCE: 67
caagcagaag acggcatacg agataggtgt acgtgactgg agttcagacg tgtgctcttc     60
cgatct                                                                66

<210> SEQ ID NO 68
<211> LENGTH: 66
<212> TYPE: DNA
<213> ORGANISM: Artificial Sequence
<220> FEATURE:
<223> OTHER INFORMATION: Reverse primer

<400> SEQUENCE: 68
caagcagaag acggcatacg agattaatgc cggtgactgg agttcagacg tgtgctcttc     60
cgatct                                                                66

<210> SEQ ID NO 69
<211> LENGTH: 66
<212> TYPE: DNA
<213> ORGANISM: Artificial Sequence
<220> FEATURE:
<223> OTHER INFORMATION: Reverse primer

<400> SEQUENCE: 69
caagcagaag acggcatacg agattcagac gagtgactgg agttcagacg tgtgctcttc     60
``` cgatct 66

<210> SEQ ID NO 70
<211> LENGTH: 66
<212> TYPE: DNA
<213> ORGANISM: Artificial Sequence
<220> FEATURE:
<223> OTHER INFORMATION: Reverse primer

<400> SEQUENCE: 70
caagcagaag acggcatacg agatgatagg ctgtgactgg agttcagacg tgtgctcttc    60
cgatct                                                               66

<210> SEQ ID NO 71
<211> LENGTH: 66
<212> TYPE: DNA
<213> ORGANISM: Artificial Sequence
<220> FEATURE:
<223> OTHER INFORMATION: Reverse primer

<400> SEQUENCE: 71
caagcagaag acggcatacg agattggtac aggtgactgg agttcagacg tgtgctcttc    60
cgatct                                                               66

<210> SEQ ID NO 72
<211> LENGTH: 66
<212> TYPE: DNA
<213> ORGANISM: Artificial Sequence
<220> FEATURE:
<223> OTHER INFORMATION: Reverse primer

<400> SEQUENCE: 72
caagcagaag acggcatacg agatcaaggt ctgtgactgg agttcagacg tgtgctcttc    60
cgatct                                                               66

<210> SEQ ID NO 73
<211> LENGTH: 66
<212> TYPE: DNA
<213> ORGANISM: Artificial Sequence
<220> FEATURE:
<223> OTHER INFORMATION: Reverse primer

<400> SEQUENCE: 73
caagcagaag acggcatacg agatgctatc ctgtgactgg agttcagacg tgtgctcttc    60
cgatct                                                               66

<210> SEQ ID NO 74
<211> LENGTH: 66
<212> TYPE: DNA
<213> ORGANISM: Artificial Sequence
<220> FEATURE:
<223> OTHER INFORMATION: Reverse primer

<400> SEQUENCE: 74
caagcagaag acggcatacg agatatggaa gggtgactgg agttcagacg tgtgctcttc    60
cgatct                                                               66

<210> SEQ ID NO 75
<211> LENGTH: 66
<212> TYPE: DNA
<213> ORGANISM: Artificial Sequence
<220> FEATURE:

```
<223> OTHER INFORMATION: Reverse primer

<400> SEQUENCE: 75
caagcagaag acggcatacg agattcaagg acgtgactgg agttcagacg tgtgctcttc      60
cgatct                                                                66

<210> SEQ ID NO 76
<211> LENGTH: 66
<212> TYPE: DNA
<213> ORGANISM: Artificial Sequence
<220> FEATURE:
<223> OTHER INFORMATION: Reverse primer

<400> SEQUENCE: 76
caagcagaag acggcatacg agatgttacg cagtgactgg agttcagacg tgtgctcttc      60
cgatct                                                                66

<210> SEQ ID NO 77
<211> LENGTH: 66
<212> TYPE: DNA
<213> ORGANISM: Artificial Sequence
<220> FEATURE:
<223> OTHER INFORMATION: Reverse primer

<400> SEQUENCE: 77
caagcagaag acggcatacg agatagtctg tggtgactgg agttcagacg tgtgctcttc      60
cgatct                                                                66

<210> SEQ ID NO 78
<211> LENGTH: 66
<212> TYPE: DNA
<213> ORGANISM: Artificial Sequence
<220> FEATURE:
<223> OTHER INFORMATION: Reverse primer

<400> SEQUENCE: 78
caagcagaag acggcatacg agatgcacgt aagtgactgg agttcagacg tgtgctcttc      60
cgatct                                                                66

<210> SEQ ID NO 79
<211> LENGTH: 66
<212> TYPE: DNA
<213> ORGANISM: Artificial Sequence
<220> FEATURE:
<223> OTHER INFORMATION: Reverse primer

<400> SEQUENCE: 79
caagcagaag acggcatacg agataacctt gggtgactgg agttcagacg tgtgctcttc      60
cgatct                                                                66

<210> SEQ ID NO 80
<211> LENGTH: 66
<212> TYPE: DNA
<213> ORGANISM: Artificial Sequence
<220> FEATURE:
<223> OTHER INFORMATION: Reverse primer

<400> SEQUENCE: 80
caagcagaag acggcatacg agatattgcg tggtgactgg agttcagacg tgtgctcttc      60
cgatct                                                                66
```

```
<210> SEQ ID NO 81
<211> LENGTH: 66
<212> TYPE: DNA
<213> ORGANISM: Artificial Sequence
<220> FEATURE:
<223> OTHER INFORMATION: Reverse primer

<400> SEQUENCE: 81
caagcagaag acggcatacg agatacctgg aagtgactgg agttcagacg tgtgctcttc    60
cgatct                                                               66

<210> SEQ ID NO 82
<211> LENGTH: 66
<212> TYPE: DNA
<213> ORGANISM: Artificial Sequence
<220> FEATURE:
<223> OTHER INFORMATION: Reverse primer

<400> SEQUENCE: 82
caagcagaag acggcatacg agatggagat gagtgactgg agttcagacg tgtgctcttc    60
cgatct                                                               66

<210> SEQ ID NO 83
<211> LENGTH: 66
<212> TYPE: DNA
<213> ORGANISM: Artificial Sequence
<220> FEATURE:
<223> OTHER INFORMATION: Reverse primer

<400> SEQUENCE: 83
caagcagaag acggcatacg agatgtactc tcgtgactgg agttcagacg tgtgctcttc    60
cgatct                                                               66

<210> SEQ ID NO 84
<211> LENGTH: 66
<212> TYPE: DNA
<213> ORGANISM: Artificial Sequence
<220> FEATURE:
<223> OTHER INFORMATION: Reverse primer

<400> SEQUENCE: 84
caagcagaag acggcatacg agatgtaacg acgtgactgg agttcagacg tgtgctcttc    60
cgatct                                                               66

<210> SEQ ID NO 85
<211> LENGTH: 66
<212> TYPE: DNA
<213> ORGANISM: Artificial Sequence
<220> FEATURE:
<223> OTHER INFORMATION: Reverse primer

<400> SEQUENCE: 85
caagcagaag acggcatacg agatattcct ccgtgactgg agttcagacg tgtgctcttc    60
cgatct                                                               66

<210> SEQ ID NO 86
<211> LENGTH: 66
<212> TYPE: DNA
<213> ORGANISM: Artificial Sequence
<220> FEATURE:
<223> OTHER INFORMATION: Reverse primer

<400> SEQUENCE: 86
```
caagcagaag acggcatacg agatgtgttc ctgtgactgg agttcagacg tgtgctcttc    60
cgatct    66

<210> SEQ ID NO 87
<211> LENGTH: 66
<212> TYPE: DNA
<213> ORGANISM: Artificial Sequence
<220> FEATURE:
<223> OTHER INFORMATION: Reverse primer

<400> SEQUENCE: 87
caagcagaag acggcatacg agataagcac tggtgactgg agttcagacg tgtgctcttc    60
cgatct    66

<210> SEQ ID NO 88
<211> LENGTH: 66
<212> TYPE: DNA
<213> ORGANISM: Artificial Sequence
<220> FEATURE:
<223> OTHER INFORMATION: Reverse primer

<400> SEQUENCE: 88
caagcagaag acggcatacg agatctagca aggtgactgg agttcagacg tgtgctcttc    60
cgatct    66

<210> SEQ ID NO 89
<211> LENGTH: 66
<212> TYPE: DNA
<213> ORGANISM: Artificial Sequence
<220> FEATURE:
<223> OTHER INFORMATION: Reverse primer

<400> SEQUENCE: 89
caagcagaag acggcatacg agattgcttc cagtgactgg agttcagacg tgtgctcttc    60
cgatct    66

<210> SEQ ID NO 90
<211> LENGTH: 66
<212> TYPE: DNA
<213> ORGANISM: Artificial Sequence
<220> FEATURE:
<223> OTHER INFORMATION: Reverse primer

<400> SEQUENCE: 90
caagcagaag acggcatacg agatgcttag ctgtgactgg agttcagacg tgtgctcttc    60
cgatct    66

<210> SEQ ID NO 91
<211> LENGTH: 66
<212> TYPE: DNA
<213> ORGANISM: Artificial Sequence
<220> FEATURE:
<223> OTHER INFORMATION: Reverse primer

<400> SEQUENCE: 91
caagcagaag acggcatacg agataaccgt tcgtgactgg agttcagacg tgtgctcttc    60
cgatct    66

<210> SEQ ID NO 92
<211> LENGTH: 66
<212> TYPE: DNA
<213> ORGANISM: Artificial Sequence

```
<220> FEATURE:
<223> OTHER INFORMATION: Reverse primer

<400> SEQUENCE: 92
caagcagaag acggcatacg agatgacatt ccgtgactgg agttcagacg tgtgctcttc      60
cgatct                                                                 66

<210> SEQ ID NO 93
<211> LENGTH: 66
<212> TYPE: DNA
<213> ORGANISM: Artificial Sequence
<220> FEATURE:
<223> OTHER INFORMATION: Reverse primer

<400> SEQUENCE: 93
caagcagaag acggcatacg agatagaccg tagtgactgg agttcagacg tgtgctcttc      60
cgatct                                                                 66

<210> SEQ ID NO 94
<211> LENGTH: 66
<212> TYPE: DNA
<213> ORGANISM: Artificial Sequence
<220> FEATURE:
<223> OTHER INFORMATION: Reverse primer

<400> SEQUENCE: 94
caagcagaag acggcatacg agatgatact gggtgactgg agttcagacg tgtgctcttc      60
cgatct                                                                 66

<210> SEQ ID NO 95
<211> LENGTH: 66
<212> TYPE: DNA
<213> ORGANISM: Artificial Sequence
<220> FEATURE:
<223> OTHER INFORMATION: Reverse primer

<400> SEQUENCE: 95
caagcagaag acggcatacg agattgcgta gagtgactgg agttcagacg tgtgctcttc      60
cgatct                                                                 66

<210> SEQ ID NO 96
<211> LENGTH: 66
<212> TYPE: DNA
<213> ORGANISM: Artificial Sequence
<220> FEATURE:
<223> OTHER INFORMATION: Reverse primer

<400> SEQUENCE: 96
caagcagaag acggcatacg agattcggtt acgtgactgg agttcagacg tgtgctcttc      60
cgatct                                                                 66

<210> SEQ ID NO 97
<211> LENGTH: 66
<212> TYPE: DNA
<213> ORGANISM: Artificial Sequence
<220> FEATURE:
<223> OTHER INFORMATION: Reverse primer

<400> SEQUENCE: 97
caagcagaag acggcatacg agatatgacg tcgtgactgg agttcagacg tgtgctcttc      60
cgatct                                                                 66
```

<210> SEQ ID NO 98
<211> LENGTH: 66
<212> TYPE: DNA
<213> ORGANISM: Artificial Sequence
<220> FEATURE:
<223> OTHER INFORMATION: Reverse primer

<400> SEQUENCE: 98
caagcagaag acggcatacg agatgctgta aggtgactgg agttcagacg tgtgctcttc    60
cgatct                                                               66

<210> SEQ ID NO 99
<211> LENGTH: 66
<212> TYPE: DNA
<213> ORGANISM: Artificial Sequence
<220> FEATURE:
<223> OTHER INFORMATION: Reverse primer

<400> SEQUENCE: 99
caagcagaag acggcatacg agatgcaatg gagtgactgg agttcagacg tgtgctcttc    60
cgatct                                                               66

<210> SEQ ID NO 100
<211> LENGTH: 66
<212> TYPE: DNA
<213> ORGANISM: Artificial Sequence
<220> FEATURE:
<223> OTHER INFORMATION: Reverse primer

<400> SEQUENCE: 100
caagcagaag acggcatacg agatatctcg ctgtgactgg agttcagacg tgtgctcttc    60
cgatct                                                               66

<210> SEQ ID NO 101
<211> LENGTH: 66
<212> TYPE: DNA
<213> ORGANISM: Artificial Sequence
<220> FEATURE:
<223> OTHER INFORMATION: Reverse primer

<400> SEQUENCE: 101
caagcagaag acggcatacg agatggctat tggtgactgg agttcagacg tgtgctcttc    60
cgatct                                                               66

<210> SEQ ID NO 102
<211> LENGTH: 66
<212> TYPE: DNA
<213> ORGANISM: Artificial Sequence
<220> FEATURE:
<223> OTHER INFORMATION: Reverse primer

<400> SEQUENCE: 102
caagcagaag acggcatacg agatggtgtc ttgtgactgg agttcagacg tgtgctcttc    60
cgatct                                                               66

<210> SEQ ID NO 103
<211> LENGTH: 66
<212> TYPE: DNA
<213> ORGANISM: Artificial Sequence
<220> FEATURE:
<223> OTHER INFORMATION: Reverse primer

<400> SEQUENCE: 103
caagcagaag acggcatacg agattcaact gggtgactgg agttcagacg tgtgctcttc    60
cgatct    66

<210> SEQ ID NO 104
<211> LENGTH: 66
<212> TYPE: DNA
<213> ORGANISM: Artificial Sequence
<220> FEATURE:
<223> OTHER INFORMATION: Reverse primer

<400> SEQUENCE: 104
caagcagaag acggcatacg agatcttcac cagtgactgg agttcagacg tgtgctcttc    60
cgatct    66

<210> SEQ ID NO 105
<211> LENGTH: 66
<212> TYPE: DNA
<213> ORGANISM: Artificial Sequence
<220> FEATURE:
<223> OTHER INFORMATION: Reverse primer

<400> SEQUENCE: 105
caagcagaag acggcatacg agatacggtc ttgtgactgg agttcagacg tgtgctcttc    60
cgatct    66

<210> SEQ ID NO 106
<211> LENGTH: 66
<212> TYPE: DNA
<213> ORGANISM: Artificial Sequence
<220> FEATURE:
<223> OTHER INFORMATION: Reverse primer

<400> SEQUENCE: 106
caagcagaag acggcatacg agattctcgc aagtgactgg agttcagacg tgtgctcttc    60
cgatct    66

<210> SEQ ID NO 107
<211> LENGTH: 66
<212> TYPE: DNA
<213> ORGANISM: Artificial Sequence
<220> FEATURE:
<223> OTHER INFORMATION: Reverse primer

<400> SEQUENCE: 107
caagcagaag acggcatacg agatggaatt gcgtgactgg agttcagacg tgtgctcttc    60
cgatct    66

<210> SEQ ID NO 108
<211> LENGTH: 66
<212> TYPE: DNA
<213> ORGANISM: Artificial Sequence
<220> FEATURE:
<223> OTHER INFORMATION: Reverse primer

<400> SEQUENCE: 108
caagcagaag acggcatacg agatacggat tcgtgactgg agttcagacg tgtgctcttc    60
cgatct    66

<210> SEQ ID NO 109
<211> LENGTH: 66
<212> TYPE: DNA

```
<213> ORGANISM: Artificial Sequence
<220> FEATURE:
<223> OTHER INFORMATION: Reverse primer

<400> SEQUENCE: 109
caagcagaag acggcatacg agatttaagc gggtgactgg agttcagacg tgtgctcttc    60
cgatct                                                               66

<210> SEQ ID NO 110
<211> LENGTH: 66
<212> TYPE: DNA
<213> ORGANISM: Artificial Sequence
<220> FEATURE:
<223> OTHER INFORMATION: Reverse primer

<400> SEQUENCE: 110
caagcagaag acggcatacg agattgcagg tagtgactgg agttcagacg tgtgctcttc    60
cgatct                                                               66

<210> SEQ ID NO 111
<211> LENGTH: 66
<212> TYPE: DNA
<213> ORGANISM: Artificial Sequence
<220> FEATURE:
<223> OTHER INFORMATION: Reverse primer

<400> SEQUENCE: 111
caagcagaag acggcatacg agatcaatcg acgtgactgg agttcagacg tgtgctcttc    60
cgatct                                                               66

<210> SEQ ID NO 112
<211> LENGTH: 66
<212> TYPE: DNA
<213> ORGANISM: Artificial Sequence
<220> FEATURE:
<223> OTHER INFORMATION: Reverse primer

<400> SEQUENCE: 112
caagcagaag acggcatacg agatgtgcca tagtgactgg agttcagacg tgtgctcttc    60
cgatct                                                               66

<210> SEQ ID NO 113
<211> LENGTH: 66
<212> TYPE: DNA
<213> ORGANISM: Artificial Sequence
<220> FEATURE:
<223> OTHER INFORMATION: Reverse primer

<400> SEQUENCE: 113
caagcagaag acggcatacg agattgttcg aggtgactgg agttcagacg tgtgctcttc    60
cgatct                                                               66

<210> SEQ ID NO 114
<211> LENGTH: 66
<212> TYPE: DNA
<213> ORGANISM: Artificial Sequence
<220> FEATURE:
<223> OTHER INFORMATION: Reverse primer

<400> SEQUENCE: 114
caagcagaag acggcatacg agattggagt tggtgactgg agttcagacg tgtgctcttc    60
cgatct                                                               66
```

<210> SEQ ID NO 115
<211> LENGTH: 66
<212> TYPE: DNA
<213> ORGANISM: Artificial Sequence
<220> FEATURE:
<223> OTHER INFORMATION: Reverse primer

<400> SEQUENCE: 115
caagcagaag acggcatacg agatacgatg acgtgactgg agttcagacg tgtgctcttc    60
cgatct                                                                66

<210> SEQ ID NO 116
<211> LENGTH: 66
<212> TYPE: DNA
<213> ORGANISM: Artificial Sequence
<220> FEATURE:
<223> OTHER INFORMATION: Reverse primer

<400> SEQUENCE: 116
caagcagaag acggcatacg agattgatgt ccgtgactgg agttcagacg tgtgctcttc    60
cgatct                                                                66

<210> SEQ ID NO 117
<211> LENGTH: 66
<212> TYPE: DNA
<213> ORGANISM: Artificial Sequence
<220> FEATURE:
<223> OTHER INFORMATION: Reverse primer

<400> SEQUENCE: 117
caagcagaag acggcatacg agattgaacc tggtgactgg agttcagacg tgtgctcttc    60
cgatct                                                                66

<210> SEQ ID NO 118
<211> LENGTH: 66
<212> TYPE: DNA
<213> ORGANISM: Artificial Sequence
<220> FEATURE:
<223> OTHER INFORMATION: Reverse primer

<400> SEQUENCE: 118
caagcagaag acggcatacg agatcttcgt tcgtgactgg agttcagacg tgtgctcttc    60
cgatct                                                                66

<210> SEQ ID NO 119
<211> LENGTH: 66
<212> TYPE: DNA
<213> ORGANISM: Artificial Sequence
<220> FEATURE:
<223> OTHER INFORMATION: Reverse primer

<400> SEQUENCE: 119
caagcagaag acggcatacg agatcttctg aggtgactgg agttcagacg tgtgctcttc    60
cgatct                                                                66

<210> SEQ ID NO 120
<211> LENGTH: 66
<212> TYPE: DNA
<213> ORGANISM: Artificial Sequence
<220> FEATURE:
<223> OTHER INFORMATION: Reverse primer

```
<400> SEQUENCE: 120
caagcagaag acggcatacg agattgctca tggtgactgg agttcagacg tgtgctcttc    60
cgatct                                                               66

<210> SEQ ID NO 121
<211> LENGTH: 66
<212> TYPE: DNA
<213> ORGANISM: Artificial Sequence
<220> FEATURE:
<223> OTHER INFORMATION: Reverse primer

<400> SEQUENCE: 121
caagcagaag acggcatacg agatagttcg tcgtgactgg agttcagacg tgtgctcttc    60
cgatct                                                               66

<210> SEQ ID NO 122
<211> LENGTH: 66
<212> TYPE: DNA
<213> ORGANISM: Artificial Sequence
<220> FEATURE:
<223> OTHER INFORMATION: Reverse primer

<400> SEQUENCE: 122
caagcagaag acggcatacg agattagcgt ctgtgactgg agttcagacg tgtgctcttc    60
cgatct                                                               66

<210> SEQ ID NO 123
<211> LENGTH: 66
<212> TYPE: DNA
<213> ORGANISM: Artificial Sequence
<220> FEATURE:
<223> OTHER INFORMATION: Reverse primer

<400> SEQUENCE: 123
caagcagaag acggcatacg agatggcgtt atgtgactgg agttcagacg tgtgctcttc    60
cgatct                                                               66

<210> SEQ ID NO 124
<211> LENGTH: 66
<212> TYPE: DNA
<213> ORGANISM: Artificial Sequence
<220> FEATURE:
<223> OTHER INFORMATION: Reverse primer

<400> SEQUENCE: 124
caagcagaag acggcatacg agatggtgat tcgtgactgg agttcagacg tgtgctcttc    60
cgatct                                                               66

<210> SEQ ID NO 125
<211> LENGTH: 66
<212> TYPE: DNA
<213> ORGANISM: Artificial Sequence
<220> FEATURE:
<223> OTHER INFORMATION: Reverse primer

<400> SEQUENCE: 125
caagcagaag acggcatacg agataacttg ccgtgactgg agttcagacg tgtgctcttc    60
cgatct                                                               66

<210> SEQ ID NO 126
<211> LENGTH: 66
```

```
<212> TYPE: DNA
<213> ORGANISM: Artificial Sequence
<220> FEATURE:
<223> OTHER INFORMATION: Reverse primer

<400> SEQUENCE: 126
caagcagaag acggcatacg agatgcaaga tcgtgactgg agttcagacg tgtgctcttc    60
cgatct                                                              66

<210> SEQ ID NO 127
<211> LENGTH: 66
<212> TYPE: DNA
<213> ORGANISM: Artificial Sequence
<220> FEATURE:
<223> OTHER INFORMATION: Reverse primer

<400> SEQUENCE: 127
caagcagaag acggcatacg agattcgcat tggtgactgg agttcagacg tgtgctcttc    60
cgatct                                                              66

<210> SEQ ID NO 128
<211> LENGTH: 66
<212> TYPE: DNA
<213> ORGANISM: Artificial Sequence
<220> FEATURE:
<223> OTHER INFORMATION: Reverse primer

<400> SEQUENCE: 128
caagcagaag acggcatacg agattgtaca ccgtgactgg agttcagacg tgtgctcttc    60
cgatct                                                              66

<210> SEQ ID NO 129
<211> LENGTH: 66
<212> TYPE: DNA
<213> ORGANISM: Artificial Sequence
<220> FEATURE:
<223> OTHER INFORMATION: Reverse primer

<400> SEQUENCE: 129
caagcagaag acggcatacg agatagctcc tagtgactgg agttcagacg tgtgctcttc    60
cgatct                                                              66

<210> SEQ ID NO 130
<211> LENGTH: 66
<212> TYPE: DNA
<213> ORGANISM: Artificial Sequence
<220> FEATURE:
<223> OTHER INFORMATION: Reverse primer

<400> SEQUENCE: 130
caagcagaag acggcatacg agatgcaatt cggtgactgg agttcagacg tgtgctcttc    60
cgatct                                                              66

<210> SEQ ID NO 131
<211> LENGTH: 66
<212> TYPE: DNA
<213> ORGANISM: Artificial Sequence
<220> FEATURE:
<223> OTHER INFORMATION: Reverse primer

<400> SEQUENCE: 131
caagcagaag acggcatacg agatcttagg acgtgactgg agttcagacg tgtgctcttc    60
```

```
cgatct                                                              66
```

<210> SEQ ID NO 132
<211> LENGTH: 66
<212> TYPE: DNA
<213> ORGANISM: Artificial Sequence
<220> FEATURE:
<223> OTHER INFORMATION: Reverse primer

<400> SEQUENCE: 132

```
caagcagaag acggcatacg agatgtccta aggtgactgg agttcagacg tgtgctcttc    60
cgatct                                                              66
```

<210> SEQ ID NO 133
<211> LENGTH: 66
<212> TYPE: DNA
<213> ORGANISM: Artificial Sequence
<220> FEATURE:
<223> OTHER INFORMATION: Reverse primer

<400> SEQUENCE: 133

```
caagcagaag acggcatacg agataacgtg gagtgactgg agttcagacg tgtgctcttc    60
cgatct                                                              66
```

<210> SEQ ID NO 134
<211> LENGTH: 66
<212> TYPE: DNA
<213> ORGANISM: Artificial Sequence
<220> FEATURE:
<223> OTHER INFORMATION: Reverse primer

<400> SEQUENCE: 134

```
caagcagaag acggcatacg agatctgtgt tggtgactgg agttcagacg tgtgctcttc    60
cgatct                                                              66
```

<210> SEQ ID NO 135
<211> LENGTH: 66
<212> TYPE: DNA
<213> ORGANISM: Artificial Sequence
<220> FEATURE:
<223> OTHER INFORMATION: Reverse primer

<400> SEQUENCE: 135

```
caagcagaag acggcatacg agatgttaag gcgtgactgg agttcagacg tgtgctcttc    60
cgatct                                                              66
```

<210> SEQ ID NO 136
<211> LENGTH: 66
<212> TYPE: DNA
<213> ORGANISM: Artificial Sequence
<220> FEATURE:
<223> OTHER INFORMATION: Reverse primer

<400> SEQUENCE: 136

```
caagcagaag acggcatacg agatcacctt acgtgactgg agttcagacg tgtgctcttc    60
cgatct                                                              66
```

<210> SEQ ID NO 137
<211> LENGTH: 66
<212> TYPE: DNA
<213> ORGANISM: Artificial Sequence
<220> FEATURE:
<223> OTHER INFORMATION: Reverse primer

<400> SEQUENCE: 137 caagcagaaag acggcatacg agattggtag ctgtgactgg agttcagacg tgtgctcttc     60
cgatct                                                                 66

<210> SEQ ID NO 138
<211> LENGTH: 66
<212> TYPE: DNA
<213> ORGANISM: Artificial Sequence
<220> FEATURE:
<223> OTHER INFORMATION: Reverse primer

<400> SEQUENCE: 138 caagcagaaag acggcatacg agatcagtga aggtgactgg agttcagacg tgtgctcttc     60
cgatct                                                                 66

<210> SEQ ID NO 139
<211> LENGTH: 66
<212> TYPE: DNA
<213> ORGANISM: Artificial Sequence
<220> FEATURE:
<223> OTHER INFORMATION: Reverse primer

<400> SEQUENCE: 139 caagcagaaag acggcatacg agatgttcaa ccgtgactgg agttcagacg tgtgctcttc     60
cgatct                                                                 66

<210> SEQ ID NO 140
<211> LENGTH: 66
<212> TYPE: DNA
<213> ORGANISM: Artificial Sequence
<220> FEATURE:
<223> OTHER INFORMATION: Reverse primer

<400> SEQUENCE: 140 caagcagaaag acggcatacg agattggcta tcgtgactgg agttcagacg tgtgctcttc     60
cgatct                                                                 66

<210> SEQ ID NO 141
<211> LENGTH: 66
<212> TYPE: DNA
<213> ORGANISM: Artificial Sequence
<220> FEATURE:
<223> OTHER INFORMATION: Reverse primer

<400> SEQUENCE: 141 caagcagaaag acggcatacg agatctggag tagtgactgg agttcagacg tgtgctcttc     60
cgatct                                                                 66

<210> SEQ ID NO 142
<211> LENGTH: 66
<212> TYPE: DNA
<213> ORGANISM: Artificial Sequence
<220> FEATURE:
<223> OTHER INFORMATION: Reverse primer

<400> SEQUENCE: 142 caagcagaaag acggcatacg agattctctt ccgtgactgg agttcagacg tgtgctcttc     60
cgatct                                                                 66

<210> SEQ ID NO 143

```
<211> LENGTH: 66
<212> TYPE: DNA
<213> ORGANISM: Artificial Sequence
<220> FEATURE:
<223> OTHER INFORMATION: Reverse primer

<400> SEQUENCE: 143
caagcagaag acggcatacg agattctaac gcgtgactgg agttcagacg tgtgctcttc     60
cgatct                                                                66

<210> SEQ ID NO 144
<211> LENGTH: 66
<212> TYPE: DNA
<213> ORGANISM: Artificial Sequence
<220> FEATURE:
<223> OTHER INFORMATION: Reverse primer

<400> SEQUENCE: 144
caagcagaag acggcatacg agatggtcag atgtgactgg agttcagacg tgtgctcttc     60
cgatct                                                                66

<210> SEQ ID NO 145
<211> LENGTH: 66
<212> TYPE: DNA
<213> ORGANISM: Artificial Sequence
<220> FEATURE:
<223> OTHER INFORMATION: Reverse primer

<400> SEQUENCE: 145
caagcagaag acggcatacg agatctctgg ttgtgactgg agttcagacg tgtgctcttc     60
cgatct                                                                66

<210> SEQ ID NO 146
<211> LENGTH: 66
<212> TYPE: DNA
<213> ORGANISM: Artificial Sequence
<220> FEATURE:
<223> OTHER INFORMATION: Reverse primer

<400> SEQUENCE: 146
caagcagaag acggcatacg agattgtggt acgtgactgg agttcagacg tgtgctcttc     60
cgatct                                                                66

<210> SEQ ID NO 147
<211> LENGTH: 66
<212> TYPE: DNA
<213> ORGANISM: Artificial Sequence
<220> FEATURE:
<223> OTHER INFORMATION: Reverse primer

<400> SEQUENCE: 147
caagcagaag acggcatacg agatcctata ccgtgactgg agttcagacg tgtgctcttc     60
cgatct                                                                66

<210> SEQ ID NO 148
<211> LENGTH: 66
<212> TYPE: DNA
<213> ORGANISM: Artificial Sequence
<220> FEATURE:
<223> OTHER INFORMATION: Reverse primer

<400> SEQUENCE: 148
caagcagaag acggcatacg agatttctct cggtgactgg agttcagacg tgtgctcttc     60
``` cgatct                                                              66

<210> SEQ ID NO 149
<211> LENGTH: 66
<212> TYPE: DNA
<213> ORGANISM: Artificial Sequence
<220> FEATURE:
<223> OTHER INFORMATION: Reverse primer

<400> SEQUENCE: 149
caagcagaag acggcatacg agatgtatgc tggtgactgg agttcagacg tgtgctcttc    60
cgatct                                                              66

<210> SEQ ID NO 150
<211> LENGTH: 66
<212> TYPE: DNA
<213> ORGANISM: Artificial Sequence
<220> FEATURE:
<223> OTHER INFORMATION: Reverse primer

<400> SEQUENCE: 150
caagcagaag acggcatacg agataagtcg aggtgactgg agttcagacg tgtgctcttc    60
cgatct                                                              66

<210> SEQ ID NO 151
<211> LENGTH: 66
<212> TYPE: DNA
<213> ORGANISM: Artificial Sequence
<220> FEATURE:
<223> OTHER INFORMATION: Reverse primer

<400> SEQUENCE: 151
caagcagaag acggcatacg agataaccga aggtgactgg agttcagacg tgtgctcttc    60
cgatct                                                              66

<210> SEQ ID NO 152
<211> LENGTH: 66
<212> TYPE: DNA
<213> ORGANISM: Artificial Sequence
<220> FEATURE:
<223> OTHER INFORMATION: Reverse primer

<400> SEQUENCE: 152
caagcagaag acggcatacg agattgttgt gggtgactgg agttcagacg tgtgctcttc    60
cgatct                                                              66

<210> SEQ ID NO 153
<211> LENGTH: 21
<212> TYPE: DNA
<213> ORGANISM: Artificial Sequence
<220> FEATURE:
<223> OTHER INFORMATION: P7 universal primer

<400> SEQUENCE: 153
caagcagaag acggcatacg a                                             21

<210> SEQ ID NO 154
<211> LENGTH: 20
<212> TYPE: DNA
<213> ORGANISM: Artificial Sequence
<220> FEATURE:
<223> OTHER INFORMATION: P5 universal primer

<400> SEQUENCE: 154
aatgatacgg cgaccaccga                                               20

<210> SEQ ID NO 155
<211> LENGTH: 70
<212> TYPE: DNA
<213> ORGANISM: Artificial Sequence
<220> FEATURE:
<223> OTHER INFORMATION: NEBNext i501 Primer

<400> SEQUENCE: 155
aatgatacgg cgaccaccga gatctacact atagcctaca ctctttccct acacgacgct   60
cttccgatct                                                          70

<210> SEQ ID NO 156
<211> LENGTH: 70
<212> TYPE: DNA
<213> ORGANISM: Artificial Sequence
<220> FEATURE:
<223> OTHER INFORMATION: NEBNext i502 Primer

<400> SEQUENCE: 156
aatgatacgg cgaccaccga gatctacaca tagaggcaca ctctttccct acacgacgct   60
cttccgatct                                                          70

<210> SEQ ID NO 157
<211> LENGTH: 70
<212> TYPE: DNA
<213> ORGANISM: Artificial Sequence
<220> FEATURE:
<223> OTHER INFORMATION: NEBNext i503 Primer

<400> SEQUENCE: 157
aatgatacgg cgaccaccga gatctacacc ctatcctaca ctctttccct acacgacgct   60
cttccgatct                                                          70

<210> SEQ ID NO 158
<211> LENGTH: 70
<212> TYPE: DNA
<213> ORGANISM: Artificial Sequence
<220> FEATURE:
<223> OTHER INFORMATION: NEBNext i504 Primer

<400> SEQUENCE: 158
aatgatacgg cgaccaccga gatctacacg gctctgaaca ctctttccct acacgacgct   60
cttccgatct                                                          70

<210> SEQ ID NO 159
<211> LENGTH: 70
<212> TYPE: DNA
<213> ORGANISM: Artificial Sequence
<220> FEATURE:
<223> OTHER INFORMATION: NEBNext i505 Primer

<400> SEQUENCE: 159
aatgatacgg cgaccaccga gatctacaca ggcgaagaca ctctttccct acacgacgct   60
cttccgatct                                                          70

<210> SEQ ID NO 160
<211> LENGTH: 70
<212> TYPE: DNA
<213> ORGANISM: Artificial Sequence

```
<220> FEATURE:
<223> OTHER INFORMATION: NEBNext i506 Primer

<400> SEQUENCE: 160
aatgatacgg cgaccaccga gatctacact aatcttaaca ctctttccct acacgacgct    60
cttccgatct                                                          70

<210> SEQ ID NO 161
<211> LENGTH: 70
<212> TYPE: DNA
<213> ORGANISM: Artificial Sequence
<220> FEATURE:
<223> OTHER INFORMATION: NEBNext i507 Primer

<400> SEQUENCE: 161
aatgatacgg cgaccaccga gatctacacc aggacgtaca ctctttccct acacgacgct    60
cttccgatct                                                          70

<210> SEQ ID NO 162
<211> LENGTH: 70
<212> TYPE: DNA
<213> ORGANISM: Artificial Sequence
<220> FEATURE:
<223> OTHER INFORMATION: NEBNext i508 Primer

<400> SEQUENCE: 162
aatgatacgg cgaccaccga gatctacacg tactgacaca ctctttccct acacgacgct    60
cttccgatct                                                          70

<210> SEQ ID NO 163
<211> LENGTH: 100
<212> TYPE: DNA
<213> ORGANISM: Artificial Sequence
<220> FEATURE:
<223> OTHER INFORMATION: UMI14_i701
<220> FEATURE:
<221> NAME/KEY: misc_feature
<222> LOCATION: (65)..(78)
<223> OTHER INFORMATION: n is a, c, g, or t

<400> SEQUENCE: 163
caagcagaag acggcatacg agatcgtgat gtgactggag ttcagacgtg tgctcttccg    60
atctnnnnnn nnnnnnnnaa cggacaggat gcagcaaaat                        100

<210> SEQ ID NO 164
<211> LENGTH: 100
<212> TYPE: DNA
<213> ORGANISM: Artificial Sequence
<220> FEATURE:
<223> OTHER INFORMATION: UMI14_i702
<220> FEATURE:
<221> NAME/KEY: misc_feature
<222> LOCATION: (65)..(78)
<223> OTHER INFORMATION: n is a, c, g, or t

<400> SEQUENCE: 164
caagcagaag acggcatacg agatacatcg gtgactggag ttcagacgtg tgctcttccg    60
atctnnnnnn nnnnnnnnaa cggacaggat gcagcaaaat                        100

<210> SEQ ID NO 165
<211> LENGTH: 100
<212> TYPE: DNA
<213> ORGANISM: Artificial Sequence
<220> FEATURE:
```

<223> OTHER INFORMATION: UMI14_i703
<220> FEATURE:
<221> NAME/KEY: misc_feature
<222> LOCATION: (65)..(78)
<223> OTHER INFORMATION: n is a, c, g, or t

<400> SEQUENCE: 165
caagcagaag acggcatacg agatgcctaa gtgactggag ttcagacgtg tgctcttccg    60
atctnnnnnn nnnnnnnnaa cggacaggat gcagcaaaat                          100

<210> SEQ ID NO 166
<211> LENGTH: 100
<212> TYPE: DNA
<213> ORGANISM: Artificial Sequence
<220> FEATURE:
<223> OTHER INFORMATION: UMI14_i704
<220> FEATURE:
<221> NAME/KEY: misc_feature
<222> LOCATION: (65)..(78)
<223> OTHER INFORMATION: n is a, c, g, or t

<400> SEQUENCE: 166
caagcagaag acggcatacg agattggtca gtgactggag ttcagacgtg tgctcttccg    60
atctnnnnnn nnnnnnnnaa cggacaggat gcagcaaaat                          100

<210> SEQ ID NO 167
<211> LENGTH: 100
<212> TYPE: DNA
<213> ORGANISM: Artificial Sequence
<220> FEATURE:
<223> OTHER INFORMATION: UMI14_i705
<220> FEATURE:
<221> NAME/KEY: misc_feature
<222> LOCATION: (65)..(78)
<223> OTHER INFORMATION: n is a, c, g, or t

<400> SEQUENCE: 167
caagcagaag acggcatacg agatcactgt gtgactggag ttcagacgtg tgctcttccg    60
atctnnnnnn nnnnnnnnaa cggacaggat gcagcaaaat                          100

<210> SEQ ID NO 168
<211> LENGTH: 100
<212> TYPE: DNA
<213> ORGANISM: Artificial Sequence
<220> FEATURE:
<223> OTHER INFORMATION: UMI14_i706
<220> FEATURE:
<221> NAME/KEY: misc_feature
<222> LOCATION: (65)..(78)
<223> OTHER INFORMATION: n is a, c, g, or t

<400> SEQUENCE: 168
caagcagaag acggcatacg agatattggc gtgactggag ttcagacgtg tgctcttccg    60
atctnnnnnn nnnnnnnnaa cggacaggat gcagcaaaat                          100

<210> SEQ ID NO 169
<211> LENGTH: 100
<212> TYPE: DNA
<213> ORGANISM: Artificial Sequence
<220> FEATURE:
<223> OTHER INFORMATION: UMI14_i707
<220> FEATURE:
<221> NAME/KEY: misc_feature
<222> LOCATION: (65)..(78)
<223> OTHER INFORMATION: n is a, c, g, or t

<400> SEQUENCE: 169

-continued

```
caagcagaag acggcatacg agatgatctg gtgactggag ttcagacgtg tgctcttccg    60
atctnnnnnn nnnnnnnnaa cggacaggat gcagcaaaat                         100
```

<210> SEQ ID NO 170
<211> LENGTH: 100
<212> TYPE: DNA
<213> ORGANISM: Artificial Sequence
<220> FEATURE:
<223> OTHER INFORMATION: UMI14_i708
<220> FEATURE:
<221> NAME/KEY: misc_feature
<222> LOCATION: (65)..(78)
<223> OTHER INFORMATION: n is a, c, g, or t

<400> SEQUENCE: 170

```
caagcagaag acggcatacg agattcaagt gtgactggag ttcagacgtg tgctcttccg    60
atctnnnnnn nnnnnnnnaa cggacaggat gcagcaaaat                         100
```

<210> SEQ ID NO 171
<211> LENGTH: 100
<212> TYPE: DNA
<213> ORGANISM: Artificial Sequence
<220> FEATURE:
<223> OTHER INFORMATION: UMI14_i709
<220> FEATURE:
<221> NAME/KEY: misc_feature
<222> LOCATION: (65)..(78)
<223> OTHER INFORMATION: n is a, c, g, or t

<400> SEQUENCE: 171

```
caagcagaag acggcatacg agatctgatc gtgactggag ttcagacgtg tgctcttccg    60
atctnnnnnn nnnnnnnnaa cggacaggat gcagcaaaat                         100
```

<210> SEQ ID NO 172
<211> LENGTH: 100
<212> TYPE: DNA
<213> ORGANISM: Artificial Sequence
<220> FEATURE:
<223> OTHER INFORMATION: UMI14_i710
<220> FEATURE:
<221> NAME/KEY: misc_feature
<222> LOCATION: (65)..(78)
<223> OTHER INFORMATION: n is a, c, g, or t

<400> SEQUENCE: 172

```
caagcagaag acggcatacg agataagcta gtgactggag ttcagacgtg tgctcttccg    60
atctnnnnnn nnnnnnnnaa cggacaggat gcagcaaaat                         100
```

<210> SEQ ID NO 173
<211> LENGTH: 100
<212> TYPE: DNA
<213> ORGANISM: Artificial Sequence
<220> FEATURE:
<223> OTHER INFORMATION: UMI14_i711
<220> FEATURE:
<221> NAME/KEY: misc_feature
<222> LOCATION: (65)..(78)
<223> OTHER INFORMATION: n is a, c, g, or t

<400> SEQUENCE: 173

```
caagcagaag acggcatacg agatgtagcc gtgactggag ttcagacgtg tgctcttccg    60
atctnnnnnn nnnnnnnnaa cggacaggat gcagcaaaat                         100
```

<210> SEQ ID NO 174

```
<211> LENGTH: 100
<212> TYPE: DNA
<213> ORGANISM: Artificial Sequence
<220> FEATURE:
<223> OTHER INFORMATION: UMI14_i712
<220> FEATURE:
<221> NAME/KEY: misc_feature
<222> LOCATION: (65)..(78)
<223> OTHER INFORMATION: n is a, c, g, or t

<400> SEQUENCE: 174
caagcagaag acggcatacg agattacaag gtgactggag ttcagacgtg tgctcttccg    60
atctnnnnnn nnnnnnnnaa cggacaggat gcagcaaaat                         100

<210> SEQ ID NO 175
<211> LENGTH: 106
<212> TYPE: DNA
<213> ORGANISM: Artificial Sequence
<220> FEATURE:
<223> OTHER INFORMATION: Exemplary Probe Sequence
<220> FEATURE:
<221> NAME/KEY: misc_feature
<222> LOCATION: (61)..(74)
<223> OTHER INFORMATION: n is a, c, g, or t

<400> SEQUENCE: 175
attcttgagg aggaagtagc gtggccgcca ggtcttgatg acacgacgct cttccgatct    60
nnnnnnnnnn nnnntgcata ctggcaagat cggaagagca cacgtc                 106
```